US012338496B2

(12) United States Patent
Bramlett et al.

(10) Patent No.: US 12,338,496 B2
(45) **Date of Patent: *Jun. 24, 2025**

(54) METHODS, SYSTEMS, COMPOSITIONS, KITS, APPARATUS AND COMPUTER-READABLE MEDIA FOR MOLECULAR TAGGING

(71) Applicant: LIFE TECHNOLOGIES CORPORATION, Carlsbad, CA (US)

(72) Inventors: Kelli Bramlett, Austin, TX (US); Dumitru Brinza, Montara, CA (US); Richard Chien, Foster City, CA (US); Dalia Dhingra, San Francisco, CA (US); Jian Gu, Austin, TX (US); Ann Mongan, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 17/389,009

(22) Filed: Jul. 29, 2021

(65) Prior Publication Data

US 2021/0363596 A1 Nov. 25, 2021

Related U.S. Application Data

(63) Continuation of application No. 16/503,262, filed on Jul. 3, 2019, now Pat. No. 11,124,842, which is a continuation of application No. 15/178,450, filed on Jun. 9, 2016, now Pat. No. 10,344,336.

(60) Provisional application No. 62/323,142, filed on Apr. 15, 2016, provisional application No. 62/311,276, filed on Mar. 21, 2016, provisional application No. 62/310,647, filed on Mar. 18, 2016, provisional application No. 62/304,530, filed on Mar. 7, 2016, provisional application No. 62/248,978, filed on Oct. 30, 2015, provisional application No. 62/207,177, filed on Aug. 19, 2015, provisional application No. 62/172,836, filed on Jun. 9, 2015.

(51) Int. Cl.

| | |
|---|---|
| ***C12Q 1/68*** | (2018.01) |
| ***C12Q 1/6827*** | (2018.01) |
| ***C12Q 1/6874*** | (2018.01) |
| ***C12Q 1/6886*** | (2018.01) |

(52) U.S. Cl.

CPC ......... *C12Q 1/6886* (2013.01); *C12Q 1/6827* (2013.01); *C12Q 1/6874* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 5,333,675 | A | 8/1994 | Mullis et al. |
| 5,508,169 | A | 4/1996 | Deugau et al. |
| 5,635,400 | A | 6/1997 | Brenner |
| 5,846,719 | A | 12/1998 | Brenner et al. |
| 5,863,722 | A | 1/1999 | Brenner |
| 5,882,856 | A | 3/1999 | Shuber |
| 6,172,214 | B1 | 1/2001 | Brenner |
| 6,207,372 | B1 | 3/2001 | Shuber |
| 6,521,428 | B1 | 2/2003 | Senapathy |
| 6,607,878 | B2 | 8/2003 | Sorge |
| 6,890,741 | B2 | 5/2005 | Fan et al. |
| 7,393,665 | B2 | 7/2008 | Brenner |
| 7,537,897 | B2 | 5/2009 | Brenner et al. |
| 7,579,154 | B2 | 8/2009 | Chun |
| 7,803,550 | B2 | 9/2010 | Makarov et al. |
| 7,948,015 | B2 | 5/2011 | Rothberg et al. |
| 8,053,192 | B2 | 11/2011 | Bignell et al. |
| 8,148,068 | B2 | 4/2012 | Brenner |

(Continued)

FOREIGN PATENT DOCUMENTS

| | | |
|---|---|---|
| CN | 103045726 A | 4/2013 |
| CN | 103748236 A | 4/2014 |

(Continued)

OTHER PUBLICATIONS

Binladen, Jonas et al., "The Use of Coded PCR Primers Enables High-Throughput Sequencing of Multiple Homolog Amplification Products by 454 Parallel Sequencing", PLoS ONE, 2(2):, 2007, e197.

Brenner, Sydney et al., "In vitro cloning of complex mixtures of DNA on microbeads: Physical separation of differentially expressed cDNAs", PNAS vol. 97 No.4 2000, 1665-1670.

Brinza, Dumitru et al., "Abstract 2402: A research approach for the detection of somatic mutations at 0.5% frequency from cfDNA and eTc DNA using a multiplex sequencing assay targeting 2000 tumor mutations", Cancer Research, vol. 75, No. 15 Supplement, Apr. 22, 2015, 2402-2402.

(Continued)

*Primary Examiner* — Suryaprabha Chunduru

(57) ABSTRACT

In some embodiments, the disclosure relates generally to methods, as well as related systems, compositions, kits, apparatuses and computer-readable media, comprising a multiplex molecular tagging procedure that employs a plurality of tags that are appended to a plurality of polynucleotides. The tags have characteristics, including a sequence, length and/or detectable moiety, or any other characteristic, that uniquely identifies the polynucleotide molecule to which it is appended, and permits tracking individual tagged molecules in a mixture of tagged molecules. For example, the tag having a unique tag sequence, can uniquely identify an individual polynucleotide to which it is appended, and distinguish the individual polynucleotide from other tagged polynucleotides in a mixture. In some embodiments, the multiplex molecular tagging procedure can be used for generating error-corrected sequencing data and for detecting a target polynucleotide which is present at low abundance in a nucleic acid sample.

20 Claims, 57 Drawing Sheets

Specification includes a Sequence Listing.

(56) References Cited

U.S. PATENT DOCUMENTS

| | | | | |
|---|---|---|---|---|
| 8,168,385 | B2 | 5/2012 | Brenner | |
| 8,182,989 | B2 | 5/2012 | Bignell et al. | |
| 8,318,433 | B2 | 11/2012 | Brenner | |
| 8,470,996 | B2 | 6/2013 | Brenner | |
| 8,476,018 | B2 | 7/2013 | Brenner | |
| 8,481,292 | B2 | 7/2013 | Casbon et al. | |
| 8,666,678 | B2 | 3/2014 | Davey et al. | |
| 8,685,678 | B2 | 4/2014 | Casbon et al. | |
| 8,685,889 | B2 | 4/2014 | Van et al. | |
| 8,715,967 | B2 | 5/2014 | Casbon et al. | |
| 8,722,368 | B2 | 5/2014 | Casbon et al. | |
| 8,728,766 | B2 | 5/2014 | Casbon et al. | |
| 8,741,606 | B2 | 6/2014 | Casbon et al. | |
| 8,822,150 | B2 | 9/2014 | Bignell et al. | |
| 8,835,358 | B2 | 9/2014 | Fodor et al. | |
| 8,865,410 | B2 | 10/2014 | Shendure et al. | |
| 9,018,365 | B2 | 4/2015 | Brenner | |
| 9,085,798 | B2 | 7/2015 | Chee | |
| 9,194,001 | B2 | 11/2015 | Brenner | |
| 9,260,753 | B2 | 2/2016 | Xie et al. | |
| 9,315,857 | B2 | 4/2016 | Fu et al. | |
| 9,340,830 | B2 | 5/2016 | Downing et al. | |
| 10,344,336 | B2 | 7/2019 | Bramlett et al. | |
| 2004/0185484 | A1 | 9/2004 | Costa et al. | |
| 2006/0263789 | A1 | 11/2006 | Kincaid et al. | |
| 2007/0020640 | A1 | 1/2007 | McCloskey et al. | |
| 2008/0261204 | A1 | 10/2008 | Lexow | |
| 2009/0318310 | A1 | 12/2009 | Liu et al. | |
| 2012/0283110 | A1 | 11/2012 | Shendure et al. | |
| 2013/0060482 | A1 | 3/2013 | Sikora et al. | |
| 2013/0090860 | A1 | 4/2013 | Sikora et al. | |
| 2013/0302801 | A1 | 11/2013 | Asbury et al. | |
| 2014/0066317 | A1* | 3/2014 | Talasaz | G16B 30/10 506/2 |
| 2014/0227705 | A1 | 8/2014 | Vogelstein et al. | |
| 2014/0255929 | A1 | 9/2014 | Zheng | |
| 2014/0274731 | A1 | 9/2014 | Raymond et al. | |
| 2014/0357499 | A1 | 12/2014 | Gordon et al. | |
| 2015/0044687 | A1 | 2/2015 | Schmitt et al. | |
| 2015/0087535 | A1 | 3/2015 | Patel | |
| 2015/0197798 | A1 | 7/2015 | Xu et al. | |
| 2015/0299812 | A1 | 10/2015 | Talasaz | |
| 2015/0322507 | A1 | 11/2015 | Zimmermann et al. | |
| 2016/0017320 | A1 | 1/2016 | Wang et al. | |
| 2016/0040229 | A1 | 2/2016 | Talasaz et al. | |
| 2016/0046986 | A1 | 2/2016 | Eltoukhy et al. | |
| 2016/0115532 | A1 | 4/2016 | Faham | |

FOREIGN PATENT DOCUMENTS

| | | | |
|---|---|---|---|
| CN | 104364392 | A | 2/2015 |
| WO | WO-03050304 | A1 | 6/2003 |
| WO | WO-2007037678 | A2 | 4/2007 |
| WO | WO-2012142213 | A2 | 10/2012 |
| WO | WO-2013130512 | A2 | 9/2013 |
| WO | WO-2013142389 | A1 | 9/2013 |
| WO | WO-2013181170 | A1 | 12/2013 |
| WO | WO-2014039556 | A1 | 3/2014 |
| WO | WO-2014130890 | A1 | 8/2014 |
| WO | WO-2015100427 | A1 | 7/2015 |

OTHER PUBLICATIONS

Church, George M. et al., "Multiplex DNA sequencing", Science vol. 240, 1988, pp. 185-188.

Craig, et al. Identification of genetic variants using bar-coded multiplexed sequencing. Nat Methods. Oct. 2008;5(10):887-93. doi: 10.1038/nmeth.1251. Epub Sep. 14, 2008.

Cronn, Richard et al., "Multiplex sequencing of plant chloroplast genomes using Solexa sequencing-by-synthesis technology", Nucleic Acids Research, vol. 36, No. 19, e122; doi:10.1093/nar/qkn502, 2008, 1-11.

Delhomme, Tiffany, "Needlestack an highly scalable and reproducible pipeline for the detection of ctDNA variants", International Agency for Research on Cancer IARC (WHO), Jun. 27, 2015, 1-31.

Eason, et al., "Characterization of synthetic DNA bar codes in *Saccharomyces cerevisiae* gene-deletion strains", Proceedings of the National Academy of Sciences, vol. 101, No. 30, Jul. 27, 2004,11046-11051.

EP19196414.7, Extended Search Report, Mar. 17, 2020, 6 pages.

Fernandez-Cuesta, Lynnette et al., "Identification of Circulating Tumor DNA for the Early Detection of Small-cell Lung Cancer", EBioMedicine, 10, 2016, 117-123.

Gray et al., "Selection of Therapeutic H5N1 Monoclonal Antibodies Following IgVH Repertoire Analysis in Mice", Antiviral Research, vol. 131, Apr. 21, 2016, pp. 100-108, XP029570500.

Harper, Diane et al., "Efficacy of a bivalent L1 virus-like particle vaccine in prevention of infection with human papillomavirus types 16 and 18 in young women: a randomised controlled trial", The Lancet, 364, 2004, 1757-65.

Hoffmann, Christian et al., "DNA bar coding and pyrosequencing to identify rare HIV drug resistance mutations", Nucleic Acids Research, vol. 35, No. 13 e91; doi:10.1093/nar/gkm435, 2007, 1-8.

Hug, Hubert et al., "Measurement of the No. of Molecules of a Single mRNA Species in a Complex mRNA Preparation", Journal of Theoretical Biolog, 221, doi:10.1006/jtbi.2003.3211, 2003, 615-624.

Kanagai-Shamanna R, et al., "Next-Generation Sequencing-Based Multi-Gene Mutation Profiling of Solid Tumors Using Fine Needle Aspiration Samples: Promises and Challenges for Routine Clinical Diagnostics", Modern Pathology, vol. 27, 2004, pp. 314-327.

Kennedy et al., "Detecting ultralow-frequency mutations by Duplex Sequencing", Nature Protocols, 2014, vol. 9, No. 11, pp. 2586-2606.

Kinde, Isaac et al., "Detection and quantification of rare mutations with massively parallel sequencing", Proceedings of the National Academy of Science, vol. 108, No. 23, 2011, 9530-9535.

Miner, Brooks et al., "Molecular barcodes detect redundancy and contamination in hairpinbisulfite PCR", Nucleic Acids Research, vol. 32, No. 17 e135, doi:10.1093/nar/gnh132, 2004, 1-4.

Morgenstern B et al., "Multiple Sequence Alignment with User-Defined Anchor Points," Algorithms for Molecular Biology, Apr. 19, 2006, vol. 1, No. 6, 12 pages.

Parameswaran, Poornima et al., "A pyrosequencing-tailored nucleotide barcode design unveils opportunities for large-scale sample multiplexing", Nucleic Acids Research, vol. 35, No. 19 e130, doi: 10.1093/nar/gkm760, 2007, 1-9.

PCT/US2016/036763, International Search Report and Written Opinion mailed Aug. 12, 2016, 15 pages.

Peng, Quan et al., "Reducing amplification artifacts in high multiplex amplicon sequencing by using molecular barcodes", BMC Genomics, 16:589, DOI 10.1186/s12864-015-1806-8, 2015, 1-12.

Pitschi F et al., "Automatic Detection of Anchor Points for Multiple Sequence Alignment," BMC Bioinformatics, Sep. 2, 2010, vol. 11, No. 445, 11 pages.

Rothberg et al., "An integrated semiconductor device enabling non-optical genome sequencing", Nature, vol. 475, No. 7356, Jul. 21, 2011, pp. 348-352.

Schmitt, Michael et al., "Detection of ultra-rare mutations by next-generation sequencing", Proceedings of the National Academy of Science, vol. 109, No. 36, 2012, 14508-14513.

Spencer, D.H. et al., J. Mol. Diagn., vol. 16, pp. 75-88 (2014).

Stiller, Mathias et al., "Direct multiplex sequencing (DMPS)—a novel method for targeted high-throughput sequencing of ancient and highly degraded DNA", Genome Research, vol. 19, 2009, 1843-1848.

* cited by examiner

| Gene | Type | 0.5% Control | 0.5% Control | 0.5% Control | 0.5% Control | 0.1% Control | 0.1% Control | 0.1% Control | 0.1% Control |
|---|---|---|---|---|---|---|---|---|---|
| EGFR | SNP | 2847 | 2896 | 3186 | 3104 | 3170 | 3061 | 3369 | 3409 |
| KRAS | SNP | 32 | 54 | 46 | 47 | 9 | 10 | 8 | 15 |
| KRAS | SNP | 32 | 54 | 46 | 45 | 9 | 10 | 9 | 15 |
| NRAS | SNP | 39 | 39 | 39 | 49 | 9 | 9 | 13 | 12 |
| NRAS | SNP | 39 | 39 | 39 | 49 | 8 | 9 | 13 | 12 |
| MET | SNP | 52 | 39 | 37 | 41 | 4 | 5 | 8 | 17 |
| MET | SNP | 40 | 45 | 42 | 39 | 6 | 8 | 12 | 0 |
| MET | SNP | 48 | 37 | 32 | 31 | 9 | 12 | 7 | 15 |
| ALK | SNP | 41 | 28 | 34 | 44 | 7 | 11 | 9 | 7 |
| TP53 | SNP | 31 | 29 | 42 | 42 | 0 | 9 | 7 | 11 |
| TP53 | SNP | 31 | 29 | 42 | 42 | 0 | 9 | 7 | 11 |
| EGFR | SNP | 29 | 35 | 33 | 39 | 4 | 8 | 4 | 11 |
| TP53 | SNP | 32 | 27 | 30 | 35 | 3 | 9 | 11 | 11 |
| PIK3CA | SNP | 30 | 40 | 26 | 27 | 4 | 5 | 12 | 14 |
| TP53 | SNP | 32 | 27 | 30 | 35 | 3 | 9 | 11 | 10 |
| TP53 | SNP | 33 | 27 | 30 | 35 | 3 | 8 | 11 | 9 |
| TP53 | SNP | 32 | 27 | 29 | 34 | 3 | 8 | 12 | 10 |
| PIK3CA | SNP | 28 | 40 | 26 | 27 | 4 | 5 | 11 | 14 |
| PIK3 CA | SNP | 28 | 40 | 26 | 27 | 4 | 5 | 11 | 14 |
| PIK3CA | SNP | 27 | 40 | 26 | 27 | 4 | 5 | 11 | 14 |
| KRAS | SNP | 25 | 37 | 35 | 23 | 9 | 3 | 13 | 6 |
| KRAS | SNP | 25 | 37 | 34 | 23 | 9 | 3 | 13 | 6 |

FIG. 6A

| | | | | | | | | | |
|---|---|---|---|---|---|---|---|---|---|
| EGFR | SNP | 35 | 21 | 31 | 30 | 7 | 5 | 0 | 5 |
| TP53 | SNP | 25 | 20 | 44 | 32 | 0 | 0 | 9 | 2 |
| ALK | SNP | 24 | 19 | 33 | 23 | 0 | 4 | 15 | 14 |
| TP53 | SNP | 24 | 20 | 44 | 32 | 0 | 0 | 7 | 2 |
| TP53;TP53_chr17 | SNP | 22 | 29 | 27 | 28 | 3 | 4 | 5 | 9 |
| TP53;TP53_chr17 | SNP | 20 | 29 | 27 | 28 | 3 | 4 | 5 | 9 |
| TP53;TP53_chr17 | SNP | 20 | 29 | 27 | 28 | 3 | 4 | 5 | 9 |
| TP53;TP53_chr17 | SNP | 19 | 29 | 27 | 28 | 3 | 4 | 5 | 9 |
| ERBB2 | SNP | 27 | 18 | 21 | 34 | 4 | 5 | 4 | 6 |
| BRAF;BRAF_chr7 | SNP | 24 | 19 | 19 | 22 | 6 | 3 | 12 | 5 |
| BRAF;BRAF_chr7 | SNP | 24 | 19 | 19 | 22 | 6 | 3 | 12 | 5 |
| BRAF;BRAF_chr7 | SNP | 24 | 19 | 19 | 22 | 6 | 3 | 11 | 5 |
| TP53;TP53_chr17 | SNP | 21 | 16 | 14 | 20 | 5 | 5 | 9 | 6 |
| TP53;TP53_chr17 | SNP | 20 | 16 | 14 | 20 | 5 | 5 | 9 | 6 |
| TP53;TP53_chr17 | SNP | 20 | 16 | 14 | 20 | 5 | 5 | 9 | 6 |
| TP53;TP53_chr17 | SNP | 20 | 15 | 14 | 21 | 5 | 5 | 9 | 6 |
| NRAS;NRAS_chr1 | SNP | 15 | 18 | 18 | 22 | 6 | 0 | 9 | 4 |
| NRAS;NRAS_chr1 | SNP | 15 | 18 | 17 | 22 | 6 | 0 | 9 | 4 |
| NRAS;NRAS_chr1 | SNP | 15 | 18 | 18 | 22 | 6 | 2 | 9 | 0 |
| **TP count** | | 41 | 41 | 41 | 41 | 36 | 37 | 40 | 39 |
| **Sensitivity** | | 100% | 100% | 100% | 100% | 88% | 90% | 98% | 95% |

FIG. 6B

Chr12:121432083

T>C 437C/40997depth

| SEQ ID NO: | Barcode | Count | Fraction |
|---|---|---|---|
| 73 | GGGACTGGGTGA | 86 | 0.016 |
| 74 | CGGACTGGGTGA | 10 | 0.007 |
| 75 | GAGACTGGGTGA | 8 | 0.012 |
| 76 | GCACTGGGTGAT | 8 | 0.019 |
| 77 | GGACTGGGTGAT | 8 | 0.010 |
| 78 | GCGACTGGGTGA | 7 | 0.013 |

FIG. 23C

Chr12:121432023

A>C 556C/45780 depth

| SEQ ID NO: | Barcode | Count | Fraction |
|---|---|---|---|
| 113 | GGGACTGGGTGA | 40 | 0.007 |
| 114 | CGGACTGGGTGA | 7 | 0.005 |
| 115 | GACTGGGTGATG | 6 | 0.012 |
| 116 | GGGACTGCGTGA | 6 | 0.013 |
| 117 | GGGACTCGGTGA | 5 | 0.013 |
| 118 | GGTACTGGGTGA | 4 | 0.019 |

FIG. 24C

| 729 M | 0.2X |
|---|---|
| Total Aligned Bases | Reference Coverage |

| | Count | % |
|---|---|---|
| Total Reads | 7,089,793 | — |
| Aligned Reads | 4,378,492 | 61.8% |
| Unaligned Reads | 2,711,301 | 38.2% |

| 1 G | 0.3X |
|---|---|
| Total Aligned Bases | Reference Coverage |

| | Count | % |
|---|---|---|
| Total Reads | 6,778,356 | — |
| Aligned Reads | 5,855,514 | 86.4% |
| Unaligned Reads | 922,842 | 13.6% |

| | |
|---|---|
| Number of mapped reads | 5,855,514 |
| Percent reads on target | 97.54% |
| Average base coverage depth | 44,085 |
| Uniformity of base coverage | 99.40% |

| Amplicon Read Coverage | |
| --- | --- |
| Number of amplicons | 129 |
| Percent assigned amplicon reads | 97.54% |
| Average reads per amplicon | 44,276 |
| Uniformity of amplicon coverage | 99.22% |
| Amplicons with at least 1 read | 100.00% |
| Amplicons with at least 20 reads | 100.00% |
| Amplicons with at least 100 reads | 100.00% |
| Amplicons with at least 500 reads | 100.00% |
| Amplicons with no strand bias | 0.00% |
| Amplicons reading end-to-end | 94.57% |

| Target Base Coverage | |
| --- | --- |
| Bases in target regions | 13,403 |
| Percent base reads on target | 58.77% |
| Average base coverage depth | 44,085 |
| Uniformity of base coverage | 99.40% |
| Target base coverage at 1x | 100.00% |
| Target base coverage at 20x | 100.00% |
| Target base coverage at 100x | 100.00% |
| Target base coverage at 500x | 100.00% |
| Target bases with no strand bias | 0.00% |
| Percent end-to-end reads | 91.75% |

FIG. 32B

METHODS, SYSTEMS, COMPOSITIONS, KITS, APPARATUS AND COMPUTER-READABLE MEDIA FOR MOLECULAR TAGGING

CROSS REFERENCE TO RELATED APPLICATIONS

This application is a continuation of U.S. Non-provisional application Ser. No. 16/503,262, filed Jul. 3, 2019, which is a continuation of U.S. Non-provisional application Ser. No. 15/178,450, filed Jun. 9, 2016, now U.S. Pat. No. 10,344,336, which claims the benefit of priority under 35 U.S.C. § 119 to U.S. Provisional Application Nos. 62/172,836, filed Jun. 9, 2015, 62/207,177, filed Aug. 19, 2015, 62/248,978, filed Oct. 30, 2015, 62/304,530, filed Mar. 7, 2016, 62/310,647, filed Mar. 18, 2016, 62/311,276, filed Mar. 21, 2016, and 62/323,142, filed Apr. 15, 2016; the disclosures of all of the which aforementioned applications are incorporated by reference in their entireties.

Throughout this application various publications, patents, and/or patent applications are referenced. The disclosures of the publications, patents and/or patent applications in their entireties are hereby incorporated by reference into this application in order to more fully describe the state of the art to which this invention pertains.

SUMMARY

In some embodiments, the disclosure relates generally to methods, as well as related systems, compositions, kits, apparatuses and computer-readable media for detecting genetic variants, identifying genetic variants and/or generating error-corrected sequencing data, which employs a molecular tagging procedure, in which polynucleotides are appended with at least one tag.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, comprising the steps: (a) forming a single reaction mixture containing: (i) a plurality of polynucleotides from the nucleic acid sample, and (ii) a plurality of oligonucleotide tags.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprises the steps: (b) generating within the single reaction mixture a plurality of tagged polynucleotides by appending at least one tag from the plurality of oligonucleotide tags to individual polynucleotides within the plurality of polynucleotides.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprises the steps: (c) generating a population of tagged amplicons by amplifying the plurality of tagged polynucleotides.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprises the steps: (d) sequencing at least a portion of the population of tagged amplicons.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprises the steps: (e) determining that the variant sequence target polynucleotide is present in the nucleic acid sample at an abundance level of 0.05-5%.

In some embodiments, the single reaction mixture of step (a) contains 1-100 ng of the plurality of polynucleotides, which includes a mixture of target and non-target polynucleotides.

In some embodiments, the plurality of oligonucleotide tags in the single reaction mixture of step (a) detects the presence of 5-100 different polynucleotides in the nucleic acid sample.

In some embodiments, the plurality of oligonucleotide tags in the single reaction mixture of step (a) detects 85-100% of the different polynucleotides that are present in the nucleic acid sample.

In some embodiments, the nucleic acid sample comprises cell-free nucleic acids from a biological fluid, nucleic acids from a biopsied tissue, nucleic acids from a needle biopsy, or nucleic acids from cells.

In some embodiments, any two of the plurality of tagged polynucleotides in step (b) are appended with tags that differ from each other. In some embodiments, any two of the plurality of tagged polynucleotides are appended with a different oligonucleotide tag at both ends. For example, the two tagged polynucleotides that are appended with tags that differ from each other are the same or different two tagged polynucleotide that are appended with a different oligonucleotide tag at both ends.

In some embodiments, at least two of the plurality of tagged polynucleotides in step (b) are appended with tags that differ from each other, wherein the at least two of the plurality of tagged polynucleotides are appended with a different oligonucleotide tag at both ends.

In some embodiments, individual oligonucleotide tags in the plurality of oligonucleotide tags in step (a) include a region having a randomer tag sequence which comprises different random tag sequences alternating with fixed tag sequences.

In some embodiments, the single reaction mixture of step (a) contains a plurality of oligonucleotide tags having $10^4$-$10^9$ different randomer tag sequences.

In some embodiments, the plurality of oligonucleotide tags in the single reaction mixture of step (a) include a randomer tag sequence which comprises the structure $(N)_n(X)_x(M)_m(Y)_y$, wherein (i) "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; (iv) wherein "Y" represents a fixed tag sequence that is the same in all of the plurality of tags, wherein the fixed tag sequence of "Y" differs from the fixed tag sequence of "X", and wherein the length "y" is 2-10; and (v) wherein the fixed tag sequences "$(X)_x$" and "$(Y)_y$" are sequence alignment anchors.

In some embodiments, the plurality of the oligonucleotide tags in the single reaction mixture that appended to individual polynucleotides in a primer extension reaction in step (b), wherein the plurality of oligonucleotide tags in the single reaction mixture comprise a plurality of single-stranded primers which include: (i) a 3' region that specifically binds a target sequence in the plurality of polynucleotides from the nucleic acid sample, and (ii) a 5' tail having a sequence that does not bind to a target sequence in the plurality of polynucleotides from the nucleic acids sample and the 5' tail includes a sequence comprising the randomer tag sequence.

In some embodiments, the plurality of oligonucleotide tags in the single reaction mixture are appended to individual polynucleotides in an enzymatic ligation reaction in step (b), wherein the plurality of oligonucleotide tags in the single reaction mixture comprise a plurality of a double-stranded linear adaptor, a stem-looped adaptor or a Y-shaped adaptor, and wherein the plurality of oligonucleotide tags includes the randomer tag sequence.

In some embodiments, the disclosure relates generally to methods, as well as related systems, compositions, kits, apparatuses and computer-readable media, further comprise: generating a plurality of tagged capture polynucleotides by appending the plurality of polynucleotides with at least one universal sequence selected from a group consisting of: an amplification primer sequence, a sequencing primer sequence, a capture primer sequence and a cleavable site.

In some embodiments, the disclosure relates generally to methods, as well as related systems, compositions, kits, apparatuses and computer-readable media, further comprise: (a) forming a plurality of captured polynucleotides, by binding the plurality of tagged capture polynucleotides to a plurality of capture primers attached to a support; and (b) sequencing the plurality of captured polynucleotides.

In some embodiments, the support includes an array of $10^4$-$10^9$ sequencing reaction sites.

In some embodiments, the sequencing reaction sites are operatively coupled to at least one CMOS sensor that detects a nucleotide incorporation event.

In some embodiments, the sequencing in step (b) further comprises: flowing one type of nucleotide onto the plurality of captured polynucleotides. For example, the one type of nucleotide is selected from a group consisting of a nucleotide labeled with an optically-detectable label, a nucleotide that is not labeled with an optically-detectable label, is terminator nucleotide, or a nucleotide that is not a terminator nucleotide.

In some embodiments, the sequencing in step (b) includes flowing 2-4 different types of nucleotides onto the plurality of captured polynucleotides. For example, at least one type of the 2-4 different types of nucleotides is selected from a group consisting of a nucleotide labeled with an optically-detectable label, a nucleotide that is not labeled with an optically-detectable label, is terminator nucleotide, or a nucleotide that is not a terminator nucleotide.

In some embodiments, the disclosure relates generally to methods, as well as related systems, compositions, kits, apparatuses and computer-readable media, further comprise: sequencing at least a portion of the population of tagged amplicons to generate a plurality of candidate sequencing reads each having the randomer tag sequence which comprises different random tag sequences alternating with fixed tag sequences, wherein the fixed tags sequences within the randomer tag sequence form a sequence alignment anchor.

In some embodiments, the disclosure relates generally to methods, as well as related systems, compositions, kits, apparatuses and computer-readable media, further comprise: aligning the sequence alignment anchors of the plurality of candidate sequencing reads.

In some embodiments, the disclosure relates generally to a plurality of tagged polynucleotides which are generated by any method described herein.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, comprising the steps: (a) forming a single reaction mixture containing: (i) a plurality of polynucleotides from the nucleic acid sample, and (ii) a plurality of oligonucleotide tags.

In some embodiments, the disclosure relates generally to methods, as well as related systems, compositions, kits, apparatuses and computer-readable media, further comprise the step: (b) generating within the single reaction mixture a plurality of tagged polynucleotides by appending at least one tag to individual polynucleotides within the plurality of polynucleotides.

In some embodiments, the disclosure relates generally to methods, as well as related systems, compositions, kits, apparatuses and computer-readable media, further comprise the step: (c) generating a population of tagged amplicons by amplifying the plurality of tagged polynucleotides.

In some embodiments, the disclosure relates generally to methods, as well as related systems, compositions, kits, apparatuses and computer-readable media, further comprise the step: (d) sequencing at least a portion of the population of tagged amplicons.

In some embodiments, the disclosure relates generally to methods, as well as related systems, compositions, kits, apparatuses and computer-readable media, further comprise the step: (e) determining that the variant sequence target polynucleotide is present in the nucleic acid sample at an abundance level of 0.05-5%.

In some embodiments, the determining in step (e) comprises determining that the variant sequence target polynucleotide is present in the nucleic acid sample at an abundance level of 0.05-0.1%.

In some embodiments, the single reaction mixture in step (a) contains 1-100 ng of the plurality of polynucleotides, which includes a mixture of target and non-target polynucleotides.

In some embodiments, the plurality of oligonucleotide tags in the single reaction mixture in step (a) detect the presence of 5-100 different polynucleotides in the nucleic acid sample.

In some embodiments, the plurality of oligonucleotide tags in the single reaction mixture in step (a) detect 85-100% of the different polynucleotides that are present in the nucleic acid sample.

In some embodiments, the nucleic acid sample in step (a) comprises cell-free nucleic acids from a biological fluid, nucleic acids from a biopsied tissue, nucleic acids from a needle biopsy, or nucleic acids from cells.

In some embodiments, the biological fluid is blood, saliva, sputum, sweat, tears, lavage fluid, amniotic fluid, cerebrospinal fluid, ascites, urine, stool, feces, or semen.

In some embodiments, the nucleic acid sample in step (a) comprises DNA or RNA, or a mixture of DNA and RNA.

In some embodiments, at least two of the plurality of tagged target polynucleotides in step (b) are appended with tags that differ from each other.

In some embodiments, the plurality of tagged target polynucleotides in step (b) are appended with a different tag at both ends.

In some embodiments, individual oligonucleotide tags in the plurality of oligonucleotide tags in step (a) include a region comprising different random tag sequences alternating with fixed tag sequences.

In some embodiments, the single reaction mixture in step (a) contains a plurality of oligonucleotide tags having $10^4$-$10^9$ different random tag sequences.

In some embodiments, the variant sequence target polynucleotide is present in the nucleic acid sample as a variant sequence, polymorphic sequence or mutant sequence.

In some embodiments, the plurality of oligonucleotide tags in the single reaction mixture in step (b) are appended to their respective target polynucleotides in a sequence-dependent manner.

In some embodiments, the plurality of oligonucleotide tags in the single reaction mixture of step (a) are appended to their respective target polynucleotides in a primer extension reaction in step (b), and the single reaction mixture includes a polymerase and a plurality of nucleotides.

In some embodiments, the plurality of oligonucleotide tags in the single reaction mixture in step (a), comprise a plurality of single-stranded primers, wherein individual single-stranded primers include: (i) a 3' region that specifically binds a target sequence in the plurality of polynucleotides from the nucleic acid sample, and (ii) a 5' tail having a sequence that is not complementary to a target sequence in the plurality of polynucleotides from the nucleic acids sample.

In some embodiments, the 5' tail of the plurality of single-stranded primers comprise the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10.

In some embodiments, the fixed tag sequences "$(X)_x$" and "$(Y)_y$" within the plurality of the single stranded primers are sequence alignment anchors.

In some embodiments, the 5' tail of the plurality of single-stranded primers comprise the structure $N_1N_2N_3X_1X_2X_3N_4N_5N_6X_4X_5X_6$, wherein: "$N_1N_2N_3$" and "$N_4N_5N_6$" represents a random tag sequence wherein each base position in the random tag sequence is independently selected from A, G, C or T; wherein "$X_1X_2X_3$" represents a first fixed tag sequence that is the same in all of the plurality of tags, wherein "$X_4X_5X_6$" represents a second fixed tag sequence that is the same in all of the plurality of tags and differs from the sequence of the first fixed tag sequence.

In some embodiments, the first fixed tag sequence "$X_1X_2X_3$" and the second fixed tag sequence "$X_4X_5X_6$" within the plurality of single-stranded tag primers are sequence alignment anchors.

In some embodiments, the 5' tail of the plurality of single-stranded primers comprise the sequence 5'-NNNACTNNNTGA-3' (SEQ ID NO:1), wherein "NNN" represents a random tag sequence wherein each base position in the random tag sequence is independently selected from A, G, C or T.

In some embodiments, the "ACT" and the "TGA" within the plurality of single-stranded tag primers are sequence alignment anchors.

In some embodiments, the determining in step (e) includes: (i) determining that the variant sequence target polynucleotide is present in the nucleic acid sample at an abundance level of 0.05-5% using the sequence alignment anchor of the plurality of the single stranded primers.

In some embodiments, the plurality of oligonucleotide tags are appended to their respective target polynucleotides in an enzymatic ligation reaction in step (b), and the single reaction mixture includes a DNA ligase or RNA ligase.

In some embodiments, the plurality of oligonucleotide tags in the single reaction mixture of step (a), comprise a plurality of a double-stranded linear adaptor, stem-looped adaptor or Y-shaped adaptor.

In some embodiments, the plurality the double-stranded linear adaptor, stem-looped adaptor or Y-shaped adaptor, comprise a region having the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10.

In some embodiments, the fixed tag sequences "$(X)_x$" and "$(Y)_y$" within the plurality of the double-stranded linear adaptor, stem-looped adaptor or Y-shaped adaptor, are a sequence alignment anchor.

In some embodiments, the 5' tail of the plurality of single-stranded primers comprise the structure $N_1N_2N_3X_1X_2X_3N_4N_5N_6X_4X_5X_6$, wherein: "$N_1N_2N_3$" and "$N_4N_5N_6$" represents a random tag sequence wherein each base position in the random tag sequence is independently selected from A, G, C or T; wherein "$X_1X_2X_3$" represents a first fixed tag sequence that is the same in all of the plurality of tags, wherein "$X_4X_5X_6$" represents a second fixed tag sequence that is the same in all of the plurality of tags and differs from the sequence of the first fixed tag sequence.

In some embodiments, the first fixed tag sequence "$X_1X_2X_3$" and the second fixed tag sequence "$X_4X_5X_6$" within the plurality of the double-stranded linear adaptor, stem-looped adaptor or Y-shaped adaptor, are a sequence alignment anchor.

In some embodiments, the 5' tail of the plurality of single-stranded primers comprise the sequence 5'-NNNACTNNNTGA-3' (SEQ ID NO:1), wherein "NNN" represents a random tag sequence wherein each base position in the random tag sequence is independently selected from A, G, C or T.

In some embodiments, the "ACT" and the "TGA" within the plurality of the double-stranded linear adaptor, stem-looped adaptor or Y-shaped adaptor, are a sequence alignment anchor.

In some embodiments, the determining in step (e) includes: (i) determining that the first target polynucleotide is present in the nucleic acid sample at an abundance level of 0.05-5% using the sequence alignment anchor of the plurality of the double-stranded linear adaptors.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprise the steps: appending the plurality of polynucleotides with at least one or any combination of a universal sequence selected from a group consisting of: an amplification primer sequence, a sequencing primer sequence, a capture primer sequence and a cleavable site.

In some embodiments, the plurality of tagged target polynucleotides, including a first and second tagged target polynucleotide, that are generated in step (b) are appended with an amplification primer sequence, a sequencing primer sequence, and a first capture primer sequence.

In some embodiments, the plurality of tagged target polynucleotides, including the first and second tagged target polynucleotides, which are generated in step (b) are appended with a second capture primer sequence having a sequence that differs from the sequence of the first capture primer sequence.

In some embodiments, the disclosure relates generally to methods, as well as related systems, compositions, kits, apparatuses and computer-readable media for detecting a target polynucleotide (e.g., a variant sequence target polynucleotide) which is present in a nucleic acid sample, further comprise the steps: (a) forming a plurality of captured polynucleotides, including forming a captured first polynucleotide by binding the first capture primer sequence of the first tagged target polynucleotides to a first capture primer which is attached to a support; (b) forming (i) a captured second polynucleotide by binding the first capture primer sequence of the second tagged target polynucleotides to a second capture primer which is attached to the same support as the first capture primer, or (ii) a captured second polynucleotide by binding the first capture primer sequence of the second tagged target polynucleotides to a second capture primer which is attached to a different support; (c) conducting a primer extension reaction; and (d) sequencing the first and the second captured polynucleotides with a plurality of polymerases and a plurality of nucleotides.

In some embodiments, the sequencing comprises a massively parallel sequencing reaction.

In some embodiments, the support comprises a substantially planar support, a flowcell, a plurality of wells, a particle or a bead.

In some embodiments, the support includes an array of $10^4$-$10^9$ sequencing reaction sites.

In some embodiments, the sequencing reaction sites are operatively coupled to at least one field effect transistor (FET) sensor.

In some embodiments, the at least one field effect transistor (FET) sensor detects a byproduct from nucleotide incorporation, wherein the byproduct includes pyrophosphate, hydrogen ions, protons, charge transfer or heat.

In some embodiments, the sequencing in step (c) further comprises: flowing one type of nucleotide onto the captured plurality of polynucleotides, including the captured first and the second polynucleotides on the support.

In some embodiments, the one type of nucleotide is labeled with an optically-detectable label, or is not labeled with an optically-detectable label.

In some embodiments, the one type of nucleotide is terminator nucleotide or is not a terminator nucleotide.

In some embodiments, the sequencing in step (c) includes flowing 2-4 different types of nucleotides onto the captured plurality of polynucleotides, including the captured first and the second polynucleotides on the support.

In some embodiments, at least one type of the 2-4 different types of nucleotides is labeled with an optically-detectable label, or is not labeled with an optically-detectable label.

In some embodiments, at least one type of the 2-4 different types of nucleotides is terminator nucleotide or none of the 2-4 different types of nucleotides are a terminator nucleotide.

In some embodiments, the sequencing in step (d) further comprises: sequencing the population of tagged amplicons to generate a plurality of candidate sequencing reads.

In some embodiments, the determining in step (e) includes: (i) comparing a reference tag sequence with the plurality of candidate sequencing reads; and (ii) culling a first candidate sequencing read from the plurality of candidate sequencing reads when a tag sequence of the first candidate sequencing read does not have 100% sequence identity with the reference tag sequence.

In some embodiments, the reference tag sequence is not used for correcting an error contained in a given candidate sequencing read.

In some embodiments, the determining in step (e) includes: (i) forming a plurality of a family of grouped sequencing reads by grouping together candidate sequencing reads having the same tag sequence.

In some embodiments, the determining in step (e) includes: (i) determining the percentage of the candidate sequencing reads within a given family of grouped sequencing reads that have a target polynucleotide sequence that is identical to a reference target polynucleotide sequence; and (ii) determining that the given family of grouped sequencing reads represents the variant target polynucleotide that is present in the nucleic acid sample, when at least 10% of the candidate sequencing reads within the given family of grouped sequencing reads have 100% sequence identity with the reference target polynucleotide.

In some embodiments, the determining in step (e) includes: (i) counting the number of different families of grouped sequencing reads having a common first target polynucleotide sequence; and (ii) retaining these different counted families of grouped sequencing read when the count equals or exceeds three.

In some embodiments, the disclosure relates generally to methods, as well as related systems, compositions, kits, apparatuses and computer-readable media for detecting a target polynucleotide (e.g., a target polynucleotide having a variant sequence) which is present in a nucleic acid sample (e.g., present at low abundance in the nucleic acid sample), comprising the steps: (a) forming a single reaction mixture containing (i) a plurality of target polynucleotides from the nucleic acid sample, wherein the plurality of target polynucleotides includes at least a first target polynucleotide and a second target polynucleotide, and (ii) a plurality of oligonucleotide tags. In some embodiments, the plurality of oligonucleotide tags includes at least a first, second, third and fourth tag. In some embodiments, individual tags from the plurality of oligonucleotide tags comprise different random tag sequences alternating with fixed tag sequences. In some embodiments, a low abundant target polynucleotide may be present in a nucleic acid sample at about 0.0001-5%.

In some embodiments, the disclosure relates generally to methods, as well as related systems, compositions, kits, apparatuses and computer-readable media, further comprise the step: (b) generating within the single reaction mixture a plurality of tagged target polynucleotides that are appended with a different tag at both ends. In some embodiments, at least two of the plurality of tagged target polynucleotides are appended with tags that differ from each other. In some embodiments, the plurality of tagged target polynucleotides that are generated in the single reaction mixture include a first and second tagged polynucleotide. In some embodiments, the first tagged target polynucleotide is generated by appending the first tag to one end of the first target polynucleotide and appending the second tag to the other end of the first target polynucleotide. In some embodiments, the second tagged target polynucleotide is generated within the same single reaction mixture by appending the third tag to one end of the second target polynucleotide and appending the fourth tag to the other end of the second target polynucleotide.

In some embodiments, the disclosure relates generally to methods, as well as related systems, compositions, kits, apparatuses and computer-readable media, further comprise the step: (c) generating a population of tagged amplicons by amplifying the plurality of tagged target polynucleotides, including generating a population of first tagged amplicons by amplifying the first tagged target polynucleotides, and generating a population of second tagged amplicons by amplifying the second tagged target polynucleotides. In some embodiments, the amplifying is conducted by PCR.

In some embodiments, the disclosure relates generally to methods, as well as related systems, compositions, kits, apparatuses and computer-readable media, further comprise the step: (d) sequencing the population of tagged amplicons to generate a plurality of candidate sequencing reads. In some embodiments, the sequencing includes sequencing the target polynucleotide regions and the tags appended thereon, including sequencing the population of the first tagged amplicons which comprises sequencing the first target polynucleotide regions and the appended first and second tag regions. In some embodiments, the sequencing includes sequencing the population of the second and tagged amplicons which comprises sequencing the second target polynucleotide regions and the appended third and fourth tag regions.

In some embodiments, the disclosure relates generally to methods, as well as related systems, compositions, kits, apparatuses and computer-readable media, further comprise the step: (e) determining that (i) the first target polynucleotide and the second target polynucleotide are present in the nucleic acid sample at an abundance level of 0.05-5%, or determining that (ii) the first target polynucleotide or the second target polynucleotide is present in the nucleic acid sample at an abundance level of 0.05-5%.

In some embodiments, the disclosure relates generally to methods, as well as related systems, compositions, kits, apparatuses and computer-readable media, wherein the plurality of oligonucleotide tags in the single reaction mixture detect the presence of 5-100, or 100-200, or 200-300, or 300-400, or 400-500 or more different target polynucleotides in the nucleic acid sample.

In some embodiments, the disclosure relates generally to methods, as well as related systems, compositions, kits, apparatuses and computer-readable media, wherein the plurality of oligonucleotide tags in the single reaction mixture detect 85-90%, or 85-95%, or 85-99%, or 85-100% of the different target polynucleotides that are present in the nucleic acid sample.

In some embodiments, the determining in step (e) comprises determining that the first target polynucleotide which is present in the nucleic acid sample at an abundance level of 0.05-0.1%. In some embodiments, the determining in step (e) comprises determining that the second target polynucleotide which is present in the nucleic acid sample at an abundance level of 0.05-0.1%. In some embodiments, the determining in step (e) comprises determining that the first and second target polynucleotide are present in the nucleic acid sample at an abundance level of 0.05-0.1%.

In some embodiments, the first or second target polynucleotide in step (a) is present in the nucleic acid sample as a variant sequence, polymorphic sequence or mutant sequence. In some embodiments, the first and second target polynucleotides in step (a) are each present in the nucleic acid sample as a variant sequence, polymorphic sequence or mutant sequence.

In some embodiments, the plurality of target polynucleotides from the nucleic acid sample in step (a) comprises cell free nucleic acids from a biological fluid, nucleic acids from a biopsied tissue, nucleic acids from a needle biopsy, or nucleic acids from cells. In some embodiments, the plurality of target polynucleotides from the nucleic acid sample in step (a) comprises DNA or RNA, or a mixture of DNA and RNA. In some embodiments, the biological fluid is blood, saliva, sputum, sweat, tears, lavage fluid, amniotic fluid, cerebrospinal fluid, ascites, urine, stool, feces, or semen.

In some embodiments, the single reaction mixture in step (a) contains 1-10 ng, or 10-30 ng, or 30-50 ng, or 50-100 ng of a plurality of polynucleotides, which includes target and non-target polynucleotides.

In some embodiments, the single reaction mixture in step (a) contains $10^4$-$10^9$ of the first tags having different random tag sequences. In some embodiments, the single reaction mixture in step (a) contains $10^4$-$10^9$ of the second tags having different random tag sequences. In some embodiments, the single reaction mixture in step (a) contains $10^4$-$10^9$ of the third tags having different random tag sequences. In some embodiments, the single reaction mixture in step (a) contains $10^4$-$10^9$ of the fourth tags having different random tag sequences.

In some embodiments, the plurality of oligonucleotide tags in the single reaction mixture in step (a), including the first, second, third and fourth tags, are appended to their respective target polynucleotides in a sequence-dependent manner. In some embodiments, the plurality of oligonucleotide tags in the single reaction mixture in step (a), including the first, second, third and fourth tags, are appended to their respective target polynucleotides in a primer extension reaction in step (b). In some embodiments, the single reaction mixture comprises a primer extension reaction which includes a plurality of single-stranded oligonucleotide tag primers, a polymerase and a plurality of nucleotides. In some embodiments, the plurality of tags in the single reaction mixture comprises a plurality of single-stranded oligonucleotide tag primers.

In some embodiments, the plurality of tags in the single reaction mixture in step (a), comprise a plurality of single-stranded oligonucleotide tag primers, wherein individual single-stranded tag primers include a 3' region that specifically binds a target sequence in the plurality of polynucleotides from the nucleic acid sample. In some embodiments, the plurality of single-stranded oligonucleotide tag primers include individual single-stranded tag primers comprising a 5' tail having a sequence that is not complementary to a target sequence in the plurality of polynucleotides from the nucleic acids sample.

In some embodiments, the plurality of single-stranded oligonucleotide tag primers, comprise a plurality of single-stranded primers which include a 5' tail having the structure $(N)_n(X)_x(M)_m(Y)_y$, and (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the 5' tail of the plurality of single-stranded tag primers comprise the structure $N_1N_2N_3X_1X_2X_3N_4N_5N_6X_4X_5X_6$, wherein "$N_1N_2N_3$" and "$N_4N_5N_6$" represents a random tag sequence wherein each base position in the random tag sequence is independently selected from A, G, C or T; wherein "$X_1X_2X_3$" represents a first fixed tag sequence that is the same in all of the plurality of tags, wherein "$X_4X_5X_6$" represents a second fixed tag sequence that is the same in all of the plurality of tags and differs from the sequence of the first fixed tag sequence. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the 5' tail of the plurality of the single-stranded tag primers comprise the sequence 5'-NNNACTNNNTGA-3' (SEQ ID NO:1), wherein "NNN" represents a random tag sequence wherein each base position in the random tag sequence is independently selected from A, G, C or T. In some embodiment, the underlined portions of 5'-<u>NNN</u>ACT<u>NNN</u>TGA-3' (SEQ ID NO:1) are a sequence alignment anchor.

In some embodiments, the determining in step (e) includes: (i) determining that the first target polynucleotide is present in the nucleic acid sample at an abundance level of 0.05-5% using the sequence alignment anchor of the first and/or second single-stranded oligonucleotide tag primers; and (ii) determining that the second target polynucleotide is present in the nucleic acid sample at an abundance level of 0.05-5% using the sequence alignment anchor of the third and/or fourth single-stranded oligonucleotide tag primers.

In some embodiments, the plurality of oligonucleotide tags in the single reaction mixture in step (a), including the first, second, third and fourth tags, are appended to their respective target polynucleotides in an enzymatic ligation reaction in step (b), and the single reaction mixture includes a DNA ligase or RNA ligase. In some embodiments, the plurality of tags in the single reaction mixture comprise a plurality of a double-stranded linear adaptor, stem-looped adaptor or Y-shaped adaptor.

In some embodiments, the plurality of the double-stranded linear adaptor, stem-looped adaptor or Y-shaped adaptor, comprise a region having the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the stem region of the stem-looped adaptor or the Y-shaped adaptor comprise the structure $(N)_n(X)_x(M)_m(Y)_y$. In some embodiments, the fixed tag sequences "$(X)_x$" and "$(Y)_y$" within the plurality of the double-stranded linear adaptor, stem-looped adaptor or Y-shaped adaptor, are a sequence alignment anchor.

In some embodiments, the plurality of the double-stranded linear adaptor, stem-looped adaptor or Y-shaped adaptor, comprise a region having the structure $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors. In some embodiments, the stem region of the stem-looped adaptor or the Y-shaped adaptor comprise the structure $N_1N_2N_3X_1X_2X_3N_4N_5N_6X_4X_5X_6$. In some embodiments, the first fixed tag sequence "$X_1X_2X_3$" and the second fixed tag sequence "$X_4X_5X_6$" within the plurality of the double-stranded linear adaptor, stem-looped adaptor or Y-shaped adaptor, are a sequence alignment anchor.

In some embodiments, the plurality of the double-stranded linear adaptor, stem-looped adaptor or Y-shaped adaptor, comprise a region having the sequence 5'-NNNACTNNNTGA-3' (SEQ ID NO:1), wherein "N" represents a random tag sequence that is generated from A, G, C or T. For example, the stem region of the stem-looped adaptor or the Y-shaped adaptor comprise the 5'-NNNACTNNNTGA-3' (SEQ ID NO:1). In some embodiment, the underlined portions of 5'-NNNACTNNNTGA-3' (SEQ ID NO: 1) are a sequence alignment anchor.

In some embodiments, the determining in step (e) includes: (i) determining that the first target polynucleotide is present in the nucleic acid sample at an abundance level of 0.05-5% using the sequence alignment anchor of the first and/or second tag (e.g., of the double-stranded linear adaptor, stem-looped adaptor or Y-shaped adaptor); and (ii) determining that the second target polynucleotide is present in the nucleic acid sample at an abundance level of 0.05-5% using the sequence alignment anchor of the third and/or fourth tags (e.g., of the double-stranded linear adaptor, stem-looped adaptor or Y-shaped adaptor).

In some embodiments, the plurality of tagged target polynucleotides that are generated in the single reaction mixture in step (b) are generated by primer extension using the plurality of single-stranded tag primers, or are generated by enzymatic ligation using the plurality of double-stranded linear adaptors, stem-looped adaptors or Y-shaped adaptors. In some embodiments, the plurality of tagged target polynucleotides are amplified to generate a population of tagged amplicons, which includes a first and second population of tagged amplicons.

In some embodiments, the sequencing in step (d) further comprises: sequencing the population of tagged amplicons to generate a plurality of candidate sequencing reads including: (i) sequencing the population of first tagged amplicons to generate a population of first candidate sequencing reads having the first target polynucleotide sequence and the first and second tag sequences, and (ii) sequencing the population of second tagged amplicons to generate a population of second candidate sequencing reads having the second target polynucleotide sequence and the third and fourth tag sequences.

In some embodiments, the determining in step (e) includes: (i) comparing a reference-first tag sequence with one of the first candidate sequencing reads from the population of first candidate sequencing reads, and culling/discarding the first candidate sequencing read when the first tag sequence of the first candidate sequencing read does not have 100% sequence identity with the reference-first tag sequence; and (ii) comparing a reference-third tag sequence with one of the second candidate sequencing reads from the population of second candidate sequencing reads, and culling/discarding the second candidate sequencing read when the third tag sequence of the second candidate sequencing read does not have 100% sequence identity with the reference-third tag sequence. In some embodiments, the reference-first tag sequence and the reference-second tag sequence each contain a known reference sequence, which includes a wild-type or variant reference sequence.

In some embodiments, the reference-first tag sequence and the reference-third tag sequence are not used for correcting an error contained in the first or second candidate sequencing reads.

In some embodiments, the determining in step (e) includes: forming a plurality of a family of grouped sequencing reads by grouping together candidate sequencing reads having the same first, second, third or fourth tag sequence, including forming a first family of grouped sequencing reads by grouping together candidate sequencing reads having the same first or second tag sequence, and including forming a second family of grouped sequencing reads by grouping together candidate sequencing reads having the same third or fourth tag sequence.

In some embodiments, the determining in step (e) includes: (i) determining the percentage of the candidate sequencing reads within a family of grouped sequencing reads that have a target polynucleotide sequence that is identical to a reference target polynucleotide sequence, including determining the percentage of the candidate sequencing reads within the first family of grouped sequencing reads that have a first target polynucleotide sequence that is identical to a reference first target polynucleotide sequence, and including determining the percentage of the candidate sequencing reads within the second family of grouped sequencing reads that have a second target polynucleotide sequence that is identical to a reference second target polynucleotide sequence; (ii) determining that the first family of grouped sequencing reads represents a first target polynucleotide that is present in the nucleic acid sample, when at least 10% of the candidate sequencing reads within the first family of grouped sequencing reads have 100% sequence identity with the reference first target polynucleotide; and (iii) determining that the second family of grouped sequencing reads represents a second target polynucleotide that is present in the nucleic acid sample, when at least 10% of the candidate sequencing reads within the second family of grouped sequencing reads have 100% sequence identity with the reference second target polynucleotide.

In some embodiments, the determining in step (e) includes: (i) counting the number of different families of grouped sequencing reads having a common first target polynucleotide sequence, and retaining the different families of grouped sequencing read when the count equals or exceeds three; and (ii) counting the number of different families of grouped sequencing reads having a common second target polynucleotide sequence, and retaining the different families of grouped sequencing read when the count equals or exceeds three.

In some embodiments, the disclosure relates generally to methods, as well as related systems, compositions, kits, apparatuses and computer-readable media, for manipulating the candidate sequencing reads (e.g., within any given family of grouped sequencing reads) to yield a high percentage of true positives while reducing the percentage of false positives by applying any one or any combination of the thresholds including the culling threshold, a grouping threshold, counting grouped reads threshold counting family threshold, difference counting threshold, pattern counting threshold non-target pattern threshold and/or family level threshold according to the present teachings.

In some embodiments, the disclosure relates generally to methods, as well as related systems, compositions, kits, apparatuses and computer-readable media, further comprise appending the plurality of polynucleotides with at least one or any combination of universal sequences selected from a group consisting of: an amplification primer sequence, a sequencing primer sequence, a capture primer sequence and a cleavable site.

In some embodiments, the plurality of tagged target polynucleotides, including the first tagged and second tagged target polynucleotides that are generated in the single reaction mixture of step (b) are further appended with an amplification primer sequence, a sequencing primer sequence, and a first capture primer sequence. Optionally, the plurality of tagged target polynucleotides, including the first tagged and second tagged target polynucleotides, that are generated in the single reaction mixture in step (b) are further appended with a second capture primer sequence having a sequence that differs from the sequence of the first capture primer sequence.

In some embodiments, the plurality of tagged target polynucleotides, including the first tagged and second tagged target polynucleotides, that are attached to an amplification primer sequence, sequencing primer sequence, first capture primer sequence and/or the second capture primer, undergo further steps including: (i) forming a plurality of captured polynucleotides, including forming a captured first polynucleotide by binding the first capture primer sequence of the first tagged target polynucleotides to a first capture primer which is attached to a support, and forming a captured second polynucleotide by binding the first capture primer sequence of the second tagged target polynucleotides to a second capture primer which is attached to the same support as the first capture primer; (ii) conducting a primer extension reaction to generate a first and second captured target polynucleotide which are attached to the same support; and (iii) sequencing the first and the second captured polynucleotides with a plurality of polymerases and a plurality of nucleotides. In some embodiments, the sequencing comprises a massively parallel sequencing reaction or a sequencing reaction that employs gel electrophoresis or a microarray. In some embodiments, the support comprises a substantially planar support, a flowcell, a plurality of wells, a particle or a bead.

In some embodiments, the plurality of tagged target polynucleotides, including the first tagged and second tagged target polynucleotides, that include the amplification primer sequence, sequencing primer sequence, first capture primer sequence and/or the second capture primer, undergo further steps including: (i) forming a plurality of captured polynucleotides, including forming a captured first polynucleotide by binding the first capture primer sequence of the first tagged target polynucleotides to a first capture primer which is attached to a first support; (ii) forming a captured second polynucleotide by binding the first capture primer sequence of the second tagged target polynucleotides to a second capture primer which is attached to a second support (e.g., the first and second supports are different supports); (iii) conducting a primer extension reaction to generate a first which is attached to the first support and to generate a second captured target polynucleotide which is attached to the second support; and (iv) sequencing the first and the second captured polynucleotides with a plurality of polymerases and a plurality of nucleotides. In some embodiments, the sequencing comprises a massively parallel sequencing reaction or a sequencing reaction that employs gel electrophoresis or a microarray. In some embodiments, the first and second supports each comprise a substantially planar support, a flowcell, a plurality of wells, a particle or a bead. In some embodiments, the first and second captured polynucleotides that are attached to the first and second bead, respectively, are deposited onto a support having one sequencing reaction site or an array of sequencing reaction sites.

In some embodiments, the support includes an array of $10^4$-$10^9$ sequencing reaction sites.

In some embodiments, the sequencing reaction sites are operatively coupled to at least one field effect transistor (FET) sensor. In some embodiments, the at least one field effect transistor (FET) sensor detects a byproduct from nucleotide incorporation, wherein the byproduct includes pyrophosphate, hydrogen ions, protons, charge transfer or heat.

In some embodiments, the sequencing in step (d) further comprises: (i) providing a support having a plurality of sequencing reaction sites that have polynucleotides captured thereon or the plurality sequencing reaction sites are deposited with beads that carry attached polynucleotides, wherein the polynucleotides on the sequencing reaction sites include the first and second captured polynucleotides; and (ii) flowing one type of nucleotide onto the sequencing reaction sites (e.g., dATP, dGTP, dCTP or dTTP). The flowed nucleotides contact the polynucleotides on the sequencing reaction sites. Optionally, the flow includes one type of nucleotide which is labeled with an optically-detectable label, or is not labeled with an optically-detectable label. Optionally, the flow includes one type of nucleotide which is a terminator nucleotide or is not a terminator nucleotide.

In some embodiments, the sequencing in step (d) further comprises: (i) providing a support having a plurality of sequencing reaction sites that have polynucleotides captured thereon or the plurality sequencing reaction sites are deposited with beads that carry attached polynucleotides, wherein the polynucleotides on the sequencing reaction sites include the first and second captured polynucleotides; and (ii) flowing 2-4 different types of nucleotides onto the sequencing reaction sites (e.g., any combination of 2-4 of dATP, dGTP, dCTP or dTTP). The flowed nucleotides contact the polynucleotides on the sequencing reaction sites. Optionally, at least one type of the 2-4 different types of nucleotides is labeled with an optically-detectable label, or is not labeled with an optically-detectable label. Optionally, at least one type of the 2-4 different types of nucleotides is terminator nucleotide or is not a terminator nucleotide.

BRIEF DESCRIPTION OF THE DRAWINGS

FIG. 6A is a table showing the number of functional families that contain positive control variants.

FIG. 6B is a continuation of the table in FIG. 6A, where FIG. 6B shows the number of functional families that contain positive control variants.

FIG. 23C is a table that lists the count and percent of sequencing reads for select barcodes (SEQ ID NOS: 73-78) for a target sequence located on chromosome 12.

FIG. 24C is a table that lists the count and percent of sequencing reads for select barcodes (SEQ ID NOS: 113-118) for a target sequence located on chromosome 12.

FIG. 32B is a table showing amplicon read coverage and target base coverage corresponding to the data show in FIG. 32A.

DETAILED DESCRIPTION

Figure 1A:
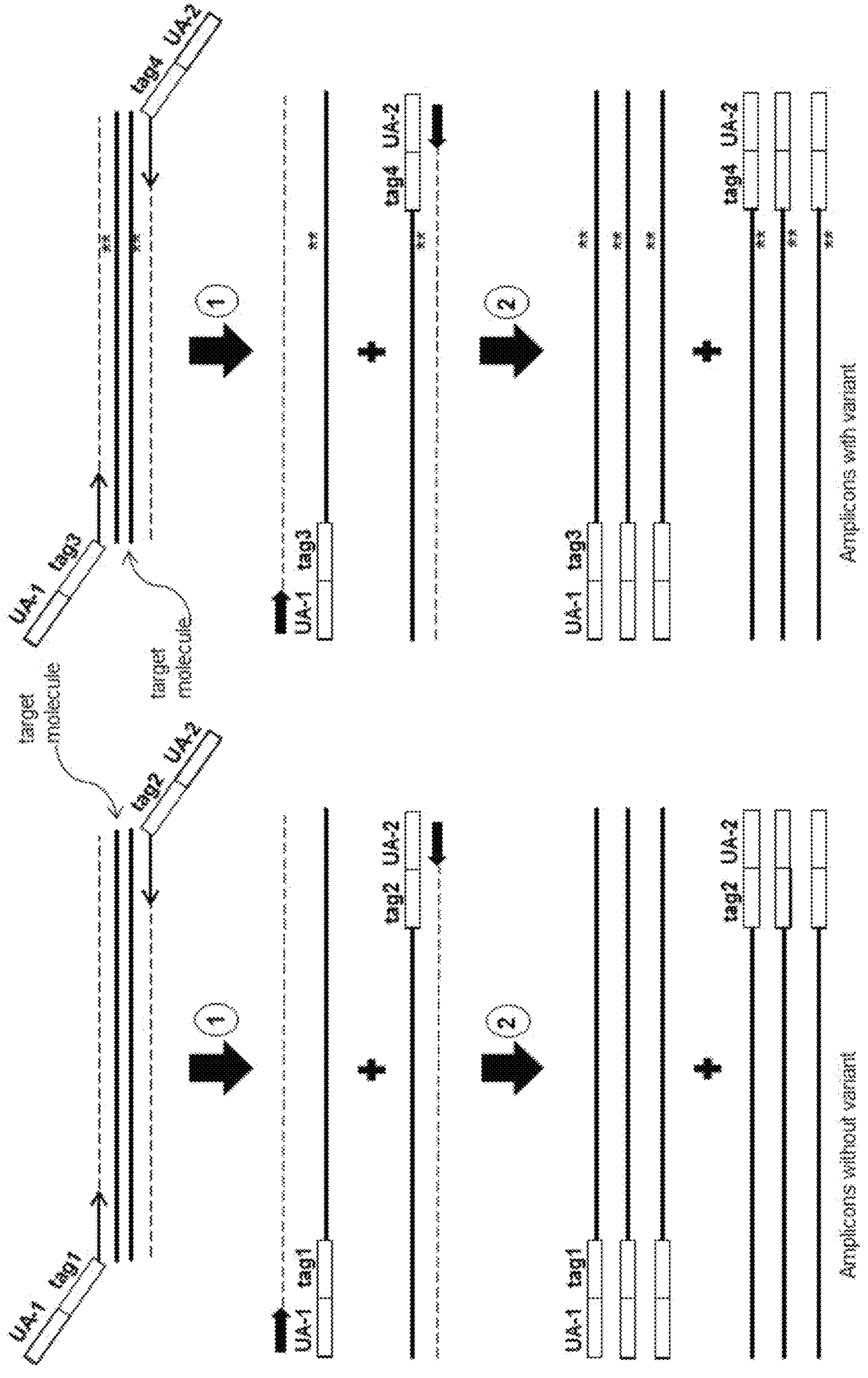
FIG. 1A is a schematic that depicts a non-limiting embodiment of a molecular tagging method.
Figure 1B:
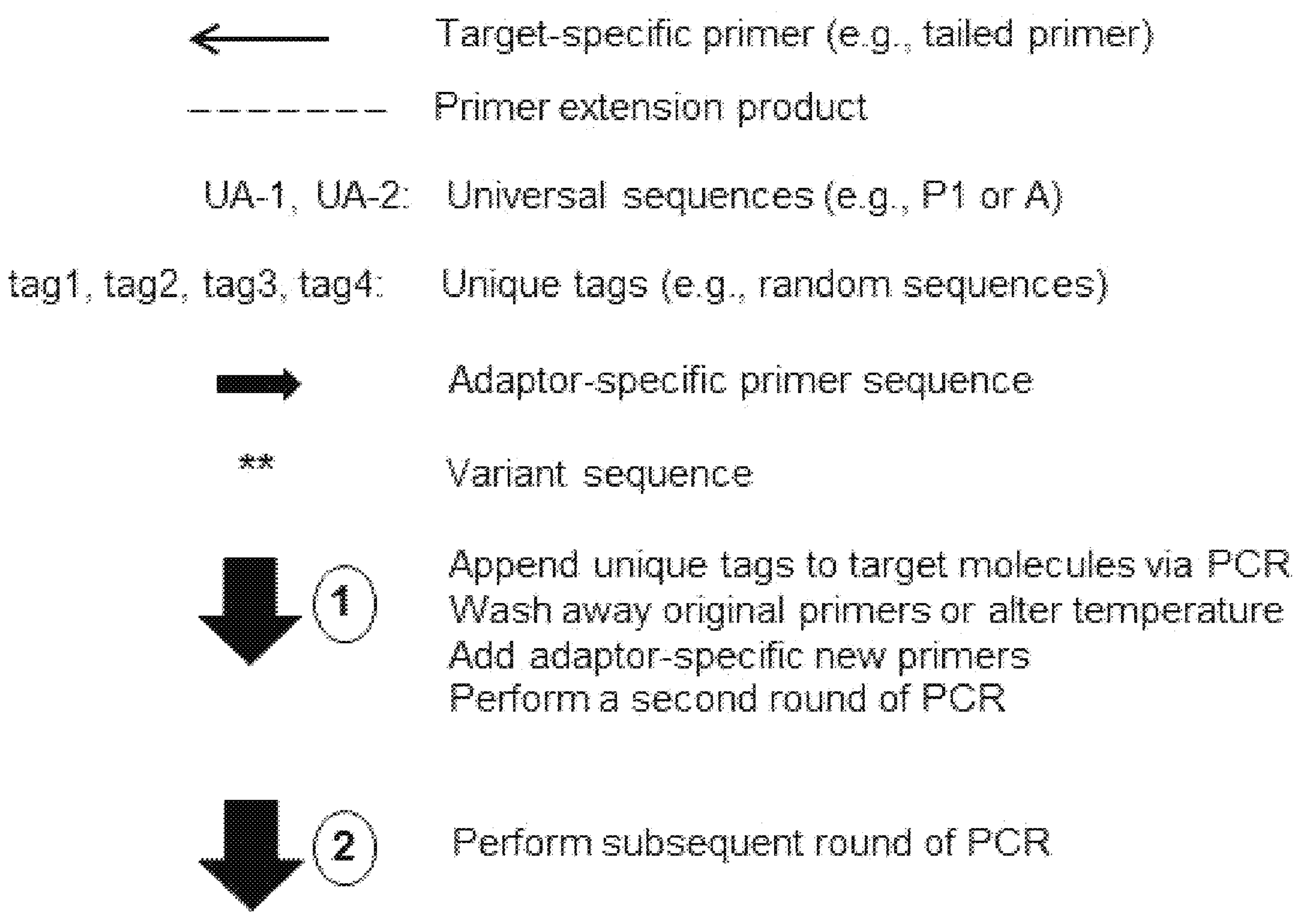
FIG. 1B is a figure legend for FIG. 1A.
Figure 2A:
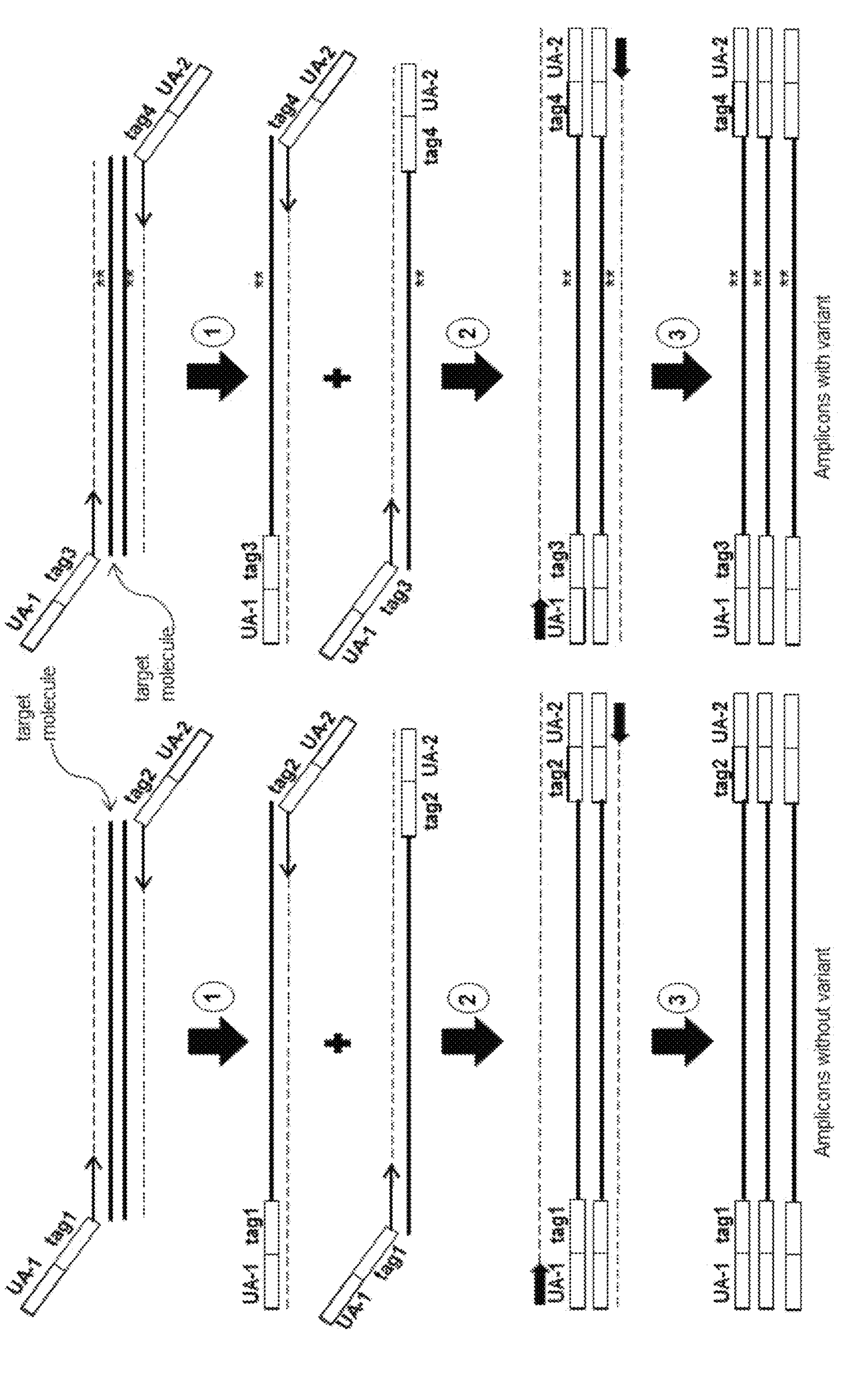
FIG. 2A is a schematic that depicts a non-limiting embodiment of a molecular tagging method.
Figure 2B:
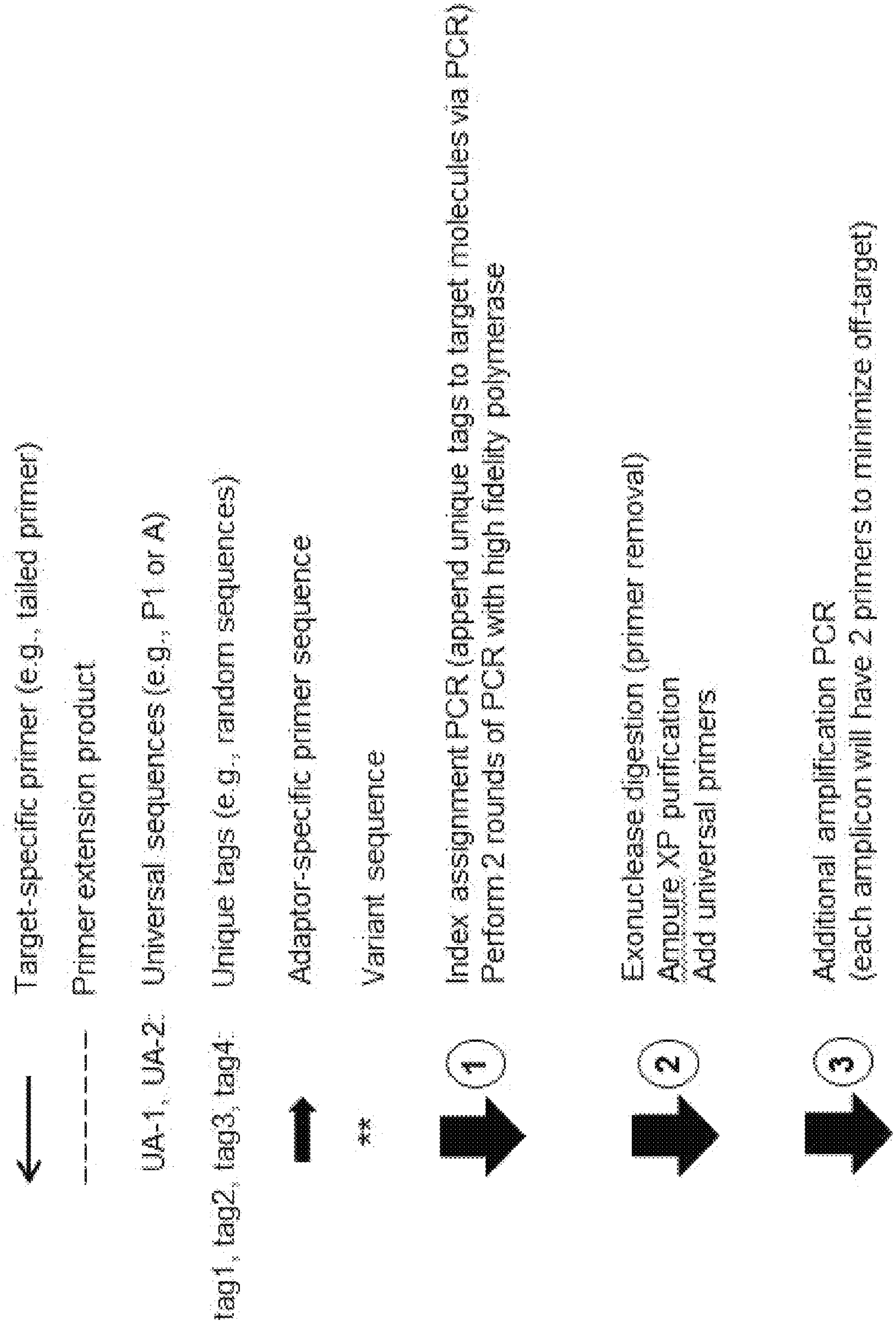
FIG. 2B is a figure legend for FIG. 2A

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As used herein the terms "amplify", "amplifying", "amplification", and other related terms include producing multiple copies of an original biomolecule. In some embodiments, nucleic acid amplification produces multiple copies of an original polynucleotide (e.g., polynucleotide), where the copies comprise a template sequence, or a sequence that is complementary to the template sequence. In some embodiments, the copies comprise a sequence that is substantially identical to a template sequence, or is substantially identical to a sequence that is complementary to the template sequence.

As used herein the terms "hybridize", "hybridizing", "hybridization", and other related terms include hydrogen bonding between two different nucleic acids, or between two different regions of a single nucleic acid molecule, to form a duplex nucleic acid. Hybridization can comprise Watson-Crick or Hoogstein binding to form a duplex nucleic acid. The two different nucleic acids, or the two different regions of a single nucleic acid, may be complementary, or partially complementary. The complementary base pairing can be the standard A-T or C-G base pairing, or can be other forms of base-pairing interactions. Duplex nucleic acids can include mismatched base-paired nucleotides. Complementary nucleic acid strands need not hybridize with each other across their entire length.

In some embodiments, conditions that are suitable for nucleic acid hybridization and/or for washing conditions include parameters such as salts, buffers, pH, temperature, GC % content of the polynucleotide and primers, and/or time. For example, conditions suitable for hybridizing or washing nucleic acids (e.g., polynucleotides and primers) can include hybridization solutions having sodium salts, such as NaCl, sodium citrate and/or sodium phosphate. In some embodiments, hybridization or wash solutions can include formamide (e.g., about 10-75%) and/or sodium dodecyl sulfate (SDS) (e.g., about 0.01-0.7%). In some embodiments, a hybridization solution can be a stringent hybridization solution which can include any combination of formamide (e.g., about 50%), 5×SSC (e.g., about 0.75 M NaCl and about 0.075 M sodium citrate), sodium phosphate (e.g., about 50 mM at about pH 6.8), sodium pyrophosphate (e.g., about 0.1%), 5×Denhardt's solution, SDS (e.g., about 0.1%), and/or dextran sulfate (e.g., about 10%). In some embodiments, the hybridization or washing solution can include BSA (bovine serum albumin). In some embodiments, hybridization or washing can be conducted at a temperature range of about 15-25° C., or about 25-35° C., or about 35-45° C., or about 45-55° C., or about 55-65° C., or about 65-75° C., or about 75-85° C., or about 85-95° C., or about 95-99° C., or higher.

In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or about 1-6 hours, or longer.

In some embodiments, hybridization or wash conditions can be conducted at a pH range of about 5-10, or about pH 6-9, or about pH 6.5-8, or about pH 6.5-7.

Methods for nucleic acid hybridization and washing are well known in the art. For example, thermal melting temperature ($T_m$) for nucleic acids can be a temperature at which half of the nucleic acid strands are double-stranded and half are single-stranded under a defined condition. In some embodiments, a defined condition can include ionic strength and pH in an aqueous reaction condition. A defined condition can be modulated by altering the concentration of salts (e.g., sodium), temperature, pH, buffers, and/or formamide. Typically, the calculated thermal melting temperature can be at about 5-30° C. below the $T_m$, or about 5-25° C. below the $T_m$, or about 5-20° C. below the $T_m$, or about 5-15° C. below the $T_m$, or about 5-10° C. below the $T_m$. Methods for calculating a $T_m$ are well known and can be found in Sambrook (1989 in "Molecular Cloning: A Laboratory Manual", 2nd edition, volumes 1-3; Wetmur 1966, J. Mol. Biol., 31:349-370; Wetmur 1991 Critical Reviews in Biochemistry and Molecular Biology, 26:227-259). Other sources for calculating a $T_m$ for hybridizing or denaturing nucleic acids include OligoAnalyze (from Integrated DNA Technologies) and Primer3 (distributed by the Whitehead Institute for Biomedical Research).

It is important to accurately detect and identify the type of variant sequence in a nucleic acid sample obtained from a source that is suspected to have a disease, infection or genetic abnormality (e.g., a somatic mutation). Sometimes the sample contains a variant sequence which arose from a rare event which manifests itself in a few copies, or a single copy, of DNA or RNA, so the variant sequence is hidden among a mixture of non-variant molecules. It is challenging to reliably detect and accurately identify the variant sequence(s) that are present in a sample that contains mostly non-variant sequences.

Detecting and identifying genetic variants (including polymorphic and mutant sequences) is often useful for diagnosing an infection, disease or genetic abnormality. Sequence analysis of such variants that are present at low abundance poses a challenge, because the abundance levels of some variants is in the range of about 0.05 to 1%, or lower abundance ranges, which is lower than the error rates of massively parallel sequencing platforms. The sources of these errors come from multiple stages of the workflow that are typically employed to yield next generation sequencing data. For example, some library preparation workflows start with physically sheared nucleic acids, where the shearing step introduces oxidative damage that can lead to formation of 8-oxoG bases, which can undergo Hoogstein base pairing with adenine bases, and can eventually lead to C-to-A and G-to-T base changes. Library prep workflows that include an end-repair step that employs a polymerase, may generate polymerase-introduced errors during nucleotide incorporation. Many library prep workflows also include at least one primer extension step for appending a tag sequence and/or for amplifying. In particular, high error rates come from nucleotide incorporation by the polymerase during a primer extension reaction using non-tailed primers for amplification, or using tailed primers to append adaptor sequences to the polynucleotides. Examples of this type of error can arise from pre-amplification and amplification steps. Additional sources of errors can be traced to nucleotide mis-incorporation during the sequencing reaction, and base-calling by the sequencing apparatus and/or software.

In some embodiments, the disclosure relates generally to methods, as well as related systems, compositions, kits, apparatuses and computer-readable media, for accurately confirming the presence of low abundance DNA and/or RNA molecules that carry variant sequences in a biological sample, where the biological sample contains nucleic acids having a mixture of target (e.g., mutant or variant) and non-target (e.g., non-mutant or non-variant) sequences. The nucleic acid molecules that carry the variant sequence may be present in a sample at only 0.0001-1%. The methods, as well as related systems, compositions, kits, apparatuses and computer-readable media, according to the present teachings generally include molecular tagging, sequencing, and analysis of the sequencing date, to confirm the presence of one or more rare abundance nucleic acid molecules having variant sequences.

In some embodiments, the disclosure relates generally to methods, as well as related systems, compositions, kits, apparatuses and computer-readable media, comprising a multiplex molecular tagging procedure that employs a plurality of tags that are appended to a plurality of polynucleotides. The tags have characteristics, including a sequence, length and/or detectable moiety, or any other characteristic, that uniquely identifies the polynucleotide molecule to which it is appended, and permits tracking individual tagged molecules in a mixture of tagged molecules. For example, the tag (e.g., having a unique tag sequence) can uniquely identify an individual polynucleotide to which it is appended, and distinguish the individual polynucleotide from other tagged polynucleotides in a mixture.

In some embodiments, the disclosure relates generally to methods, as well as related systems, compositions, kits, apparatuses and computer-readable media for detecting genetic variants, identifying genetic variants and/or generating error-corrected sequencing data. In some embodiments, the detecting genetic variants, identifying genetic variants and/or error-corrected sequencing data is generated by practicing a single-plex or multi-plex molecular tagging procedure to generate a plurality of individual polynucleotides that are appended with at least one unique tag. In some embodiments, the methods, as well as related systems, compositions, kits, apparatuses and computer-readable media for detecting genetic variants, identifying genetic variants and/or generating error-corrected sequencing data further comprise amplifying the tagged polynucleotides to generate a plurality of tagged amplicons. In some embodiments, the methods, as well as related systems, compositions, kits, apparatuses and computer-readable media for detecting genetic variants, identifying genetic variants and/or generating error-corrected sequencing data further comprise sequencing the tagged amplicons to generate a plurality of sequencing reads. In some embodiments, the methods, as well as related systems, compositions, kits, apparatuses and computer-readable media for detecting genetic variants, identifying genetic variants and/or generating error-corrected sequencing data further comprise manipulating the sequencing reads, which can include applying at least one threshold, which can reduce errors in the sequencing reads. In some embodiments, manipulation of the sequencing reads includes culling, sorting, grouping, counting grouped reads, counting family of reads, and other manipulation steps. In some embodiments, the manipulation steps can be based on tag-specific reference sequences and/or polynucleotide-specific reference sequences. The resulting error-corrected sequencing data is reduced in the number of sequencing errors that typically arise during the library prep and/or sequencing workflow. By reducing the error rate in the sequencing data to a level that is similar to (or even less than) the frequency level of a target polynucleotide (e.g., a low abundance allele, variant or mutant) in a mixture of nucleic acids, then detection and identification of low abundant target polynucleotides that are present in a mixture of nucleic acids is attainable.

In some embodiments, the methods, as well as related systems, compositions, kits, apparatuses and computer-readable media for detecting genetic variants, identifying genetic variants and/or generating error-corrected sequencing data can be implemented on a nucleic acid sample obtained from any type of fluid (e.g., a biological fluid) or solid biological sample, or any organism, or from water, soil or food.

In some embodiments, the methods, as well as related systems, compositions, kits, apparatuses and computer-readable media for detecting genetic variants, identifying genetic variants and/or generating error-corrected sequencing data can be implemented on any type of nucleic acid sample, including nucleic acids isolated from biopsied tissue, fresh or frozen tissue, archived tissue (e.g., FFPE-preserved), and biological fluids containing a single cell or a few dozen cells, cell-free nucleic acids (DNA and/or RNA), or nucleic acids isolated from circulating tumor cell(s). In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the methods, as well as related systems, compositions, kits, apparatuses and computer-readable media for detecting genetic variants, identifying genetic variants and/or generating error-corrected sequencing data can be implemented on a nucleic acid sample having as little as 1-100 ng of polynucleotides, including DNA and RNA or a mixture of DNA and RNA.

In some embodiments, the methods, as well as related systems, compositions, kits, apparatuses and computer-readable media for detecting genetic variants, identifying genetic variants and/or generating error-corrected sequencing data can accurately detect and identify low abundant polynucleotides that are present at about 0.0001-1%, or at about 0.001-1%, or about 0.01-1%, or about 0.1-1%, or about 0.1-5% (or abundance ranges lower than 0.0001%) in a nucleic acid sample.

In some embodiments, the methods, as well as related systems, compositions, kits, apparatuses and computer-readable media for detecting genetic variants, identifying genetic variants and/or generating error-corrected sequencing data can detect about 85-95%, or about 95-99%, or about 100% of the different target polynucleotides (e.g., including genetic variants) that may be present in the initial nucleic acid sample.

In some embodiments, the methods, as well as related systems, compositions, kits, apparatuses and computer-readable media for detecting genetic variants, identifying genetic variants and/or generating error-corrected sequencing data can be implemented on a nucleic acid sample using a single reaction mixture (e.g., single tube reaction) using a single-plex or multi-plex format.

In some embodiments, the methods, as well as related systems, compositions, kits, apparatuses and computer-readable media for detecting genetic variants, identifying genetic variants and/or generating error-corrected sequencing data can be practiced by appending at least one adaptor, from a repertoire of adaptors, to individual polynucleotides in the nucleic acid sample, optionally by enzymatic ligation.

In some embodiments, the methods, as well as related systems, compositions, kits, apparatuses and computer-readable media for detecting genetic variants, identifying genetic variants and/or generating error-corrected sequencing data can be practiced by appending at least one unique tag sequence using at least one primer, from a repertoire of primers, to individual polynucleotides in the nucleic acid sample, optionally by primer extension. The primers can be designed to selectively target a different sequence of interest in the initial nucleic acid sample.

In some embodiments, the methods, as well as related systems, compositions, kits, apparatuses and computer-readable media for detecting genetic variants, identifying genetic variants and/or generating error-corrected sequencing data can be practiced using a repertoire of adaptors or primers which contain at least one unique tag sequence, optionally including at least one random or degenerate tag sequence. In some embodiments, the tag (e.g., a randomer tag) contains at least one random sequence and at least one fixed sequence, or comprises a random sequence flanked on both sides by a fixed sequence, or comprises a fixed sequence flanked on both sides by a random sequence.

The molecular tagging procedures described in the present teachings offer advantages over conventional solid tissue biopsy procedures. The level of detection of the molecular tagging methods is sensitive enough to permit use of a biological fluid such as blood, to obtain the initial nucleic acid sample. Obtaining blood samples (or other biological fluids) offers a non-invasive approach, poses less risk, and is less expensive when compared to an invasive tissue biopsy procedure. Also, the molecular tagging method, using blood as a source of the initial nucleic acid sample, can produce results in a few days, compared to 3 or more weeks for tissue biopsy.

In some embodiments, the disclosure relates generally to methods, as well as related systems, compositions, kits, apparatuses and computer-readable media for detecting genetic variants, identifying genetic variants and/or generating error-corrected sequencing data are useful for:

(1) Improving the quality of sequencing data generated by any type of massively parallel sequencing procedure by generating error-corrected sequencing data, where the massively parallel sequencing procedures, includes for example, sequencing by oligonucleotide probe ligation and detection (e.g., SOLiD™ from Life Technologies, WO 2006/084132), probe-anchor ligation sequencing (e.g., Complete Genomics or Polonator™), sequencing-by-synthesis (e.g., Genetic Analyzer™ and HiSeq™ from Illumina (Bentley 2006 Current Opinion Genetics & Development 16:545-552; and Bentley, et al., 2008 Nature 456:53-59; and U.S. Pat. No. 7,566,537)), pyrophosphate sequencing (e.g., Genome Sequencer FLX™ from 454 Life Sciences (U.S. Pat. Nos. 7,211,390, 7,244,559 and 7,264,929)), ion-sensitive sequencing (e.g., Personal Genome Machine (Ion PGM™) and Ion Proton™ Sequencer, both from Ion Torrent Systems, Inc.), and single molecule sequencing platforms (e.g., Heliscope™ from Helicos);

(2) Detecting, identifying and/or counting one or more target polynucleotides in a nucleic acid sample that contains target and non-target polynucleotides, or the nucleic acid sample lacks non-target polynucleotides;

(3) Determining if a target polynucleotide is present in the initial nucleic acid sample, or if it arose from spurious events during the sample prep and/or sequencing workflow;

(4) Increasing the sensitivity of detecting low-abundance target polynucleotides in a nucleic acid sample, where for example the target polynucleotides are present at about 0.0001-1%, or at about 0.001-1%, or about 0.01-1%, or about 0.1-1%, or about 0.1-5%, or abundance ranges lower than 0.0001%;

(5) Determining the abundance level of a target polynucleotide and its related polymorphic forms that are present within the initial nucleic acid sample, where the polymorphic forms can include allelic, variant and/or mutant forms;

(6) Counting the number of a target polynucleotide that are present in a nucleic acid sample, which for example, can be used for copy number variation analysis of cell-free circulating DNA (or DNA isolated from circulating tumor cells) in a biological fluid (e.g., blood) from a subject, and where the cell-free DNA (or DNA from the tumor cells) originated from any source include fetus, tumor or infectious organism;

(7) Detecting the presence of polymorphic forms of a target polynucleotides (e.g., wild-type, allelic, variant and/or mutant forms) in a nucleic acid sample from a subject, where the variant and/or mutant forms are associate (or not associated) with an infection or disease, and optionally diagnosing the infection or disease in the subject;

(8) Monitoring the progression of an infection or disease that may be associated with a change in the genetic variation in a disease by detecting the appearance and/or disappearance of the genetic variants in a nucleic acid sample from a subject;

(9) Determining the heterogeneity of target polynucleotide in a nucleic acid sample;

(10) Monitoring the efficacy of a medical treatment for an infection or disease (e.g., therapy monitoring);

(11) Selecting a therapy based on the genetic variants that are discovered;

(12) Detecting residual disease in a subject;

(13) Detecting disease recurrence in a subject;

(14) Detecting a copy number variation of a target polynucleotide;

(15) Detecting an indication of graft rejection in an organ transplant recipient by detecting donor DNA in the transplant recipient.

(16) Detecting and characterizing (e.g., sequencing) cell-free circulating fetal DNA present in maternal blood.

(17) Annual broad-based screening (e.g., for cancer or other diseases).

One skilled in the art will recognize that the methods, as well as related systems, compositions, kits, apparatuses and computer-readable media of the present teachings have many other uses as well.

In some embodiments, the disclosure relates generally to methods, as well as related systems, compositions, kits, apparatuses and computer-readable media for detecting genetic variants, identifying genetic variants and/or generating error-corrected sequencing data employs a molecular tagging procedure, in which polynucleotides are appended with at least one tag. In some embodiments, the tag-appending reaction is stochastic. In some embodiments, the polynucleotides are appended with at least one tag that is randomly selected from a repertoire of diverse tags (e.g., a plurality of tags). In some embodiments, the tag-appending reaction can be performed with an excess of tags compared to the number of polynucleotide molecules. The tag-appending event for one polynucleotide can be independent of a tag-appending event for a different polynucleotide, for example if the supply of tags is substantially non-depleting. The diversity of the tags and the number of copies of identical polynucleotides, along with the statistics of random selection, will dictate the frequency of uniquely-tagged polynucleotides. For example, random selection can influence the frequency of uniquely-tagged polynucleotides that are generated by ligating polynucleotides to tag-carrying adaptors (e.g., where the tag can be a randomer tag), or are generated by primer extension using tag-carrying primers. When the diversity of the tag-carrying adaptors greatly exceeds the number of polynucleotide molecules present in a tag-appending reaction, then substantially every tagged molecule will be appended to a unique tag. Although it is challenging to obtain yields of 100% of the tagged molecules being uniquely tagged, a substantial percentage of the tagged molecules will be appended to a unique tag, where about 10-30%, or about 30-50%, or about 50-70%, or about 70-80%, or about 80-90%, or about 90-95%, or about 95-99% of the tagged polynucleotide molecules that are generated from a tag-appending reaction are uniquely tagged.

In some embodiments, other types of molecular tagging procedures are not necessarily controlled by random selection. For example, a molecular tagging procedure that is conducted with tailed primers in a primer extension reaction (e.g., PCR) can be a selective process that is controlled by the 3' portion of the tailed primers which can contain a target-specific sequence that selectively hybridizes to a portion of a target polynucleotide. The 5' portion of the tailed primer can contain a sequence that does not hybridize substantially to a target sequence. The 5' portion of the tailed primer can contain at least one tag sequence (e.g., randomer tag sequence) which is designed to exhibit minimal hybridization to the target polynucleotide. In some embodiments, a set of tailed primers can include the same 3' target-specific sequence and different 5' randomer tag sequences. When the sequence of the 3' region of the tailed primer is designed to exhibit minimal hybridization to non-target polynucleotides, then the primer extension reaction will generate a population of tagged polynucleotides that are selectively enriched for target sequences that correspond to the sequences in the 3' region of the primers. The 3' target-specific region of a tailed primer can have perfect complementarity with its target sequence, or can be partially complementary with its target sequence which includes at least 50%, 60%, 70%, 80%, 90%, 95% or 99% complementarity with its target sequence. Typically, but not necessarily, a forward and reverse primer are employed in a primer extension reaction (e.g., PCR) to generate amplicons (e.g., tagged amplicons). Thus, a primer extension reaction can be a form of an enrichment step that primarily generates tagged polynucleotides having certain selected target sequences and reduces the number of non-target polynucleotides. In some embodiments, the 3' regions of the forward and reverse primers can selectively hybridize to a region of a target polynucleotide (e.g., target DNA or RNA polynucleotide) that can be used in a primer extension reaction (e.g., PCR) to generate tagged amplicons that span an intron, exon, junction intron-exon, coding, non-coding, or fusion sequences. The primer extension reaction can be performed with an excess of tag primers compared to the number of polynucleotide molecules. The primer extension reaction can be performed using a repertoire of primers having unique tag sequences in the 5' tail region so that different polynucleotide molecules having the same sequence can be appended to different tag sequences.

In some embodiments, a set of tailed primers can contain numerous members that have a common 3' region that selectively hybridizes to a particular portion of a specific target polynucleotide. In some embodiments, a set of tailed primers can include multiple forward and reverse tailed primers.

The members of the set of tailed primers can carry a 5' tail having the same tag sequences or different tag sequences. When a set of tailed primers carries a common 3' region and different tag sequences in their 5' region, then a primer extension reaction can generate a population of tagged polynucleotides molecules having the same target polynucleotide sequence, and many of the tagged molecules will be appended to a different tag. When the diversity of the tag-carrying primers (e.g., tailed primers) greatly exceeds the number of polynucleotide molecules present in a tagging reaction, then substantially every tagged molecule will be appended to a unique tag. Using this diverse set of primers in a molecular tagging procedure can generate a population of tagged polynucleotides that are selectively enriched for target sequences that corresponds to the 3' region of the primers, but substantially each tagged polynucleotide carries a unique tag. By contrast, when a set of tailed primers carries a common 3' region and a common tag sequence in their 5' region, then a primer extension reaction can generate a population of tagged polynucleotides molecules having the same target polynucleotide sequence, and substantially each tagged molecule is appended to the same tag.

In some embodiments, the disclosure relates generally to methods, as well as related systems, compositions, kits, apparatuses and computer-readable media, for detecting genetic variants, identifying genetic variants and/or generating error-corrected sequencing data by: (a) providing a nucleic acid sample containing a plurality of polynucleotides, including target and non-target polynucleotides, or the nucleic acid sample lack non-target polynucleotides; (b) generating a plurality of tagged polynucleotides (parent tagged polynucleotides) by appending at least one unique tag to individual polynucleotide molecules from the plurality of polynucleotides, and (c) generating tagged amplicons by amplifying the plurality of tagged polynucleotides, where the tagged amplicons are progeny tagged molecules that arose from the parent tagged polynucleotides molecules. In some embodiments, the unique tag(s) are appended to the nucleic acids in a one-step tagging procedure or a multiple-step tagging procedure. In some embodiments, the nucleic acid sample is obtained from a biological sample or a synthesized (e.g., engineered) sample, or a mixture of both. In some embodiments, the nucleic acid sample contains DNA, RNA or a mixture of DNA and RNA (e.g., total nucleic acid sample). In some embodiments, the mixture of DNA and RNA are obtained from the same biological sample. In some embodiments, the nucleic acid sample contains cfDNA, cfRNA, or a mixture of both.

In some embodiments, the disclosure relates generally to methods, as well as related systems, compositions, kits, apparatuses and computer-readable media, further comprise sequencing the amplicons to generate a plurality of candidate sequencing reads. Optionally, the sequencing step can be performed using massively parallel sequencing procedures or size fractionation procedures (e.g., gel electrophoresis).

In some embodiments, the disclosure relates generally to methods, as well as related systems, compositions, kits, apparatuses and computer-readable media, further comprise manipulating the candidate sequencing reads (e.g., sorting, grouping, culling and/or counting) to produce a set of error-corrected sequencing reads, which can be used to determine that a particular polynucleotide is present in the initial nucleic acid sample, and to identify the sequence of the particular polynucleotide (e.g., wild-type, polymorphic variant or mutant). The plurality of candidate sequencing reads can be sorted and/or grouped into different families of sequencing reads based on a common reference sequence of one or more unique tags. The candidate sequencing reads that do not match a reference tag sequence can optionally be discarded (e.g., culled), or can be assigned to a group of sequence reads if the criterion for requiring an exact match is relaxed. The candidate sequencing reads that remain in any given family of sequencing reads, form a set of error-corrected sequencing reads. Within any given family of sequencing reads, the polynucleotide portion of the sequencing reads can be compared to a polynucleotide reference sequence. The sequencing reads can be counted to determine the percentage of sequencing reads, within any given family, that have a polynucleotide portion that is substantially identical to the polynucleotide reference sequence. When the calculated percentage of sequencing reads that are substantially identical to the polynucleotide reference sequence exceeds a threshold level, a determination can be made that the polynucleotide (represented by the family of sequencing reads) is a true positive and is present in the initial nucleic acid sample. The amplification step combined with the massively parallel sequencing procedure, can generate a large initial data set of sequencing reads that can be manipulated (e.g., sorting, grouping, culling and/or counting) to enable a statistical analysis for generating error-corrected sequencing data which can increase the confidence in determining if a particular polynucleotide is present in the initial nucleic acid sample, and can be used to identify the sequence of the particular polynucleotide.

During the amplification step, a parent tagged polynucleotide that carries a variant sequence will give rise to progeny molecules that also carry the same variant sequence. Some of the progeny molecules may also carry a spurious mutant sequence that is not found in the parent polynucleotide but was introduced during the workflow. The spurious mutant sequence may be found in the tag and/or the polynucleotide. The spurious mutant sequences can contribute to the error rate of the sequencing data. In some embodiments, one or more threshold settings can be applied, which are used to manipulate the candidate sequencing reads to reduce the error rate.

During the amplification step, a parent tagged polynucleotide having a sequence that matches that of a reference sequence, may give rise to progeny molecules that carry a variant sequence (e.g., spurious mutant). The spurious mutant sequence that is not found in the parent polynucleotide may have been introduced during the workflow. The spurious mutant sequence may be found in the tag and/or the polynucleotide. The spurious mutant sequences can contribute to the error rate of the sequencing data. In some embodiments, one or more threshold settings can be applied, which are used to manipulate the candidate sequencing reads to reduce the error rate.

Figure 18A:
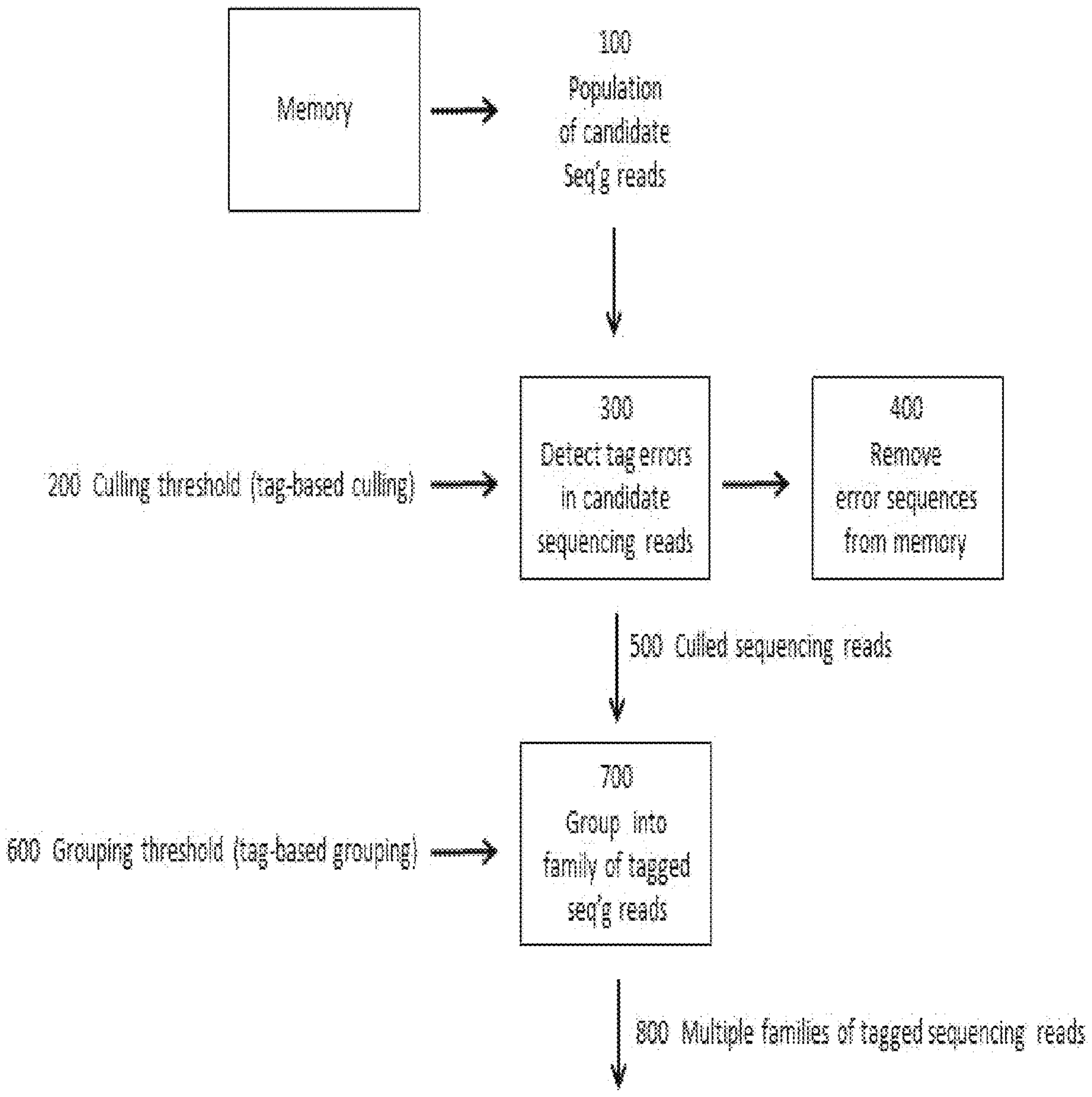
FIG. 18A is a block diagram that depicts a non-limiting block diagram of processing steps applied to sequencing reads for generating error-corrected sequencing data.
Figure 20A:
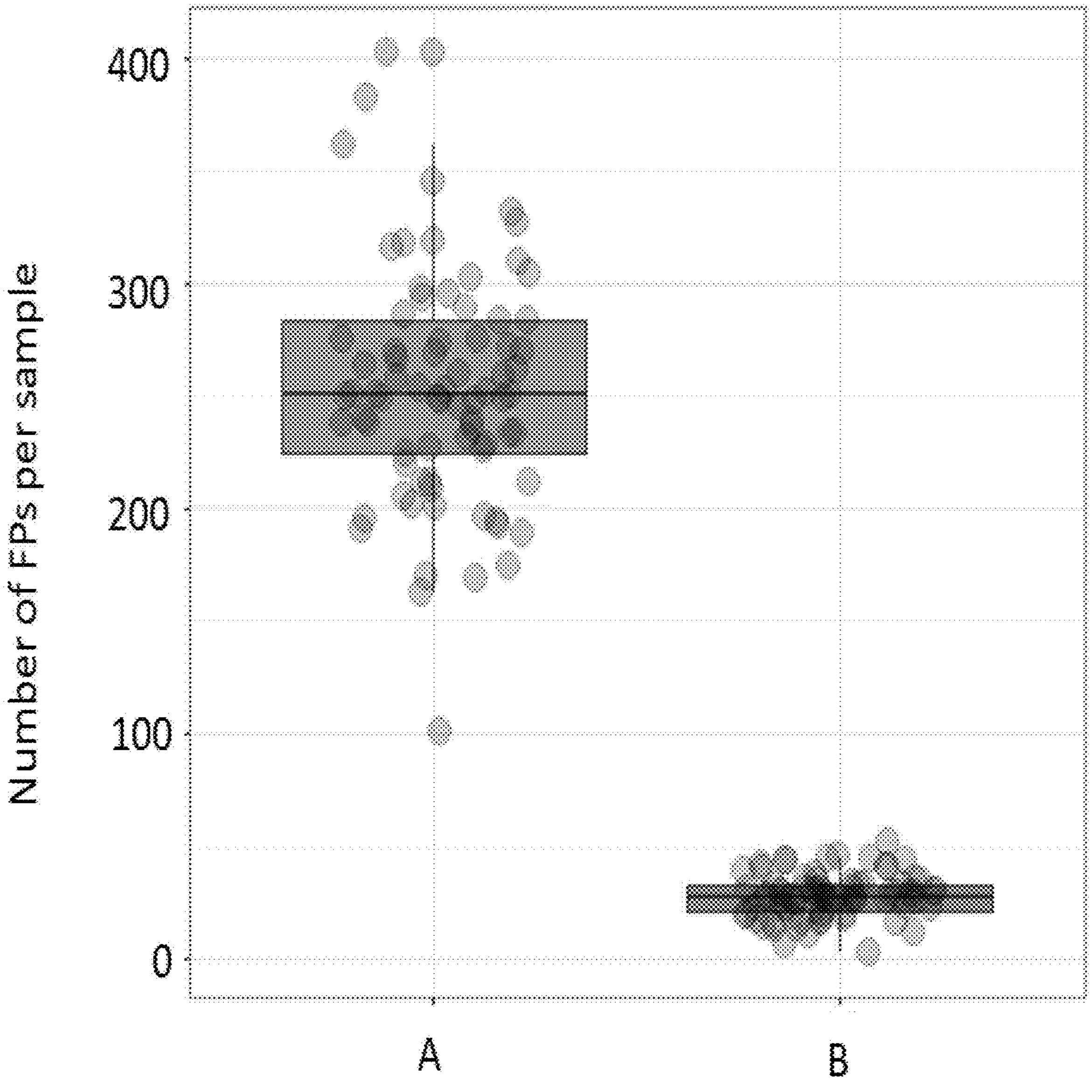
FIG. 20A is a histogram showing the number of whole target false positive (FP) called for 0.1% allelic frequency in a 0.1% MegaMix dilution sample.

In some embodiments, the disclosure relates generally to methods, as well as related systems, compositions, kits, apparatuses and computer-readable media, for applying one or more thresholds to improve the accuracy and/or sensitivity of a sequencing workflow. In some embodiments, the threshold(s) can be established using the sequence of at least one reference sequence, including a portion of at least one tag (e.g., a randomer tag) that is appended to a polynucleotide and/or using at least a portion of the polynucleotide itself. The known sequence of a tag can be used as a reference tag sequence which is compared to tag sequences in a set of candidate sequencing reads. In a similar manner, the known sequence of a polynucleotide can be used as a reference polynucleotide sequence which is compared to polynucleotide sequences in a set of candidate sequencing reads. One or more threshold criteria can be applied to a set of candidate sequencing reads in any order, to generate a set of error corrected sequencing reads in which the number of false positives is reduced. In some embodiments, the candidate sequencing reads can be manipulated according to the teachings described herein to yield a high percentage of true positives while reducing the percentage of false positives (FIGS. 20A and B). For example, a set of candidate sequencing reads may be subjected to any one or any combination of a culling threshold, a grouping threshold, counting grouped reads threshold counting family threshold, difference counting threshold, pattern counting threshold and/or non-target pattern threshold, which may be applied in any order (FIGS. 18A, B and C). Optionally, the order of thresholds applied to the candidate sequencing reads includes: (1) culling, grouping, counting grouped reads, and counting family thresholds; (2) grouping, culling, counting grouped reads, and counting family thresholds; (3) culling, grouping, and counting grouped reads; (4) grouping, culling, and counting grouped reads; (5) culling, grouping, and counting family thresholds; or (6) grouping, culling and counting family thresholds. In some embodiments, a family of grouped candidate sequencing reads may be subjected to any one or any combination of a difference counting threshold, a pattern counting threshold and/or a non-target pattern threshold, which may be applied in any order. In some embodiments, an error-corrected family of grouped candidate sequencing reads may be subjected to any one or any combination of a family level threshold and a multi-family threshold. One skilled in the art will recognize that many other combinations and order of thresholds can be applied to the candidate sequencing reads to determine that a particular polynucleotide is present in the initial nucleic acid sample, and to identify the sequence of the particular polynucleotide.

In some embodiments, a culling threshold can be used to guide a decision to retain or remove a candidate sequencing read (FIG. 18A, (100)) that contains a sequence that varies from a reference sequence (e.g., a spurious variant tag or polynucleotide sequence). In some embodiments, a tag error can be detected in the candidate sequencing reads (FIG. 18A, (300)). In some embodiments, the criterion of the culling threshold (FIG. 18A, (200)) can require that a candidate sequencing read has 100% sequence identity with a reference tag or reference polynucleotide sequence in order to be retained. In some embodiments, the criterion for the culling threshold can require that a sequence read is discarded if it differs by 1, 2, 3, 4, 5, 6, 7, 8, 9 or 10 base positions compared to a reference sequence. In some embodiments, the criterion of the culling threshold can require that a candidate sequencing read has about 50-60%, or about 60-70%, or about 70-80%, or about 80-90%, or about 90-99%, sequence identity with a reference tag or reference polynucleotide sequence in order to be retained. Removing at least one sequencing read from a set of candidate sequencing reads (FIG. 18A, (400)), may yield a set of sequencing reads having a reduced error rate (FIG. 18A, (500)).

In some embodiments, a grouping threshold can be used to guide which candidate sequencing reads are grouped together, based on a tag-based and/or polynucleotide-based reference sequence, to form at least one family of grouped sequencing reads. An exemplary tag-based grouping threshold is shown in FIG. 18A (600). For example, a first group of sequencing reads can share a common first tag sequence, and a second group of sequencing reads can share a common second tag sequence, where the first and second tag sequences differ from each other. In another example, a first group of sequencing reads can share a common first and second tag sequence (e.g., a tag at both ends of a first polynucleotide), and a second group of sequencing reads can share a common third and fourth tag sequence (e.g., a tag at both ends of a second polynucleotide), where at least two of the tag sequences differ from each other. In some embodiments, the criterion of the grouping threshold can require that all members of a group of sequencing reads have 100% sequence identity with a tag or polynucleotide reference sequence. In some embodiments, the criterion of the grouping threshold can require that all members of a group of sequencing reads differ from a tag or polynucleotide reference sequence by no more than 1, 2, 3, 4, 5, or 6 base positions. In some embodiments, the criterion of the grouping threshold can require that all members of a group of sequencing reads have about 50-60%, or about 60-70%, or about 70-80%, or about 80-90%, or about 90-99%, sequence identity with a tag or polynucleotide reference sequence. Generating at least one group of sequencing reads may yield a set of sequencing reads having a reduced error rate.

In some embodiments, an error-corrected family of sequencing reads (or sometimes called a family of error-corrected sequencing reads) contains a plurality of sequencing reads that have been grouped together based on a common tag-based and/or target polynucleotide-based reference sequence. Optionally, candidate sequencing reads that do not meet or exceed the criterion of the grouping threshold are discarded and are therefore not placed in a family of sequencing reads. Optionally, an error-correction algorithm is applied to a candidate sequencing read that does not meet or exceed the criterion of the grouping threshold, to correct the error (e.g., error in the tag and/or target polynucleotide region), and the now-corrected sequencing read is placed in a family of sequencing reads. The exemplary block diagram in FIG. 18A (700) shows tagged sequencing reads grouped into a family based on a common tag sequence. The grouping threshold is applied to a plurality of tagged sequencing reads to generate many different grouped families. The exemplary block diagram in FIG. 18A (800) shows multiple different families of sequencing reads each formed by grouping tagged sequencing reads having a given common tag sequence.

In some embodiments, a sequencing read that does not meet or exceed a threshold can be discarded from a group of sequencing reads. In some embodiments, an entire group of sequencing reads (e.g., a family of grouped sequencing reads) can be discarded if a single sequencing read within that group differs from a polynucleotide reference sequence by two or more base positions.

In some embodiments, a counting grouped reads threshold can be used to determine if a polynucleotide molecule having a particular sequence was present in the initial nucleic acid sample. For example, a family of grouped sequencing reads can be analyzed, using a counting grouped reads threshold, to determine if a polynucleotide was present in the initial nucleic acid sample. Within the family of grouped sequencing reads, the number of candidate sequencing reads that match a reference sequence can be counted, and the count can be converted into a percent. The reference sequence can be based on one particular known target polynucleotide sequence, or on a consensus sequence. The match between the candidate sequencing reads and the reference sequence can be 100% identity, or the match requirement can be relaxed so that the match is about 65-75%, or about 75-85%, or about 85-95%, or about 95-99%, or about 99-100% sequence identity. The percent of sequencing reads in that group that match the reference sequence can be compared to a threshold which may require, for example, that at least 1%, 5%, 10%, 20%, 30%, 40%, 50%, 60%, 70%, 80%, 90%, 95%, 97%, 98%, 99% or 100% of the members in a group must match the reference sequence, then it may be concluded that a particular sequencing read is a true positive, and that the polynucleotide having that sequence was present in the initial nucleic acid sample. In some embodiments, the counting grouped reads threshold can be used to determine if a sequencing read (e.g., containing a variant sequence) is a true positive sequencing read and if it corresponds to a polynucleotide that is present in the initial nucleic acid sample.

In some embodiments, a counting family threshold can be used to determine if a polynucleotide molecule having a particular sequence was present in the initial nucleic acid sample. For example, a molecular tagging procedure can produce multiple families of sequencing reads that, within a family, the sequencing reads are grouped together based on a common tag and/or target polynucleotide sequence that is unique to each different family. More than one of the families may contain sequencing reads of the same target polynucleotide. For example, the initial nucleic acid sample can include multiple copies of a particular target polynucleotide, where each of the particular target polynucleotides is appended with a unique tag. Amplification will produce progeny molecules, whose sequences can be grouped together (into a family) based on a common unique tag. The number of different families having the same target polynucleotide sequence can be counted, and if this number exceeds a counting family threshold, then the target polynucleotide sequence is deemed to represent a true positive sequencing read that corresponds to a polynucleotide that is present in the initial nucleic acid sample. For example, the minimum number of different families having the same target polynucleotide sequence can be a set having 2, 3, 4, 5, 6, 7, 8, 9, 10, 11-20, 20-30 or more different families. The family of sequencing reads that are inferred to represent a true positive sequencing read may be retained, and may be subjected to further analysis. When the number of different families having the same target polynucleotide sequence does not exceed a counting family threshold, then the target polynucleotide sequence may be deemed to represent a false positive sequencing read so it may be inferred that it was not present in the initial nucleic acid sample. The family of sequencing reads that are inferred to represent a false positive sequencing read may be discarded. In some embodiments, the candidate sequencing reads can be manipulated according to the teachings described herein to yield a high percentage of true positives while reducing the percentage of false positives (FIGS. 20A and B).

Figure 16A:
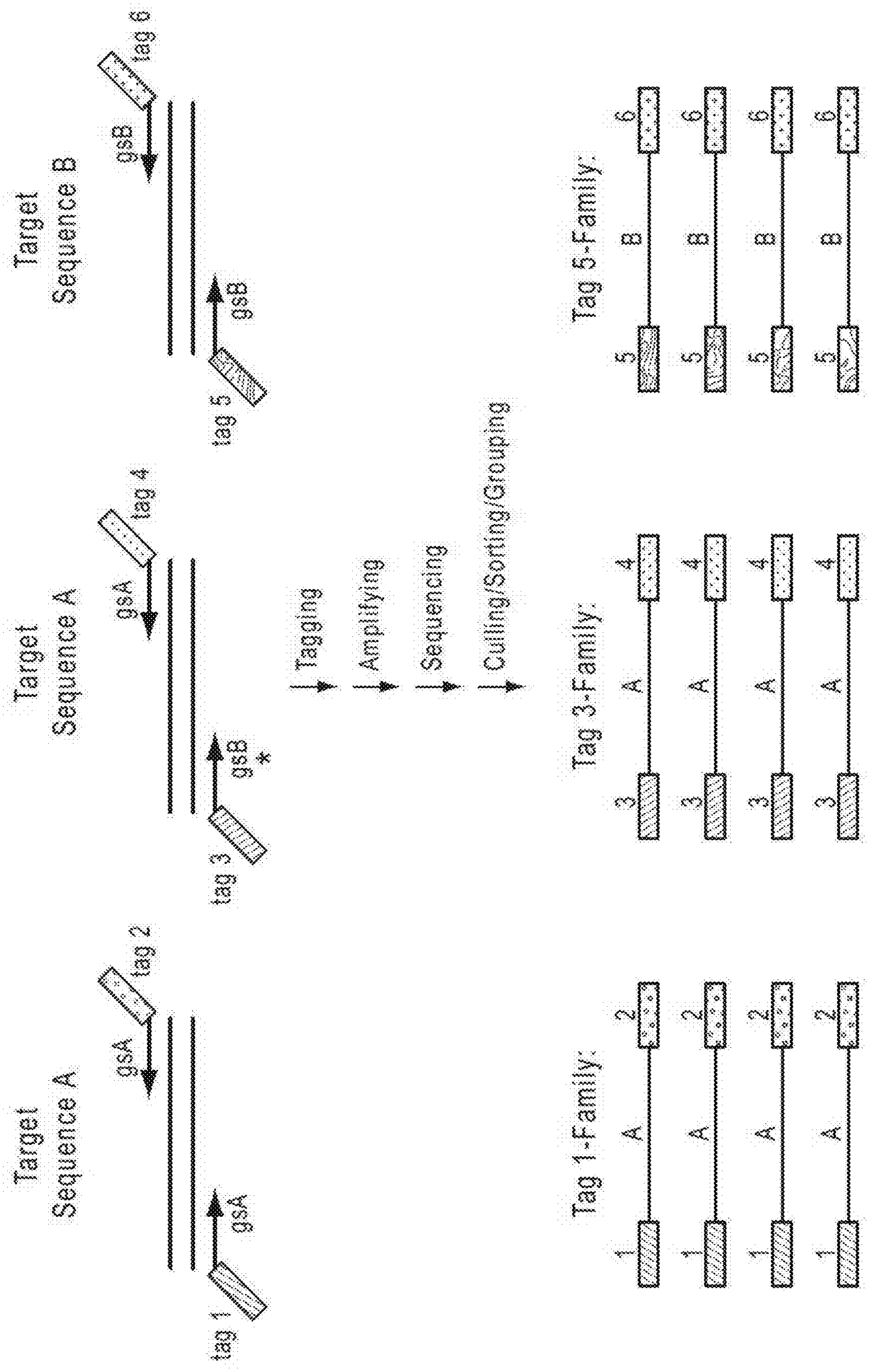
FIG. 16A is a schematic that depicts a non-limiting embodiment of a mis-tagging event.

In some embodiments, a family of grouped sequencing reads, such as a family formed using a grouping threshold, may include mistagged sequencing reads that include a common tag sequence but correspond to a different region of a target polynucleotide or a non-target polynucleotide due to a tag-appending error, including an error arising from tag adaptor ligation or tag primer extension, or other error (FIGS. 16A and B). A mistagged sequencing read may include one or more base positions where nucleotides differ from a reference polynucleotide sequence or correctly tagged sequencing reads for the family.

One embodiment of a mis-tagging event is shown in FIG. 16A, which shows a multiplex single reaction tagging mixture containing target sequences A and B, and tailed primers that are designed to hybridize to a portion of target sequence A or B. The “gsA” denotes the region of a tailed primer that will hybridize to a portion of target sequence A, and the “gsB” denotes the region of a tailed primer that will hybridize to a portion of target sequence B. The tailed primers also contain different 5' tag sequence (tags 1, 2, 3, 4, 5 or 6) that do not exhibit substantial hybridization to target sequence A or B. In FIG. 16A, the tailed primer (e.g., tailed primer gsB) having a 3' gene-specific region which is designed to hybridize specifically to polynucleotide B, instead hybridizes to a region of polynucleotide A (target sequence A). The mis-tagging event is denoted with an (*). The gsB tailed primer undergoes primer extension to append the tag 3 sequence onto the target A sequence thereby generating a spurious mis-tagged product having polynucleotide A appended to tags 3 and 4. The mis-tagged product undergoes amplifying, sequencing and manipulation of the sequencing reads (e.g., culling, sorting and grouping, in any order). The tag 3 family of grouped sequencing reads represents spurious polynucleotides having target sequence A appended to tags 3 and 4. Since a second copy of the tailed primer tag 3-gsB (if it is present in the tagging reaction) does not hybridize to a target sequence B, then the tag 3 family of grouped sequencing reads does not include a target B sequence appended with a tag 3 sequence.

Figure 16B:
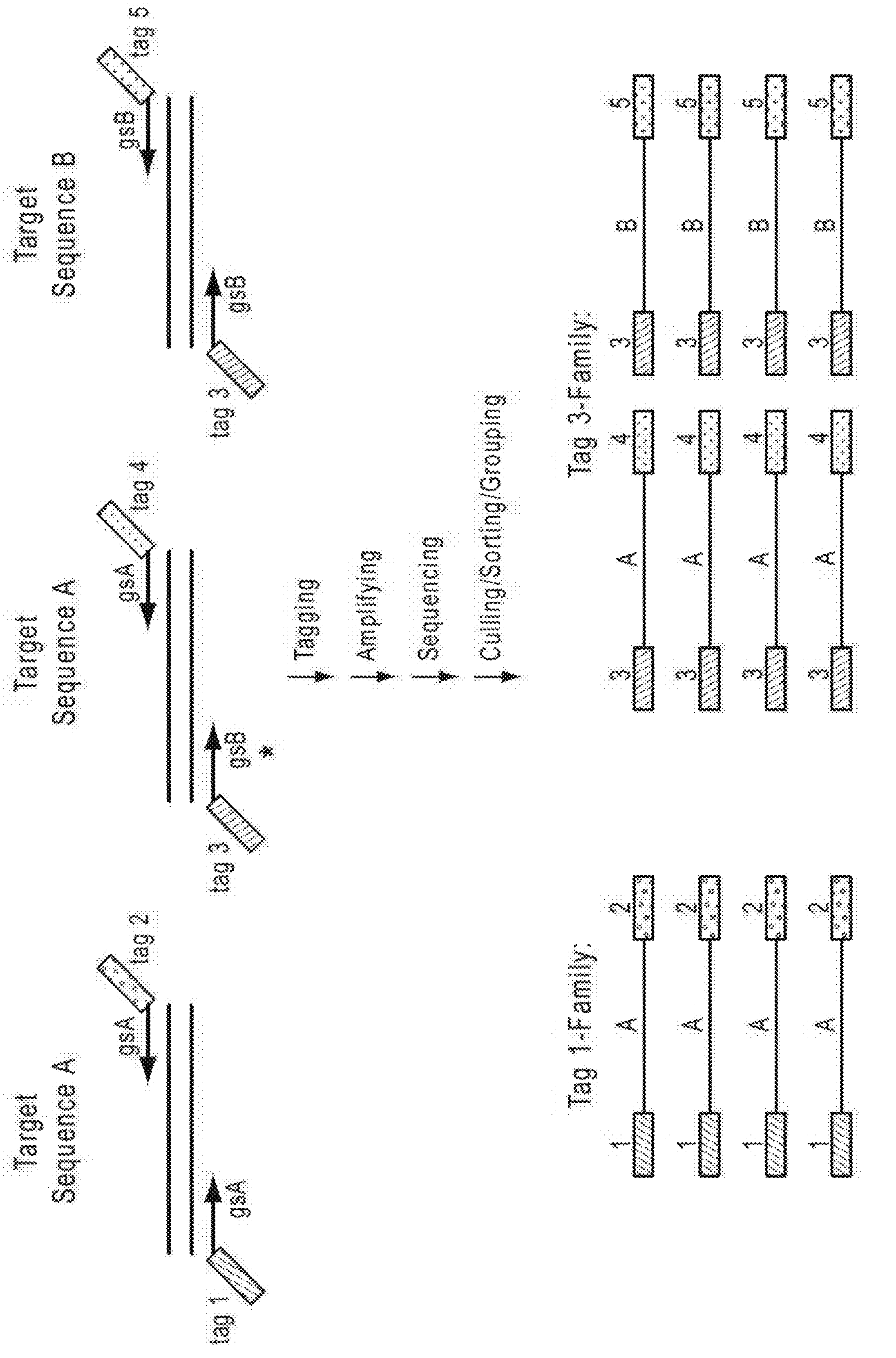
FIG. 16B is a schematic that depicts another non-limiting embodiment of a mis-tagging event.

Another embodiment of a mis-tagging event is shown in FIG. 16B, which shows a multiplex single reaction tagging mixture containing target sequences A and B, and tailed primers that are designed to hybridize to a portion of target sequence A or B. The “gsA” denotes the region of a tailed primer that will hybridize to a portion of target sequence A, and the “gsB” denotes the region of a tailed primer that will hybridize to a portion of target sequence B. The tailed primers also contain different 5' tag sequence (tags 1, 2, 3, 4 or 5) that do not exhibit substantial hybridization to target sequence A or B. In FIG. 16B, the tailed primer (e.g., tailed primer gsB) having a 3' gene-specific region which is designed to hybridize specifically to polynucleotide B, hybridizes to a region of polynucleotide A (target sequence A) and to a region of polynucleotide B (target sequence B). The mis-tagging event is denoted with an (*). Both of the gsB tailed primers undergo primer extension to append the tag 3 sequence onto the target A sequence and the target B sequence, thereby generating two types of tagged products: (i) a spurious mis-tagged product having polynucleotide A appended to tags 3 and 4, and (ii) a properly-tagged product having polynucleotide B appended to tags 3 and 5. The mis-tagged and properly-tagged products undergo amplifying, sequencing and manipulation of the sequencing reads (e.g., culling, sorting and grouping, in any order). The tag 3 family of grouped sequencing reads represents two types of tagged molecules: (i) spurious polynucleotides having target sequence A appended to tags 3 and 4 (mis-tagged products) and (ii) polynucleotides having target sequence B appended to tags 3 and 5 (properly-tagged products).

Figure 18B:
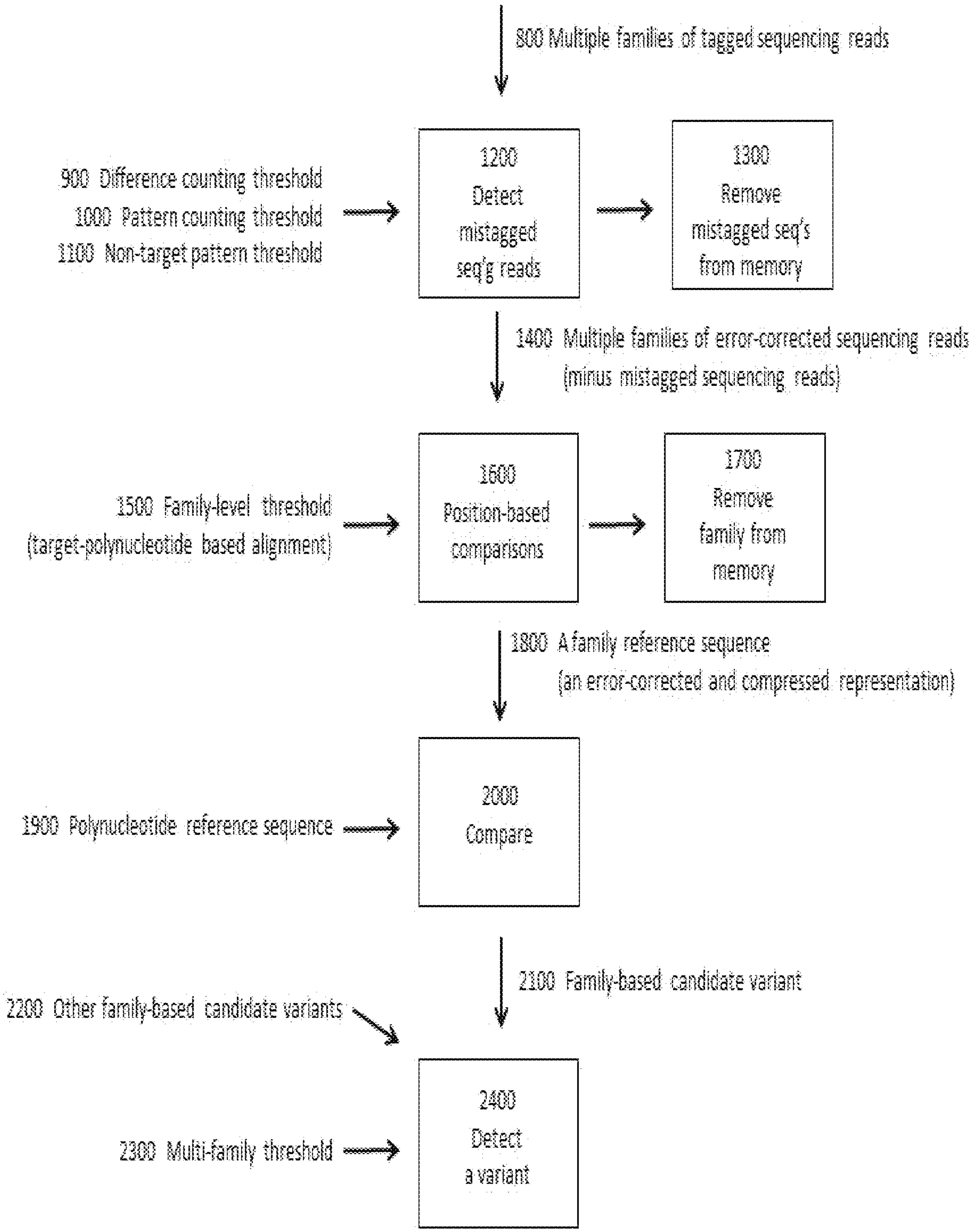
FIG. 18B is a block diagram that depicts a non-limiting block diagram of processing steps applied to families of candidate sequencing reads for generating error-corrected sequencing data.

In some embodiments, a difference counting threshold (FIG. 18B, (900)) can be used to identify which candidate sequencing reads may be a mistagged sequencing read (1200). For example, determining a number of nucleotides that differ between a candidate sequencing read and the reference sequence for the target polynucleotide and comparing the number to the difference counting threshold can identify a mistagged sequencing read. The difference counting threshold may be applied prior or subsequent to the grouping threshold. Applying the difference counting threshold to a set of candidate sequencing reads and removing an identified mistagged sequencing read (1300) may yield a set of sequencing reads having a reduced error rate. Applying the difference counting threshold to a family of grouped sequencing reads and removing an identified mistagged sequencing read may yield a family of sequencing reads having a reduced error rate (1400).

In some embodiments, a pattern counting threshold (FIG. 18B, (1000)) can be used to identify which candidate sequencing reads may be mistagged sequencing reads (1200) having a common pattern of variants. For example, determining a number of sequencing reads having a common pattern of variants in their polynucleotide sequences and comparing the number to a pattern counting threshold can be used to identify a group of mistagged sequencing reads. The pattern counting threshold may be applied prior or subsequent to the grouping threshold. Applying the pattern counting threshold to a set of candidate sequencing reads and removing an identified mistagged sequencing read (1300) may yield a set of sequencing reads having a reduced error rate. Applying the pattern counting threshold to a family of grouped sequencing reads and removing an identified mistagged sequencing read may yield a family of sequencing reads having a reduced error rate (1400).

In some embodiments, a non-target pattern threshold (FIG. 18B, (1100)) can be used to identify which candidate sequencing reads may be mistagged sequencing reads (1200). Mistagged sequencing reads may have a pattern of differences that is similar to a pattern of expected differences between the reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Comparing a pattern of differences in a candidate mistagged sequencing read to a pattern of expected differences and applying a non-target pattern threshold can identify a mistagged sequencing read. The non-target pattern threshold may be applied prior or subsequent to the grouping threshold. Applying the non-target pattern threshold to a set of candidate sequencing reads and removing an identified mistagged sequencing read (1300) may yield a set of sequencing reads having a reduced error rate. Applying the non-target pattern threshold to a family of grouped sequencing reads and removing an identified mistagged sequencing read may yield a family of sequencing reads having a reduced error rate (1400).

In some embodiments, a family level threshold can be used to identify a candidate variant within an error-corrected family of sequencing reads. For example, an error-corrected family of sequencing reads can be formed by detecting and removing mistagged sequencing reads using a difference counting threshold, pattern counting threshold and/or non-target pattern threshold. For example, aligning the error-corrected sequencing reads to a reference sequence for the error-corrected family, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, a family level threshold (FIG. 18B, (1500)) can be used to identify a candidate variant within an error-corrected family of sequencing reads. For example, an error-corrected family of sequencing reads can be formed by detecting and removing mistagged sequencing reads using any one or any combination of: a difference counting threshold, pattern counting threshold and/or non-target pattern threshold (FIG. 18B, (900), (1000) and (1100), respectively). For example, aligning the error-corrected sequencing reads to a reference sequence for the error-corrected family, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, a family level threshold (FIG. 18B, (1500)) can be used to determine a representative base for each base position to produce a family reference sequence. For example, in an error-corrected family of sequencing reads, for each position in the aligned sequences counting a number of aligned sequences having a particular base at the position (1600) and applying the family level threshold to the number to identify a representative base for that position. A number below the family level threshold indicates a base error at the position in the particular aligned sequence. A grouped family of sequencing reads that does not meet the family level threshold may be discarded (1700). In the families that are retained, the representative bases identified for each position can be used to generate a family reference sequence containing the representative base for each position. The family reference sequence is a single sequencing read that is error-corrected and is a compressed representation (1800) of the sequencing reads for the retained family. The family reference sequence can be stored in memory.

In some embodiments, the family reference sequence is compared to the polynucleotide-specific reference sequence to identify a family-based candidate variant. When the representative base at a given position differs from a base at the corresponding position in the polynucleotide-specific reference sequence, a family-based candidate variant at the given position is identified.

In some embodiments, a multi-family threshold (FIG. 18B, (2300)) can guide a decision to identify a variant that may be present in the initial nucleic acid sample. For example, applying a counting family threshold can identify the number of different error-corrected families having the same target polynucleotide sequence. In some instances, the family level threshold applied for different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, a multi-family threshold (2300) can be applied to the family-based candidate variants (2100) identified using the family reference sequences from multiple families (2200) to identify a variant that may be present in the initial nucleic acid sample. In some instances, the family-based candidate variants identified using family reference sequences for different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

FIG. 18A is a block diagram of processing steps applied to a plurality of candidate sequencing reads for error correction and family grouping in accordance with an exemplary embodiment. A memory stores a plurality of candidate sequencing reads (100) for analysis by a processor configured to apply operations implementing these steps. A first stage of error correction operations detects erroneous sequencing reads by comparing the corresponding portions of the sequencing reads to a tag-specific reference sequence and/or a polynucleotide-specific reference and applying a culling threshold (200). The sequencing reads that do not meet the criterion (300) of the culling threshold are removed from memory (400). After the first stage of error correction, a subset of candidate sequencing reads remains for further processing (500). The grouping operations (600) compare tag sequences of the candidate sequencing reads with a reference tag sequence. Candidate sequencing reads that share a common tag sequence are grouped into a given family, where the common tag sequence is unique to that family (700). The grouping operation generates multiple families of tagged sequencing reads (800).

FIG. 18B is a block diagram of additional processing steps which follow the processing steps shown in FIG. 18A. The processing steps are applied to families of candidate sequencing reads in accordance with an exemplary embodiment. Another stage of error correction operations identifies mistagged sequences that may be present in the grouped families of candidate sequencing reads by applying any one or any combination of the difference counting threshold (900), pattern counting threshold (1000) and/or non-target pattern threshold (1100). The identified mistagged sequences that are contained in the grouped families are removed from memory (1300).

Yet another stage of error correction includes position-based comparison operations (1600) which can create a family reference sequence for each family that is analyzed. The family reference sequence (1800) is a single sequencing read that is error-corrected and is a compressed representation of the sequencing reads for the retained family. For each base position that is analyzed, counting the number of aligned sequences having a particular base at the position and applying a family level threshold to the number can identify a representative base for that position. A number below the family level threshold at a given position indicates a base error in the aligned sequence. The family level threshold may be set based on a level of error tolerated. For example, for 20% error, the family level threshold is set to 80% of the sequencing reads for a given position. For a family containing 5 or 4 grouped sequencing reads, at least 80% of the sequencing reads for a given position gives the family level threshold equal to 4 for both. For a family containing 3 grouped sequencing reads, at least 80% of the sequencing reads for the position gives the family level threshold equal to 3.

A family reference sequence (1800) is generated by assembling the representative bases determined for each position into an array. A base error in a particular position in any of the candidate sequencing reads is not represented in the family reference sequence. The family reference sequence represents an error-corrected sequence for the family. The candidate sequencing reads of the family may be removed from memory (1700) while the family reference sequence is stored in memory. Storing the family reference sequence while discarding the candidate sequencing reads saves space in memory, resulting in a compression ratio of N:1, where N is the number of candidate sequencing reads in the family.

Returning to FIG. 18B, comparing (2000) the family reference sequence (1800) to the polynucleotide-specific reference sequence (1900) at each position and detecting a different base for a given position can identify a family-based candidate variant (2100) at the given position. Performing the comparison for each of the families corresponding to the polynucleotide-specific reference can generate multiple family-based candidate variants (2200). Counting the number of error-corrected families having a particular family-based candidate variant and applying a multi-family threshold (2300) to the number of error-corrected families can identify the variant at the given position (2400). The value of the multi-family threshold the nearest integer to a product of a percent factor multiplied by a number of different families corresponding to the same target polynucleotide. The percent factor can be in a range of 0.0001 to 0.1%, 0.001 to 0.1%, 0.01 to 0.1%, 0.02 to 0.08%, 0.03 to 0.07%, 0.04 to 0.06%, 0.045 to 0.055%, 0.0001 to 2.5%, 0.1 to 2.5%, 1 to 2.5%, 1.5 to 2.5%, 1.8 to 2.2%, 1.9 to 2.1%, or 1.95% to 2.05%, or a subinterval of one of these ranges.

Figure 18C:
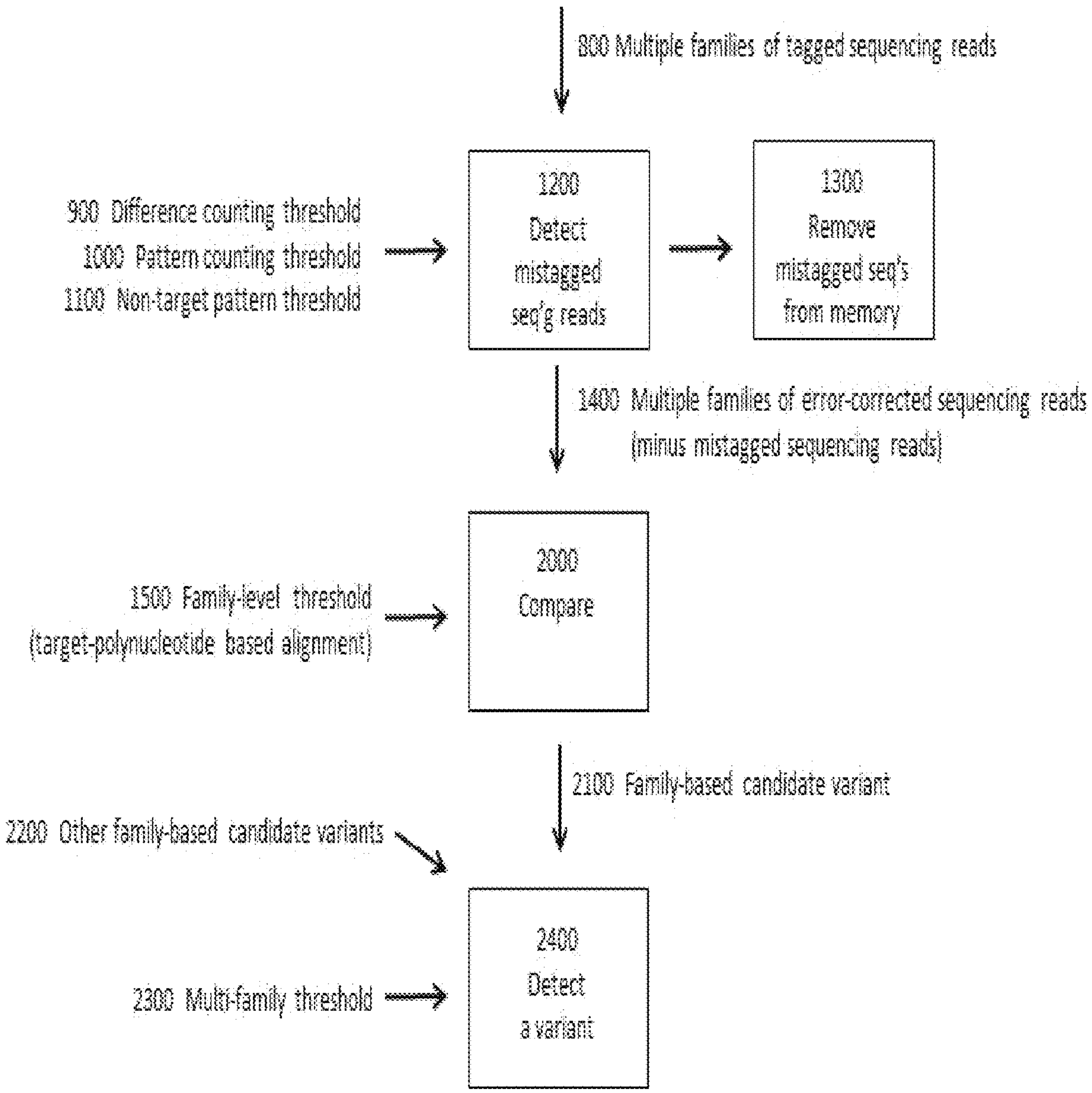
FIG. 18C is a block diagram that depicts a non-limiting block diagram of processing steps applied to families of candidate sequencing reads for generating error-corrected sequencing data.

In some embodiments, the processing steps shown in FIG. 18C follow those shown in FIG. 18A. As in FIG. 18B, another stage of error correction includes operations to identify mistagged sequencing reads that may be present in the grouped families of candidate sequencing reads. The example shown in FIG. 18C does not include the position-based comparisons to determine a family reference sequence. For determining the family-based variant, the candidate sequencing reads of the error-corrected family are each compared to a polynucleotide specific reference sequence. The comparing operation determines a base position where one or more aligned sequencing reads and the polynucleotide reference sequence have different bases. Counting the number of aligned sequences having a particular base difference at the base position and applying a family level threshold can identify a family-based candidate variant. When the number of base differences is below the family level threshold, no family-based candidate variant is identified. The operations for detecting a variant using multiple family-based candidate variants are the same as described for FIG. 18B.

Figure 19A:
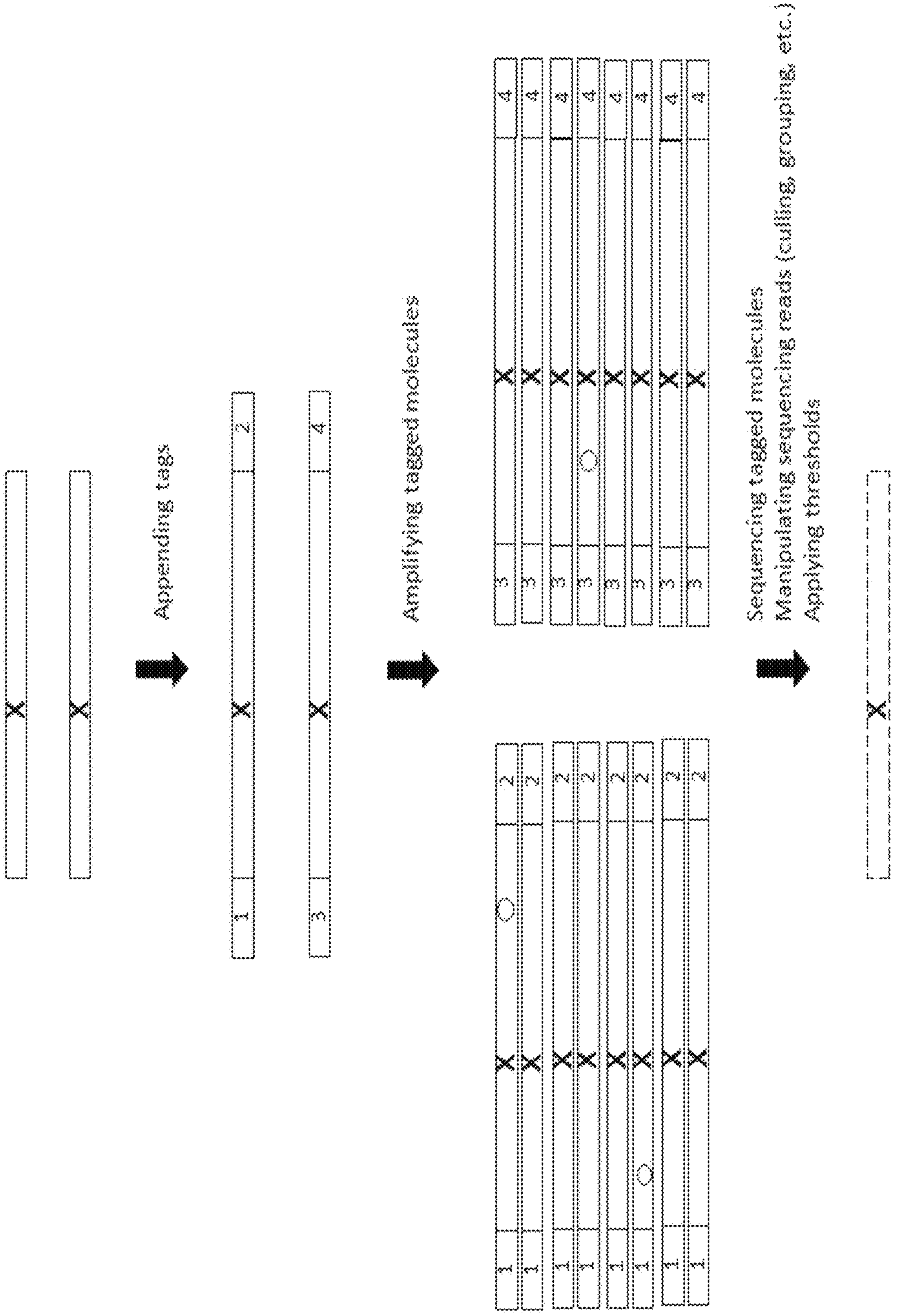
FIG. 19A is non-limiting schematic that depicts a molecular tagging workflow for generating a family reference sequence.
Figure 19B:
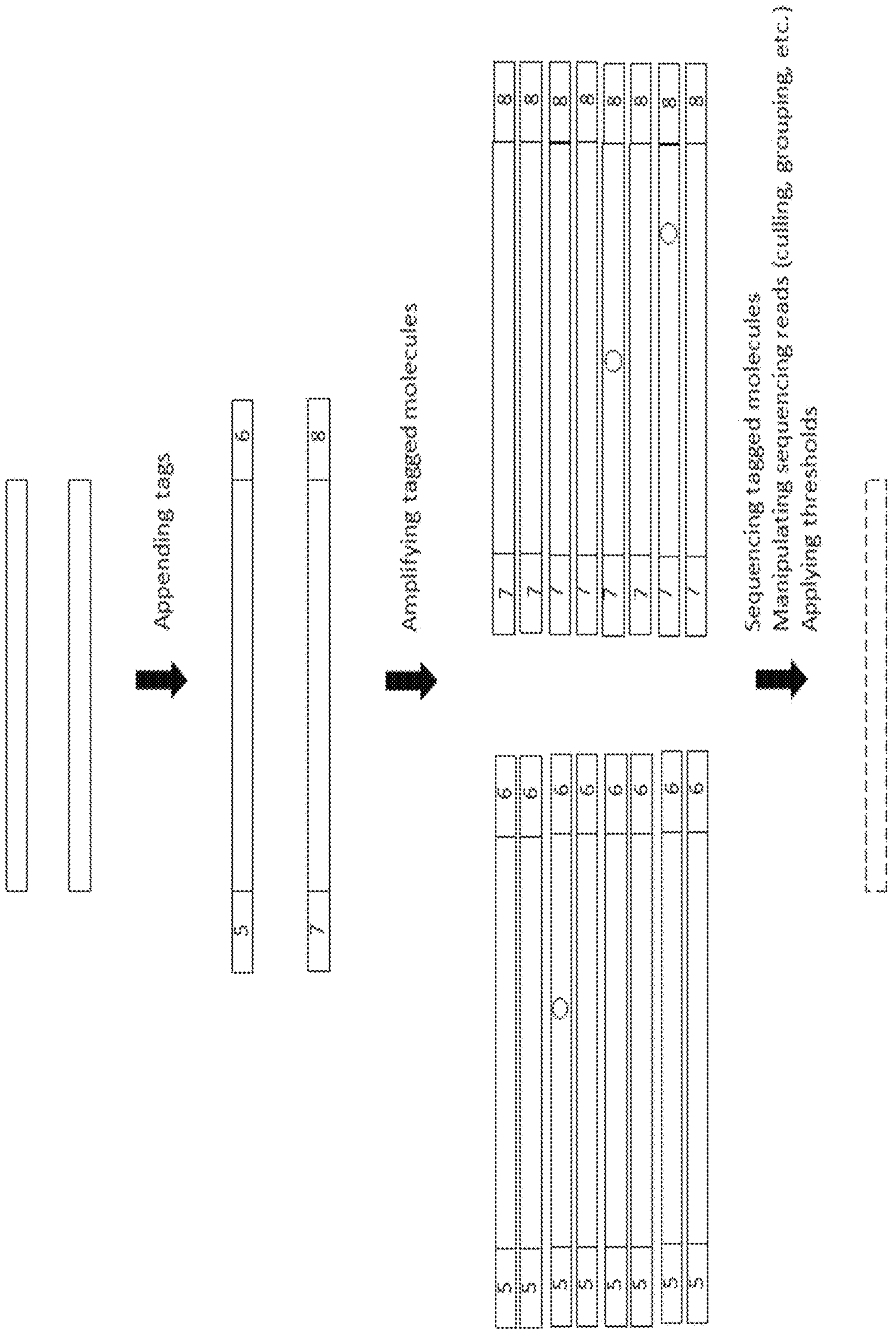
FIG. 19B is non-limiting schematic that depicts a molecular tagging workflow for generating a family reference sequence.

FIGS. 19A and B are non-limiting schematics that depict a molecular tagging workflow. The two target polynucleotides at the top of FIG. 19A carry the same mutant sequence which is denoted with an "X". The two target polynucleotides at the top of FIG. 19B carry the same wild-type sequence. The target polynucleotides at the top of FIGS. 19A and B are each appended at both ends to unique tags (e.g., randomer tags 1-8) in the same tag-appending reaction mixture via adaptor ligation or primer extension. The tagged molecules are amplified in the same reaction mixture to generate a plurality of tagged amplicons, some of which now carry spurious mutant sequences that were produced during the amplification step. The spurious mutant sequences in FIGS. 19A and B are denoted with an "O". The plurality of tagged amplicons is sequenced to generate a plurality of candidate tagged sequencing reads. Thus the sequences of the original two mutant and wild-type molecules are contained in multiple candidate tagged sequencing reads. The candidate tagged sequencing reads are manipulated by applying any one or any combination of the culling threshold, a grouping threshold, counting grouped reads threshold counting family threshold, difference counting threshold, pattern counting threshold non-target pattern threshold and/or family level threshold to reduce the multiple candidate tagged sequencing reads to a single sequencing read (e.g., the family reference sequence) that is error-corrected and is a compressed representation of the multiple candidate tagged sequencing reads in the family. The family reference sequence which represents the mutant candidate tagged sequencing reads is denoted by a dashed rectangular box at the bottom of FIG. 19A. The family reference sequence which represents the wild-type candidate tagged sequencing reads is denoted by a dashed rectangular box at the bottom of FIG. 19B. Both the mutant and wild-type family reference sequences can be stored in memory.

It will be appreciated by the skilled artisan that any threshold can be adjusted based on one or on several factors, including: the number of sequencing reads that are generated, the percent of sequencing reads that are culled and/or retained, the number of different groups of sequencing reads, and the size of the groups.

A multi-family threshold can guide a decision to identify a variant that may be present in the nucleic acid sample. In some instances, different families for a given target polynucleotide sequence may identify a particular candidate variant. Counting the number of families supporting the particular candidate variant and applying a multi-family threshold can identify the candidate variant as a variant that was present in the nucleic acid sample. The value of the multi-family threshold is a product of a percent factor multiplied by a number of different families corresponding to the same target polynucleotide. The percent factor can be in a range of 0.0001 to 0.1%, 0.001 to 0.1%, 0.01 to 0.1%, 0.02 to 0.08%, 0.03 to 0.07%, 0.04 to 0.06%, 0.045 to 0.055%, 0.0001 to 2.5%, 0.1 to 2.5%, 1 to 2.5%, 1.5 to 2.5%, 1.8 to 2.2%, 1.9 to 2.1%, or 1.95% to 2.05%, or a subinterval of one of these ranges.

In some embodiments, the disclosure relates generally to methods, as well as related systems, compositions, kits, apparatuses and computer-readable media, for detecting genetic variants, identifying genetic variants and/or reducing the error rate of sequencing data, which can enable increasing the sensitivity level for detecting and identifying genetic variants, for example by leveraging the massively parallel analysis capability of next generation sequencing platforms.

In some embodiments, the disclosure relates generally to methods, as well as related systems, compositions, kits, apparatuses and computer-readable media, for detecting low abundance genetic variants that are present within a nucleic acid sample, at a sensitivity level of about 0.0001-1%, or at about 0.001-1%, or about 0.01-1%, or about 0.1-1%, or about 0.1-5%, or about 5-10% in a nucleic acid sample, or about 0.05-0.1%, or about 0.048-0.1%, or about 0.046-0.1%, or about, 0.044-0.1%, or about 0.042-0.1%, or about 0.040-0.1%, or about 0.025-0.05%, or about 0.0125-0.025%, or less than 0.0125% (or lower abundance ranges).

In some embodiments, the starting nucleic acid sample contains about 1-7 ng, or about 5-12 ng, or about 10-105 ng, or about 100 ng-1 ug of polynucleotides. In some embodiments, the starting nucleic acid sample contains about 0.0001-5 ng of polynucleotides. Optionally, the starting nucleic acid sample can be approximately 1-50 ng and can be obtained from a biological fluid, solid biological sample, any organism, or from water, soil or food.

In some embodiments, the disclosure relates generally to methods, as well as related systems, compositions, kits, apparatuses and computer-readable media, for detecting genetic variants, identifying genetic variants and/or generating error-corrected sequencing data, comprising: (a) providing a nucleic acid sample containing a plurality of polynucleotides; and (b) generating a plurality of tagged polynucleotides by appending to at least some of the plurality of polynucleotides at least one tag. The tagged polynucleotides can be generated by conducting a one-step tagging reaction or a multiple-step tagging reaction. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a full-length universal sequence. The two-step tagging procedure includes performing a first ligation or primer extension reaction using tags that contain a unique tag sequence or a partial-length universal sequence, and performing a subsequent ligation or primer extension reaction using tags that contain a unique tag sequence or a universal sequence.

In some embodiments, the disclosure relates generally to methods, as well as related systems, compositions, kits, apparatuses and computer-readable media, further comprise the step: (c) amplifying the tagged polynucleotides to generate tagged amplicons.

In some embodiments, the disclosure relates generally to methods, as well as related systems, compositions, kits, apparatuses and computer-readable media, further comprise the step: (d) determining the sequence of at least some of the tagged amplicons to generate a population of candidate sequencing reads.

In some embodiments, the disclosure relates generally to methods, as well as related systems, compositions, kits, apparatuses and computer-readable media, further comprise the step: manipulating the candidate sequencing reads to generate error-corrected sequencing reads. Optionally, the manipulating includes applying at least one threshold to the candidate sequencing reads. Optionally, the manipulated sequencing reads can be used to determine that a particular polynucleotide is present in the initial nucleic acid sample, and to identify the sequence of the particular polynucleotide.

In some embodiments, the disclosure relates generally to methods, as well as related systems, compositions, kits, apparatuses and computer-readable media, further comprise the step: culling one or more candidate sequencing reads from the population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate error-corrected sequencing reads.

In some embodiments, the disclosure relates generally to methods, as well as related systems, compositions, kits, apparatuses and computer-readable media, further comprise the step: grouping a subset of the population of candidate sequencing reads into different families of candidate sequencing reads, where the different families of candidate sequencing reads include a common tag sequence. The grouped sequencing reads can be used to generate a family of error-corrected sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence.

In some embodiments, the disclosure relates generally to methods, as well as related systems, compositions, kits, apparatuses and computer-readable media, further comprise the step: determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample.

In some embodiments, the disclosure relates generally to methods, as well as related systems, compositions, kits, apparatuses and computer-readable media, further comprise the step: counting the number of different families (of sequencing grouped sequencing reads) having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the disclosure relates generally to methods, as well as related systems, compositions, kits, apparatuses and computer-readable media, further comprise the step: removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the disclosure relates generally to methods, as well as related systems, compositions, kits, apparatuses and computer-readable media, further comprise the step: identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate.

In some embodiments, the disclosure relates generally to methods, as well as related systems, compositions, kits, apparatuses and computer-readable media, further comprise the step: identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate.

In some embodiments, the disclosure relates generally to methods, as well as related systems, compositions, kits, apparatuses and computer-readable media, further comprise the step: identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate.

In some embodiments, the disclosure relates generally to methods, as well as related systems, compositions, kits, apparatuses and computer-readable media, further comprise the step: identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate.

In some embodiments, the disclosure relates generally to methods, as well as related systems, compositions, kits, apparatuses and computer-readable media, further comprise the step: identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the disclosure relates generally to methods, as well as related systems, compositions, kits, apparatuses and computer-readable media, further comprise the step: identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the plurality of polynucleotides are appended with the at least one tag in a single reaction mixture.

In some embodiments, the single reaction mixture contains 1-6 unique tags, or 4-105 unique tags, or 100-510 unique tags, or 500-1010 unique tags, or 1000-5010 unique tags, or 5000-10,010 unique tags, or more than 10,000 unique tags.

In some embodiments, the plurality of oligonucleotide tags in the single reaction mixture detect the presence of 5-105, or 100-205, or 200-305, or 300-405, or 400-505 or more different target polynucleotides in the nucleic acid sample.

In some embodiments, amplicons that contain a target polynucleotide sequence appended to at least one tag, are about 30-105 bases, or about 100-305 bases, or about 300-605 bases, or about 600-1,000 bases in length.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least one target polynucleotides and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the target and non-target polynucleotides or lacks non-target polynucleotides.

In some embodiments, the abundance level of the target polynucleotide is present in the nucleic acid sample at about 0.0001-1%, or about 0.001-1%, or about 0.01-1%, or about 0.1-1%, or about 0.1-5%, or lower abundance ranges.

In some embodiments, the nucleic acid sample contains a plurality of target polynucleotides including wild-type forms and its related polymorphic forms which include allelic, variant and/or mutant forms.

In some embodiments, the error-corrected sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the target polynucleotide and are present in the nucleic acid sample.

In some embodiments, the error-corrected family of sequencing reads is used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, is used to detect and identify about 85-95%, or about 95-99%, or about 100%, of the different target polynucleotides, (e.g., including genetic variants) that may be present in the initial nucleic acid sample.

In some embodiments, at least two of the tagged polynucleotide molecules in the plurality of tagged polynucleotides are uniquely tagged, that is at least two of the tagged polynucleotide molecules in the plurality of tagged polynucleotides are appended with different tags. The two tagged polynucleotide can include a target polynucleotide having the same or different sequence. In some embodiments, each of the tagged polynucleotide molecules in a plurality of tagged polynucleotides are appended with a tag that differs from a tag that is appended to substantially every other tagged polynucleotide.

In some embodiments, at least two tagged polynucleotides in the plurality of tagged polynucleotides are appended at both ends with a different tag.

In some embodiments, the plurality of polynucleotides that are appended with the at least one tag (e.g., tag adaptor) by enzymatic ligation.

In some embodiments, substantially every polynucleotide is appended to the at least one tag (e.g., tag adaptor) by enzymatic ligation.

In some embodiments, substantially every polynucleotide that is appended with the at least one tag, includes about 10-30%, or about 30-50%, or about 50-70%, or about 70-80%, or about 80-90%, or about 90-95%, or about 95-99% of the individual polynucleotide molecules within the plurality of polynucleotides are appended with at least one tag.

In some embodiments, the enzymatic ligation non-selectively appends at least one tag to the plurality of polynucleotides. For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the plurality of polynucleotides that are appended with the at least one tag by primer extension reaction using at least one tag primer having a target-specific sequence that selectively hybridizes to at least one region of a target polynucleotide within the nucleic acid sample, and the at least one tag primer includes at least one unique tag sequence. Optionally, the tag primer includes a portion that does not selectively hybridize to the target polynucleotide. For example, the 3' region of a tag primer includes a target-specific sequence that selectively hybridizes to a portion of the target polynucleotide, and the 5' region includes a unique tag sequence which does not selectively hybridize to the target polynucleotide.

In some embodiments, the primer extension reaction further comprises a polymerase and a plurality of nucleotides.

In some embodiments, a subset of the plurality of polynucleotides are selectively appended to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in a tag adaptor or primer) comprises a randomer tag having at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags in a plurality of tags have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3$ $N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-<u>NNN</u>ACT<u>NNN</u>TGA-3' (SEQ ID NO:1) are a sequence alignment anchor.

In some embodiments, the fixed sequences within the randomer tag sequence can serve as a sequence alignment anchor that is used to generate error-corrected sequencing data, including to generate a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the tagged amplicons.

Optionally, the determining step includes sequencing one or both strands that correspond to the tagged amplicons.

Optionally, the determining step includes sequencing at least a portion of the polynucleotide and/or at least a portion of the at least one tag that is appended to the polynucleotide.

Optionally, the determining step includes sequencing at least a portion of the polynucleotide and at least a portion of two tags that are appended to the polynucleotide.

Optionally, the determining step includes generating a population of candidate sequencing reads that contain at least a portion of the polynucleotide and/or at least a portion of the at least one tag that are appended to the polynucleotide.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a target polynucleotides in a nucleic acid sample, comprising: (a) generating a plurality of tagged polynucleotides, by appending at least one tag to each end of individual polynucleotides from a plurality of polynucleotides. Optionally, the nucleic acid sample includes target polynucleotide and non-target polynucleotides or lack non-target polynucleotides. The tagged polynucleotides can be generated by conducting a one-step tagging reaction or a multiple-step tagging reaction. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a full-length universal sequence. The two-step tagging procedure includes performing a first ligation or primer extension reaction using tags that contain a unique tag sequence or a partial-length universal sequence, and performing a subsequent ligation or primer extension reaction using tags that contain a unique tag sequence or a universal sequence.

In some embodiments, the disclosure relates generally to methods, as well as related systems, compositions, kits, apparatuses and computer-readable media, further comprise the step: (b) generating a population of tagged amplicons by amplifying the plurality of tagged polynucleotides.

In some embodiments, the disclosure relates generally to methods, as well as related systems, compositions, kits, apparatuses and computer-readable media, further comprise the step: (c) determining that the target polynucleotide is present in the nucleic acid sample.

In some embodiments, the determining step includes sequencing at least a portion of the polynucleotide and/or at least a portion of the at least one tag that is appended to the polynucleotide.

In some embodiments, the determining step includes sequencing at least a portion of the polynucleotide and at least a portion of two tags that are appended to the polynucleotide.

In some embodiments, the determining step includes generating a population of candidate sequencing reads that contain at least a portion of the polynucleotide and/or at least a portion of the at least one tag that is appended to the polynucleotide.

In some embodiments, the determining step includes manipulating the population of candidate sequencing reads to generate error-corrected sequencing reads, for example by applying one or more thresholds including culling, grouping, counting grouped reads, difference counting, pattern counting and/or non-target pattern counting family thresholds. Optionally, the manipulating includes applying at least one threshold to the candidate sequencing reads. Optionally, the manipulated sequencing reads can be used to determine that a particular polynucleotide is present in the initial nucleic acid sample, and to identify the sequence of the particular polynucleotide. Optionally, the manipulated sequencing reads can be used to detect a variant that may be present in the initial nucleic acid sample, for example by applying a family-level threshold and/or a multi-family threshold.

In some embodiments, the determining step includes culling one or more candidate sequencing reads from the population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate error-corrected sequencing reads.

In some embodiments, the determining step includes grouping a subset of the population of candidate sequencing reads into different families of candidate sequencing reads, where the different families of candidate sequencing reads include a common tag sequence. The grouped sequencing reads can be used to generate an error-corrected family of sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence.

In some embodiments, the determining step includes determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample.

In some embodiments, the determining step includes counting the number of different families (of sequencing grouped sequencing reads) having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the determining step includes removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the determining step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate.

In some embodiments, the determining step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate.

In some embodiments, the determining step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate.

In some embodiments, the determining step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the appending the at least one tag to each end of the individual polynucleotides from the plurality of polynucleotides is conducted in a single reaction mixture.

In some embodiments, the single reaction mixture contains 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, the plurality of oligonucleotide tags in the single reaction mixture detect the presence of 5-100, or 100-200, or 200-300, or 300-400, or 400-500 or more different target polynucleotides in the nucleic acid sample.

In some embodiments, amplicons that contain a target polynucleotide sequence appended to at least one tag, are about 30-100 bases, or about 100-300 bases, or about 300-600 bases, or about 600-1,000 bases in length.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least one target polynucleotides and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the target and non-target polynucleotides or lacks non-target polynucleotides.

In some embodiments, the abundance level of the target polynucleotide is present in the nucleic acid sample at about 0.0001-1%, or about 0.001-1%, or about 0.01-1%, or about 0.1-1%, or about 0.1-5%, or lower abundance ranges In some embodiments, the nucleic acid sample contains a plurality of target polynucleotides including wild-type forms and its related polymorphic forms which include allelic, variant and/or mutant forms.

In some embodiments, the error-corrected sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the target polynucleotide and are present in the nucleic acid sample.

In some embodiments, the error-corrected sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify about 85-95%, or about 95-99%, or about 100%, of the different target polynucleotides (e.g., including genetic variants) that may be present in the initial nucleic acid sample.

In some embodiments, at least two of the tagged polynucleotide molecules in the plurality of tagged polynucleotides are uniquely tagged, that is at least two of the tagged polynucleotide molecules in the plurality of tagged polynucleotides are appended with different tags. The two tagged polynucleotide can include a target polynucleotide having the same or different sequence. In some embodiments, each of the tagged polynucleotide molecules in a plurality of tagged polynucleotides are appended with a tag that differs from a tag that is appended to substantially every other tagged polynucleotide.

In some embodiments, at least two tagged polynucleotides in the plurality of tagged polynucleotides are appended at both ends with a different tag.

In some embodiments, the plurality of polynucleotides that are appended at each end with the at least one tag (e.g., tag adaptor) by enzymatic ligation.

In some embodiments, substantially every polynucleotide is appended at each end to the at least one tag (e.g., tag adaptor) by enzymatic ligation.

In some embodiments, substantially every polynucleotide that is appended with the at least one tag, includes 10-30%, or about 30-50%, or about 50-70%, or about 70-80%, or about 80-90%, or about 90-95%, or about 95-99% of the individual polynucleotide molecules within the plurality of polynucleotides are appended with at least one tag.

In some embodiments, the enzymatic ligation non-selectively appends at least one tag to the plurality of polynucleotides. For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the plurality of polynucleotides that are appended at each end with the at least one tag by primer extension reaction using at least one tag primer having a target-specific sequence that selectively hybridizes to at least one region of a target polynucleotide within the nucleic acid sample, and the at least one tag primer includes at least one unique tag sequence. Optionally, the tag primer includes a portion that does not selectively hybridize to the target polynucleotide. For example, the 3' region of a tag primer includes a target-specific sequence that selectively hybridizes to a portion of the target polynucleotide, and the 5' region includes a unique tag sequence which does not selectively hybridize to the target polynucleotide.

In some embodiments, the primer extension reaction comprises a polymerase and a plurality of nucleotides.

In some embodiments, a subset of the plurality of polynucleotides are selectively appended at each end to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in a tag adaptor or primer) comprises a randomer tag having at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags in a plurality of tags have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3$ $N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the fixed sequences within the randomer tag sequence can serve as a sequence alignment anchor that is used to generate error-corrected sequencing data, including generating a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the tagged amplicons.

Optionally, the determining step includes sequencing one or both strands that correspond to the tagged amplicons.

Optionally, the determining step includes sequencing at least a portion of the polynucleotide and/or at least a portion of the at least one tag that is appended to the polynucleotide.

Optionally, the determining step includes sequencing at least a portion of the polynucleotide and at least a portion of two tags that are appended to the polynucleotide.

Optionally, the determining step includes generating a population of candidate sequencing reads that contain at least a portion of the polynucleotide and/or at least a portion of the at least one tag that are appended to the polynucleotide.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a target polynucleotides in a nucleic acid sample, comprising: (a) generating a plurality of tagged polynucleotides, by contacting (i) a plurality of polynucleotides that include a first polynucleotide and a second polynucleotide with (ii) a plurality of tags that include a first, second, third and fourth tag, and appending the first tag to one end of the first polynucleotide and appending the second tag to the other end of the first polynucleotide, and appending the third tag to one end of the second polynucleotide and appending the fourth tag to the other end of the second polynucleotide. In some embodiments, the nucleic acid sample includes target polynucleotides and non-target polynucleotides, or lacks non-target polynucleotides. The tagged polynucleotides can be generated by conducting a one-step tagging reaction or a multiple-step tagging reaction. In some embodiments, individual polynucleotides (e.g., the first and second polynucleotides) are appended with a unique tag sequence (e.g., first, second, third or fourth unique tag) and a universal tag sequence (e.g., first, second, third or fourth universal tag) using a one-step or multiple-step (e.g., two-step) tagging procedure.

In some embodiments, individual polynucleotides (e.g., the first polynucleotide) are appended with unique tag sequences (e.g., first and second unique tags) and universal tag sequences (e.g., first and second universal tags) using a one-step or multiple-step (e.g., two-step) tagging procedure. In some embodiments, individual polynucleotides (e.g., the second polynucleotide) are appended with unique tag sequences (e.g., third and fourth unique tags) and universal tag sequences (e.g., third and fourth universal tags) using a one-step or multiple-step (e.g., two-step) tagging procedure.

For example, the one-step tagging procedure includes performing a ligation or primer extension reaction with the first polynucleotide using (i) the first tag that contains the first unique tag sequence and the full-length first universal sequence and (ii) the second tag that contains the second unique tag sequence and the full-length second universal sequence.

In the same reaction mixture, the one-step tagging procedure includes performing a ligation or primer extension reaction with the second polynucleotide using (i) the third tag that contains the third unique tag sequence and the full-length third universal sequence and (ii) the fourth tag that contains the fourth unique tag sequence and the full-length fourth universal sequence. The first, second, third and fourth tags contain the same or different universal sequences.

The two-step tagging procedure includes performing a first ligation or primer extension reaction with the first polynucleotide using (i) the first tag that contains the first unique tag sequence and optionally at least a portion of the first universal sequence and (ii) the second tag that contains the second unique tag sequence and optionally at least a portion of the second universal sequence.

In the same reaction mixture, the first ligation or primer extension reaction is performed with the second polynucleotide using (i) the third tag that contains the third unique tag sequence and optionally at least a portion of the third universal sequence and (ii) the fourth tag that contains the fourth unique tag sequence and optionally at least a portion of the fourth universal sequence.

A second ligation or primer extension reaction is performed using the first polynucleotide (which is now tagged) and (iii) a tag that contains at least a portion of the first universal sequence and (iv) a tag that contains at least a portion of the second universal sequence.

A second ligation or primer extension reaction is performed using the second polynucleotide (which is now tagged) and (iii) a tag that contains at least a portion of the third universal sequence and (iv) a tag that contains at least a portion of the fourth universal sequence.

The first, second, third and fourth tags contain the same or different universal sequences.

In some embodiments, the disclosure relates generally to methods, as well as related systems, compositions, kits, apparatuses and computer-readable media, further comprise the step: (b) generating a population of first tagged amplicons by amplifying the first tagged polynucleotides, and generating a population of second tagged amplicons by amplifying the second tagged polynucleotides.

In some embodiments, the disclosure relates generally to methods, as well as related systems, compositions, kits, apparatuses and computer-readable media, further comprise the step: (c) determining that the first target polynucleotide and/or that the second target polynucleotide is present in the nucleic acid sample.

In some embodiments, the determining step includes sequencing at least a portion of the first polynucleotide and/or at least the portion of the first tag and/or at least a portion of the second tag, where the first and second tags are appended to the first polynucleotide.

In some embodiments, the determining step includes sequencing at least a portion of the second polynucleotide and/or at least the portion of the third tag and/or at least a portion of the fourth tag, where the third and fourth tags are appended to the second polynucleotide.

In some embodiments, the determining step includes generating a population of candidate sequencing reads that contain at least a portion of the first polynucleotide and/or at least the portion of the first tag and/or at least a portion of the second tag.

In some embodiments, the determining step includes generating a population of candidate sequencing reads that contain at least a portion of the second polynucleotide and/or at least the portion of the third tag and/or at least a portion of the fourth tag.

In some embodiments, the determining step includes manipulating the population of candidate sequencing reads to generate error-corrected sequencing reads, for example by applying one or more thresholds including culling, grouping, counting grouped reads, counting family, difference counting, pattern counting and/or non-target pattern thresholds. Optionally, the manipulating includes applying at least one threshold to the candidate sequencing reads. Optionally, the manipulated sequencing reads can be used to determine that a particular polynucleotide is present in the initial nucleic acid sample, and to identify the sequence of the particular polynucleotide. Optionally, the manipulated sequencing reads can be used to detect a variant that may be present in the initial nucleic acid sample, for example by applying a family-level threshold and/or a multi-family threshold.

In some embodiments, the determining step includes culling one or more candidate sequencing reads from the population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate error-corrected sequencing reads. Optionally, the culling threshold can be used to retain or remove the first candidate sequencing read, which corresponds to the first tagged polynucleotide, to generate error-corrected sequencing reads. Optionally, the culling threshold can be used to retain or remove the second candidate sequencing read, which corresponds to the second tagged polynucleotide, to generate error-corrected sequencing reads.

In some embodiments, the determining step includes grouping a subset of the population of candidate sequencing reads into different families of candidate sequencing reads, where the different families of candidate sequencing reads include a common tag sequence. The grouped sequencing reads can be used to generate an error-corrected family of sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence. Optionally, the candidate sequencing reads can be grouped by applying a grouping threshold to generate a first family of grouped sequencing reads, where the members of the first family of grouped sequencing reads share a common tag and/or polynucleotide sequence. Optionally, the candidate sequencing reads can be grouped by applying a grouping threshold to generate a second family of grouped sequencing reads, where the members of the second family of grouped sequencing reads share a common tag and/or polynucleotide sequence.

In some embodiments, the determining step includes determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample. Optionally, a first family of grouped sequencing reads can be subjected to the counting grouped reads threshold to determine the percent of the first grouped sequencing reads that match (e.g., are similar or identical to) a reference sequence, in order to determine if the first family of grouped sequencing reads contains true positive sequencing reads. Optionally, a second family of grouped sequencing reads can be subjected to the counting grouped reads threshold to determine the percent of the second grouped sequencing reads that match (e.g., are similar or identical to) a reference sequence, in order to determine if the second family of grouped sequencing reads contains true positive sequencing reads.

In some embodiments, the determining step includes counting the number of different families (of sequencing grouped sequencing reads) having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the determining step includes removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the determining step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate. Optionally, the difference counting threshold can be used to retain or remove a first candidate sequencing read, which corresponds to the first tagged polynucleotide, to generate error-corrected sequencing reads. Optionally, the difference counting threshold can be used to retain or remove a second candidate sequencing read, which corresponds to the second tagged polynucleotide, to generate error-corrected sequencing reads. Optionally, a first family of grouped sequencing reads can be subjected to the difference counting threshold to identify a mistagged sequencing read in the first family, where the members of the first family of grouped sequencing reads share a common tag and/or polynucleotide sequence. Optionally, a second family of grouped sequencing reads can be subjected to the difference counting threshold to identify a mistagged sequencing read in the second family, where the members of the second family of grouped sequencing reads share a common tag and/or polynucleotide sequence.

In some embodiments, the determining step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate. Optionally, the pattern counting threshold can be used to retain or remove a first candidate sequencing read, which corresponds to the first tagged polynucleotide, to generate error-corrected sequencing reads. Optionally, the pattern counting threshold can be used to retain or remove a second candidate sequencing read, which corresponds to the second tagged polynucleotide, to generate error-corrected sequencing reads. Optionally, a first family of grouped sequencing reads can be subjected to the pattern counting threshold to identify a mistagged sequencing read in the first family, where the members of the first family of grouped sequencing reads share a common tag and/or polynucleotide sequence. Optionally, a second family of grouped sequencing reads can be subjected to the pattern counting threshold to identify a mistagged sequencing read in the second family, where the members of the second family of grouped sequencing reads share a common tag and/or polynucleotide sequence.

In some embodiments, the determining step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate. Optionally, the difference counting threshold and the pattern counting threshold can be used to retain or remove a first candidate sequencing read, which corresponds to the first tagged polynucleotide, to generate error-corrected sequencing reads. Optionally, the difference counting threshold and the pattern counting threshold can be used to retain or remove a second candidate sequencing read, which corresponds to the second tagged polynucleotide, to generate error-corrected sequencing reads. Optionally, a first family of grouped sequencing reads can be subjected to the difference counting threshold and the pattern counting threshold to identify a mistagged sequencing read in the first family, where the members of the first family of grouped sequencing reads share a common tag and/or polynucleotide sequence. Optionally, a second family of grouped sequencing reads can be subjected to the difference counting threshold and the pattern counting threshold to identify a mistagged sequencing read in the second family, where the members of the second family of grouped sequencing reads share a common tag and/or polynucleotide sequence.

In some embodiments, the determining step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate. Optionally, the non-target pattern threshold can be used to retain or remove a first candidate sequencing read, which corresponds to the first tagged polynucleotide, to generate error-corrected sequencing reads. Optionally, the non-target pattern threshold can be used to retain or remove a second candidate sequencing read, which corresponds to the second tagged polynucleotide, to generate error-corrected sequencing reads. Optionally, a first family of grouped sequencing reads can be subjected to the non-target pattern threshold to identify a mistagged sequencing read in the first family, where the members of the first family of grouped sequencing reads share a common tag and/or polynucleotide sequence. Optionally, a second family of grouped sequencing reads can be subjected to the non-target pattern threshold to identify a mistagged sequencing read in the second family, where the members of the second family of grouped sequencing reads share a common tag and/or polynucleotide sequence.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants. Optionally, a first error-corrected family of grouped sequencing reads can be subjected to the family level threshold to identify a first candidate variant in the first family, where the members of the first family of grouped sequencing reads share a common tag and/or polynucleotide sequence. Optionally, a second error-corrected family of grouped sequencing reads can be subjected to the family level threshold to identify a second candidate variant in the second family, where the members of the second family of grouped sequencing reads share a common tag and/or polynucleotide sequence.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample. Optionally, a first set of error-corrected families of grouped sequencing reads supporting a particular first candidate variant can be subjected to a multi-family threshold to identify a first variant in the first set of families, where members of families the first set of grouped sequencing reads share a common tag and/or polynucleotide sequence. Optionally, a second set of error-corrected families of grouped sequencing reads supporting a particular second candidate variant can be subjected to a multi-family threshold to identify a second candidate variant in the second set of families, where members of families the second set of grouped sequencing reads share a common tag and/or polynucleotide sequence.

In some embodiments, the appending step is conducted in a single reaction mixture, where the first tag is appended to one end of the first polynucleotide and the second tag is appended to the other end of the first polynucleotide, and the third tag is appended to one end of the second polynucleotide and the fourth tag is appended to the other end of the second polynucleotide.

In some embodiments, the single reaction mixture contains 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, the plurality of oligonucleotide tags in the single reaction mixture detect the presence of 5-100, or 100-200, or 200-300, or 300-400, or 400-500 or more different target polynucleotides in the nucleic acid sample.

In some embodiments, amplicons that contain a first target polynucleotide sequence appended to a first and second tag, are about 30-100 bases, or about 100-300 bases, or about 300-600 bases, or about 600-1,000 bases in length. In some embodiments, amplicons that contain a second target polynucleotide sequence appended to a third and fourth tag, are about 30-100 bases, or about 100-300 bases, or about 300-600 bases, or about 600-1,000 bases in length.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least one target polynucleotides and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the target and non-target polynucleotides or lacks non-target polynucleotides.

In some embodiments, the abundance level of the target polynucleotide is present in the nucleic acid sample at about 0.0001-1%, or about 0.001-1%, or about 0.01-1%, or about 0.1-1%, or about 0.1-5%, or lower abundance ranges.

In some embodiments, the nucleic acid sample contains a plurality of target polynucleotides including wild-type forms and its related polymorphic forms which include allelic, variant and/or mutant forms.

In some embodiments, the error-corrected sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the target polynucleotide and are present in the nucleic acid sample.

In some embodiments, the error-corrected family of sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify about 85-95%, or about 95-99%, or about 100%, of the different target polynucleotides (e.g., including genetic variants) that may be present in the initial nucleic acid sample.

In some embodiments, the first tagged polynucleotide in the plurality of tagged polynucleotides is appended with tags at each end (e.g., first and second tags) that differ from other tags that are appended to substantially every other tagged polynucleotide.

In some embodiments, the second tagged polynucleotide in the plurality of tagged polynucleotides is appended with tags at each end (e.g., third and fourth tags) that differ from other tags that are appended to substantially every other tagged polynucleotide.

In some embodiments, the first tagged polynucleotide in the plurality of tagged polynucleotides is appended with a different tag at each end (e.g., first and second tags).

In some embodiments, the second tagged polynucleotide in the plurality of tagged polynucleotides is appended with a different tag at each end (e.g., third and fourth tags).

In some embodiments, the first tagged polynucleotide in the plurality of tagged polynucleotides is appended with a first tag and a second tag that differ from each other.

In some embodiments, the second tagged polynucleotide in the plurality of tagged polynucleotides is appended with a third and fourth tag that differ from each other.

In some embodiments, the first polynucleotide is appended with the first and second tags (e.g., first and second tag adaptors) by enzymatic ligation.

In some embodiments, the second polynucleotide is appended with the third and fourth tags (e.g., third and fourth tag adaptors) by enzymatic ligation.

In some embodiments, substantially every polynucleotide, including the first and second polynucleotides, are appended at each end to the at least one tag (e.g., tag adaptor) by enzymatic ligation.

In some embodiments, substantially every polynucleotide (including the first and second polynucleotides) that is appended at each end with the at least one tag, includes about 10-30%, or about 30-50%, or about 50-70%, or about 70-80%, or about 80-90%, or about 90-95%, or about 95-99% of the individual polynucleotide molecules within the plurality of polynucleotides are appended at each end with at least one tag.

In some embodiments, the enzymatic ligation non-selectively appends at least one tag to each end of the plurality of polynucleotides. For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the first target polynucleotide is appended with the first and second tag primers by primer extension reaction using a first and second tag primer, where the first and second tag primers include a target-specific sequence that selectively hybridizes to at least one region of a first target polynucleotide within the nucleic acid sample, and the first tag primer includes at least a first unique tag sequence and the second tag primer includes at least a second unique tag sequence. The first and second tag primers can hybridize to a different region of the first target polynucleotide. Optionally, the first tag primer includes a portion that does not selectively hybridize to the first target polynucleotide. Optionally, the second tag primer includes a portion that does not selectively hybridize to the first target polynucleotide. For example, the 3' region of the first tag primer includes a target-specific sequence that selectively hybridizes to a portion of the first target polynucleotide, and the 5' region includes a unique tag sequence which does not selectively hybridize to the first target polynucleotide. The 3' region of the second tag primer includes a target-specific sequence that selectively hybridizes to a portion of the first target polynucleotide, and the 5' region includes a unique tag sequence which does not selectively hybridize to the first target polynucleotide. Optionally, the 3' regions of the first and second tag primers hybridize to different portions of the first polynucleotide.

In some embodiments, the second target polynucleotide is appended with the third and fourth tag primers by primer extension reaction using a third and fourth tag primer, where the third and fourth tag primers include a target-specific sequence that selectively hybridizes to at least one region of a second target polynucleotide within the nucleic acid sample, and the third tag primer includes at least a third unique tag sequence and the fourth tag primer includes at least a fourth unique tag sequence. The third and fourth tag primers can hybridize to a different region of the second target polynucleotide. Optionally, the third tag primer includes a portion that does not selectively hybridize to the second target polynucleotide. Optionally, the fourth tag primer includes a portion that does not selectively hybridize to the second target polynucleotide. For example, the 3' region of the third tag primer includes a target-specific sequence that selectively hybridizes to a portion of the second target polynucleotide, and the 5' region includes a unique tag sequence which does not selectively hybridize to the second target polynucleotide. The 3' region of the fourth tag primer includes a target-specific sequence that selectively hybridizes to a portion of the second target polynucleotide, and the 5' region includes a unique tag sequence which does not selectively hybridize to the second target polynucleotide. Optionally, the 3' regions of the third and fourth tag primers hybridize to different portions of the first polynucleotide.

In some embodiments, the primer extension reaction comprises a polymerase and a plurality of nucleotides.

In some embodiments, a subset of the plurality of polynucleotides, where the subset includes the first and second target polynucleotides, are selectively appended at each end to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in a tag adaptor or contained in a first, second, third and fourth tag primer) comprises a randomer tag, where the random tag includes at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags in a plurality of tags have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3$ $N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the fixed sequences within the randomer tag sequence can serve as a sequence alignment anchor that is used to generate error-corrected sequencing data, including generating a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the tagged amplicons, including the first and second tagged amplicons.

Optionally, the determining step includes sequencing one or both strands that correspond to the tagged amplicons. Optionally, the determining step includes sequencing one or both strands of the first and second tagged amplicons.

Optionally, the determining step includes sequencing at least a portion of the first tagged polynucleotide. Optionally, the determining step includes sequencing at least a portion of the first target polynucleotide and/or at least a portion of first tag and/or at least a portion of the second tag, where the first and second tags are part of the first tagged polynucleotide.

Optionally, the determining step includes sequencing at least a portion of the second tagged polynucleotide. Optionally, the determining step includes sequencing at least a portion of the second target polynucleotide and/or at least a portion of third tag and/or at least a portion of the fourth tag, where the third and fourth tags are part of the second tagged polynucleotide.

Optionally, the determining step includes generating a population of candidate sequencing reads that contain at least a portion of the first tagged polynucleotide. Optionally, the determining step includes generating a population of candidate sequencing reads that contain at least a portion of the first target polynucleotide and/or at least a portion of first tag and/or at least a portion of the second tag, where the first and second tags are part of the first tagged polynucleotide.

Optionally, the determining step includes generating a population of candidate sequencing reads that contain at least a portion of the second tagged polynucleotide. Optionally, the determining step includes generating a population of candidate sequencing reads that contain at least a portion of the second target polynucleotide and/or at least a portion of third tag and/or at least a portion of the fourth tag, where the third and fourth tags are part of the second tagged polynucleotide.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a target polynucleotides in a nucleic acid sample, comprising: (a) forming a single reaction mixture containing: (i) a plurality of polynucleotides and (ii) a plurality of tags; and (b) generating within the single reaction mixture a plurality of tagged polynucleotides by appending at least one tag to individual polynucleotides within the plurality of polynucleotides. In some embodiments, the nucleic acid sample includes target polynucleotides and non-target polynucleotides, or lacks non-target polynucleotides. In some embodiments, the plurality of polynucleotides and the plurality of tags are placed in one reaction mixture to perform the tag-appending reaction. In some embodiments, separate reaction vessels can be set up where each reaction vessel contains a plurality of polynucleotides and/or a plurality of tags, and then the separate reaction vessels can be mixed together in any combination to generate one or more combinatorial mixtures, where the combinatorial mixtures are used as the single reaction mixture for conducting the tag-appending reaction.

The tagged polynucleotides can be generated in the single reaction mixture by conducting a one-step tagging reaction or a multiple-step tagging reaction. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a full-length universal sequence. The two-step tagging procedure includes performing a first ligation or primer extension reaction using tags that contain a unique tag sequence or a partial-length universal sequence, and performing a subsequent ligation or primer extension reaction using tags that contain a unique tag sequence or a universal sequence.

In some embodiments, the disclosure relates generally to methods, as well as related systems, compositions, kits, apparatuses and computer-readable media, further comprise the step: (c) generating a population of tagged amplicons by amplifying the plurality of tagged polynucleotides.

In some embodiments, the disclosure relates generally to methods, as well as related systems, compositions, kits, apparatuses and computer-readable media, further comprise the step: (d) determining that the target polynucleotide is present in the nucleic acid sample.

In some embodiments, the determining step includes sequencing at least a portion of one or more polynucleotides and/or at least a portion of the at least one tag that is appended to the polynucleotide.

In some embodiments, the determining step includes generating a population of candidate sequencing reads that contain at least a portion of the polynucleotide and/or at least a portion of the at least one tag that is appended to the polynucleotide.

In some embodiments, the determining step includes manipulating the population of candidate sequencing reads to generate error-corrected sequencing reads, for example by applying one or more thresholds including culling, grouping, counting grouped reads counting family, difference counting, pattern counting and/or non-target pattern thresholds. Optionally, the manipulating includes applying at least one threshold to the candidate sequencing reads. Optionally, the manipulated sequencing reads can be used to determine that a particular polynucleotide is present in the initial nucleic acid sample, and to identify the sequence of the particular polynucleotide. Optionally, the manipulated sequencing reads can be used to detect a variant that may be present in the initial nucleic acid sample, for example by applying a family-level threshold and/or a multi-family threshold.

In some embodiments, the determining step includes culling one or more candidate sequencing reads from the population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate error-corrected sequencing reads.

In some embodiments, the determining step includes grouping a subset of the population of candidate sequencing reads into different families of candidate sequencing reads, where the different families of candidate sequencing reads include a common tag sequence. The grouped sequencing reads can be used to generate an error-corrected family of sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence.

In some embodiments, the determining step includes determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample.

In some embodiments, the determining step includes counting the number of different families (of sequencing grouped sequencing reads) having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the determining step includes removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the determining step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate.

In some embodiments, the determining step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate.

In some embodiments, the determining step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate.

In some embodiments, the determining step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the single reaction mixture contains 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, the plurality of oligonucleotide tags in the single reaction mixture detect the presence of 5-100, or 100-200, or 200-300, or 300-400, or 400-500 or more different target polynucleotides in the nucleic acid sample.

In some embodiments, amplicons that contain a target polynucleotide sequence appended to at least one tag, are about 30-100 bases, or about 100-300 bases, or about 300-600 bases, or about 600-1,000 bases in length.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least one target polynucleotides and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the target and non-target polynucleotides or lacks non-target polynucleotides.

In some embodiments, the abundance level of the target polynucleotide is present in the nucleic acid sample at about 0.0001-1%, or about 0.001-1%, or about 0.01-1%, or about 0.1-1%, or about 0.1-5%, or lower abundance ranges In some embodiments, the nucleic acid sample contains a plurality of target polynucleotides including wild-type forms and its related polymorphic forms which include allelic, variant and/or mutant forms.

In some embodiments, the error-corrected sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the target polynucleotide and are present in the nucleic acid sample.

In some embodiments, the error-corrected family of sequencing reads are used to detect and identify a target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify about 85-95%, or about 95-99%, or about 100%, of the different target polynucleotides (e.g., including genetic variants) that may be present in the initial nucleic acid sample.

In some embodiments, at least two of the tagged polynucleotide molecules in the plurality of tagged polynucleotides are uniquely tagged, that is at least two of the tagged polynucleotide molecules in the plurality of tagged polynucleotides are appended with different tags. The two tagged polynucleotide can include a target polynucleotide having the same or different sequence. In some embodiments, each of the tagged polynucleotide molecules in a plurality of tagged polynucleotides are appended with a tag that differs from a tag that is appended to substantially every other tagged polynucleotide.

In some embodiments, at least two tagged polynucleotides in the plurality of tagged polynucleotides are appended at both ends with a different tag.

In some embodiments, the plurality of polynucleotides that are appended at each end with the at least one tag (e.g., tag adaptor) by enzymatic ligation.

In some embodiments, substantially every polynucleotide is appended at each end to the at least one tag (e.g., tag adaptor) by enzymatic ligation.

In some embodiments, substantially every polynucleotide that is appended with the at least one tag, includes about 10-30%, or about 30-50%, or about 50-70%, or about 70-80%, or about 80-90%, or about 90-95%, or about 95-99% of the individual polynucleotide molecules within the plurality of polynucleotides are appended with at least one tag.

In some embodiments, the enzymatic ligation non-selectively appends at least one tag to the plurality of polynucleotides. For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the plurality of polynucleotides that are appended at each end with the at least one tag by primer extension reaction using at least one tag primer having a target-specific sequence that selectively hybridizes to at least one region of a target polynucleotide within the nucleic acid sample, and the at least one tag primer includes at least one unique tag sequence. Optionally, the tag primer includes a portion that does not selectively hybridize to the target polynucleotide. For example, the 3' region of the tag primer includes a target-specific sequence that selectively hybridizes to a portion of the target polynucleotide, and the 5' region includes a unique tag sequence which does not selectively hybridize to the target polynucleotide.

In some embodiments, the primer extension reaction comprises a polymerase and a plurality of nucleotides.

In some embodiments, a subset of the plurality of polynucleotides are selectively appended at each end to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in a tag adaptor or primer) comprises a randomer tag having at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags in a plurality of tags have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides.

Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the fixed sequences within the randomer tag sequence can serve as a sequence alignment anchor that is used to generate error-corrected sequencing data, including generating a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the tagged amplicons.

Optionally, the determining step includes sequencing one or both strands that correspond to the tagged amplicons.

Optionally, the determining step includes sequencing at least a portion of the polynucleotide and/or at least a portion of the at least one tag that is appended to the polynucleotide.

Optionally, the determining step includes sequencing at least a portion of the polynucleotide and at least a portion of two tags that are appended to the polynucleotide.

Optionally, the determining step includes generating a population of candidate sequencing reads that contain at least a portion of the polynucleotide and/or at least a portion of the at least one tag that are appended to the polynucleotide.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) forming a single reaction mixture containing: (i) a plurality of polynucleotides including at least a first polynucleotide and a second polynucleotide, and (ii) a plurality of tags; and (b) generating within the single reaction mixture a plurality of tagged polynucleotides, including a first tagged polynucleotide by appending a first pair of tags to the first polynucleotide, and generating within the single reaction mixture a second tagged polynucleotide by appending a second pair of tags to the second polynucleotide. In some embodiments, the nucleic acid sample includes target polynucleotides and non-target polynucleotides, or lacks non-target polynucleotides. The tagged polynucleotides can be generated by conducting a one-step tagging reaction or a multiple-step tagging reaction. In some embodiments, individual polynucleotides (e.g., first and second polynucleotides) are appended with a unique tag sequence and a universal tag sequence using a one-step or multiple-step (e.g., two-step) tagging procedure. For example, the one-step tagging procedure includes performing a ligation or primer extension reaction using a pair of tags each containing a unique tag sequence and an optional full-length universal sequence. The two-step tagging procedure includes performing a first ligation or primer extension reaction using a pair of tags each containing a unique tag sequence and an optional partial-length universal sequence, and performing a subsequent ligation or primer extension reaction using a pair of tags each containing a unique tag sequence an optional universal sequence.

In some embodiments, the disclosure relates generally to methods, as well as related systems, compositions, kits, apparatuses and computer-readable media, further comprising the step: (c) generating a population of first tagged amplicons by amplifying the first tagged polynucleotides, and generating a population of second tagged amplicons by amplifying the second tagged polynucleotides.

In some embodiments, the disclosure relates generally to methods, as well as related systems, compositions, kits, apparatuses and computer-readable media, further comprising the step: (d) determining that the first target polynucleotide and/or that the second target polynucleotide is present in the nucleic acid sample.

In some embodiments, the determining step includes sequencing at least a portion of the first tagged polynucleotide and/or at least a portion of one or both of the first pair of tags that are appended to the first polynucleotide.

In some embodiments, the determining step includes sequencing at least a portion of the second tagged polynucleotide and/or at least a portion of one or both of the second pair of tags that are appended to the second polynucleotide.

In some embodiments, the determining step includes generating a population of candidate sequencing reads that contain at least a portion of the first tagged polynucleotide and/or at least a portion of one or both of the tags from the first pair of tags that are appended to the first polynucleotide.

In some embodiments, the determining step includes generating a population of candidate sequencing reads that contain at least a portion of the second tagged polynucleotide and/or at least a portion of one or both of the tags from the second pair of tags that are appended to the second polynucleotide.

In some embodiments, the determining step includes manipulating the population of candidate sequencing reads to generate error-corrected sequencing reads, for example by applying one or more thresholds including culling, grouping, counting grouped reads, counting family, difference counting, pattern counting and/or non-target pattern thresholds. Optionally, the manipulating includes applying at least on threshold to the candidate sequencing reads. Optionally, the manipulated sequencing reads can be used to determine that a particular polynucleotide is present in the initial nucleic acid sample, and to identify the sequence of the particular polynucleotide. Optionally, the manipulated sequencing reads can be used to detect a variant that may be present in the initial nucleic acid sample, for example by applying a family-level threshold and/or a multi-family threshold.

In some embodiments, the determining step includes culling one or more candidate sequencing reads from the population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate an error-corrected family of sequencing reads.

In some embodiments, the determining step includes grouping a subset of the population of candidate sequencing reads into different families of candidate sequencing reads, where the different families of candidate sequencing reads include a common tag sequence. The grouped sequencing reads can be used to generate an error-corrected family of sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence.

In some embodiments, the determining step includes determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample.

In some embodiments, the determining step includes counting the number of different families having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the determining step includes removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the determining step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate.

In some embodiments, the determining step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate.

In some embodiments, the determining step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate.

In some embodiments, the determining step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the single reaction mixture contains 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, the plurality of oligonucleotide tags in the single reaction mixture detect the presence of 5-100, or 100-200, or 200-300, or 300-400, or 400-500 or more different target polynucleotides in the nucleic acid sample.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least a first target polynucleotide and one or more non-target polynucleotides, or the nucleic acid sample lacks any non-target polynucleotides.

In some embodiments, the nucleic acid sample contains at least a second target polynucleotide and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the first target and non-target polynucleotides, or the nucleic acid sample lacks non-target polynucleotides.

In some embodiments, the nucleic acid sample contains about 0.001 ng-100 ug, or about 1-500 ng of polynucleotides, which includes the second target and non-target polynucleotides, or the nucleic acid sample lacks non-target polynucleotides.

In some embodiments, the abundance level of the first target polynucleotide is present in the nucleic acid sample at about 0.0001-1%, or about 0.001-1%, or about 0.01-1%, or about 0.1-5%, or about 0.1-1%, or lower abundance ranges.

In some embodiments, the abundance level of the second target polynucleotide is present in the nucleic acid sample at about 0.0001-1%, or about 0.001-1%, or about 0.01-1%, or about 0.1-1%, or about 0.1-5%, or lower abundance ranges.

In some embodiments, the nucleic acid sample contains a plurality of target polynucleotides (e.g., the first target polynucleotide) including wild-type forms and its related polymorphic forms which include allelic, variant and/or mutant forms.

In some embodiments, the nucleic acid sample contains a plurality of target polynucleotides (e.g., the second target polynucleotide) including wild-type forms and its related polymorphic forms which include allelic, variant and/or mutant forms.

In some embodiments, the error-corrected sequencing reads, or the error-corrected family of sequencing reads, are used to detect and identify the first target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the first target polynucleotide and are present in the nucleic acid sample.

In some embodiments, the error-corrected sequencing reads, or the error-corrected family of sequencing reads, are used to detect and identify the second target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the second target polynucleotide and are present in the nucleic acid sample.

In some embodiments, the error-corrected sequencing reads, or the error-corrected family of sequencing reads, are used to detect and identify the first target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify the second target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify about 85-95%, or about 95-99%, or about 100%, of the different target polynucleotides (e.g., including genetic variants) of the first polynucleotide that may be present in the initial nucleic acid sample.

In some embodiments, the error-corrected sequencing reads, or the error-corrected family of sequencing reads, are used to detect and identify about 85-95%, or about 95-99%, or about 100%, of the different polynucleotides (e.g., including genetic variants) of the second polynucleotide that may be present in the initial nucleic acid sample.

In some embodiments, the first tagged polynucleotides in the plurality of tagged polynucleotides are appended with a first pair of tags, one tag at each end, that differ from substantially every other tagged polynucleotide.

In some embodiments, the second tagged polynucleotides in the plurality of tagged polynucleotides are appended with a second pair of tags, one tag at each end, that differ from substantially every other tagged polynucleotide.

In some embodiments, the first tagged polynucleotides in the plurality of tagged polynucleotides are appended with a different tag at each end.

In some embodiments, the second tagged polynucleotides in the plurality of tagged polynucleotides are appended with a different tag at each end.

In some embodiments, the first tagged polynucleotides in the plurality of tagged polynucleotides are appended with a first pair of tags that differ from each other.

In some embodiments, the second tagged polynucleotides in the plurality of tagged polynucleotides are appended with a second pair of tags that differ from each other.

In some embodiments, the plurality of polynucleotides, that are appended at each end with the at least one tag (e.g., tag adaptor) by enzymatic ligation.

In some embodiments, the first polynucleotides are appended with a first pair of tags (e.g., a first pair of tag adaptors) by enzymatic ligation.

In some embodiments, the second polynucleotides are appended with a second pair of tags (e.g., a second pair of tag adaptors) by enzymatic ligation.

In some embodiments, substantially every polynucleotide in the single reaction mixture is appended at each end to the at least one tag (e.g., tag adaptor) by enzymatic ligation.

In some embodiments, substantially every polynucleotide in the single reaction mixture that is appended with the at least one tag (e.g., the first tagged polynucleotide and the second tagged polynucleotide), includes about 10-30%, or about 30-50%, or about 50-70%, or about 70-80%, or about 80-90%, or about 90-95%, or about 95-99% of the individual polynucleotide molecules within the plurality of polynucleotides are appended with at least one tag.

In some embodiments, the enzymatic ligation non-selectively appends the first pair of tags to the first polynucleotide.

In some embodiments, the enzymatic ligation non-selectively appends the second pair of tags to the second polynucleotide.

For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the first polynucleotide is appended with a first pair of tags, (e.g., one tag at each end) by primer extension reaction, where one or both tags in the first pair of tags includes a target-specific sequence that selectively hybridizes to at least one region of the first target polynucleotide, and where one or both tags in the first pair of tags includes at least one unique tag sequence. Optionally, one or both tags in the first pair of tags includes a portion that does not selectively hybridize to the first target polynucleotide. For example, the 3' region of both tag primers in the first pair of tag primers include a target-specific sequence that selectively hybridizes to different portions of the first target polynucleotide, and optionally, one or both tag primers in the first pair of tag primers includes a 5' region containing a unique tag sequence which does not selectively hybridize to the first target polynucleotide.

In some embodiments, the second polynucleotide is appended with a second pair of tags, (e.g., one tag at each end) by primer extension reaction, where one or both tags in the second pair of tags includes a target-specific sequence that selectively hybridizes to at least one region of the second target polynucleotide, and where one or both tags in the second pair of tags includes at least one unique tag sequence. Optionally, one or both tags in the second pair of tags includes a portion that does not selectively hybridize to the second target polynucleotide. For example, the 3' region of both tag primers in the second pair of tag primers include a target-specific sequence that selectively hybridizes to different portions of the second target polynucleotide, and optionally, one or both tag primers in the second pair of tag primers includes a 5' region containing a unique tag sequence which does not selectively hybridize to the second target polynucleotide.

In some embodiments, the primer extension reaction comprises a polymerase and a plurality of nucleotides.

In some embodiments, a subset of the plurality of polynucleotides are selectively appended at each end to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in the first pair of tag adaptors or primers) comprises a randomer tag having at least one random sequence and at least one fixed sequence, or comprises a random sequence flanked on both sides by a fixed sequence, or comprises a fixed sequence flanked on both sides by a random sequence.

In some embodiments, the at least one tag (e.g., contained in the second pair of tag adaptors or primers) comprises a randomer tag having at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags in a plurality of tags have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3$ $N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the fixed sequences within the randomer tag sequence can serve as a sequence alignment anchor that is used to generate error-corrected sequencing data, including generating a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the first tagged amplicons.

In some embodiments, the determining step includes sequencing at least two of the second tagged amplicons.

Optionally, the determining step includes sequencing one or both strands that correspond to the first tagged amplicons.

Optionally, the determining step includes sequencing one or both strands that correspond to the second tagged amplicons.

Optionally, the determining step includes sequencing at least a portion of the first polynucleotide and/or at least a portion of one or both of the tags of the first pair of tags that is appended to the first polynucleotide.

Optionally, the determining step includes sequencing at least a portion of the second polynucleotide and/or at least a portion of one or both of the tags of the second pair of tags that is appended to the second polynucleotide.

Optionally, the determining step includes generating a population of candidate sequencing reads that contain at least a portion of the first polynucleotide and/or at least a portion of one or both of the tags of the first pair of tags that are appended to the first polynucleotide.

Optionally, the determining step includes generating a population of candidate sequencing reads that contain at least a portion of the second polynucleotide and/or at least a portion of one or both of the tags of the second pair of tags that are appended to the second polynucleotide.

Optionally, the determining step includes counting the number of sequencing reads within the error-corrected family of sequencing reads.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) forming a single reaction mixture containing (i) a plurality of polynucleotides including at least a first polynucleotide and a second polynucleotide, and (ii) a plurality of tags including at least a first, second, third and fourth tag; and (b) generating within the single reaction mixture a first tagged polynucleotide by appending the first tag to one end of the first polynucleotide and appending the second tag to the other end of the first polynucleotide, and generating within the single reaction mixture a second tagged polynucleotide by appending the third tag to one end of the second polynucleotide and appending the fourth tag to the other end of the second polynucleotide. In some embodiments, the nucleic acid sample contains target and non-target polynucleotides, or lacks non-target polynucleotides. The tagged polynucleotides can be generated by conducting a one-step tagging reaction or a multiple-step tagging reaction.

In some embodiments, individual polynucleotides (e.g., the first polynucleotide) are appended with unique tag sequences (e.g., first and second unique tags) and universal tag sequences (e.g., first and second universal tags) using a one-step or multiple-step (e.g., two-step) tagging procedure. In some embodiments, individual polynucleotides (e.g., the second polynucleotide) are appended with unique tag sequences (e.g., third and fourth unique tags) and universal tag sequences (e.g., third and fourth universal tags) using a one-step or multiple-step (e.g., two-step) tagging procedure.

For example, the one-step tagging procedure includes performing a ligation or primer extension reaction with the first polynucleotide using (i) the first tag that contains the first unique tag sequence and the full-length first universal sequence and (ii) the second tag that contains the second unique tag sequence and the full-length second universal sequence.

In the same reaction mixture, the one-step tagging procedure includes performing a ligation or primer extension reaction with the second polynucleotide using (i) the third tag that contains the third unique tag sequence and the full-length third universal sequence and (ii) the fourth tag that contains the fourth unique tag sequence and the full-length fourth universal sequence. The first, second, third and fourth tags contain the same or different universal sequences.

The two-step tagging procedure includes performing a first ligation or primer extension reaction with the first polynucleotide using (i) the first tag that contains the first unique tag sequence and optionally at least a portion of the first universal sequence and (ii) the second tag that contains the second unique tag sequence and optionally at least a portion of the second universal sequence.

In the same reaction mixture, the first ligation or primer extension reaction is performed with the second polynucleotide using (i) the third tag that contains the third unique tag sequence and optionally at least a portion of the third universal sequence and (ii) the fourth tag that contains the fourth unique tag sequence and optionally at least a portion of the fourth universal sequence.

A second ligation or primer extension reaction is performed using the first polynucleotide (which is now tagged) and (iii) a tag that contains at least a portion of the first universal sequence and (iv) a tag that contains at least a portion of the second universal sequence.

A second ligation or primer extension reaction is performed using the second polynucleotide (which is now tagged) and (iii) a tag that contains at least a portion of the third universal sequence and (iv) a tag that contains at least a portion of the fourth universal sequence.

The first, second, third and fourth tags contain the same or different universal sequences.

In some embodiments, the disclosure relates generally to methods, as well as related systems, compositions, kits, apparatuses and computer-readable media, further comprising the step: (c) generating a population of first tagged amplicons by amplifying the first tagged polynucleotides, and generating a population of second tagged amplicons by amplifying the second tagged polynucleotides.

In some embodiments, the disclosure relates generally to methods, as well as related systems, compositions, kits, apparatuses and computer-readable media, further comprising the step: (d) determining that the first target polynucleotide and/or that the second target polynucleotide is present in the nucleic acid sample.

In some embodiments, the determining step includes sequencing at least a portion of the first target polynucleotide and/or at least the portion of the first tag and/or at least a portion of the second tag, where the first and second tags are appended to the first target polynucleotide.

In some embodiments, the determining step includes sequencing at least a portion of the second target polynucleotide and/or at least the portion of the third tag and/or at least a portion of the fourth tag, where the third and fourth tags are appended to the second target polynucleotide.

In some embodiments, the determining step includes generating a first population of candidate sequencing reads that contain at least a portion of the first polynucleotide and/or at least the portion of the first tag and/or at least a portion of the second tag.

In some embodiments, the determining step includes generating a second population of candidate sequencing reads that contain at least a portion of the second polynucleotide and/or at least the portion of the third tag and/or at least a portion of the fourth tag.

In some embodiments, the determining step includes manipulating the first and/or second population of candidate sequencing reads to generate error-corrected sequencing reads, for example by applying one or more thresholds including culling, grouping, counting grouped reads counting family, difference counting, pattern counting and/or non-target pattern thresholds. Optionally, the manipulating includes applying at least one threshold to the candidate sequencing reads. Optionally, the manipulated sequencing reads can be used to determine that a particular polynucleotide is present in the initial nucleic acid sample, and to identify the sequence of the particular polynucleotide. Optionally, the manipulated sequencing reads can be used to detect a variant that may be present in the initial nucleic acid sample, for example by applying a family-level threshold and/or a multi-family threshold.

In some embodiments, the determining step includes culling one or more candidate sequencing reads from the first and/or second population of candidate sequencing reads, based on a tag-specific reference sequence and/or based on a polynucleotide-specific reference sequence. The candidate sequencing reads can be culled by applying a culling threshold. For example, a culling threshold can be used to retain or remove at least one candidate sequencing read, to generate error-corrected sequencing reads. Optionally, the culling threshold can be used to retain or remove the first candidate sequencing read, which corresponds to the first tagged polynucleotide, to generate error-corrected sequencing reads. Optionally, the culling threshold can be used to retain or remove the second candidate sequencing read, which corresponds to the second tagged polynucleotide, to generate error-corrected sequencing reads.

In some embodiments, the determining step includes grouping a subset of the first and/or second population of candidate sequencing reads into different families of candidate sequencing reads, where the different families of candidate sequencing reads include a common tag sequence. The grouped sequencing reads can be used to generate an error-corrected family of sequencing reads. The candidate sequencing reads can be grouped by applying a grouping threshold. For example, the grouping threshold can be based on a reference tag sequence or a reference polynucleotide sequence. The different sequencing reads that are grouped into a given family of sequencing reads share a common tag and/or polynucleotide sequence. Optionally, the candidate sequencing reads can be grouped by applying a grouping threshold to generate a first family of grouped sequencing reads, where the members of the first family of grouped sequencing reads share a common tag and/or polynucleotide sequence. Optionally, the candidate sequencing reads can be grouped by applying a grouping threshold to generate a second family of grouped sequencing reads, where the members of the second family of grouped sequencing reads share a common tag and/or polynucleotide sequence.

In some embodiments, the determining step includes determining the percent of sequencing reads within a grouped family that match (e.g., are similar or identical to) a reference sequence using a counting grouped reads threshold. For example, the counting grouped reads threshold can be based on a particular polynucleotide sequence or a tag sequence. When the percent of sequencing reads within a grouped family that match (e.g., are similar or identical to) the reference sequence meets or exceeds the counting grouped reads threshold, then it may be concluded that the sequencing reads are true positive sequencing reads, and that a polynucleotide having that sequence was present in the initial nucleic acid sample. Optionally, a first family of grouped sequencing reads can be subjected to the counting grouped reads threshold to determine the percent of the first grouped sequencing reads that match (e.g., are similar or identical to) a reference sequence, in order to determine if the first family of grouped sequencing reads contains true positive sequencing reads. Optionally, a second family of grouped sequencing reads can be subjected to the counting grouped reads threshold to determine the percent of the second grouped sequencing reads that match (e.g., are similar or identical to) a reference sequence, in order to determine if the second family of grouped sequencing reads contains true positive sequencing reads.

In some embodiments, the determining step includes counting the number of different families (of sequencing grouped sequencing reads) having the same target polynucleotide sequence and applying the counting family threshold. If the number of counted families exceeds the counting family threshold, then the target polynucleotide sequence is deemed to represent a true positive sequencing read that corresponds to a polynucleotide that is present in the initial nucleic acid sample.

In some embodiments, the determining step includes removing mistagged sequencing reads from a set of candidate sequencing reads or a grouped family of sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the determining step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. The difference counting threshold may be applied prior or subsequent to the grouping threshold. Applying the difference counting threshold to a set of candidate sequencing reads and removing an identified mistagged sequencing read may yield a set of sequencing reads having a reduced error rate. Applying the difference counting threshold to a family of grouped sequencing reads and removing an identified mistagged sequencing read may yield a family of sequencing reads having a reduced error rate.

In some embodiments, the determining step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. The pattern counting threshold may be applied prior or subsequent to the grouping threshold. Applying the pattern counting threshold to a set of candidate sequencing reads and removing an identified mistagged sequencing read may yield a set of sequencing reads having a reduced error rate. Applying the pattern counting threshold to a family of grouped sequencing reads and removing an identified mistagged sequencing read may yield a family of sequencing reads having a reduced error rate.

In some embodiments, the determining step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. The difference counting threshold and the pattern counting threshold may be applied prior or subsequent to the grouping threshold. Applying the difference counting threshold and the pattern counting threshold to a set of candidate sequencing reads and removing an identified mistagged sequencing read may yield a set of sequencing reads having a reduced error rate. Applying the difference counting threshold and the pattern counting threshold to a family of grouped sequencing reads and removing an identified mistagged sequencing read may yield a family of sequencing reads having a reduced error rate.

In some embodiments, the determining step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. The non-target pattern threshold may be applied prior or subsequent to the grouping threshold. Applying the non-target pattern threshold to a set of candidate sequencing reads and removing an identified mistagged sequencing read may yield a set of sequencing reads having a reduced error rate. Applying the non-target pattern threshold to a family of grouped sequencing reads and removing an identified mistagged sequencing read may yield a family of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the appending step is conducted in a single reaction mixture, where the first tag is appended to one end of the first polynucleotide and the second tag is appended to the other end of the first polynucleotide.

In some embodiments, the appending step is conducted in a single reaction mixture, where the third tag is appended to one end of the second polynucleotide and the fourth tag is appended to the other end of the second polynucleotide.

In some embodiments, the single reaction mixture contains 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, the plurality of oligonucleotide tags in the single reaction mixture detect the presence of 5-100, or 100-200, or 200-300, or 300-400, or 400-500 or more different target polynucleotides in the nucleic acid sample.

In some embodiments, amplicons that contain a first target polynucleotide sequence appended to a first and second tag, are about 30-100 bases, or about 100-300 bases, or about 300-600 bases, or about 600-1,000 bases in length. In some embodiments, amplicons that contain a second target polynucleotide sequence appended to a third and fourth tag, are about 30-100 bases, or about 100-300 bases, or about 300-600 bases, or about 600-1,000 bases in length.

In some embodiments, the nucleic acid sample is obtained from any type of biological fluid or solid biological sample, or any organism, or from water, soil or food. In some embodiments, a biological sample includes a biological fluid or solid tissue obtained by biopsy, swab, needle biopsy (e.g., fine needle biopsy or fine needle aspirate), smear, or even air borne nucleic acids.

In some embodiments, the nucleic acid sample includes DNA, RNA, a mixture of RNA and DNA, cfDNA, DNA from circulating tumor cells, or cfRNA.

In some embodiments, the nucleic acid sample contains at least one target polynucleotides and one or more non-target polynucleotides, or the nucleic acid sample lacks any non-target polynucleotides.

In some embodiments, the nucleic acid sample contains about 0.001 ng-100 ug, or about 1-500 ng of polynucleotides, which includes the target and non-target polynucleotides, or the nucleic acid sample lacks non-target polynucleotides.

In some embodiments, the abundance level of the target polynucleotide is present in the nucleic acid sample at about 0.0001-1%, or about 0.001-1%, or about 0.01-1%, or about 0.1-1%, or about 0.1-5%, or lower abundance ranges.

In some embodiments, the nucleic acid sample contains a plurality of first target polynucleotides including wild-type forms and its related polymorphic forms which include allelic, variant and/or mutant forms.

In some embodiments, the nucleic acid sample contains a plurality of second target polynucleotides including wild-type forms and its related polymorphic forms which include allelic, variant and/or mutant forms.

In some embodiments, the error-corrected sequencing reads, or the error-corrected family of sequencing reads, are used to detect and identify the first target polynucleotide that is present in the nucleic acid sample at an abundance level of about 0.0001-1%, or about 0.001-1%, or about 0.01-1%, or about 0.1-1%, or lower abundance ranges, relative to a population of polymorphic polynucleotides that are related to the first target polynucleotide and are present in the nucleic acid sample.

In some embodiments, the error-corrected sequencing reads, or the error-corrected family of sequencing reads, are used to detect and identify the second target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to a population of polymorphic polynucleotides that are related to the second target polynucleotide and are present in the nucleic acid sample.

In some embodiments, the error-corrected sequencing reads, or the error-corrected family of sequencing reads, are used to detect and identify the first target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads, or the error-corrected family of sequencing reads, are used to detect and identify the second target polynucleotide that is present in the nucleic acid sample at an abundance level of about 0.0001-1%, or about 0.001-1%, or about 0.01-1%, or about 0.1-1%, or about 0.1-5%, or lower abundance ranges, relative to the total population of polynucleotides in the nucleic acid sample.

In some embodiments, the error-corrected sequencing reads are used to detect and identify about 85-95%, or about 95-99%, or about 100%, of the different target polynucleotides (e.g., including genetic variants) of the first polynucleotide that may be present in the initial nucleic acid sample.

In some embodiments, the error-corrected sequencing reads are used to detect and identify about 85-95%, or about 95-99%, or about 100%, of the different target polynucleotides (e.g., including genetic variants) of the second polynucleotide that may be present in the initial nucleic acid sample.

In some embodiments, the first tagged polynucleotide in the plurality of tagged polynucleotides is appended with the first and second tags that differ from other tags that are appended to substantially every other tagged polynucleotide.

In some embodiments, the second tagged polynucleotide in the plurality of tagged polynucleotides is appended with the third and fourth tags that differ from other tags that are appended to substantially every other tagged polynucleotide.

In some embodiments, the first tagged polynucleotide in the plurality of tagged polynucleotides is appended with a different tag at each end (e.g., first and second tags).

In some embodiments, the second tagged polynucleotide in the plurality of tagged polynucleotides is appended with a different tag at each end (e.g., third and fourth tags).

In some embodiments, the first tagged polynucleotide in the plurality of tagged polynucleotides is appended with a first tag and a second tag that differ from each other.

In some embodiments, the second tagged polynucleotide in the plurality of tagged polynucleotides is appended with a third and fourth tag that differ from each other.

In some embodiments, the plurality of polynucleotides are appended at each end with the at least one tag (e.g., tag adaptor) by enzymatic ligation.

In some embodiments, the first polynucleotide is appended with the first and second tags (e.g., first and second tag adaptors) by enzymatic ligation.

In some embodiments, the second polynucleotide is appended with the third and fourth tags (e.g., third and fourth tag adaptors) by enzymatic ligation.

In some embodiments, substantially every polynucleotide, including the first and second polynucleotides, are appended at each end to the at least one tag (e.g., tag adaptor) by enzymatic ligation.

In some embodiments, substantially every polynucleotide (including the first and second polynucleotides) that is appended at each end with the at least one tag, includes about 10-30%, or about 30-50%, or about 50-70%, or about 70-80%, or about 80-90%, or about 90-95%, or about 95-99% of the individual polynucleotide molecules within the plurality of polynucleotides are appended at each end with at least one tag.

In some embodiments, the enzymatic ligation non-selectively appends the first and second tags to the first polynucleotide.

In some embodiments, the enzymatic ligation non-selectively appends the third and fourth tags to the second polynucleotide.

For example, a blunt-ended ligation reaction can be used to append at least one tag to individual polynucleotides from a plurality of polynucleotides. In another example, tags having a 5' or 3' overhang end can be appended to individual polynucleotides from a plurality of polynucleotides using enzymatic ligation.

In some embodiments, the appending step includes enzymatically ligating at least one adaptor (e.g., tag adaptor) to the at least one end of individual polynucleotides to produce a plurality of tagged polynucleotides. Optionally, the molecular tagging procedure includes conducting multiple separate ligation reactions (e.g., about 1-6) to append at least one adaptor (e.g., tag adaptor) to the at least one end of individual polynucleotides. Optionally, the at least one adaptor (e.g., tag adaptor) can be appended to one or both ends of individual polynucleotides in the first, second, third, or subsequent round of enzymatic ligation reactions.

In some embodiments, the first target polynucleotide is appended with the first and second tag primers by primer extension reaction using a first and second tag primer, where the first and second tag primers include a target-specific sequence that selectively hybridizes to at least one region of a first target polynucleotide within the nucleic acid sample, and the first tag primer includes at least a first unique tag sequence and the second tag primer includes at least a second unique tag sequence. The first and second tag primers can hybridize to a different region of the first target polynucleotide. Optionally, the first tag primer includes a portion that does not selectively hybridize to the first target polynucleotide. Optionally, the second tag primer includes a portion that does not selectively hybridize to the first target polynucleotide. For example, the 3' region of the first and second tag primers include a target-specific sequence that selectively hybridizes to different portions of the first target polynucleotide, and the first and/or second tag primers includes a 5' region containing a unique tag sequence which does not selectively hybridize to the first target polynucleotide.

In some embodiments, the second target polynucleotide is appended with the third and fourth tag primers by primer extension reaction using a third and fourth tag primer, where the third and fourth tag primers include a target-specific sequence that selectively hybridizes to at least one region of a second target polynucleotide within the nucleic acid sample, and the third tag primer includes at least a third unique tag sequence and the fourth tag primer includes at least a fourth unique tag sequence. The third and fourth tag primers can hybridize to a different region of the second target polynucleotide. Optionally, the first tag primer includes a portion that does not selectively hybridize to the second target polynucleotide. Optionally, the second tag primer includes a portion that does not selectively hybridize to the second target polynucleotide. For example, the 3' region of the third and fourth tag primers include a target-specific sequence that selectively hybridizes to different portions of the second target polynucleotide, and the third and/or fourth tag primers includes a 5' region containing a unique tag sequence which does not selectively hybridize to the second target polynucleotide.

In some embodiments, the primer extension reaction comprises a polymerase and a plurality of nucleotides.

In some embodiments, a subset of the plurality of polynucleotides, where the subset includes the first target polynucleotide, are selectively appended at each end to at least one tag by primer extension.

In some embodiments, a subset of the plurality of polynucleotides, where the subset includes the second target polynucleotide, are selectively appended at each end to at least one tag by primer extension.

In some embodiments, the appending step includes conducting a primer extension reaction with primers (e.g., tag primers) to produce a plurality of tagged polynucleotides having at least one end appended with a tag sequence. Optionally, the molecular tagging procedure includes conducting multiple separate rounds of primer extension reactions to append at least one tag sequence to the at least one end of individual polynucleotides. For example, 2-4 rounds of primer extension (e.g., PCR) are conducted with a repertoire of tag primers to generate a plurality of tagged polynucleotides, where individual tagged polynucleotides have each end appended with a unique tag sequence, and optionally one or both ends of the individual tagged polynucleotides can also include the same or different universal sequences. Additional rounds of primer extension (e.g., PCR) can be conducted with tailed primers to append additional unique tag sequences, barcodes sequences and/or universal sequences. The tailed primers used in the additional rounds of primer extension can include a sequence in their 3' region that hybridizes with a tag sequence from the previous primer extension reaction. About 2-40 additional rounds of primer extension reactions can be conducted. Optionally, one or more rounds of primer extension reactions can be conducted to append at least one barcode or universal sequence to the polynucleotides, followed by one or more rounds of primer extension reactions can be conducted to append at least one unique tag sequence to the polynucleotides.

In some embodiments, unique tag sequences can be appended to the polynucleotides using a combination of enzymatic ligation using tag adaptors and/or primer extension (e.g., PCR) using tag primers.

In some embodiments, the at least one tag (e.g., contained in a tag adaptor or contained in a first, second, third and fourth tag primer) comprises a randomer tag, where the random tag includes at least one random sequence and at least one fixed sequence, or comprises a random sequence flanked on both sides by a fixed sequence, or comprises a fixed sequence flanked on both sides by a random sequence. The randomer tag can include a fixed sequence that is 2-2000 nucleotides or base-pairs in length. The randomer tag can include a random sequence that is 2-2000 nucleotides or base-pairs in length.

In some embodiments, the tags include a sequence having at least one random sequence interspersed with fixed sequences. In some embodiments, individual tags, including the first, second, third and fourth tags, in a plurality of tags, have the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3$ $N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the randomer tag comprises the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the fixed sequences within the randomer tag sequence can serve as a sequence alignment anchor that is used to generate error-corrected sequencing data, including generating a family of error-corrected sequencing reads.

In some embodiments, the randomer tag sequence is not used to correct any sequencing read, but instead, the candidate sequencing read that contains an error (e.g., an error in the randomer tag sequence) is discarded.

In some embodiments, the amplifying comprises isothermal or thermo-cycling amplification, or a combination of isothermal and thermo-cycling amplification. Optionally, the amplifying includes a recombinase (e.g., T4 uvsX), with or without recombinase accessory factors (e.g., T4 uvsY and/or gp32 protein).

In some embodiments, the determining step includes sequencing at least two of the tagged amplicons, including the first and second tagged amplicons.

Optionally, the determining step includes sequencing one or both strands that correspond to the tagged amplicons. Optionally, the determining step includes sequencing one or both strands of the first and second tagged amplicons.

Optionally, the determining step includes sequencing at least a portion of the first tagged polynucleotide. Optionally, the determining step includes sequencing at least a portion of the first target polynucleotide and/or at least a portion of first tag and/or at least a portion of the second tag, where the first and second tags are part of the first tagged polynucleotide.

Optionally, the determining step includes sequencing at least a portion of the second tagged polynucleotide. Optionally, the determining step includes sequencing at least a portion of the second target polynucleotide and/or at least a portion of third tag and/or at least a portion of the fourth tag, where the third and fourth tags are part of the second tagged polynucleotide.

Optionally, the determining step includes generating a population of candidate sequencing reads that contain at least a portion of the first tagged polynucleotide. Optionally, the determining step includes generating a population of candidate sequencing reads that contain at least a portion of the first target polynucleotide and/or at least a portion of first tag and/or at least a portion of the second tag, where the first and second tags are part of the first tagged polynucleotide.

Optionally, the determining step includes generating a population of candidate sequencing reads that contain at least a portion of the second tagged polynucleotide. Optionally, the determining step includes generating a population of candidate sequencing reads that contain at least a portion of the second target polynucleotide and/or at least a portion of third tag and/or at least a portion of the fourth tag, where the third and fourth tags are part of the second tagged polynucleotide.

Optionally, the determining step includes counting the number of sequencing reads within the error-corrected sequencing reads. If the number of sequencing reads within the error-corrected sequencing reads does not exceed a threshold, then the error-corrected sequencing reads will not be included in further data analysis.

Optionally, the determining step includes calculating a percentage of the number of sequencing reads within the error-corrected sequencing reads relative to the number of candidate sequencing reads prior to the culling step.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) providing a nucleic acid sample containing a plurality of polynucleotides which includes target and non-target polynucleotides, or lacks non-target polynucleotides; (b) generating a plurality of tagged polynucleotides (e.g., parent tagged polynucleotides) by appending at least one unique tag to individual polynucleotide molecules from the plurality of polynucleotides, wherein the appending is conducted within a single reaction mixture; (c) generating tagged amplicons by amplifying the plurality of tagged polynucleotides, where the tagged amplicons are progeny molecules that arose from the parent tagged polynucleotides; (d) determining the sequence of at least some of the tagged amplicons to generate a population of candidate sequencing reads; (e) culling at least some of the candidate sequencing reads by removing one or more candidate sequencing reads from the population of candidate sequencing reads, based on a tag-specific reference sequence and/or based on a polynucleotide-specific reference sequence, to generate an error-corrected family of sequencing reads; (f) grouping a subset of the error-corrected family of sequencing reads into different families of candidate sequencing reads, where each of the different families of candidate sequencing reads include a common tag sequence that is unique to a given family of candidate sequencing reads; and (g) determining that a given polynucleotide is present in the nucleic acid sample, by using the error-corrected family of sequencing reads. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a universal sequence. The two-step tagging procedure includes performing a first ligation or primer extension reaction using tags that contain a unique tag sequence or a universal sequence, and performing a subsequent ligation or primer extension reaction using tags that contain a unique tag sequence or a universal sequence. In some embodiments, the unique tag includes a randomer sequence (e.g., a randomer tag) comprising at least one random sequence and at least one fixed sequence, or comprises a random sequence flanked on both sides by a fixed sequence, or comprises a fixed sequence flanked on both sides by a random sequence. The random sequence within a randomer tag is represented by "N", and the fixed sequence is represented by "X". The randomer tag can include a fixed sequence that is 2-2000 nucleotides or base-pairs in length. The randomer tag can include a random sequence that is 2-2000 nucleotides or base-pairs in length. Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the randomer tag comprises the sequence 5'-NNNACTNNNTGA-3' (SEQ ID NO:1), where "N" represents a position within the random sequence that is generated randomly from A, G, C or T. In some embodiments, the fixed sequences within the randomer tag sequence can serve as a sequence alignment anchor that is used to generate error-corrected sequencing data, including generating a family of error-corrected sequencing reads. In some embodiments, the randomer tag sequence is not used to correct any sequencing read, but instead, the candidate sequencing read that contains an error (e.g., an error in the randomer tag sequence) is discarded.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) providing a nucleic acid sample containing a plurality of polynucleotides which includes target and non-target polynucleotides, or lacks non-target polynucleotides; (b) generating a plurality of tagged polynucleotides (e.g., parent tagged polynucleotides) by appending at least one unique tag to individual polynucleotide molecules from the plurality of polynucleotides, wherein the appending is conducted within a single reaction mixture; (c) generating tagged amplicons by amplifying the plurality of tagged polynucleotides, where the tagged amplicons are progeny molecules that arose from the parent tagged polynucleotides; (d) determining the sequence of at least some of the tagged amplicons to generate a population of candidate sequencing reads; (e) culling at least some of the candidate sequencing reads by removing one or more candidate sequencing reads from the population of candidate sequencing reads, based on a tag-specific reference sequence and/or based on a polynucleotide-specific reference sequence, to generate an error-corrected family of sequencing reads; (f) grouping a subset of the error-corrected family of sequencing reads into different families of candidate sequencing reads, where each of the different families of candidate sequencing reads include a common tag sequence that is unique to a given family of candidate sequencing reads; and (g) determining that a given polynucleotide is present in the nucleic acid sample, by using the error-corrected family of sequencing reads. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a universal sequence. The two-step tagging procedure includes performing a first ligation or primer extension reaction using tags that contain a unique tag sequence or a universal sequence, and performing a subsequent ligation or primer extension reaction using tags that contain a unique tag sequence or a universal sequence. In some embodiments, the unique tag includes a randomer sequence (e.g., a randomer tag) comprising at least one random sequence and at least one fixed sequence, or comprises a random sequence flanked on both sides by a fixed sequence, or comprises a fixed sequence flanked on both sides by a random sequence. The random sequence within a randomer tag is represented by "N", and the fixed sequence is represented by "X". The randomer tag can include a fixed sequence that is 2-2000 nucleotides or base-pairs in length. The randomer tag can include a random sequence that is 2-2000 nucleotides or base-pairs in length. Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the randomer tag comprises the sequence 5'-NNNACTNNNTGA-3' (SEQ ID NO:1), where "N" represents a position within the random sequence that is generated randomly from A, G, C or T. In some embodiments, the fixed sequences within the randomer tag sequence can serve as a sequence alignment anchor that is used to generate error-corrected sequencing data, including generating a family of error-corrected sequencing reads. In some embodiments, the randomer tag sequence is not used to correct any sequencing read, but instead, the candidate sequencing read that contains an error (e.g., an error in the randomer tag sequence) is discarded. In some embodiments, the culling step includes removing mistagged sequencing reads from a set of candidate sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the culling step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. Applying the difference counting threshold to a set of candidate sequencing reads and removing an identified mistagged sequencing read may yield a set of sequencing reads having a reduced error rate.

In some embodiments, the culling step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. Applying the pattern counting threshold to a set of candidate sequencing reads and removing an identified mistagged sequencing read may yield a set of sequencing reads having a reduced error rate.

In some embodiments, the culling step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. Applying the difference counting threshold and the pattern counting threshold to a set of candidate sequencing reads and removing an identified mistagged sequencing read may yield a set of sequencing reads having a reduced error rate.

In some embodiments, the culling step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. Applying the non-target pattern threshold to a set of candidate sequencing reads and removing an identified mistagged sequencing read may yield a set of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) providing a nucleic acid sample containing a plurality of polynucleotides which includes target and non-target polynucleotides, or lacks non-target polynucleotides; (b) generating a plurality of tagged polynucleotides (e.g., parent tagged polynucleotides) by appending at least one unique tag to individual polynucleotide molecules from the plurality of polynucleotides, wherein the appending is conducted within a single reaction mixture; (c) generating tagged amplicons by amplifying the plurality of tagged polynucleotides, where the tagged amplicons are progeny molecules that arose from the parent tagged polynucleotides; (d) determining the sequence of at least some of the tagged amplicons to generate a population of candidate sequencing reads; (e) grouping a subset of the population of candidate sequencing reads into different families of candidate sequencing reads, where each of the different families of candidate sequencing reads include a common tag sequence that is unique to a given family of candidate sequencing reads; (f) culling at least one of the family of candidate sequencing reads by removing one or more candidate sequencing reads from family of candidate sequencing reads, based on a tag-specific reference sequence and/or based on a polynucleotide-specific reference sequence, to generate an error-corrected family of sequencing reads; and (g) determining that a polynucleotide is present in the nucleic acid sample, by using the error-corrected family of sequencing reads. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a universal sequence. The two-step tagging procedure includes performing a first ligation or primer extension reaction using tags that contain a unique tag sequence or a universal sequence, and performing a subsequent ligation or primer extension reaction using tags that contain a unique tag sequence or a universal sequence. In some embodiments, the unique tag includes a randomer sequence (e.g., a randomer tag) comprising at least one random sequence and at least one fixed sequence, or comprises a random sequence flanked on both sides by a fixed sequence, or comprises a fixed sequence flanked on both sides by a random sequence. The random sequence within a randomer tag is represented by "N", and the fixed sequence is represented by "X". The randomer tag can include a fixed sequence that is 2-2000 nucleotides or base-pairs in length. The randomer tag can include a random sequence that is 2-2000 nucleotides or base-pairs in length. Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the randomer tag comprises the sequence 5'-NNNACTNNNTGA-3' (SEQ ID NO:1), where "N" represents a position within the random sequence that is generated randomly from A, G, C or T. In some embodiments, the fixed sequences within the randomer tag sequence can serve as a sequence alignment anchor that is used to generate error-corrected sequencing data, including generating a family of error-corrected sequencing reads. In some embodiments, the randomer tag sequence is not used to correct any sequencing read, but instead, the candidate sequencing read that contains an error (e.g., an error in the randomer tag sequence) is discarded.

In some embodiments, the disclosure relates generally to methods, as well as related systems, compositions, kits, apparatuses and computer-readable media, for detecting a first target polynucleotide and a second target polynucleotide in a nucleic acid sample, comprising: (a) providing a nucleic acid sample containing a plurality of polynucleotides which includes target and non-target polynucleotides, or lacks non-target polynucleotides; (b) generating a plurality of tagged polynucleotides (e.g., parent tagged polynucleotides) by appending at least one unique tag to individual polynucleotide molecules from the plurality of polynucleotides, wherein the appending is conducted within a single reaction mixture; (c) generating tagged amplicons by amplifying the plurality of tagged polynucleotides, where the tagged amplicons are progeny molecules that arose from the parent tagged polynucleotides; (d) determining the sequence of at least some of the tagged amplicons to generate a population of candidate sequencing reads; (e) grouping a subset of the population of candidate sequencing reads into different families of candidate sequencing reads, where each of the different families of candidate sequencing reads include a common tag sequence that is unique to a given family of candidate sequencing reads; (f) culling at least one of the family of candidate sequencing reads by removing one or more candidate sequencing reads from family of candidate sequencing reads, based on a tag-specific reference sequence and/or based on a polynucleotide-specific reference sequence, to generate an error-corrected family of sequencing reads; and (g) determining that a polynucleotide is present in the nucleic acid sample, by using the error-corrected family of sequencing reads. In some embodiments, individual polynucleotides are appended with a unique tag sequence and a universal tag sequence using a one-step or multiple-step (e.g., two-step) tagging procedure. For example, the one-step tagging procedure includes performing a ligation or primer extension reaction using tags that contain a unique tag sequence and a universal sequence. The two-step tagging procedure includes performing a first ligation or primer extension reaction using tags that contain a unique tag sequence or a universal sequence, and performing a subsequent ligation or primer extension reaction using tags that contain a unique tag sequence or a universal sequence. In some embodiments, the unique tag includes a randomer sequence (e.g., a randomer tag) comprising at least one random sequence and at least one fixed sequence, or comprises a random sequence flanked on both sides by a fixed sequence, or comprises a fixed sequence flanked on both sides by a random sequence. The random sequence within a randomer tag is represented by "N", and the fixed sequence is represented by "X". The randomer tag can include a fixed sequence that is 2-2000 nucleotides or base-pairs in length. The randomer tag can include a random sequence that is 2-2000 nucleotides or base-pairs in length. Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the randomer tag comprises the sequence 5'-NNNACTNNNTGA-3' (SEQ ID NO:1), where "N" represents a position within the random sequence that is generated randomly from A, G, C or T. In some embodiments, the fixed sequences within the randomer tag sequence can serve as a sequence alignment anchor that is used to generate error-corrected sequencing data, including generating a family of error-corrected sequencing reads. In some embodiments, the randomer tag sequence is not used to correct any sequencing read, but instead, the candidate sequencing read that contains an error (e.g., an error in the randomer tag sequence) is discarded. In some embodiments, the culling step includes removing mistagged sequencing reads from a grouped family of candidate sequencing reads. In some instances, a given family of sequencing reads may include mistagged sequencing reads that include a common tag sequence but correspond to a different region of a target polynucleotide or a non-target polynucleotide due to a tag-appending error, including an error arising from tag adaptor ligation or tag primer extension, or other error. A mistagged sequencing read would include one or more base positions where nucleotides differ from a reference polynucleotide sequence or correctly tagged sequencing reads.

In some embodiments, the culling step includes identifying a mistagged sequencing read by comparing the sequencing reads to a reference sequence for the target polynucleotide and applying a difference counting threshold. For example, determining a number of nucleotides that differ between the sequencing read and the reference polynucleotide and comparing the number to the difference counting threshold can identify a mistagged sequencing read. The mistagged sequencing read may be retained or removed. Applying the difference counting threshold to a family of grouped sequencing reads and removing an identified mistagged sequencing read may yield a family of sequencing reads having a reduced error rate.

In some embodiments, the culling step includes identifying mistagged sequencing reads having a common pattern of variants by comparing a sequencing read to other sequencing reads and applying a pattern counting threshold. For example, determining a number of sequencing reads having a common pattern of variants in their polynucleotide sequences and comparing the number to a pattern counting threshold can identify a group of mistagged sequencing reads. The mistagged sequencing reads may be retained or removed. Applying the pattern counting threshold to a family of grouped sequencing reads and removing an identified mistagged sequencing read may yield a family of sequencing reads having a reduced error rate.

In some embodiments, the culling step includes identifying candidate mistagged sequencing reads by comparing the sequencing reads to a reference sequence for the target polynucleotide and applying a difference counting threshold. Comparing a candidate mistagged sequencing read to one or more other identified candidate mistagged sequencing reads and applying a pattern counting threshold can detect a common pattern of variants that may be present in the candidate mistagged sequences. For example, determining a number of candidate mistagged sequencing reads having a particular pattern of variants in their polynucleotide sequences and comparing the number to a pattern counting threshold can identify a group of mistagged sequencing reads. The mistagged sequencing reads may be retained or removed. Applying the difference counting threshold and the pattern counting threshold to a family of grouped sequencing reads and removing an identified mistagged sequencing read may yield a family of sequencing reads having a reduced error rate.

In some embodiments, the culling step includes identifying mistagged sequencing reads by comparing a pattern of differences in a candidate mistagged sequencing read to a pattern of expected differences between a reference sequence for the target polynucleotide and an expected sequence for a non-target polynucleotide or a different region of the target polynucleotide. For example, a pattern of expected differences between a reference sequence for the target polynucleotide and an expected sequence for a non-target polynucleotide can be predetermined and stored in a lookup table. Optionally, comparing the sequencing reads to the reference sequence and applying a difference counting threshold can identify a candidate mistagged sequencing read. Comparing a pattern of differences in the candidate mistagged sequencing read to a pattern of expected differences and applying a non-target pattern threshold can identify a mistagged sequencing read. The mistagged sequencing reads may be retained or removed. Applying the non-target pattern threshold to a family of grouped sequencing reads and removing an identified mistagged sequencing read may yield a family of sequencing reads having a reduced error rate.

In some embodiments, the determining step includes identifying a family-based candidate variant. The error-corrected families of sequencing reads can be used to detect and identify variants that may be present in the initial nucleic acid sample. For example, for a given error-corrected family, aligning the sequencing reads to a reference sequence for the target polynucleotide, determining a base position where one or more aligned sequencing reads and the reference sequence have different bases, counting the number of aligned sequences having a particular base difference in the base position and applying a family level threshold can identify a family-based candidate variant. When the number of base differences is below the family level threshold, no family-based candidate variant is identified. In some instances, applying the family level threshold may identify one or more candidate variants.

In some embodiments, the determining step includes identifying a genetic variant. Candidate variants from multiple error-corrected families can be used to identify a variant that may be present in the initial nucleic acid sample. For example, applying a counting family threshold can identify the number of different error-corrected families having the same target polynucleotide sequence. In some instances, different error-corrected families for a given target polynucleotide sequence may identify a particular candidate variant. Counting the number of error-corrected families supporting the particular candidate variant and applying a multi-family threshold can identify the candidate variant as a variant that was present in the initial nucleic acid sample.

In some embodiments, the molecular tagging methods described in the present teachings can be used to detect copy number variation, including aneuploidy, such as monosomy, trisomy or higher orders of aneuploidy. Take for example, parents having the genotype BC and BB, and their progeny who carries a duplication genotype BBC. In some embodiments, polynucleotide samples can be obtained from both parents and their progeny (e.g., cfDNA or DNA from blood or a tissue sample), and each of the three samples is separately subjected to the molecular tagging methods described in the present teachings, using a repertoire of unique tags and a sample-specific barcode tag that identifies/distinguishes polynucleotides obtained from either parent or the progeny. The three separately tagged samples can be pooled together and sequenced to generate sequencing data (e.g., sequencing reads). For example the tagged sample can be sequenced using a massively parallel sequencing method or one that employs gel electrophoresis or microarray. The sequencing reads can be manipulated by applying culling, sorting, grouping, counting grouped reads, counting family of reads, and other manipulation steps, to yield error-corrected sequencing data. For the heterozygous parent BC, the number of unique tag sequences that are associated with the target sequence allele-B and with the target sequence allele-C can be counted and compared. The expected ratio of B to C alleles is approximately 1:1 for the BC parent, since half of the total allele counts come from allele-B and half from allele-C. In a similar analysis for the BB parent, the number of unique tag sequences that are associates with the allele-B can be counted and compared. Since the BB parent is homozygous, the expected ratio of B to C alleles is 2:0, since all of the allele counts come from allele-B. For the aneuploid progeny, the number of unique tag sequences that are associated with the allele-B and allele-C can be counted and compared. The expected ratio of B to C alleles is 2:1, since the one of the allele-B and the allele-C contribute to the allele count and the extra allele-B also contributes to the allele count.

In some embodiments, the disclosure relates generally to methods, as well as related systems, compositions, kits, apparatuses and computer-readable media for attaching a unique identifying tag, including any of the randomer tags described herein, to any type of macromolecule. The tagged macromolecules may be useful for distinguishing the different tagged macromolecules from each other, and to permit tracking individual tagged macromolecules in a workflow or in a mixture of macromolecules. For example, the macromolecule to be tagged include sugars, carbohydrates, lipids, phospholipids, oligonucleotides, polynucleotides, peptides, polypeptides, peptides, and hormones. The macromolecules also includes drug candidates, prodrugs, drugs, pharmaceutical candidates, and drug metabolites. The macromolecules include antibodies, antigens, cell-signaling molecules, serum proteins, glycoproteins, cholesterol, glycolipids, polysaccharides, lectins, growth factors, cytokines, steroids, and vitamins. The randomer tags include various forms, such as single-stranded oligonucleotide primers and double-stranded adaptors. The randomer tags contain at least one random sequence interspersed with fixed sequences, including a random sequence flanked on both sides by a fixed sequence, or a fixed sequence flanked on both sides by a random sequence. The randomer tags can be attached to a macromolecule using procedures well known to the skilled artisan, which include using chemical modification of the sugar to generate oligonucleotides carrying one or more modified 2' sugars such as 2'-fluoro, 2'-O-methyl, 2'-methoxyethyl substituents and bicyclic sugars locked nucleic acids (LNA) for making oligonucleotide-peptide conjugates. Other methods for generating oligonucleotide-peptide conjugates include using peptide nucleic acids (PNA) or introducing (2-aminoethyl)-glycine peptide backbone and replacing the corresponding ribose or deoxyribose rings. Many methods are well known for conjugating oligonucleotides to macromolecules (U.S. Pat. No. 6,444,806; U.S. published application Nos. 2010/0167290 and 2004/0038331; Winkler 2013 Therapeutic Delivery 4(7):791-809, and Juliano, Ming and Nakagawa 2012 Accounts of Chemical Research 45(7):1067-1076).

In some embodiments, the disclosure relates generally to methods, as well as related systems, compositions, kits, apparatuses and computer-readable media, for performing an enrichment procedure to enrich for the target polynucleotides. In some embodiments, the enrichment procedure can be conducted prior to or after the tag-appending procedure.

For example, enrichment can include a solid phase capture procedure to enrich for the target polynucleotides. In some embodiments, the target polynucleotides can be selectively captured by hybridizing a nucleic acid sample (e.g., which contains at least one target polynucleotide) with a capture primer that is attached to a support (e.g., planar support or beads). The polynucleotides in the nucleic acid sample can include at least one universal sequence appended to one or both ends, or the nucleic acids lack a universal sequence. The support can include immobilized capture primers having the same sequence or different primer sequences. The capture primers, which are attached to the support, can be contacted with the nucleic acid sample under conditions suitable to selectively hybridize to a portion of the target polynucleotides or to a portion of the universal sequence. The non-hybridized polynucleotides can optionally be removed by washing or by enzymatic degradation, and the target polynucleotide remain hybridized to the capture primers. The captured polynucleotides can optionally be eluted from the support. The eluted polynucleotides can be subjected to any one of the molecular tagging procedures described in the present teachings to generate tagged polynucleotides.

In another example, enrichment can include an in-solution capture procedure to enrich for the target polynucleotides. In some embodiments, the target polynucleotides can be selectively captured by hybridizing a nucleic acid sample (e.g., which contains at least one target polynucleotide) with a soluble capture primer. Optionally, the soluble capture primer is attached to an affinity moiety (e.g., biotin). The polynucleotides in the nucleic acid sample can include at least one universal sequence appended to one or both ends, or the nucleic acids lack a universal sequence. The soluble capture primers can include the same sequence or different sequences. The soluble capture primers can be contacted with the nucleic acid sample under conditions suitable to selectively hybridize to a portion of the target polynucleotides or to a portion of the universal sequence. The non-hybridized polynucleotides can optionally be removed by washing or by enzymatic degradation, and the target polynucleotide remains hybridized to the soluble capture primers. The captured polynucleotides can optionally be eluted from the soluble capture primers. The eluted polynucleotides can be subjected to any one of the molecular tagging procedures described in the present teachings to generate tagged polynucleotides. Optionally, the captured polynucleotides can be removed from the non-capture polynucleotides by contacting the affinity moiety (e.g., biotin) which attached to the soluble capture primer, with its cognate affinity receptor (e.g., an avidin-like molecule) to form a soluble capture primer/affinity complex. The soluble capture primer/affinity complex can be washed to remove the non-captured polynucleotides. If the cognate affinity receptor is attached to a paramagnetic bead, then the soluble capture primer/affinity complex can be removed from the non-captured polynucleotides using a magnetic source to attract the paramagnetic beads.

In some embodiments, the disclosure relates generally to methods, as well as related systems, compositions, kits, apparatuses and computer-readable media, for appending a polynucleotide with at least one tag. At least one tag can be appended to a polynucleotide to generate a tagged polynucleotide. The tagged polynucleotide contains a polynucleotide covalently or non-covalently joined, or associated, to at least one tag. The polynucleotide can be appended to at least one tag via covalent, ionic, hydrogen, dipole-dipole, hydrophilic, hydrophobic, affinity bonding, or bonds or associations involving van der Waals forces.

In some embodiments, at least one primer containing one or more tag sequences can be appended to a polynucleotide by hybridization to the polynucleotide. For example, the primer can be a tailed primer having a target-specific 3' region that hybridizes with a portion of the polynucleotide, and a 5' region that does not hybridize with the polynucleotide (the 5' tail). The 5' tail can include at least one tag sequence.

In some embodiments, at least one tag can be appended to a polynucleotide by conducting a primer extension reaction, for example using one or more primers, at least one type of polymerase and a plurality of nucleotides. The primers can include at least one tag sequence (e.g., unique tag sequence). The primer can include a region that can selectively hybridize to a portion of the polynucleotide (e.g., a target-specific sequence in the 3' region of the primer). The primer can also include a region that is designed to exhibit minimal hybridization to a portion of the polynucleotide (e.g., a non-target specific sequence in the 5' region of the primer). For example, the primer can be a tailed primer. The primer can include at least one tag sequence in the 5' tail region.

In some embodiments, at least one adaptor containing one or more tags can be appended to a polynucleotide via enzymatic ligation, for example using a DNA ligase, including T4 DNA ligase, T7 DNA ligase, Taq ligase, a ligase from a Quick Ligase™ Kit (New England Biolabs), or Electro-Ligase™ (New England Biolabs). In some embodiments, at least one adaptor containing one or more tags can be appended to a polynucleotide via enzymatic ligation, for example using an RNA, including T4 RNA ligase 1 or 2, T4 ligase 2 truncated (e.g., K227Q or KQ), or thermostable AppDNA/RNA ligase.

In some embodiments, a transposon-mediated tagmentation reaction can be used to insert a tag sequence at a random location into a polynucleotide, and make a double-stranded cut in the polynucleotide, to yield a polynucleotide fragment appended at one or both ends with at least one tag. For example, a transposon complex can be formed by contacting a polynucleotide with a transposase which is bound to two transposon end sequences each containing at least one tag. The transposon complex can be incubated under conditions that permit a tagmentation reaction to occur. The transposase and transposon end sequences can be derived from MuA (U.S. application Ser. Nos. 13/553,395 and 14/480,419, or PCT Application No. PCT/EP2014/079473, or U.S. Pat. No. 6,593,113) or Tn5 (U.S. published application Nos. 2014/0162897; 2014/0031261; 2013/0196860; 2011/0287435; and 2010/0120098).

In some embodiments, at least one tag can be appended to the polynucleotide by interactions between binding partners. For example, a biotinylated tag can bind a polynucleotide that is conjugated to streptavidin, or the polynucleotide can be biotinylated and the tag can be conjugated to streptavidin. The biotin/streptavidin binding partners can be substituted with one of many other binding partners.

In some embodiments, the disclosure relates generally to methods, as well as related systems, compositions, kits, apparatuses and computer-readable media for detecting genetic variants, identifying genetic variants and/or generating error-corrected sequencing data, for appending a polynucleotide with at least one tag using an in vitro transposon-mediated fragmenting and tagging (e.g., "tagmentation").

In some embodiments, the disclosure relates generally to methods, as well as related systems, compositions, kits, apparatuses and computer-readable media for fragmenting and tagging nucleic acids from a nucleic acid sample in an in vitro reaction, comprising: (a) providing a plurality of transpososome complexes, including a first and second transpososome complex, wherein individual transpososome complexes include (i) a plurality of transposases, (ii) a first transposon end sequence, wherein the first transposon end sequence is capable of binding to a transposase from the plurality of transposases and includes a first tag sequence having different random tag sequences alternating with fixed tag sequences, and wherein the first transposon end sequence optionally contains at least one nick, gap, apurinic site or apyrimidinic site, (iii) a second transposon end sequence, wherein the second transposon end sequence is capable of binding to a transposase from the plurality of transposases and includes a second tag sequence having different random tag sequences alternating with fixed tag sequences, and wherein the second transposon end sequence optionally contains at least one nick, gap, apurinic site or apyrimidinic site, and wherein the first and second tag sequence contain different random tag sequences.

In some embodiments, the methods fragmenting and tagging nucleic acids further comprise: (b) contacting, in a single reaction mixture, the plurality of transpososome complexes with a plurality of polynucleotides from the nucleic acid sample which includes at least a first target polynucleotide, wherein the contacting is performed under conditions that are suitable for (i) transposing the plurality of transpososome complexes into the plurality of polynucleotides, including transposing the first and second transposon end sequences or the first and second transpososome complexes (respectively) into different positions of the first target polynucleotide, (ii) and fragmenting the plurality of polynucleotides including fragmenting the first target polynucleotide.

In some embodiments, the methods further comprise: (c) producing a plurality of tagged polynucleotides that are appended with a different tag sequences at both ends, wherein at least two of the plurality of tagged polynucleotides are appended with tag sequences that differ from each other. The plurality of tagged polynucleotides that are generated in the single reaction mixture include a first tagged polynucleotide, wherein the first tagged target polynucleotide is generated by transposing and fragmenting the first transposon end sequences into the first target polynucleotide at a first position and attaching the first transposon end sequence to the end of the fragmented first target polynucleotide, and by transposing and fragmenting the second transposon end sequences into the first target polynucleotide at a second position and attaching the second transposon end sequence to the other end of the fragmented first target polynucleotide, wherein the plurality of tagged polynucleotides includes the first transposon end sequence having at least one nick, gap, apurinic site or apyrimidinic site, and a second end having at least one nick, gap, apurinic site or apyrimidinic site.

In some embodiments, (i) the first transpososome complex includes a first pair of double-stranded transposon end sequences wherein the double-stranded transposon end sequences in the first pair have a first random tag sequence; and (ii) the second transpososome complex includes a second pair of double-stranded transposon end sequences wherein the double-stranded transposon end sequences in the second pair have a second random tag sequence, and wherein the first random tag sequence differs from the second random tag sequence.

In some embodiments, the method further comprises: (d) generating a population of tagged amplicons by amplifying the plurality of tagged polynucleotides, including generating a population of first tagged amplicons by amplifying the first tagged target polynucleotides.

In some embodiments, the method further comprises: (e) sequencing the population of tagged amplicons which comprises sequencing the target polynucleotide regions and the tags appended thereon, including sequencing the population of the first tagged amplicons which comprises sequencing the first target polynucleotide regions and the appended first and second tag regions.

In some embodiments, the method further comprises: (f) determining that the first target polynucleotide is present in the nucleic acid sample at an abundance level of 0.05-5%.

In some embodiments, the methods, as well as related systems, compositions, kits, apparatuses and computer-readable media described in WO 2015/113725 can be used to generate a population of transpososome complexes with MuA or Tn5 transpososomes, and individual transpososome complexes contains two double-stranded transposon end sequences, wherein each double-stranded transposon end sequence includes at least one random sequence interspersed with fixed sequences, and having the structure $(N)_n(X)_x(M)_m(Y)_y$. For example, the double-stranded transposon end sequences include the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

In some embodiments, the double-stranded transposon end sequence includes a random sequence which is represented by "N", and a fixed sequence which is represented by "X". Thus, the double-stranded transposon end sequence includes a randomer tag that can be represented by the structure $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

In some embodiments, the double-stranded transposon end sequence comprises a randomer tag which includes the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, the molecular tagging procedure can be performed using a limited number of primer extension cycles. For example, to reduce the nucleotide misincorporation errors that are potentially introduced into a tagged polynucleotides, the target polynucleotides can be appended with at least one tag using a limited number of primer extension cycles. For example, at least one tag is appended to a target polynucleotide (e.g., via primer extension with a tailed tag primer) under conditions that limit the number of primer extension reactions to 2-4 cycles. Optionally, a PCR reaction can be limited to about two cycles to append a tag to one end, and append a second tag to the other end of a target polynucleotide. Optionally, the first and second tags that are appended to the polynucleotide have the same or different tag sequence. In some embodiments, about 1-100 PCR cycles, or about 1-50 PCR cycles, or about 1-25 PCR cycles, or about 1-15 PCR cycles, can be employed to append the target polynucleotides with at least one tag.

In some embodiments, when performing any of the molecular tagging procedures of described in the present teachings, only the tagged polynucleotides will be sequenced. Thus, any un-tagged polynucleotides will not be detected. Optimizing the tag-appending conditions can increase the likelihood that more polynucleotides in the initial nucleic acid sample will be detected by sequencing. Optimizing the tag-appending conditions may ensure that a maximum number of polynucleotide molecules are appended with at least one tag, so that about 5-10%, or about 10-25%, or about 25-50%, or about 50-75%, or about 75-90%, or about 90-99.99% of the polynucleotides are appended to at least one tag. One way to increase the number of tagged polynucleotides is to increase the amount of input nucleic acids, but this is not always feasible for biological samples containing scant amounts of nucleic acids with low abundant variant species. The tagging reaction can contain an excess of tags compared to the amount of input polynucleotides. Another way to increase the yield of tagged polynucleotides is to improve the tag-appending conditions. For example, when appending a tag to a polynucleotide via an enzymatic ligation reaction, parameters such as blunt-end vs. sticky-end ligation, tag concentration relative to the polynucleotides, and temperature can be modulated to increase the percent of polynucleotides that are tagged. In another example, target polynucleotides-of-interest can be selectively appended to one or more tags using tailed primers in a primer extension reaction (thermo-cycling or isothermal). The specificity of hybridization between the target-specific portion of the tailed primer and the target polynucleotide can be optimized by adjusting parameters such as time, temperature, salts (e.g., monovalent cations), organic solvents (e.g., formamide), pH, as well as the length of the target-specific region and the concentrations of the tailed primers and input polynucleotides. Yet another way to increase the yield of tagged polynucleotides is to reduce the concentration of the nucleic acids in the tag-appending reaction relative to the concentration of the adaptor tags or tag primers. For example, the nucleic acid sample can be split into 2-20 or more separate pools, and the nucleic acid within each pool are placed into a single reaction mixture. The single reaction mixture can be used to append at least one tag (e.g., adaptors or primers) to the polynucleotides within the nucleic acid sample. Within each pool, the polynucleotides (from the nucleic acid sample) can be contacted with a set of a mixture of different tags (e.g., adaptors or primers), so that each pool has a different set of tags or each pool has the same or an overlapping set of tags. In some embodiments, if the initial nucleic acid sample contains a mixture of different polynucleotides, then the probability that any two polynucleotides having the same sequence are appended with the same one tag is quite low, and the probability that any two polynucleotides having the same sequence are appended with the same two tags is even lower. Thus, a tag-appending reaction performed in separate pools using the same set of tags will likely generate tagged polynucleotides where substantially every tagged polynucleotides that is appended with a different tag.

In some embodiments, the disclosure relates generally to methods, as well as related systems, compositions, kits, apparatuses and computer-readable media, for depositing an aliquot of the nucleic acid sample into two or more separate reaction vessels, to perform separate tag-appending reactions in each reaction vessel. For example, each reaction vessel contains a separate single reaction mixture that receives a separate aliquot of polynucleotides from the nucleic acid sample, for generating a plurality of tagged polynucleotides and optionally for generating tagged amplicons. In some embodiments, each reaction vessel can contain the same or different repertoire of tags (e.g., randomer tags). In some embodiments, the separately tagged polynucleotides can be separately amplified, then pooled. In some embodiments, the separately tagged polynucleotides can be pooled and then amplified. In some embodiments, the separately tagged amplicons can be pooled and then sequenced.

In some embodiments, the disclosure relates generally to methods, and related compositions, systems, kits, apparatuses and computer-readable media that further include a step to remove excess primers (e.g., tag primers) that are un-hybridized to a target polynucleotide after conducting a primer extension reaction (e.g., PCR). For example, any enzyme that degrades single-stranded oligonucleotides can be used, including single-stranded exonucleases, for example include Rec$J_f$, T5 exonuclease, lambda exonuclease, *E. coli* exonuclease I, *E. coli* exonuclease III, exonuclease VII or recBCD nuclease.

In some embodiments, the disclosure relates generally to methods, and related compositions, systems, kits, apparatuses and computer-readable media that further include at least one washing step. The washing step can be conducted at any time during the workflow, for example before, during or after any tag-appending or amplifying step. In some embodiments, a washing step can remove excess or unreacted components of the appending, amplifying and/or determining steps.

In some embodiments, any of the appending, amplifying and/or determining steps, according to the present teachings, can be conducted manually or by automation. In some embodiments, any one or any combination of the steps can be conducted manually or by automation, including: (1) forming a single reaction mixture, (2) appending at least one tag to a polynucleotide, (3) amplifying, (4) washing and/or (5) determining. For example, any reagents for the forming-a-single-reaction-mixture, appending, amplifying or washing steps can be deposited into, or removed from, a reaction vessel via manual or automated modes. In some embodiments, reagents for nucleic acid synthesis include any one or any combination of tags, nucleic acid sample, polynucleotides, enzymes (e.g., ligases or polymerases), nucleotides, divalent cations, binding partners, and/or buffer.

In some embodiments, any tagged amplicons produced using the methods, systems, compositions or kits of the present teachings can be used to detect mutations associated with cancer that are located in at least one of the genes selected from ABI1; ABL1; ABL2; ACSL3; ACSL6; AFF1; AFF3; AFF4; AKAP9; AKT1; AKT2; ALK; APC; ARHGAP26; ARHGEF12; ARID1A; ARNT; ASPSCR1; ASXL1; ATF1; ATIC; ATM; AXIN2; BAP1; BARD1; BCAR3; BCL10; BCL11A; BCL11B; BCL2; BCL3; BCL6; BCL7A; BCL9; BCR; BIRC3; BLM; BMPR1A; BRAF;

BRCA1; BRCA2; BRD3; BRD4; BRIP1; BUB1B; CARD11; CARS; CASC5; CBFA2T3; CBFB; CBL; CBLB; CBLC; CCDC6; CCNB1IP1; CCND1; CCND2; CD74; CD79A; CDC73; CDH1; CDH11; CDK4; CDK6; CDKN2A; CDKN2B; CDKN2C; CDX2; CEBPA; CEP110; CHEK1; CHEK2; CHIC2; CHN1; CIC; CIITA; CLP1; CLTC; CLTCL1; COL1A1; CREB1; CREB3L2; CREBBP; CRTC1; CRTC3; CSF1R; CTNNB1; CXCR7; CYLD; CYTSB; DCLK3; DDB2; DDIT3; DDR2; DDX10; DDX5; DDX6; DEK; DGKG; DICERI; DNMT3A; EEF1B2, EGFR; EIF4A2; ELF4; ELL; ELN; EML4; EP300; EPS15; ERBB2; ERBB4; ERC1; ERCC2; ERCC3; ERCC4; ERCC5; ERG; ETV1; ETV4; ETV5; ETV6; EWSR1; EXT1; EXT2; EZH2; FAM123B; FANCA; FANCC; FANCD2; FANCE; FANCF; FANCG; FAS; FBXW7; FCRL4; FGFR1; FGFR10P; FGFR2; FGFR3; FH; FIP1L1; FLCN; FLI1; FLT1; FLT3; FNBP1; FOXL2; FOXO1; FOXO3; FOXO4; FOXP1; FUS; GAS7; GATA1; GATA2; GATA3; GMPS; GNAQ; GNAS; GOLGA5; GOPC; GPC3; GPHNGPR124; HIP1; HIST1H4I; HLF; HNF1A; HNRNPA2B1; HOOK3; HOXA11; HOXA13; HOXA9; HOXC11; HOXC13; HOXD13; HRAS; HSP90AA1; HSP90AB1; IDH1; IDH2; IKZF1; IL2; IL21R; IL6ST; IRF4; ITGA10; ITGA9; ITK; JAK1; JAK2; JAK3; KDM5A; KDM5C; KDM6A; KDR; KDSR; KIAA1549; KIT; KLF6; KLK2; KRAS; KTN1; LASP1; LCK; LCP1; LHFP; LIFR; LMO2; LPP; MAF; MALT1; MAML2; MAP2K1; MAP2K4; MDM2; MDM4; MECOM; MEN1; MET; MITF; MKL1; MLH1; MLL; MLLT1; MLLT10; MLLT3; MLLT4; MLLT6; MN1; MPL; MRE11A; MSH2; MSH6; MSI2; MSN; MTCP1; MTOR; MUC1; MYB; MYC; MYCL1; MYCN; MYH11; MYH9; MYST3; MYST4; NACA; NBN; NBPF10, NCOA1; NCOA2; NCOA4; NEK9; NF1; NF2; NFE2L2; NFKB2; NIN; NKX2-1; NLRP1; NONO; NOTCH1; NOTCH2; NPM1; NR4A3; NRAS; NSD1; NTRK1; NTRK3; NUMA1; NUP214; NUP98; OLIG2; OMD; PAFAH1B2; PALB2; PATZ1; PAX3; PAX5; PAX7; PAX8; PBRM1; PBX1; PCM1; PDE4DIP; PDGFB; PDGFRA; PDGFRB; PER1; PHOX2B; PICALM; PIK3CA; PIK3R1; PIM1; PLAG1; PML; PMS1; PMS2; POU2AF1; POU5F1; PPARG; PPP2R1A; PRCC; PRDM16; PRF1; PRF19; PRKAR1A; PRRX1; PSIP1; PTCH1; PTEN; PTPN11; RABEP1; RAD50; RAD5IL1; RAF1; RANBP17; RAP1GDS1; RARA; RB1; RBM15; RECQL4; REL; RET; RHOH; RNF213; ROS1; RPN1; RPS6KA2; RSBN1L; RUNX1; RUNX1T1; SBDS; SDHAF2; SDHB; SETD2; SFPQ; SFRS3; SH3GL1; SLC6A18; SLC45A3; SMAD4; SMARCA4; SMARCB1; SMO; SOCS1; SRC; SRGAP3; SS18; SS18L1; STIL; STK11; STK36; SUFU; SYK; TAF15; TAF1L; TAL1; TAL2; TCF12; TCF3; TCL1A; TET1; TET2; TEX14; TFE3; TFEB; TFG; TFRC; THRAP3; TLX1; TLX3; TMPRSS2; TNFAIP3; TOP1; TP53; TPM3; TPM4; TPR; TRIM27; TRIM33; TRIP11; TSC1; TSC2; TSHR; USP6; VHL; WAS; WASH3P; WHSC1L1; WRN; WT1; XPA; XPC; ZBTB16; ZMYM2; ZNF331; ZNF384; and ZNF521.

In some embodiments, any tagged amplicons produced using the methods, systems, compositions or kits of the present teachings can be used to detect mutations associated with cancer that are located in at least one of the genes selected from ABL1; AKT1; ALK; APC; ATM; BRAF; CDH1; CDKN2A; CSF1R; CTNNB1; EGFR; ERBB2; ERBB4; FBXW7; FGFR1; FGFR2; FGFR3; FLT3; GNAS; HNF1A; HRAS; IDH1; JAK2; JAK3; KDR; KIT; KRAS; MAP2K1; MET; MLH1; MPL; NOTCH1; NPM1; NRAS; PIC3CA; PDGFRA; PIK3CA; PTEN; PTPN11; RB1; RET; ROS1, SMAD4; SMARCB1; SMO; SRC; STK11; TP53; and VHL.

In some embodiments, any tagged amplicons produced using the methods, systems, compositions or kits of the present teachings can be used to detect mutations, including for example at least one of the following: EGFR (Leu858Arg), TP53 (Arg158Leu), TP53 (Tyr220Cys), MET (Thr1010Ile), and/or KRAS (Gly12Cys).

In some embodiments, the disclosure relates generally to compositions, and related methods, systems, kits, apparatuses and computer-readable media, comprising a support. In some embodiments, the support can include a surface which is an outer or top-most layer or boundary of an object. In some embodiments, a surface can be interior to the boundary of the support.

In some embodiments, a support can be a substantially planar support, as well as concave, convex, or any combination thereof. In some embodiments, a support can be a bead, particle, microparticle, sphere, filter, flowcell, well, microwell, groove, channel reservoir, gel or inner wall of a capillary. In some embodiments, a support includes the inner walls of a capillary, a channel, a well, microwell, groove, channel, reservoir. In some embodiments, a support can include texture (e.g., etched, cavitated, pores, three-dimensional scaffolds or bumps). In some embodiments, a support includes a plurality of reaction sites arranged in an organized or random array. In some embodiments, the plurality of reaction sites can be arranged on the support in a random pattern, organized pattern, rectilinear pattern, hexagonal pattern, or addressable array pattern. For example, the plurality of reaction sites can be used for solid phase amplification (e.g., amplification reaction sites) or for sequencing (e.g., sequencing reaction sites).

In some embodiments, a support can be porous, semi-porous or non-porous.

In some embodiments, particles can have a shape that is spherical, hemispherical, cylindrical, barrel-shaped, toroidal, rod-like, disc-like, conical, triangular, cubical, polygonal, tubular, wire-like or irregular.

In some embodiments, a support can be made from any material, including glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond).

In some embodiments, a support can be magnetic or paramagnetic. In some embodiments, a support can be paramagnetic beads (particle) attached with streptavidin, for example DYNABEADS M-270 (from Invitrogen, Carlsbad, CA). A bead or particle can have an iron core, or comprise a hydrogel or agarose (e.g., SEPHAROSE).

In some embodiments, the support (including interior scaffolds of a bead or particle) can be attached with a plurality of a capture primer. A support can be coated with an acrylamide, carboxylic or amine compound for attaching a nucleic acid (e.g., a capture primer). In some embodiments, an amino-modified nucleic acid (e.g., primer) can be attached to a support that is coated with a carboxylic acid. In some embodiments, an amino-modified nucleic acid can be reacted with ethyl (dimethylaminopropyl) carbodiimide (EDC) or EDAC for attachment to a carboxylic acid coated support (with or without N-hydoxysuccinimide (NHS)). A capture primer can be immobilized to an acrylamide compound coating on a support. The particles can be coated with an avidin-like compound (e.g., streptavidin) for binding biotinylated nucleic acids.

In some embodiments, a support can be a well, microwell, groove, channel reservoir, gel or inner wall of a capillary. The surface of the support can be formed of a semi-metal or metal or oxide or nitride ceramic thereof. Exemplary metals or semi-metals include silicon, gallium, aluminum, hafnium, titanium, tungsten, tantalum, zirconium, or any alloy or combination thereof. Such exemplary metals or semi-metals can also form ceramic oxides, nitrides, or oxynitrides. In a particular example, the surface can be further treated with a surface agent including functionality, such a phosphate, phosphonate, catechol, nitrocatechol, boronate, phenylboronate, imidazole, silanol or silane functionality.

In some embodiments, the support can be treated or coated with a surface agent that enhances signal detection of nucleotide incorporation by products such as pyrophosphate, hydrogen ions, protons, charge transfer or heat.

In an example, a surface agent including silane functionality can have the formula R—[(CH2)n]-Si—[X1X2X3] where R is an organofunctional group, [(CH2)n] is a hydrocarbon linker (n=1 to 20) Si is a silicon atom, and [X1X2X3] comprises one or more independent hydrolysable groups, including alkoxy or halogen groups. In another embodiment, the silane group may be R—[(C2H4O)n]-Si—[X1X2X3] where R is an organofunctional group, [(C2H4O)n](n=1 to 100) is a polyether linker, Si is a silicon atom, and [X1X2X3] comprises one or more hydrolysable groups, including alkoxy or halogen groups. In either of the embodiments, organofunctional groups R include, but are not limited to methyl, methylene, phenyl, benzyl, anilino, amino, amide, hydroxyl, aldehyde, alkoxy, halo, mercapto, carboxy, acyl, vinyl, allyl, styryl, epoxy, isocyanato, glycidoxy, and acryloxy. See, for example, U.S. Pat. No. 8,647,577, incorporated herein by reference.

In another example, the surface agent can bind as a monolayer over one or more of the surfaces. In particular, the surface agent includes a functional group reactive with the Bronsted base or Lewis acid functionality formed on the surfaces. See, for example, U.S. Patent Publication No. 2016/0003768, incorporated herein by reference. An exemplary surface reactive functional group of the surface agent can include a silane, phosphates, phosphonic acid, phosphinic acid, bisphosphonic acid, multidentate phosphates or phosphonates, polyphosphates/phosphonates, isocyanate, catechol, hydroxamate, alkoxy derivatives thereof, or any combination thereof. Exemplary alkoxy groups include methoxy, ethoxy, or combinations thereof. In another example, a combination of a clodronic acid and a functionalized primary amine can be used in place of a surface reactive functional group. In an example, silanes can functionalize many ceramic and metallic surfaces. In a particular example, silanes, isocyanates, hydroxamates, and clodronic acid can functionalize silica surfaces. In another example, phosphates, catechols, and hydroxamates can be used to functionalize titania surfaces. In further examples, particular surface reactive functional groups may preferentially deposit on one or more metal or ceramic surfaces relative to other metal or ceramic surfaces.

Distal from the functional group, the surface agent can include a functional group that does not include a donor pair of electron or that lacks Bronsted base or acid activity. The distal functional group can be a positively charged functional group or can be a neutral functional group. Exemplary neutral functional groups include alkyl, branched alkyl, or cyclic aromatic groups. Exemplary positively charged groups that lack a donor pair of electrons include salts of quaternary ammonium ions derived from secondary amines, tertiary amines or heterocyclic groups incorporating nitrogen. In another example, the distal functional group can be a nitroso functional group. Exemplary heterocyclic groups incorporating nitrogen include quaternary amines derived from pyrrolidine, pyrrole, imidazole, piperidine, pyridine, pyrimidine, purine, triazolium, or combinations thereof. In particular, the salt can include a halide salt of the quaternary ammonium ions, such as a bromide salt. The secondary, tertiary, or quaternary amines can be conjugated to alkyl groups including methyl, ethyl, propyl, butyl, or tert-butyl alkyl groups. In another example, the distal functional group can include hindered primary, secondary or tertiary amines, such as amines hindered by proximal phosphate, phosphonate, phosphinate, or silane groups, or combinations thereof. In a particular example, the distal functional group can include biotin or a derivative thereof.

In an example, the distal functional group can be bound to the surface reactive functional group by an amide, alkyl, alkoxy, aryl, or polyether or thioether moiety, or a combination thereof. For example, the distal functional group can be separated from the surface reactive functional group by an alkyl moiety having 1 to 16 carbons, such as 1 to 12 carbons. In an example, the alkyl moiety can have 8 to 12 carbons, such as 10 to 12 carbons. In another example, the alkyl moiety can have 1 to 6 carbons, such as 1 to 4 carbons, or 1 to 3 carbons. In particular, surface agents including hindered amine distal functionality can have an alkyl moiety having 1 to 6 carbons, such as 1 to 4 carbons, or 1 to 3 carbons. In another example, the alkoxy moiety can have a number of carbons in a range similar to that of the alkyl moiety. In an additional example, a polyether moiety can have between 1 and 10 ether units, each having between 1 and 4 carbons, such as between 1 and 3 carbons. For example, the polyether moiety can have between 1 and 6 ether units, such as between 1 and 4 ether units.

In a particular example, the surface agent includes a silane surface reactive functional group. Exemplary surface agents include alkyl trialkoxy silane, such as octyldecyl triethoxysilane, octyldecyl trimethoxy silanes, propyl trimethoxy silane, or combinations thereof, salts of quaternary ammonium alkyl alkoxy silanes, such as butyl ammonium trimethoxy silane, methyl ammonium benzo trimethoxy silanes, uronium-silane or thiouronium-silane, methoxy-N silane, short butyl ammonium trimethoxy silanes, or a combination thereof, fluorinated or chlorinated derivatives thereof; derivatives thereof, or combinations thereof. Exemplary quaternary salts include chlorine or bromine salts of such quaternary ammonium alkyl trialkoxysilanes. Such silane surface agents can bind to semi-metal or metal oxides. Some silane-based surface agents can bind indiscriminately to sidewalls surface or sensor surfaces.

In another example, the surface agent can be a phosphonic acid-based surface agent. An exemplary surface agent includes alkyl phosphonic acids, such as octadecyl phosphonic acid; chlorine or bromine salts of quaternary amino phosphonic acids, such as imidazole phosphonic acids (e.g., 1-methyl-3-(dodecylphosphonic acid) imidazolium, or 1-methyl-3-(hexylphosphonic acid) imidazolium), (12-dodecylphosphonic acid) trimethylammonium bromide, methyl ammonium phosphonic acid, ethyl ammonium phosphonic acid, (12-dodecylphosphonic acid)tripropylammonium bromide, (12-dodecylphosphonic acid)tributylammonium bromide; (12-dodecylphosphonic acid) methyltriazolium bromide; (6-hexylphosphonic acid) imidazolium; pyridine alkyl phosphonic acids; benzo alkyl phosphonic acids; (1-amino-1-phenylmethyl) phosphonic acid; fluorinated or chlorinated derivatives thereof, derivatives thereof, or any combination thereof. In another example, the surface agent can be a biotin alkyl phosphonic acid. In an example, phosphates and phosphonates can preferentially bind to sensor surfaces.

In a further example, the phosphonic acid-based surface agent can include more than one phosphonic acid surface active functional group. For example, the surface agent can be a bisphosphonic acid, including two phosphonic acid surface active functional groups, such as alendronic acid or a derivative thereof. In particular, the surface agent can be a multidentate phosphonic acid-based surface agent, for example, including more than one phosphonic acid functional group coupled to a central moiety functioning as the distal group, such as a tertiary amine or alkyldiamine. For example, the surface agent can be a functionalized amino bis(alkyl phosphonic acid), such as a biotin functionalized amino bis(methylene phosphonic acid), nitrilotris (alkyl phosphonic acid), e.g. nitrilotris (methylene phosphonic acid), an ether derivative thereof, or a combination thereof. In another example, the surface agent can be alkyldiamine tetrakis (alkyl phosphonic acid), such as ethylene diamine tetrakis (methylene phosphonic acid). In a further example, the surface agent can be diethylenetriamine penta(methylene phosphonic acid), hexamethylenediamine tetra(methylene phosphonic acid), tetramethylenediamine tetra(methylene phosphonic acid), or any combination thereof. In an additional example, the surface agent is a phenyl diphosphonic acid, a functionalized derivative thereof, or a combination thereof.

In a further example, the surface agent can be a catechol, such as a catecholamine, nitrocatechol, nitrocatecholamine, derivatives thereof, or a combination thereof. For example, the catechol can include a dopamine, nitrodopamine, norepinephrine, epinephrine, esters thereof, or a combination thereof. In a particular example, the catechol is dopamine or nitrodopamine.

In an additional example, the surface agent can include an isocyanate or hydroxamate surface active functionality.

In particular embodiments, support materials, such as polymeric materials can be deposited into surface support structures, such as a well, microwell, groove, channel reservoir, gel or inner wall of a capillary. For example, polymer beads can be deposited into wells, microwells, groove, channels, or capillaries. In another example, a polymer can be coated over such surface structures. For example, a polymer matrix can be formed over the surface structures. See, for example, US Patent Publication No. 2015/0160153, incorporated herein by reference.

For example, the polymer matrix can be formed from matrix precursors, such as a radically polymerizable monomer, for example, a vinyl-based monomer. In particular, the monomer can include a hydrophilic monomer, such as an acrylamide, vinyl acetate, hydroxyalkylmethacrylate, variations or derivatives thereof, copolymers thereof, or any combination thereof. In a particular example, the hydrophilic monomer is an acrylamide, such as an acrylamide functionalized to include hydroxyl groups, amino groups, carboxyl groups, halogen groups, or a combination thereof. In an example, the hydrophilic monomer is an aminoalkyl acrylamide, an acrylamide functionalized with an amine terminated polyalkyl glycol, an acrylopiperazine, or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide, N-(hydroxymethyl)acrylamide, or a combination thereof. The acrylamide functionalized with an amine terminated polyalkyl glycol can include between 1 and 20 units of an alkyl glycol, such as ethylene glycol, propylene glycol, or a combination thereof. In another example, a comonomer can include a halogen modified acrylate or acrylamide, such as a N-(5-bromoacetamidylpentyl)acrylamide (BRAPA). While BRAPA is illustrated as including a bromoacetamide group, a bromoalkylamide including an alkyl group of 2 to 20 carbons can be used. Further, the pentyl group of BRAPA can be replaced with another alkyl group having a carbon length in a range of 2 to 20. In another example, a comonomer can include an oligonucleotide modified acrylate or acrylamide monomer. In a further example, a mixture of monomers, such as a mixture of hydroxyalky acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1. In another example, the amine functionalize acrylamide can be included in a ratio of hydroxyalkyl acrylamide:bromine functionalized acrylamide or acrylamide:bromine functionalized acrylamide in a range of 100:1 to 1:1, such as a range of 100:1 to 2:1, a range of 50:1 to 3:1, a range of 50:1 to 5:1 or even a range of 50:1 to 10:1.

In a further example, an oligonucleotide functionalized acrylamide or acrylate monomer, such as an Acrydite™ monomer, can be included to incorporate oligonucleotides into the polymer matrix.

Another exemplary matrix precursor includes a crosslinker. In an example, the crosslinker is included in a mass ratio of monomer to crosslinker in a range of 15:1 to 1:2, such as a range of 10:1 to 1:1, a range of 6:1 to 1:1, or even a range of 4:1 to 1:1. In particular, the crosslinker can be a divinyl crosslinker. For example, a divinyl crosslinker can include a diacrylamide, such as N,N'-(ethane-1,2-diyl)bis(2-hydroxyl ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a protected derivative thereof, or a combination thereof.

Polymerization can be initiated by an initiator within the solution. For example, the initiator can be a water-based. In another example, the initiator can be a hydrophobic initiator, preferentially residing in a hydrophobic phase. An exemplary initiator includes ammonium persulfate and TEMED (tetramethylethylenediamine). TEMED can accelerate the rate of formation of free radicals from persulfate, in turn catalyzing polymerization. The persulfate free radicals, for example, convert acrylamide monomers to free radicals which react with unactivated monomers to begin the polymerization chain reaction. The elongating polymer chains can be randomly crosslinked, resulting in a gel with a characteristic porosity which depends on the polymerization conditions and monomer concentrations. Riboflavin (or riboflavin-5'-phosphate) can also be used as a source of free radicals, often in combination with TEMED and ammonium persulfate. In the presence of light and oxygen, riboflavin is converted to its leuco form, which is active in initiating polymerization, which is usually referred to as photochemical polymerization.

In another example, an azo initiator can be used to initiate polymerization. In particular, the azo initiator can be azobisisobutyronitrile (AIBN).

In a further example, precursors to the polymer matrix can include surface reactive additives to enhance binding with surface. Exemplary additives include functionalize acrylic monomers or functionalized acrylamide monomers. For example, an acrylic monomer can be functionalized to bind with a surface material, such as a ceramic material forming the bottom or sidewall of a well. In an example, the additive can include an acryl-phosphonate, such as methacrylphosphonate. In another example, the additive can include dimethylacrylamide or polydimethylacrylamide. In a further example, the additive can include a polylysine modified with polymerizable groups, such as acrylate groups.

In another example, polymerization can be facilitated using an atom transfer radical polymerization (ATRP). The ATRP system can include a chain transfer agent (CTA), monomer, a transition metal ion, and a ligand. An exemplary transition metal ion complex includes a copper-based complex. An exemplary ligand includes 2,2'-bipyridine, 4,4'-di-5-nonyl-2,2'-bipyridine, 4,4',4"-tris(5-nonyl)-2,2' 6',2"-terpyridine, N,N,N',N',N"-pentamethyldiethylenetriamine, 1,1,4,7,10,10-hexamethyltriethylenetetramine, tris(2-dimethylaminoethyl)amine, N,N-bis(2-pyridylmethyl)octadecylamine, N,N,N',N'-tetra[(2-pyridyl)methyl]ethylenediamine, tris[(2-pyridyl)methyl]amine, tris(2-aminoethyl)amine, tris(2-bis(3-butoxy-3-oxopropyl)aminoethyl)amine, tris(2-bis(3-(2-ethylhexoxy)-3-oxopropyl)aminoethyl)amine, tris(2-bis(3-dodecoxy-3-oxopropyl)aminoethyl)amine, aliphatic, aromatic and heterocyclic/heteroaromatic amines, variations and derivatives thereof, or combinations thereof. An exemplary CTA includes 2-bromopropanitrile, ethyl 2-bromoisobutyrate, ethyl 2-bromopropionate, methyl 2-bromopropionate, 1-phenyl ethylbromide, tosyl chloride, 1-cyano-1-methylethyldiethyldithiocarbamate, 2-(N,N-diethyldithiocarbamyl)-isobutyric acid ethyl ester, dimethyl 2,6-dibromoheptanedioate, and other functionalized alkyl halides, variations or derivatives thereof, or any combination thereof. Optionally, the BRAPA monomer can function as a branching agent in the presence of an ATRP system.

In an example, ATRP is initiated at a surface to directly bond the polymer to the surface. For example, acrylate monomers, acrylamide monomers, Acrydite™ monomers, succinimidyl acrylates, bis-acrylate or bis-acrylamide monomers, derivatives thereof, or combinations thereof can be applied in solution to the initiated surface in the presence of a transition metal ion/ligand complex.

In another, the ATRP system can be used to attach a polymer to a surface of the well using a modified phosphonate, sulfonate, silicate, titanate, or zirconate compounds. In particular, an amine or hydroxyl terminated alkyl phosphonate or an alkoxy derivative thereof can be applied to a surface and initiated using an initiator. The catalyst complex and monomers can be applied, extending the surface compound.

In an exemplary method, an aqueous solution including precursors to the polymer matrix can be applied into wells of the structure defining an array of wells. The aqueous solution in the wells can be isolated by providing an immiscible fluid over the wells and initiating polymerization of the polymer precursors within the solution within the wells.

Many examples of methods for preparing supports treated or coated with at least one surface agent that can be that enhances signal detection of nucleotide incorporation byproducts can be found in U.S. published application Nos. 2012/0045368, published Feb. 23, 2012; 2016/0032371, published Feb. 4, 2016; and 2016/0003768, published Jan. 7, 2016.

In some embodiments, the disclosure relates generally to methods, as well as related systems, compositions, kits, apparatuses and computer-readable media, for appending a polynucleotide with at least one tag using a nucleic acid amplification reaction, which includes a polymerase chain reaction (PCR) (U.S. Pat. Nos. 4,683,195 and 4,683,202 both granted to Mullis), ligase chain reaction (LCR) (Barany 1991 Proceedings National Academy of Science USA 88:189-193; Barnes 1994 Proceedings National Academy of Science USA91:2216-2220), or isothermal self-sustained sequence reaction (Kwoh 1989 Proceedings National Academy of Science USA 86:1173-1177; WO 1988/10315; and U.S. Pat. Nos. 5,409,818, 5,399,491, and 5,194,370), or recombinase polymerase amplification (RPA) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, the disclosure relates generally to methods, as well as related systems, compositions, kits, apparatuses and computer-readable media, for appending a polynucleotide with at least one tag using circularized nucleic acids. In some embodiments, the polynucleotides from the nucleic acid sample can be circularized, for example by intramolecular ligation or use of a splint molecule or a padlock structure. The circularized molecules can be used to generate the tagged amplicons by rolling circle amplification, vector-mediated procedure, padlock structure formation, or hairpin adaptor-mediated procedure.

In some embodiments, the nucleic acid amplification reaction includes rolling circle amplification (RCA). For example, tailed primer having a 3' region that hybridizes to a portion of a circular polynucleotide and a 5' unique tail, can be used to conduct the amplification reaction to generate concatemers having a tag in their 5' region. Examples of rolling circle amplification are described in Fire and Xu 1995 Proceedings of the National Academy of Science 92:4641-4645; Lizardi 1998 Nature Genetics 19:225; Baner 1998 Nucleic Acids Research 26:5073; Zhao 2008 Agnewandte Chemie International Edition 47:6330-6337; and Nilsson 2008 Trends in Biochemistry 24:83-88.

In some embodiments, the nucleic acid amplification reaction includes a vector-mediate method in which a portion of a target polynucleotide (target sequence) is inserted into a vector, and the target sequence is joined on one or both sides with a unique tag, to generate a circular molecule. The circular molecule is subjected to bi-directional RCA using forward and reverse primers that selectively hybridize to the target sequence, to generate forward and reverse concatemers (Bielas and Ericson, U.S. Application Publication No. 2015/0126376). The concatemers can be sequenced and the sequencing reads can be manipulated using the methods described in the present teachings. Alternatively, the circular molecule is subjected to uni-directional RCA using a primer specific for the tag sequence or the target sequence (U.S. Pat. Nos. 6,287,824; 6,480,791; 8,221,982; 8,383,345; 8,865, 410).

In some embodiments, the nucleic acid amplification reaction includes ligating a target polynucleotide with at least one tag to form a circular molecule. RCA is performed using a primer that hybridizes to the tag or target sequence (U.S. Pat. Nos. 6,480,791; 7,537,897; 8,003,330; 8,383,345; 8,497,069; 8,835,358; and 8,865,410).

In some embodiments, the nucleic acid amplification reaction includes forming a padlock structure using a pre-circle probe containing at least one tag. The pre-circle probe is hybridized to a target polynucleotide to form a padlock structure having a nick. The nick is closed with a ligase, and primer extension is performed with a primer specific for the tag or target sequence (U.S. Pat. Nos. 6,830,884; 7,498,131; and 7,790,388).

In some embodiments, the nucleic acid amplification reaction includes ligating hairpin adaptors to both ends of a double-stranded target polynucleotide, where the hairpin adaptors contain at least one tag. The resulting ligation product can form a single-stranded circular molecule that can undergo RCA (U.S. Pat. No. 8,309,330).

In some embodiments, the nucleic acid amplification reaction includes utilizing a LoxP/Cre system, in which a LoxP sequence is joined to at least one tag and a Cre recombinase is used to generate a circular molecule having a tag insert. The circular molecule can be subjected to RCA (U.S. Pat. No. 6,448,017).

In some embodiments, the disclosure relates generally to methods, as well as related systems, compositions, kits, apparatuses and computer-readable media, for appending a polynucleotide with at least one tag using and inverse PCR reaction. For example, an inverse PCR reaction incudes: (a) providing a nucleic acid sample containing a plurality of polynucleotides; (b) randomly-fragmenting the plurality of polynucleotides to generate fragments having (i) at least one region having a known sequence flanked by unknown sequences, and (ii) terminal ends having unique sequences; (c) appending a first universal sequence to one end of the fragmented polynucleotides and appending a second universal sequence to the other end of the fragmented polynucleotides, for example by adaptor ligation, to generate adaptor-joined fragments; (d) amplifying the adaptor-joined fragments using PCR and primers that hybridize to the first or second universal sequences of the adaptor-joined fragments, to generate adaptor-joined amplicons; (e) circularizing the adaptor-joined amplicons to generate a plurality of circular molecules that contain (i) at least one region having a known sequence flanked by unknown sequences, (ii) a first terminal end having a first unique sequence which is joined to the first universal sequence, and (iii) a second terminal end having a second unique sequence which is joined to the second universal sequence; (f) amplifying the circular molecules by rolling circle amplification using tailed primers that hybridize to the known sequence, to generate linear molecules (e.g., concatemers) having (i) a first terminal end having a first unique sequence which is joined to the first universal sequence, (ii) a second terminal end having a second unique sequence which is joined to the second universal sequence, (iii) a region having a known sequence flanked by unknown sequences; and (g) sequencing the linear molecules to produce a plurality of candidate sequencing reads. In some embodiments, methods, as well as related systems, compositions, kits, apparatuses and computer-readable media, further comprise manipulating the sequencing reads and applying at least one threshold, which can reduce errors in the sequencing reads. In some embodiments, the manipulating of the candidate sequencing reads includes culling, sorting, grouping, counting grouped reads, counting family of reads, and other manipulation steps. In some embodiments, randomly-fragmenting step can be conducted by shearing or transposon-mediated tagmentation. In some embodiments, the manipulating steps can be based on tag-specific reference sequences and/or polynucleotide-specific reference sequences. In some embodiments, other variations of the inverse PCR methods can be practiced, based on methods described in U.S. 2014/0227705 (Vogelstein); Ochman 1988 Genetics 120:621-623; Triglia 1988 Nucleic Acids Research 16:8186; or Silver and Keerikatte 1989 Journal of Virology 63:1924-1928).

In some embodiments, any tagged-target polynucleotides (including tagged amplicons) that have been generated according to the present teachings, can be attached to a solid support. For example, a bridge amplification reaction can be conducted to attach the tagged-target nucleic acids to a substantially planar support (e.g., flowcell) or beads. Individual tagged-target nucleic acids include at least one tag adaptor sequence and a first universal adaptor sequence at one end and at least another tag adaptor sequence and a second universal adaptor sequence at the other end. In some embodiments, the tag portion of the first and second tag-adaptors have different sequences. In some embodiments, the first and/or second tag-adaptors include a universal amplification and/or sequencing primer sequences. In some embodiments, at least two of the tagged-target nucleic acids include target sequence portions having different sequences. The population of tagged nucleic acids are amplified to generate a population of tagged-target amplicons. The population of tagged-target amplicons is rendered single-stranded to generate a population of single-stranded tagged-target nucleic acids. At least a portion of the population of the single-stranded tagged-target nucleic acids is hybridized to capture primers that are attached to a support. The support can include a plurality of first and second capture primers having different sequences, for example, the first capture primers hybridize to the first universal sequence and the second capture primers hybridize to the second universal sequence. In the hybridization step, the first universal adaptor (e.g., attached to the first polynucleotide) hybridizes with the first capture primer, and a primer extension reaction extends the first capture primer to generate a first capture primer extension product having a complementary sequence of the second adaptor at one end. The primer extension reaction employs the captured target nucleic acid as a template. The template molecule is removed. The first capture primer extension product bends (e.g., arches) so that the second adaptor sequence can hybridize to a nearby second capture primer, and a primer extension reaction extends the second capture primer to generate a second capture primer extension product having a complementary sequence of the first adaptor at one end, and forming a double-stranded bridge molecule. The double-stranded bridge is denatured to yield two single-stranded, immobilized target nucleic acids. One of the single-stranded, immobilized target nucleic acids has a first primer (or complementary sequence thereof) which is attached to the support and the other end of the molecule has a second primer sequence (or complementary sequence thereof), and the second primer sequence can hybridize to a nearby second capture primer to start another bridge amplification reaction. The other single-stranded, immobilized target nucleic acids has a second primer (or complementary sequence thereof) which is attached to the support and the other end of the molecule has a first primer sequence (or complementary sequence thereof), and the first primer sequence can hybridize to a nearby first capture primer to start another bridge amplification reaction. Repeat cycles of bridge amplification produce a plurality of amplified target nucleic acids that are attached to the support. The cycles of bridge amplification can be conducted under isothermal conditions. Examples of compositions and methods for bridge amplification are found in U.S. Pat. Nos. 7,790,418, 7,985,565, 8,143,008 and 8,895,249.

In some embodiments, any tagged-target polynucleotides (including tagged amplicons) that have been generated according to the present teachings, can be attached to a solid support. For example, a template walking reaction can be conducted to attach the tagged target nucleic acids to a substantially planar support (e.g., flowcell) or beads. Individual tagged target nucleic acids include at least one tag sequence and a first universal adaptor sequence at one end and at least another tag sequence and a second universal adaptor sequence at the other end. In some embodiments, the first and second universal adaptors have different sequences. In some embodiments, the first and/or second adaptor includes a universal amplification primer sequence. In some embodiments, the first and/or second adaptor includes a universal sequencing primer sequence. In some embodiments, at least two of the tagged target nucleic acids have different target sequences. In some embodiments, the template walking reaction includes: providing a support attached with a plurality of capture primers. The support can include a plurality of capture primers that are attached to the support by their 5' ends. The support can include a plurality of immobilized capture primers, where the 3' end of the capture primers includes the same sequence. In some embodiments, the 3' end of the capture primers includes a sequence having a low $T_m$(melting temperature) sequence. The plurality of capture primers can hybridize with at least a portion of the first universal adaptor sequence. In some embodiments, the template walking reaction includes: rendering a population of tagged target nucleic acids single-stranded. In some embodiments, the template walking reaction includes: hybridizing at least a portion of the population of single-stranded tagged target nucleic acids to the capture primers that are attached to a support. In the hybridization step, the first universal adaptor hybridizes with a first immobilized capture primer, and a primer extension reaction extends the first capture primer to generate a first captured primer extension product having a complementary sequence of the second adaptor at one end. The primer extension reaction employs the tagged target nucleic acid as a template. The template molecule (which is hybridized along its length to the first extension product) undergoes localized denaturation at the first adaptor region that contains the low $T_m$ region, and the first universal adaptor region rehybridizes to a nearby capture primer (e.g., a second capture primer), while the remainder of the template molecule is hybridized to the first extension product. Primer extension of the second capture primer, serves to denature the portion of the template molecule that is still hybridized with the first extension product, and generates a second captured primer extension product. Repeat cycles of template walking include hybridizing the first universal adaptor region to a nearby capture primer, primer extension, localized denaturation at the first universal adaptor region that contains the low $T_m$ region, re-hybridization with a different nearby capture primer, and primer extension, to produce a plurality of amplified target nucleic acids that are attached to the support. The cycles of template walking can be conducted under isothermal conditions.

For example, a method for template walking, comprises:

(a) providing a support with immobilized a plurality of capture primers which includes a first and a second capture primer, wherein the plurality of the capture primers have an identical sequence or have an identical 3' portion, and wherein the 5' ends of the plurality of the capture primers are attached to the support, and wherein the plurality of the capture primers contain a region having a low melting temperature sequence;

(b) providing a plurality of single-stranded tagged target nucleic acids which includes a first single-stranded tagged target nucleic acid, wherein the plurality of single-stranded tagged target nucleic acids having (i) a first universal adaptor and a first tag attached to one end of the target nucleic acids, and (ii) a second universal adaptor and a second tag attached to the other end of the target nucleic acids;

(c) hybridizing the first capture primer to the first universal adaptor of the first single-stranded tagged target nucleic acid;

(d) extending the first capture primer by conducting a primer extension reaction to generate a duplex first extension product which is hybridized along the length of the first extension product;

(e) separating a portion of the first capture primer (e.g., that includes the low melting temperature sequence) from the hybridized first universal adaptor by local denaturation;

(f) re-hybridizing the first universal adaptor to the second capture primer while the remainder of the duplex first extension product remains in duplex form;

(g) extending the second capture primer by conducting a primer extension reaction that separates the remainder of the duplex first extension product and generates a duplex second extension product which is hybridized along the length of the second extension product;

(h) separating a portion of the second capture primer (e.g., that includes the low melting temperature sequence) from the hybridized first universal adaptor by local denaturation;

(i) re-hybridizing the first universal adaptor to another of the immobilized capture primers while the remainder of the duplex second extension product remains in duplex form; and (j) extending the immobilized capture primer by conducting a primer extension reaction that separates the remainder of the duplex second extension product and generates a duplex third extension product which is hybridized along the length of the third extension product. In some embodiments, steps (a)-(j) can be conducted under isothermal conditions. Examples of compositions and methods for nucleic acid template walking are found in U.S. published application Nos. 2012/0156728 and 2013/0203607.

In some embodiments, any tagged-target polynucleotides (including tagged amplicons) that have been generated according to the present teachings, can be attached to a solid support. For example, a recombinase-polymerase amplification (RPA) reaction can be conducted under aqueous conditions to attach the tagged target nucleic acids to any type of support including a substantially planar support (e.g., flowcell) or beads. Individual tagged target nucleic acids include at least one tag sequence and a first universal adaptor sequence at one end and at least another tag sequence and a second universal adaptor sequence at the other end. In some embodiments, the first and second adaptors have different sequences. In some embodiments, the first and/or second adaptor includes a universal sequencing primer sequence. In some embodiments, the first adaptor includes a universal amplification primer sequence that differs from the universal amplification sequence in the second adaptor. In some embodiments, at least two of the tagged-target nucleic acids have different target sequences. The population of tagged-target nucleic acids is rendered single-stranded. In a single reaction mixture (an aqueous reaction mixture), the single-stranded tagged-nucleic acids are reacted/contacted with: (i) a plurality of supports (e.g., beads) having a plurality of capture primers attached thereon, wherein the capture primers on the plurality of supports have the same sequence and can hybridize to the first universal adaptor sequence of the tagged nucleic acids; (ii) a plurality of soluble reverse primers that are identical to or can hybridize to the second universal adaptor sequence of the tagged nucleic acids; (iii) polymerase; and (iv) a plurality of nucleotides. In some embodiments, the single reaction mixture further includes a recombinase (e.g., T4 uvsX), and optionally accessory proteins, including recombinase loading factor (e.g., T4 uvsY) and/or single-stranded binding protein (T4 gp32). The single reaction mixture can be incubated under conditions suitable for conducting nucleic acid amplification. The recombinase and accessory proteins can mediate D-loop formation between the first universal adaptor sequence and the capture primer. The first universal adaptor sequence region of the single-stranded tagged-target nucleic acid hybridizes to one of the plurality of capture primers on the support (e.g., bead), and primer extension produces a captured primer extension product. A soluble reverse primer hybridizes to the second universal adaptor region of the captured primer extension product, and a primer extension reaction produces a reverse primer extension product. The recombinase and accessory proteins can mediate D-loop formation between the second universal adaptor sequence and the soluble reverse primer. The reverse primer extension product can dissociate (e.g., denature) from the captured primer extension product, and re-hybridize with a different capture primer on the same support (e.g., bead), for another primer extension reaction. Repeat cycles of the RPA-bead amplification reaction yields beads that are attached with multiple copies of the tagged-target nucleic acid to yield individual beads that are attached with substantially monoclonal copies of one tagged-target nucleic acid. Optionally, different beads are attached with copies of different tagged-target nucleic acids (e.g., polyclonality).

In some embodiments, the capture primers are attached to a support (e.g., planar-like support) and the recombinase-polymerase reaction is conducted in a manner similar to the RPA-bead method, where the aqueous single reaction mixture contacts the surface of the support having the attached capture primers, where the aqueous single reaction mixture contains template nucleic acids, fusion primers (or lacking fusion primers), reverse primers, polymerase, nucleotides, recombinase and accessory proteins.

Optionally, the RPA single reaction mixture also includes a forward fusion primer which serves as a splint molecule that can hybridize to a capture primer and the first universal adaptor sequence which is joined to the tagged nucleic acid. In embodiments using the forward fusion primer, the first universal adaptor sequence (which is joined to the target nucleic acid) can hybridize with a portion of the fusion primer, but the first adaptor lacks a sequence that can hybridize to the capture primer on the support (e.g., bead). In some embodiments, the fusion primer hybridizes to the first universal adaptor sequence, and a primer extension reaction yields a fusion primer extension product which includes a sequence that can hybridize to the capture primer on the support (e.g., bead). The soluble reverse primer hybridizes with the fusion primer extension product, and a primer extension reaction yields a reverse primer extension product. The reverse primer extension product can hybridize to one of the plurality of capture primers on the support (e.g., bead), and a primer extension reaction yields a capture primer extension product which is attached to the support (e.g., bead) and includes a sequence that is complementary to the reverse primer extension product.

In some embodiments, the RPA-bead method includes an water-and-oil emulsion, where droplets of the aqueous reaction mixture are surrounded by an immiscible fluid (e.g., oil) so that the aqueous droplets provide compartmentalized reaction mixtures containing: one or more beads that are attached with capture primers; template nucleic acids; fusion primers (or lacking fusion primers); reverse primers; polymerase; nucleotides; and recombinase and accessory proteins.

In some embodiments, cycles of an RPA reaction, using beads or a support, with or without an emulsion, can be conducted under isothermal amplification conditions. Examples of compositions and methods for recombinase-polymerase amplification (RPA) reactions are found in U.S. published application Nos. 2013/0225421 and 2014/0080717, and in U.S. Pat. Nos. 7,399,590, 7,666,598, 8,637,253, 8,809,021, and 9,057,097.

In some embodiments, any tagged-target polynucleotides (including tagged amplicons) that have been generated according to the present teachings, can be attached to a solid support. For example, an emulsion PCR reaction can be conducted to attach the tagged target nucleic acids to any type of support including particles or beads. Individual tagged target nucleic acids include at least one tag sequence and a first universal adaptor sequence at one end and at least another tag sequence and a second universal adaptor sequence at the other end. In some embodiments, the first and second adaptors have different sequences. In some embodiments, the first and/or second adaptor includes a universal sequencing primer sequence. In some embodiments, the first adaptor includes a universal amplification primer sequence that differs from the universal amplification sequence in the second adaptor. In some embodiments, at least two of the tagged-target nucleic acids have different target sequences.

The emPCR-bead method is conducted in an water-and-oil emulsion, where droplets of the aqueous reaction mixture are surrounded by an immiscible fluid (e.g., oil) so that individual aqueous droplets provide compartmentalized reaction mixtures containing: one or more beads that are attached with capture primers; template nucleic acids (e.g., tagged nucleic acids); fusion primers (or lacking fusion primers); reverse primers; polymerase; and nucleotides. Optionally, the tagged nucleic acids are diluted so that, individual aqueous droplets contain only one tagged nucleic acid molecule. The emulsion PCR reaction is conducted under thermocycling conditions to render the tagged-target nucleic acids single-stranded. During emulsion PCR, the single-stranded tagged-nucleic acids are reacted/contacted with: (i) a plurality of supports (e.g., beads) having a plurality of capture primers attached thereon, wherein the capture primers on the plurality of supports have the same sequence and can hybridize to the first universal adaptor sequence of the tagged nucleic acids; (ii) a plurality of soluble reverse primers that are identical to or can hybridize to the second universal adaptor sequence of the tagged nucleic acids; (iii) polymerase; and (iv) a plurality of nucleotides. The first universal adaptor sequence region of the single-stranded tagged-target nucleic acid hybridizes to one of the plurality of capture primers on the support (e.g., bead), and primer extension produces a captured primer extension product. A soluble reverse primer hybridizes to the second universal adaptor region of the captured primer extension product, and a primer extension reaction produces a reverse primer extension product. The reverse primer extension product can dissociate (e.g., denature) from the captured primer extension product, and re-hybridizes with a different capture primer on the same support (e.g., bead), for another primer extension reaction. Repeat cycles of the emPCR-bead amplification reaction yields beads that are attached with multiple copies of the tagged-target nucleic acid to yield individual beads that are attached with substantially monoclonal copies of one tagged-target nucleic acid. Optionally, different beads are attached with copies of different tagged-target nucleic acids (e.g., polyclonality). Upon completion of amplification, the emulsion droplets can be contacted with a breaking solution to rupture/break the droplet and release the beads that are attached with tagged nucleic acids.

Optionally, the emPCR-bead amplification reaction mixture also includes a forward fusion primer which serves as a splint molecule that can hybridize to a capture primer and the first universal adaptor sequence which is joined to the target nucleic acid. In embodiments using the forward fusion primer, the first universal adaptor sequence (which is joined to the tagged nucleic acid) can hybridize with a portion of the fusion primer, but the first adaptor lacks a sequence that can hybridize to the capture primer on the support (e.g., bead) therefor the tagged nucleic acid cannot bind the capture primer on the support. In some embodiments, the fusion primer hybridizes to the first universal adaptor sequence, and a primer extension reaction yields a fusion primer extension product which includes a sequence that can hybridize to the capture primer on the support (e.g., bead). The soluble reverse primer hybridizes with the fusion primer extension product, and a primer extension reaction yields a reverse primer extension product. The reverse primer extension product can hybridize to one of the plurality of capture primers on the support (e.g., bead), and a primer extension reaction yields a capture primer extension product which is attached to the support (e.g., bead) and includes a sequence that is complementary to the reverse primer extension product. Examples of compositions and methods for emPCR-bead amplification reactions may be found in U.S. Pat. Nos. 7,323,305; 7,638,276; 7,842,457; 8,012,690; 8,153,402; 8,158,359; 8,748,102; 8,765,380; and PCT published application No. WO 2012/138926.

In some embodiments, the disclosure relates generally to compositions, and related methods, systems, kits, apparatuses and computer-readable media, comprising a nucleic acid synthesis or nucleic acid amplification reaction (amplification condition) that can be conducted under thermo-cycling or isothermal conditions, or a combination of both types of conditions. For example, the amplification condition can include alternating between thermocycling and isothermal amplification conditions, in any order.

In some embodiments thermo-cycling amplification conditions comprise a nucleic acid amplification reaction mixture that is subjected to an elevated temperature for a period of time that is sufficient to denature at least about 30-95% of the double-stranded target nucleic acids, and then subjected to a lower temperature for a period of time that is sufficient to permit hybridization between the single-stranded target nucleic acids and any of the primers (e.g., capture primer, reverse solution-phase primer, or fusion primer). In some embodiments, the increase and decrease temperature cycle is repeated at least once.

In some embodiments isothermal amplification conditions comprise a nucleic acid amplification reaction mixture that is subjected to a temperature variation which is constrained within a limited range during at least some portion of the amplification, including for example a temperature variation is within about 20° C., or about 10° C., or about 5° C., or about 1-5° C., or about 0.1-1° C., or less than about 0.1° C.

In some embodiments, an isothermal nucleic acid amplification reaction can be conducted for about 2, 5, 10, 15, 20, 30, 40, 50, 60 or 120 minutes, or longer.

In some embodiments, an isothermal nucleic acid amplification reaction can be conducted at about 15-30° C., or about 30-45° C., or about 45-60° C., or about 60-75° C., or about 75-90° C., or about 90-93° C., or about 93-99° C.

In some embodiments, an isothermal amplification reaction mixture includes a recombinase (e.g., T4 uvsX), with or without recombinase accessory factors (e.g., T4 uvsY and/or gp32 protein).

In some embodiments, a sufficient number of the tagged-target nucleic acids (including amplicons thereof) can be sequenced (e.g., sampling) to ensure the probability that any target polynucleotide that is present in the plurality of tagged polynucleotides will be represented in a set of sequencing reads and can therefore be detected. To accomplish this goal, many thousands, many tens-of-thousands, or many millions of tagged amplicons need to be sequenced, which can optionally be achieved by employing a massively parallel sequencing procedure. The capability of sequencing many thousands, many tens-of-thousands, or many millions of tagged amplicons increases the probability to about 10-25%, or about 25-50%, or about 50-75%, or about 75-90%, or about 90-99.99%, that a tagged polynucleotide will be represented in a set of sequencing reads and can therefore be detected and analyzed.

In some embodiments, the disclosure relates generally to methods, and related compositions, systems, kits, apparatuses and computer-readable media, which further include a sequencing reaction. In some embodiments, any tagged-target nucleic acids (including amplicons thereof) that are prepared according to the present teachings can be sequenced.

In some embodiments, any type of sequencing platform can be employed, including massively parallel sequencing platforms or older versions of sequencing, such as: Sanger sequencing, sequencing by oligonucleotide probe ligation and detection (e.g., SOLiD™ from Life Technologies, WO 2006/084132), probe-anchor ligation sequencing (e.g., Complete Genomics or Polonator™), sequencing-by-synthesis (e.g., Genetic Analyzer™ and HiSeg™ from Illumina (Bentley 2006 Current Opinion Genetics & Development 16:545-552; and Bentley, et al., 2008 Nature 456:53-59; and U.S. Pat. No. 7,566,537)), pyrophosphate sequencing (e.g., Genome Sequencer FLX™ from 454 Life Sciences (U.S. Pat. Nos. 7,211,390, 7,244,559 and 7,264,929)), ion-sensitive sequencing (e.g., Personal Genome Machine (Ion PGM™) and Ion Proton™ Sequencer, both from Ion Torrent Systems, Inc.), and single molecule sequencing platforms (e.g., Heliscope™ from Helicos).

In some embodiments, a sequencing platform that employs sequence-by-synthesis includes attaching a plurality of tagged polynucleotides to a support (e.g., immobilized tagged polynucleotides). The tagged polynucleotides can include a universal capture sequence (e.g., universal amplification sequence), and the support can include capture primers attached thereon. The tagged polynucleotides can be attached to the support by binding the capture sequence of the tagged polynucleotide to the capture primer on the support. The plurality of tagged polynucleotides can be covalently attached to the support via the bridge amplification reaction described herein. The support can be a part of a flowcell, and the support includes a substantially planar surface, grooves or a plurality of wells (e.g., microwells or nanowells) arranged in an array. A sequencing reaction site includes any site on the support where a sequencing reaction is conducted. A plurality of sequencing reaction sites can be located at any location on the planar surface, on any region of the grooves, or within any of the wells. Sequencing primers can be hybridized to the plurality of immobilized tagged polynucleotides. An aqueous solution that contains one, two, three or four types of nucleotides (e.g., deoxyribose triphosphate nucleotides) can be flowed onto the plurality of immobilized tagged polynucleotides, and in the presence of a polymerase that binds the tagged polynucleotides and catalyzes nucleotide incorporation, the sequencing reaction begins. A nucleotide that is complementary to template strand is incorporated onto the primer, an optional wash step removes non-incorporated nucleotides, and the identity of the incorporated nucleotide is determined. In some embodiments, the nucleotides in the flow are attached to an optically-detectable label. For example, the different types of nucleotides (e.g., A, G, C and T) can be attached to a different label that differentiates one type of nucleotide from the other types. The optically-detectable label can be attached to the base of the nucleotides. The different types of nucleotides can also optionally be attached to a blocking moiety that confers the ability to inhibit or block further nucleotide incorporations (e.g., a terminator blocking moiety). The blocking moiety can be attached to the 2' or 3' sugar position. The linker that attaches the label to the base, and attaches the blocking moiety to the sugar, can be the same or different type of linker. After a nucleotide is incorporated, the identity of the incorporated nucleotide is determined by exposing the incorporated nucleotide with radiation energy (e.g., light) and the emitted signal from the label is detected. The optically-detectable label and/or the blocking moiety are removed from the incorporated nucleotide by reacting the linker with a cleaving agent. If the same type of linker is used to attach the label to the base and attach the blocking moiety to the sugar, then one type of cleaving agent can be used to remove the label and blocking moiety. If a different type of linker is used to attach the label to the base and attach the blocking moiety to the sugar, then two types of cleaving agent can be used to remove the label and blocking moiety. The next sequencing cycle begins by performing a subsequent nucleotide flow, and the washing, identifying, and linker cleaving steps are repeated. In some embodiments, the sequence-by-synthesis methods include those described by Illumina (U.S. Pat. Nos. 7,057,026; 7,566,537; 7,785,796; 8,158,346; 7,541,444; 7,057,026; 7,592,435; 7,414,116; 7,427,673 and 8,399,188) and described by Jingyu Ju (U.S. Pat. Nos. 7,713,698; 7,790,869; 8,088,575; 7,635,578; and 7,883,869) which are all expressly incorporated herein by reference as if set forth in full.

The tagged-target nucleic acid described herein can be detected or sequenced using a suitable electrical or optical detector. In some embodiments, any of the tagged-target nucleic acids (and amplicons thereof) that have been synthesized according to the present teachings can be sequenced or detected by any sequencing method or detection means, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrosequencing or pyrophosphate detection sequencing, capillary electrophoresis, gel electrophoresis, next-generation, massively parallel sequencing platforms, sequencing platforms that detect hydrogen ions or other sequencing by-products, and sequencing platforms that can detect single molecule sequencing platforms. In some embodiments, a sequencing reaction can be conducted using at least one sequencing primer that can hybridize to any portion of the tagged amplicons, including a nucleic acid adaptor (e.g., universal sequence) or a target polynucleotide sequence.

In some embodiments, the disclosure relates generally to methods, as well as related systems, compositions, kits and apparatuses, for conducting sequencing reaction on a support having one or more reaction sites coupled to a sensor.

In some embodiments, any tagged-target nucleic acid produced according to the present teachings can be detected for its presence in a detection system using any of the technology described herein. For example, an array using CMOS technology may be used to simply detect the presence of a specific nucleic acid sequence, such as through qPCR or dPCR. The presence of the nucleic acid sequence may be detected through non-optical (detecting reaction byproducts) or optical methods. The optical methods may include dye-labeled tags on the sequences or on any nucleotides hybridized to the sequence.

In some embodiments, any tagged-target nucleic acids produced according to the present teachings can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992). In addition detection may be based on a change in capacitance, impedance or conductivity or voltammetry.

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as “pH-based” or “ion-based” nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time or two or more different types, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion PGM™, Jon Proton™, and Ion S5sequencer (Ion Torrent™ Systems, Thermo Fisher Scientific).

In some embodiments, any tagged-target nucleic acids produced using the methods, systems, compositions or kits of the present teachings can be used as a substrate for a biological or chemical reaction that is detected and/or monitored by a sensor including a field-effect transistor (FET). In various embodiments the FET is a chemFET, FinFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20. A Fin Field Effect Transistor or "FinFET" is a type of non-planar or three-dimensional transistor. Additionally, a nanowire may be used either alone or in conjunction with the FET.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells. Exemplary embodiments of FET sensor arrays can be found in U.S. Pat. Nos. 7,948,015; 8,262,900; 8,776,573; 8,208,712.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET, FinFET, or an ISFET. The FET (FinFET or chemFET or ISFET) and/or reaction chamber can be an array of FETs or reaction chambers, respectively.

In some embodiments, a biological or chemical reaction can be carried out in a two-dimensional or three-dimensional array of reaction chambers, wherein each reaction chamber can be coupled to a FET, and each reaction chamber is no greater than 10 $\mu m^3$ (i.e., 1 μL) in volume. In some embodiments each reaction chamber is no greater than 0.34 μL, 0.096 μL or even 0.012 μL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion PGM™ or Ion Proton™, or Ion S5® sequencer (Ion Torrent™ Systems, Thermo Fisher Scientific).

In some embodiments, the disclosure relates generally to methods for sequencing any of the tagged amplicons produced by the teachings provided herein. In one exemplary embodiment, the disclosure relates generally to a method for obtaining sequence information from tagged amplicons, comprising: (a) generating tagged-target nucleic acids (or amplicons thereof); and (b) sequencing the tagged-target nucleic acids or amplicons by performing template-dependent nucleic acid synthesis using at least one of the tagged-target nucleic acids or amplicons produced during step (a) as a template. The amplifying can optionally be performed according to any of the amplification methods described herein.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a) attaching tagged-target nucleic acids to sequencing particles by amplifying the tagged-target nucleic acids in the presence of sequencing particles to generate at least one particle attached with a substantially monoclonal polynucleotide population containing a portion of one of the tagged-target nucleic acids, according to the teachings disclosed herein; and (b) disposing the particles into a reaction chambers, wherein one or more of the reaction chambers are in contact with a field effect transistor (FET). Optionally, the method further includes contacting the substantially monoclonal polynucleotide population, which are disposed into one of the reaction chambers, with a polymerase thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (ISFET) and chemically-sensitive FET (chemFET).

In some embodiments, the disclosure relates generally to methods (and related compositions, systems, kits and apparatuses) for nucleic acid sequencing, comprising identifying a series of contiguous nucleotides in a nucleic acid template according to any of the methods disclosed herein.

One exemplary system involving sequencing via detection of ionic byproducts of nucleotide incorporation is the Ion PGM™ or Ion Proton™ or Ion S5 ® sequencer (Ion Torrent System, Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion PGM™ Ion Proton™, or Ion S5@ sequencer detects the nucleotide incorporations by detecting the hydrogen ion byproducts of the nucleotide incorporations. The Ion PGM™, Ion Proton™, or Ion S5@ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Alternatively, one type of nucleotide can be flowed into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion PGM™ or Jon Proton™ or Ion S5™ or Ion S5XL™ sequencers can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the tagged-target nucleic acid templates, optionally bound to a polymerase, are distributed, deposited or positioned to different sites of the array. The sites of the array include primers and the methods can include hybridizing different templates to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the Ion PGM™, Ion Proton™, or Ion S5® sequencer. Example 3 provides one exemplary protocol for ion-based sequencing using the Ion PGM™ sequencer (Ion Torrent™ Systems, Thermo Fisher Scientific).

In some embodiments, a CMOS sensor can detect a nucleotide incorporation event, including detect nucleotide incorporation byproducts. In some embodiments, in addition to using CMOS technology to detect reaction byproducts, such as hydrogen ions, phosphate ions, pyrophosphate ions or phosphate chains, CMOS technology may be used as sensor to detect other measureable signals. For example, CMOS technology may be used to detect fluorescence, phosphorescence, luminescence, bio-luminescence. In some embodiments, the surface of the sensors may have receptors or may be treated with a surface treatment so that the sensor surface may attract and/or bind to any molecules being detected. The surface treatment may be used to improve the signal to noise ratio (SNR) of the system. In some embodiments, the sensors may be combined with nanowires.

In some embodiments, the disclosure relates generally to methods for sequencing a population of template polynucleotides, comprising: (a) generating a plurality of amplicons by clonally amplifying a plurality of target polynucleotides onto a plurality of particles, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal in nature. In some embodiments, a sufficient number of substantially monoclonal amplicons are produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the disclosure relates generally to compositions, as well as related systems, methods, kits, apparatuses and computer-readable media, comprising a tag, for example an oligonucleotide having a tag sequence. Optionally, the tag is a randomer tag.

In some embodiments, the disclosure relates generally to compositions, as well as related systems, methods, kits, apparatuses and computer-readable media, comprising a pair of tags. Optionally, the pair of tags includes a forward and reverse tag primer, or a left and a right tag adaptor. Optionally the pair of tags can be used in a primer extension reaction (e.g., a PCR reaction) or an enzymatic ligation reaction. Optionally, in the pair of tags, one or both are a randomer tag.

In some embodiments, the randomer tag comprises an oligonucleotide having a randomer tag which includes at least one random sequence (e.g., degenerate sequence) and at least one fixed sequence, or comprises a random sequence flanked on both sides by a fixed sequence, or comprises a fixed sequence flanked on both sides by a random sequence. In some embodiments, the randomer tag comprises an oligonucleotide having at least two random sequences alternating with at least two fixed sequences. In some embodiments, the randomer tag comprises 3 random sequences alternating with 3 fixed sequences, or 4 random sequences alternating with 4 fixed sequences. One skilled in the art will recognize that the randomer tag can include any number of random sequence units alternating with any number of fixed sequence units.

In some embodiments, the fixed sequence within the randomer tag comprises 1-20 or more nucleotides, or analogs thereof. In some embodiments, the random sequence within the randomer tag comprises 1-20 or more nucleotides, or analogs thereof. In some embodiments, each position within the random sequence of the randomer tag is a nucleotide selected from A, T, G, C, I, U, or analogs thereof.

In some embodiments, the tags (or randomer tags) are soluble tags (e.g., tags in solution) or the tags are attached to a support, including tags attached to a substantially planar support or bead support.

In some embodiments, the disclosure relates generally to compositions, as well as related systems, methods, kits, apparatuses and computer-readable media, comprising a plurality of tags. Optionally, the plurality of tags includes at least two randomer tags.

In some embodiments, the plurality of randomer tags comprise a plurality of oligonucleotides, where individual randomer tags include at least one random sequence (e.g., degenerate sequence) and at least one fixed sequence, or comprises a random sequence flanked on both sides by a fixed sequence, or comprises a fixed sequence flanked on both sides by a random sequence. Optionally, the randomer tag comprises an oligonucleotide having at least two random sequences alternating with at least two fixed sequences.

In some embodiments, one or more tags includes a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the disclosure relates generally to compositions, as well as related systems, methods, kits, apparatuses and computer-readable media, comprising a single-stranded or double-stranded primer containing at least one tag sequence. Optionally, the tag is a randomer tag. Optionally, the primer includes a target-specific sequence that can hybridize with at least a portion of a target polynucleotide. For example the target-specific sequence is located in the 3' region of the primer. Optionally, the primer includes an extendible 3' end, for example a terminal 3' OH. Optionally, the 5' region of the primer includes at least one tag (e.g., randomer tag). Optionally, the primer includes at least one barcode sequence, amplification primer sequence, sequencing primer sequence, capture primer sequence, or cleavable site.

In some embodiments, the disclosure relates generally to compositions, as well as related systems, methods, kits, apparatuses and computer-readable media, comprising a single-stranded or double-stranded adaptor containing at least one tag sequence (e.g., a tag adaptor). Optionally, the tag is a randomer tag.

Optionally, the double-stranded adaptor includes at least one blunt end. Optionally, the double-stranded adaptor includes at least one 5' or 3' overhang end. Optionally, the 5' or 3' overhang end can hybridize with a terminal region of at least one target polynucleotide.

Optionally, at least one end of the adaptor is ligatable to another nucleic acid (e.g., a target polynucleotide). Optionally, one strand of the adaptor includes a terminal 5' phosphate group. Optionally, one strand of the adaptor includes a terminal 3' OH group.

Optionally, the adaptor includes at least one barcode sequence, universal sequence, amplification primer sequence, sequencing primer sequence, capture primer sequence or cleavable site.

In some embodiments, any of the primers containing at least one tag (e.g., at least one randomer tags) include a gene-specific region in their 3' regions that can selectively hybridize to a portion of at least one target polynucleotide, where the target polynucleotide contains a mutation that is associated with cancer that are located in at least one of the genes selected from ABI1; ABL1; ABL2; ACSL3; ACSL6; AFF1; AFF3; AFF4; AKAP9; AKT1; AKT2; ALK; APC; ARHGAP26; ARHGEF12; ARID1A; ARNT; ASPSCR1; ASXL1; ATF1; ATIC; ATM; AXIN2; BAP1; BARD1; BCAR3; BCL10; BCL11A; BCL11B; BCL2; BCL3; BCL6; BCL7A; BCL9; BCR; BIRC3; BLM; BMPR1A; BRAF; BRCA1; BRCA2; BRD3; BRD4; BRIP1; BUB1B; CARD11; CARS; CASC5; CBFA2T3; CBFB; CBL; CBLB; CBLC; CCDC6; CCNB1IP1; CCND1; CCND2; CD74; CD79A; CDC73; CDH1; CDH11; CDK4; CDK6; CDKN2A; CDKN2B; CDKN2C; CDX2; CEBPA; CEP110; CHEK1; CHEK2; CHIC2; CHN1; CIC; CIITA; CLP1; CLTC; CLTCL1; COL1A1; CREB1; CREB3L2; CREBBP; CRTC1; CRTC3; CSF1R; CTNNB1; CXCR7; CYLD; CYTSB; DCLK3; DDB2; DDIT3; DDR2; DDX10; DDX5; DDX6; DEK; DGKG; DICERI; DNMT3A; EEF1B2, EGFR; EIF4A2; ELF4; ELL; ELN; EML4; EP300; EPS15; ERBB2; ERBB4; ERC1; ERCC2; ERCC3; ERCC4; ERCC5; ERG; ETV1; ETV4; ETV5; ETV6; EWSR1; EXT1; EXT2; EZH2; FAM123B; FANCA; FANCC; FANCD2; FANCE; FANCF; FANCG; FAS; FBXW7; FCRL4; FGFR1; FGFR1OP; FGFR2; FGFR3; FH; FIP1L1; FLCN; FLI1; FLT1; FLT3; FNBP1; FOXL2; FOXO1; FOXO3; FOXO4; FOXP1; FUS; GAS7; GATA1; GATA2; GATA3; GMPS; GNAQ; GNAS; GOLGA5; GOPC; GPC3; GPHNGPR124; HIP1; HIST1H4I; HLF; HNF1A; HNRNPA2B1; HOOK3; HOXA11; HOXA13; HOXA9; HOXC11; HOXC13; HOXD13; HRAS; HSP90AA1; HSP90AB1; IDH1; IDH2; IKZF1; IL2; IL21R; IL6ST; IRF4; ITGA10; ITGA9; ITK; JAK1; JAK2; JAK3; KDM5A; KDM5C; KDM6A; KDR; KDSR; KIAA1549; KIT; KLF6; KLK2; KRAS; KTN1; LASP1; LCK; LCP1; LHFP; LIFR; LMO2; LPP; MAF; MALT1; MAML2; MAP2K1; MAP2K4; MDM2; MDM4; MECOM; MEN1; MET; MITF; MKL1; MLH1; MLL; MLLT1; MLLT10; MLLT3; MLLT4; MLLT6; MN1; MPL; MRE11A; MSH2; MSH6; MSI2; MSN; MTCP1; MTOR; MUC1; MYB; MYC; MYCL1; MYCN; MYH11; MYH9; MYST3; MYST4; NACA; NBN; NBPF10, NCOA1; NCOA2; NCOA4; NEK9; NF1; NF2; NFE2L2; NFKB2; NIN; NKX2-1; NLRP1; NONO; NOTCH1; NOTCH2; NPM1;

NR4A3; NRAS; NSD1; NTRK1; NTRK3; NUMA1; NUP214; NUP98; OLIG2; OMD; PAFAH1B2; PALB2; PATZ1; PAX3; PAX5; PAX7; PAX8; PBRM1; PBX1; PCM1; PDE4DIP; PDGFB; PDGFRA; PDGFRB; PER1; PHOX2B; PICALM; PIK3CA; PIK3R1; PIM1; PLAG1; PML; PMS1; PMS2; POU2AF1; POU5F1; PPARG; PPP2R1A; PRCC; PRDM16; PRF1; RF19; PRKAR1A; PRRX1; PSIP1; PTCH1; PTEN; PTPN11; RABEP1; RAD50; RAD5IL1; RAF1; RANBP17; RAP1GDS1; RARA; RB1; RBM15; RECQL4; REL; RET; RHOH; RNF213; ROS1; RPN1; RPS6KA2; RSBN1L; RUNX1; RUNX1T1; SBDS; SDHAF2; SDHB; SETD2; SFPQ; SFRS3; SH3GL1; SLC6A18; SLC45A3; SMAD4; SMARCA4; SMARCB1; SMO; SOCS1; SRC; SRGAP3; SS18; SS18L1; STIL; STK11; STK36; SUFU; SYK; TAF15; TAF1L; TAL1; TAL2; TCF12; TCF3; TCL1A; TET1; TET2; TEX14; TFE3; TFEB; TFG; TFRC; THRAP3; TLX1; TLX3; TMPRSS2; TNFAIP3; TOP1; TP53; TPM3; TPM4; TPR; TRIM27; TRIM33; TRIP11; TSC1; TSC2; TSHR; USP6; VHL; WAS; WASH3P; WHSC1L1; WRN; WT1; XPA; XPC; ZBTB16; ZMYM2; ZNF331; ZNF384; and ZNF521.

In some embodiments, any of the primers containing at least one tag (e.g., at least one randomer tags) include a gene-specific region in their 3' regions that can selectively hybridize to a portion of at least one target polynucleotide, where the target polynucleotide contains a mutation that is associated with cancer that are located in at least one of the genes selected from ABL1; AKT1; ALK; APC; ATM; BRAF; CDH1; CDKN2A; CSF1R; CTNNB1; EGFR; ERBB2; ERBB4; FBXW7; FGFR1; FGFR2; FGFR3; FLT3; GNAS; HNF1A; HRAS; IDH1; JAK2; JAK3; KDR; KIT; KRAS; MAP2K1; MET; MLH1; MPL; NOTCH1; NPM1; NRAS; PIC3CA; PDGFRA; PIK3CA; PTEN; PTPN11; RB1; RET; ROS1, SMAD4; SMARCB1; SMO; SRC; STK11; TP53; and VHL.

In some embodiments, the disclosure relates generally to compositions, as well as related systems, methods, kits, apparatuses and computer-readable media, comprising a single-stranded or double-stranded polynucleotide appended to at least one tag, including tagged-nucleic acids. Optionally, the tag is a randomer tag. Optionally, the polynucleotide is appended at one end to a first randomer tag, and appended to the other end to a second randomer tag. Optionally, one or both ends further comprise at least one barcode tag.

In some embodiments, the disclosure relates generally to compositions, as well as related systems, methods, kits, apparatuses and computer-readable media, comprising a single reaction mixture containing (i) a plurality of polynucleotides including at least a first polynucleotide and a second polynucleotide, and (ii) a plurality of tags (e.g., randomer tags) including at least a first, second, third and fourth randomer tag. The plurality of tags comprises tagged-single-stranded primers or tagged-double-stranded adaptors.

In some embodiments, the plurality of polynucleotides comprises a mixture of different polynucleotides or polynucleotides having the same sequence. The plurality of polynucleotides includes target and non-target polynucleotides, or lack non-target polynucleotides.

In some embodiments, the plurality of randomer tags comprises a mixture of different randomer tags.

Optionally, the single reaction mixture further comprises any one or any combination of reagents for appending the randomer tags to the polynucleotides, including: ligase, ATP, polymerase (e.g., recombinant polymerase), nucleotides, and/or cations for enhancing a primer extension reaction (e.g., magnesium and/or manganese). Optionally, the single reaction mixture further comprises reagents for transposon-mediated insertion and fragmentation (e.g., tagmentation), including at least one transposome complex which includes a plurality of transposases and a plurality of transposon end sequences. Optionally, the single reaction mixture includes at least one polynucleotide appended to one or more randomer tags (e.g., at least one tagged polynucleotide). Optionally, the single reaction mixture includes at least one amplicon generated from a tagged polynucleotide.

In some embodiments, the disclosure relates generally to compositions, as well as related systems, methods, kits, apparatuses and computer-readable media, comprising one or more nucleic acid samples containing polynucleotides, for example a nucleic acid sample that includes a mixture of target and/or non-target polynucleotides. The polynucleotides in the nucleic sample can include DNA and/or RNA. The polynucleotides in the nucleic sample can include any one or any combination of single-stranded and/or double-stranded polynucleotides. The polynucleotides in the nucleic sample can include cDNA. The nucleic acid sample can originate from a biological sample, including a biological fluid, cell culture, solid tissue or solid tumor. The nucleic acid sample can originate from a single tube of drawn blood (e.g., approximately 7.5-10 mL). The nucleic acid sample can originate from multiple tubes of drawn blood that are pooled together as a source of polynucleotides to undergo a tag-appending reaction. The nucleic acid sample can originate from any organism including human, canine, feline, bovine, equine, murine, porcine, caprine, lupine, ranine, piscine, simian, ape, plant, insect, bacteria, virus or fungus. The nucleic acid sample can originate from water, soil or food.

In some embodiments, the nucleic acid sample can originate from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

In some embodiments, the nucleic acid sample originate from a biological sample, including a biological fluid obtained from blood, serum, plasma, saliva, sputum, sweat, tears, lavage fluid, amniotic fluid (e.g., from a pregnant female), cerebrospinal fluid, ascites, urine, stool, feces, semen and the like. For example, blood, serum and plasma include fractions or processed portions thereof. Optionally, the nucleic acid sample can be a formalin fixed paraffin-embedded (FFPE) sample, which contains polynucleotides.

In some embodiments, a biological sample includes a biological fluid or solid tissue obtained by biopsy, swab, needle biopsy (e.g., fine needle biopsy or fine needle aspirate), biopsy via microforceps, smear, or air borne nucleic acids. In some embodiments, the solid tissue includes healthy or diseased tissue (e.g., tumor) or fluid, or a mixture of healthy and diseased tissue or fluid.

In some embodiments, the nucleic acid sample originates from a biological sample that contains cells, bacteria, virus, fungus and/or cell-free nucleic acids or nucleic acids isolated from circulating tumor cell(s).

In some embodiments, the nucleic acid sample is isolated from the same source (e.g., the same subject) at different time points. For example, a nucleic acid sample is obtained from the same subject, tissue, tumor, cell or biological fluid at multiple time points. The nucleic acid sample is obtained at a different second, minute, hour, day, week, month, or year. The tumor includes any one or any combination of non-malignant, pre-malignant and/or malignant cells.

In some embodiments, the nucleic acid sample is isolated from a different source (e.g., different subjects) over different time points. For example, (1) at a first time point, a nucleic acid sample is obtained from a first subject, tissue, tumor, cell or biological fluid, and (2) at a second time point, a nucleic acid sample is obtained from a second subject, tissue, tumor, cell or biological fluid. At subsequent time points, additional nucleic acid samples can be obtained. The different time points include a different second, minute, hour, day, week, month, or year.

In some embodiments, the nucleic acid sample can undergo a separate processing step to extract the polynucleotides, and the extracted polynucleotides can be used to conduct a tag-appending reaction. Optionally, an optional enrichment step can be performed to remove the cellular debris. For example, cells contained within a biological fluid can be lysed to release the polynucleotides which are then enriched or purified to remove the cellular debris. In some embodiments, the nucleic acid sample can be used directly in a tag-appending reaction without any separate polynucleotide extraction step. For example, a nucleic acid sample (e.g., a biological fluid containing cells or cell-free nucleic acids) can be added directly to a reaction vessel along with various reagents for conducting any tag-appending and/or amplification step as described in the present teachings. Alternatively, cell-free nucleic acids can be extracted from a biological source and added to a reaction vessel along with various reagents for conducting any tag-appending and/or amplification step as described in the present teachings. In some embodiments, a separate cell lysis step is not practiced, or a lysis step is conducted prior to the tag-appending step.

In some embodiments, the nucleic acid sample can be a reference standard. For example, the reference standard is manufactured from engineered cell lines that are known to carry mutant sequences (e.g., cancer cell line) or from engineered cell lines that do not carry mutant sequences of interest, or the reference standard is manufactured from recombinant nucleic acids. Optionally, the reference standard is fragmented to an average size (e.g., about 160 bp) that is similar to the size of cfDNA extracted from a biological fluid (e.g., blood). One example of a reference standard is commercially-available from Horizon Diagnostics (Cambridge, United Kingdom).

In some embodiments, the disclosure relates generally to compositions, as well as related systems, methods, kits, apparatuses and computer-readable media, comprising a plurality of polynucleotides. The plurality of polynucleotides can include single-stranded or double-stranded polynucleotides, or a mixture of both. The plurality of polynucleotides can include cDNA. The plurality of polynucleotides comprise DNA, cfDNA (e.g., cell-free DNA), ctDNA (e.g., circulating tumor DNA), cfRNA (cell-free RNA), cDNA (e.g., copy DNA synthesized from RNA), RNA, RNA/DNA, or nucleic acid analogs. The plurality of polynucleotides comprises mRNA, miRNA, rRNA, tRNA or a mixture of any of these nucleic acids (e.g., a mixture of RNA and DNA). The plurality of polynucleotides can include polynucleotides having the same sequence or a mixture of different sequences. The plurality of polynucleotides can include polynucleotides having the same or different lengths. The plurality of polynucleotides can include about 2-10, or about 10-50, or about 50-100, or about 100-500, or about 500-1,000, or about 1,000-5,000, or about $10^3$-$10^6$, or about $10^6$-$10^{10}$ or more polynucleotide molecules. The plurality of polynucleotides comprises polymers of deoxyribonucleotides, ribonucleotides, and/or analogs thereof. The plurality of polynucleotides comprise naturally-occurring, synthetic, recombinant, cloned, fragmented, un-fragmented, amplified, unamplified or archived (e.g., preserved) forms. The plurality of polynucleotides can be randomly fragmented using enzymatic, chemical or mechanical procedures (e.g., mechanical shearing, sonication, nebulization, or acoustics). Fragmentation can be predetermined using any one or a combination of different restriction endonucleases. Fragmentation of the plurality of polynucleotides can be random using a nick translation reaction which employs one or more enzymes that couple nucleic acid nicking and nick translating activities in the presence of nucleotides that lack a detectable moiety, or in the presence of labeled nucleotides. In some embodiments, nick translation conditions conducted according to the present teachings produce unlabeled nucleic acid fragments (U.S. 2012/0301926, Chen). For example, the present teachings can include nick translation conditions comprising a nicking enzyme (e.g., DNase I) and a polymerase having 5'→3' degradation/polymerization activity, or can include a nicking enzyme (e.g., DNase I) and a polymerase having 5'→3' strand displacing activity (e.g., Taq polymerase). A nick translation reaction according to the present teachings can further include one or more unlabeled nucleotides (e.g., dATP, dTTP, dCTP, dGTP, dUTP, or analogs thereof). A nick translation reaction can include a cation, such as magnesium, manganese or calcium. The nick translation reaction can include at least one single-stranded binding protein, including phage T4 gp 32 protein, *Sulfolobus solfataricus* single-stranded binding protein, *Methanococcus jannaschii* single-stranded binding protein, or *E. coli* single-stranded binding protein. Fragment sizes can be about 20-10,000 base-pairs in length.

In some embodiments, the disclosure relates generally to compositions, as well as related systems, methods, kits, apparatuses and computer-readable media, comprising a plurality of polynucleotides that include target and non-target polynucleotides, or lacks non-target polynucleotides. For example, a target polynucleotide is a polynucleotide-of-interest, and a non-target polynucleotide is a polynucleotide not-of-interest. The plurality of polynucleotides can include at least one group of target polynucleotides which contain a target polynucleotide and its related variants. For example, the group of target polynucleotides can include a target polynucleotide which is a wild-type form and its related polymorphic forms, which can include variant, allelic and/or mutant forms. The related variant forms contain at least one genetic point mutation, insertion, deletion, substitution, inversion, rearrangement, splice, sequence fusion (e.g., gene fusion or RNA fusion), truncation, transversion, translocation, non-sense mutation, sequence repeat, single nucleotide polymorphism (SNP), or other genetic rearrangement. The mutant or variant sequences also include copy number variation, aneuploidy, partial aneuploidy, or polyploidy.

In some embodiments, the disclosure relates generally to compositions, as well as related systems, methods, kits, apparatuses and computer-readable media, comprising a tag which can be appended to a polynucleotide. In some embodiments, a tag comprises an oligonucleotide, including a single-stranded or double-stranded oligonucleotide.

In some embodiments, the disclosure relates generally to compositions, as well as related systems, methods, kits, apparatuses and computer-readable media, comprising a plurality of tags which can be appended to a plurality of polynucleotides. The different tags in the plurality of tags can have the same characteristics or different characteristics.

The tag can include characteristics, including a sequence, length and/or detectable moiety, or any other characteristic that identifies the polynucleotide molecule to which it is appended.

For example, the tag (e.g., having a unique tag sequence) can uniquely identify an individual polynucleotide to which it is appended, and distinguish the individual polynucleotide from other tagged polynucleotides in a mixture.

In another example, the tag (e.g., having a sample-specific sequence or a sample-specific barcode sequence) that is appended to multiple polynucleotides can identify the polynucleotides derived from a common sample or source. In some embodiments, substantially all of the tagged molecules in a single reaction mixture can be appended with the same barcode sequence.

The tag can be appended to a double-stranded polynucleotide to identify one or both of the strands.

In some embodiments, the junction sequence of a tagged polynucleotide can be used to identify the polynucleotide. For example, a junction sequence that contains at least a portion of the tag (e.g., a unique tag or sample-specific tag) and a portion of the polynucleotide (e.g., an endogenous polynucleotide sequence) that is juxtaposed to the tag, can be used to identify the polynucleotide. The junction sequence can include a portion of the tag and at least 2-20, or about 20-50, or about 50-100 or more nucleotides of the polynucleotide. Optionally, one or both ends of a polynucleotide are appended to one or more tags. Optionally, one or both junction sequences can be used to identify the polynucleotide.

In some embodiments, the tags comprise DNA, RNA or both DNA and RNA, or analogs thereof. The tags comprise a single-stranded or double-stranded nucleic acid, or analog thereof. The tags can be naturally-occurring, synthetic, recombinant forms.

For tags that include both DNA and RNA, the 5' end of the tags is RNA or DNA. For tags that include both DNA and RNA, the 3' end of the tags is RNA or DNA.

In some embodiments, at least one end of a double-stranded tag is a blunt end or an overhang end, including a 5' or 3' overhang end.

The tags can be any length, including 2-2000 nucleotides or base-pairs, or 2-1000 nucleotides or base-pairs, or 2-100 nucleotides or base-pairs, or 2-75 nucleotides or base-pairs, or 2-50 nucleotides or base-pairs, or 2-25 nucleotides or base-pairs, or 2-10 nucleotides or base-pairs. The tag can be about 100-200 nucleotides or longer.

In some embodiments, a plurality of tags includes tags having the same or different lengths.

In some embodiments, a plurality of tags includes tags having the same or different sequences.

In some embodiments, a plurality of tags includes tags having the same or different detectable moieties.

Optionally, a tag can include a nucleotide analog or linkage between nucleotides that render the tag resistant to a nuclease. Optionally, the tag includes at least one phosphorothiolate, phosphorothioate, and/or phosphoramidate linkage.

Optionally, a tag includes moiety includes a blocking group attached to the 2' or 3' sugar group of a nucleotide, where the blocking group inhibits nucleotide incorporation.

Optionally, the 3' end of a tag can include a 3'OH.

Optionally, the 5' end of a tag can include a phosphate group.

Optionally, a tag can be biotinylated at either end or any internal location within the tag.

Optionally, a tag can include a cleavage site, including a restriction endonuclease sequence, a nicking enzyme sequence, a type IIs sequence, or at least one uracil base. For example, a tag containing at least one uracil base is cleavable with uracil DNA glycosylase (UDG) and formamidopyrimidine DNA glycosylase (Fpg).

Optionally, a tag can include at least one unique tag sequence, at least one barcode sequence (e.g., a sample-specific tag sequence), at least one universal sequence which includes an amplification primer sequence, a sequencing primer sequence, cleavable site and/or a sequence for grafting to a support (e.g., capture primer sequence).

In some embodiments, a tag is not substantially self-hybridizing so it does not easily form a hairpin, stem-loop, or circular structure.

In some embodiments, a tag is a linear nucleic acid molecule.

In some embodiments, a tag is self-hybridizing so it can form a hairpin, stem-loop, or circular structure.

In some embodiments, the tag can be part of an amplification or sequencing primer, or part of an adaptor, or a tag can be a separate nucleic acid.

In some embodiments, the tag can be synthesized using recombinant or chemical-synthesis technology, or by combinatorial synthesis methodology.

Optionally, a mixture of different tags can be made by hand-mixing or machine-mixing different batches of tags.

In some embodiments, at least one tag can be appended to a linear or circular polynucleotide molecule.

A tag can be inserted into an interior region of a polynucleotide, or appended to one or both ends of a polynucleotide.

In some embodiments, the sequence of a tag can be designed to hybridize to a portion of a polynucleotide, or exhibit minimal hybridization to a polynucleotide. Optionally, a tag does not substantially hybridize with any polynucleotide sequence.

In some embodiments, a set of tags (e.g., a repertoire of tags) can include a plurality of tags having the same sequence, or at least two of the tags in the set contain different sequences.

In some embodiments, a set of tags includes about 1-4 unique tags, or 4-100 unique tags, or 100-500 unique tags, or 500-1000 unique tags, or 1000-5000 unique tags, or 5000-10,000 unique tags, or more than 10,000 unique tags.

In some embodiments, a set of tags include about $10^5$ or $10^6$ or $10^7$ or $10^8$ or $10^9$ or $10^{10}$ or $10^{11}$ or $10^{12}$ more unique tags.

In some embodiments, a set of tags can detect the presence of 5-100, or 100-200, or 200-300, or 300-400, or 400-500 or more different target polynucleotides in the nucleic acid sample.

The set of tags can include a plurality of tags having the same length, or at least two of the tags in the set have different lengths.

At least two tags within a set are distinguishable from each other by their sequence, length and/or detectable moieties.

At least two tags within a set have melting temperatures that are substantially the same, where the melting temperatures are within about 10-5° C. of each other, or within about 5-2° C. of each other, or within about 2-0.5° C. of each other, or less than about 0.5° C. of each other.

At least one tag, in a set of tags, is labeled with a detectable moiety, or all tags in a set are unlabeled.

At least two of the tags in a set exhibit minimal cross-hybridization.

At least one tag, in a set of tags, contains at least 1, 2, 3 or 4 bases that differ from another tag in the set.

In some embodiments, the disclosure relates generally to compositions, as well as related systems, methods, kits, apparatuses and computer-readable media, comprising a tag which is a randomer tag that can be appended to a polynucleotide.

In some embodiments, the disclosure relates generally to compositions, as well as related systems, methods, kits, apparatuses and computer-readable media, comprising a plurality of tags which are randomer tags that can be appended to a plurality of polynucleotides. The different randomer tags in the plurality of randomer tags can have the same characteristics or different characteristics.

In some embodiments, a tag containing at least one random sequence is a randomer tag.

In some embodiments, the randomer tag includes at least one random sequence and at least one fixed sequence, or comprises a random sequence flanked on both sides by a fixed sequence, or comprises a fixed sequence flanked on both sides by a random sequence. In some embodiments, the randomer tag comprises an oligonucleotide having at least two random sequences alternating with at least two fixed sequences. In some embodiments, the randomer tag comprises 2 random sequences alternating with 2 fixed sequences, or the randomer tag comprises 3 random sequences alternating with 3 fixed sequences, or 4 random sequences alternating with 4 fixed sequences. One skilled in the art will recognize that the randomer tag can include any number of units having a random sequence alternating with any number of units having a fixed sequence.

In some embodiments, a randomer tag that contains a unit of 3 nucleotides that encodes an amino acid, or encodes a stop codon, or does not encode an amino acid or a stop codon.

The randomer tag can include a fixed sequence that is 2-2000 nucleotides or base-pairs, or 2-1000 nucleotides or base-pairs, or 2-100 nucleotides or base-pairs, or 2-75 nucleotides or base-pairs, or 2-50 nucleotides or base-pairs, or 2-25 nucleotides or base-pairs, or 2-10 nucleotides or base-pairs in length.

The randomer tag can include a random sequence that is 2-2000 nucleotides or base-pairs, or 2-1000 nucleotides or base-pairs, or 2-100 nucleotides or base-pairs, or 2-75 nucleotides or base-pairs, or 2-50 nucleotides or base-pairs, or 2-25 nucleotides or base-pairs, or 2-10 nucleotides or base-pairs in length.

The randomer tag can include at least one random sequence interspersed with fixed sequences.

In some embodiments, the randomer tag comprises the structure $(N)_n(X)_x(M)_m(Y)_y$, and (i) wherein "N" represents a random tag sequence that is generated from A, G, C, T, U or I, and wherein "n" is 2-10 which represents the nucleotide length of the "N" random tag sequence; (ii) wherein "X" represents a fixed tag sequence, and wherein "x" is 2-10 which represents the nucleotide length of the "X" random tag sequence; (iii) wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and (iv) wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of the single stranded primers are sequence alignment anchors.

The random sequence within a randomer tag is represented by "N", and the fixed sequence is represented by "X". Thus, a randomer tag can be represented by $N_1N_2N_3X_1X_2X_3$ or by $N_1N_2N_3X_1X_2X_3N_4N_5N_6$ or by $N_1N_2N_3X_1X_2X_3$ $N_4N_5N_6X_4X_5X_6$ or by $N_1N_2N_3X_1X_2X_3N_4N_5N_6X_4$ $X_5X_6N_7N_8N_9$. These are not intended to represent limiting examples of a randomer tag, as the skilled artisan will recognize that many other structures are possible. The randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. The randomer tag can have a random sequence in which some or all of the nucleotide positions can be randomly selected from a subset (e.g., a constrained set) of A, G, C, T, U or I. For example, a nucleotide for each position within a random sequence can be independently selected from a subset containing any two nucleotides selected from A, G, C, T, U and I. A nucleotide for each position within a random tag sequence can be independently selected from a subset containing any three, four or five nucleotides selected from A, G, C, T, U and I. Non-limiting examples of subsets of two nucleotides include C and T, or A and G. One skilled in the art will recognize that many other subsets are possible. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of single-stranded tag primers are sequence alignment anchors.

By generating a large number of unique randomer tags, it is possible to increase the probability that a substantial percentage of the polynucleotides (or target polynucleotides) in a nucleic acid sample will be appended with at least one randomer tag. The presence of one random sequence within a randomer tag serves to increase the number of possible unique randomer tags. It follows that the presence of more than one random sequence further increases the diversity of a repertoire of randomer tags. The number of possible unique randomer tags will be dictated by the length of the random sequence and the number of possible different nucleotide bases that can be used to generate the random sequence, along with the length of the fixed sequence. For example, a 12-mer randomer tag having the sequence 5'-NNNACTNNNTGA-3' (SEQ ID NO:1), where "N" represents a position within the random sequence that is generated randomly from A, G, C or T, the number of possible distinct randomer tags is calculated to be $4^6$ (or 4^6) is about 4096, and the number of possible different combinations of two randomer tags is $4^{12}$ (or 4^12) is about 16.78 million. In some embodiment, the underlined portions of 5'-NNNACTNNNTGA-3' (SEQ ID NO:1) are a sequence alignment anchor.

In some embodiments, different randomer tags can include at least one fixed sequence that is the same or different among the different randomer tags.

In some embodiments, different randomer tags can include at least one fixed sequence having the same or different length among the different randomer tags.

There are several advantages to using randomer tags that are designed to contain random sequences interspersed with fixed sequences. For example, the fixed sequences can be designed to contain certain sequences, length and spacing the will reduce primer-primer interaction and/or primer dimer formation during the primer extension or amplification steps. Optionally, a randomer tag having a short fixed length, 2-10 nucleotides in length, may reduce primer-primer interaction and/or primer dimer formation during the primer extension or amplification steps.

In another example, the random sequences that are disperse among the fixed sequences will increase the diversity of a set of randomer tags while maintaining a short overall length of the randomer tag, which will require less time and reagents for sequencing through the randomer tag region but will still deliver the sequencing information that will be used to generate error-corrected sequencing data.

An advantage of performing a molecular tagging procedure using randomer tags that contain alternating unit sequences of fixed and random sequences, is that the randomer tag sequence can be used for error-correction of the sequencing reads (e.g., error-correction of a family of sequencing reads). For example, the candidate sequencing reads can be grouped into families based on a common randomer tag sequence. The fixed sequences within the randomer tag sequences can be used as a sequence alignment anchor to impose a strict requirement that all members of any given tag family must contain the length, sequence and spacing that is identical to a reference sequence of the fixed sequences. The candidate sequencing reads that do not meet this requirement may be removed from further analysis. For example, in a reference randomer tag having the sequence 5'-NNNACTNNNTGA-3' (SEQ ID NO:1), the length, sequence and spacing of the two fixed sequences 5'-ACT-3' and 5'-TGA-3' can be used as sequence alignment anchors for comparison with the tag sequence portion of a candidate sequencing read. If the tag sequence portion of the candidate sequencing read does not match the length, sequence and spacing of the two fixed sequences, then the candidate sequencing read may be discarded. This type of comparison with a randomer tag sequence, and decision to retain or discard a sequencing read, can be applied to any candidate sequencing read. The candidate sequencing reads that do not carry a match for the fixed sequences will likely correspond to polynucleotide products of primer extension or amplification having spurious errors that are introduced by polymerase-mediated nucleotide mis-incorporation or strand slippage. Strand slippage may result from secondary structure formation (e.g., loop formation) of the nascent strand or the template strand during primer extension. Thus, the fixed sequences within the randomer tag sequence can serve as a sequence alignment anchor that is used to generate error-corrected sequencing data, including generating a family of error-corrected sequencing reads. A molecular tagging procedure which uses tags that lack alternating fixed and random sequences cannot identify sequencing reads carrying errors in the tag region, and therefore cannot generate error-corrected sequencing data in this manner.

In some embodiments, the reference sequence of a randomer tag is used to correct the sequence of a randomer tag in a candidate sequencing read. For example, if a candidate sequencing read shows that a randomer tag sequence is 5'-NNNACTNNNTGC-3' (SEQ ID NO:2), and the reference sequence is known to be 5'-NNNACTNNNTGA-3' (SEQ ID NO:1), then an error-correction algorithm would be applied to change the erroneous base from C to A, to yield an error-corrected sequencing read which is 5'-NNNACTNNNTGA-3' (SEQ ID NO:1). In some embodiments, the randomer tag sequence is not used to correct any sequencing read, but instead, the candidate sequencing read that contains an error (e.g., an error in the randomer tag sequence) is discarded.

Another advantage of using randomer tags having more than one unit of a random sequence, is that a population of randomer tags will provide enough sequence diversity to serve as a substantially non-depleting population of unique tag sequences. The presence of more than one random sequence increases the diversity of a repertoire of randomer tag sequences. The number of possible unique randomer tags will be dictated by the length of the random sequence and the number of possible different nucleotide bases that can be used to generate the random sequence, along with the length of the fixed sequence. Additionally, the overall length of a randomer tag, which contains alternating fixed/random sequences, can be minimized to reduce the amount of time and reagents needed to sequence one or both tags and the target sequence, while enabling error-corrected sequencing data.

In some embodiments, the disclosure relates generally to compositions, as well as related systems, methods, kits, apparatuses and computer-readable media, comprising one or more primers containing at least one tag (e.g., at least one randomer tag).

In some embodiments, the primer comprises an oligonucleotide containing DNA, RNA both DNA and RNA, or analogs there. Optionally, the primer is single-stranded or double-stranded. Optionally, the primer can be naturally-occurring or synthesized using chemical synthesis or recombinant procedures. Optionally, the primer includes an extendible 3' end or a non-extendible 3' end, where the terminal nucleotide at the non-extendible end carries a blocking moiety at the 2' or 3' sugar position.

In some embodiments, the primer can include a region that can selectively hybridize to a portion of the polynucleotide (e.g., a target-specific sequence in the 3' region of the primer). The primer can also include a region that is designed to exhibit minimal hybridization to a portion of the polynucleotide (e.g., a non-target specific sequence in the 5' region of the primer). For example, the primer can be a tailed primer. The primer can include at least one tag in the 5' tail region.

In some embodiments, a pair of primers includes a forward and a reverse primer that can be used in an amplification reaction (e.g., PCR). For example, a first primer (e.g., the forward primer) in the pair of primers can hybridize to a first position of a polynucleotide, and a second primer (e.g., the reverse primer) in the same pair of primers can hybridize to a second position of the same polynucleotide (or complementary strand), so that the first and second primers are separated by about 10-500 base pairs, or about 10-2000 base pairs, or about 2000-5000 base pairs, or about 5000-10,000 base pairs, or longer separation distances of a polynucleotide in its double-stranded form. These embodiments are applicable to a second pair of primers that includes a third primer (e.g., forward primer) and fourth primer (e.g., reverse primer).

In some embodiments, the first and second primers in any given pair of primers can hybridize to a polynucleotide so that the location of their hybridization positions will flank a target region of the polynucleotide.

In some embodiments, a first and/or second pair of primers (e.g., tailed primers) can be used in a primer extension reaction to generate polynucleotides appended with at least one tag. Optionally, the primer extension reactions can be conducted under isothermal or thermo-cycling conditions, or a combination of isothermal and thermo-cycling conditions.

In some embodiments, the extension products from the primer extension reaction are about 10-2000 nucleotides, or about 2000-5000 nucleotides, or about 5000-10,000 nucleotides in length.

In some embodiments, the primer extension reaction can be performed on DNA, RNA or a mixture of DNA and RNA, using forward and reverse primers (e.g., tailed primers) that can selectively hybridize to a region of a target polynucleotide (e.g., target DNA or RNA polynucleotide) to generate tagged amplicons that span an intron, exon, junction intron-exon, coding, non-coding, or fusion sequences.

In some embodiments, the disclosure relates generally to compositions, as well as related systems, methods, kits, apparatuses and computer-readable media, comprising at least one adaptor.

In some embodiments, the disclosure relates generally to compositions, as well as related systems, methods, kits, apparatuses and computer-readable media, comprising at least one adaptor appended to a polynucleotide.

In some embodiments, the adaptor can include at least one tag (e.g., at least one randomer tag).

In some embodiments, the polynucleotides are joined or appended to at least one adaptor, or lack any adaptor. In some embodiments, one or more adaptors can be joined to the polynucleotide by ligation.

In some embodiments, the adaptor comprises a nucleic acid, including DNA, RNA, RNA/DNA molecules, or analogs thereof. In some embodiments, the adaptor can include one or more deoxyribonucleoside or ribonucleoside residues. In some embodiments, the adaptor can be single-stranded or double-stranded nucleic acids, or can include single-stranded and/or double-stranded portions. In some embodiments, the adaptor can have any structure, including linear, hairpin, forked (Y-shaped), or stem-loop. For example, Y-shaped adaptors can include a first oligonucleotide having one end portion hybridized to an end portion of a second oligonucleotide to form a duplex stem portion, and the other end portions of the first and second oligonucleotides are not hybridized to each other. Examples of Y-shaped adaptors include U.S. Pat. No. 8,563,478 (Gormley), U.S. Pat. No. 8,053,192 (Bignell), U.S. Pat. No. 7,741,463 (Gormley), U.S. Pat. No. 8,182,989 (Bignell), U.S. Pat. No. 6,287,825 (Weissman), U.S. Pat. No. 8,420,319 (Mikawa) and U.S. Pat. No. 7,993,842 (McKernan)

Optionally, a linear, hairpin, stem-looped, or Y-shaped adaptor contains at least one tag sequence (e.g., at least one randomer tag sequence). For example the stem portion of the hairpin, stem-looped or Y-shaped adaptor contains at least one tag (e.g., at least one randomer tag). Examples of Y-shaped adaptors used for molecular tagging methods can be found in U.S Application Publication Nos. 2015/0044687; 2015/0031559; 2014/0155274; 2014/0227705; and International Publication Nos. WO 2013/181170 and WO 2015/100427.

In some embodiments, the adaptor can have any length, including fewer than 10 bases in length, or about 10-20 bases in length, or about 20-50 bases in length, or about 50-100 bases in length, or longer.

In some embodiments, the adaptor can have any combination of blunt end(s) and/or sticky end(s). In some embodiments, at least one end of the adaptor can be compatible with at least one end of a nucleic acid fragment. In some embodiments, a compatible end of the adaptor can be joined to a compatible end of a nucleic acid fragment. In some embodiments, the adaptor can have a 5' or 3' overhang end.

In some embodiments, the adaptor can have a 5' or 3' overhang tail. In some embodiments, the tail can be any length, including 1-50 or more nucleotides in length.

In some embodiments, the adaptor can include an internal nick. In some embodiments, the adaptor can have at least one strand that lacks a terminal 5' phosphate residue. In some embodiments, the adaptor lacking a terminal 5' phosphate residue can be joined to a nucleic acid fragment to introduce a nick at the junction between the adaptor and the nucleic acid fragment.

In some embodiments, the adaptor can include a nucleotide sequence that is identical or complementary to any portion of the polynucleotide, capture primer, fusion primer, solution-phase primer, amplification primer, or a sequencing primer.

In some embodiments, the adaptor can include an oligo-dA, oligo-dT, oligo-dC, oligo-dG or oligo-U sequences.

In some embodiments, the adaptor can include a unique identifier sequence (e.g., barcode sequence). In some embodiments, a plurality of barcoded adaptors (e.g., plurality of different barcoded adaptors) can be used for constructing a multiplex library of polynucleotides. In some embodiments, the barcoded adaptors can be appended to a polynucleotide and used for sorting or tracking the source of the polynucleotide. For example, a population of polynucleotides can be appended to a common barcoded adaptor which identifies the polynucleotides as being obtained from a common source. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, the adaptor can include degenerate sequences. In some embodiments, the adaptor can include one or more inosine residues.

In some embodiments, the adaptor can include at least one scissile linkage. In some embodiments, the scissile linkage can be susceptible to cleavage or degradation by an enzyme or chemical compound. Optionally, the adaptor includes at least one uracil base. In some embodiments, the adaptor can include at least one phosphorothiolate, phosphorothioate, and/or phosphoramidate linkage. For example, a tag containing at least one uracil base is cleavable with uracil DNA glycosylase (UDG) and formamidopyrimidine DNA glycosylase (Fpg).

In some embodiments, the adaptor can include any type of restriction enzyme recognition sequence, including type I, type II, type IIs, type IIB, type III, type IV restriction enzyme recognition sequences, or recognition sequences having palindromic or non-palindromic recognition sequences.

In some embodiments, the adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, any primer (e.g., tailed primer) or adaptor can be compatible for use in any type of sequencing platform including chemical degradation, chain-termination, sequence-by-synthesis, pyrophosphate, massively parallel, ion-sensitive, and single molecule platforms. In some embodiments, any primer or adaptor can be compatible for use in any type of sequencing procedure including: sequencing by oligonucleotide probe ligation and detection (e.g., SOLiD™ from Life Technologies, WO 2006/084132), probe-anchor ligation sequencing (e.g., Complete Genomics or Polonator™), sequence-by-synthesis (e.g., Illumina's Genetic Analyzer™ or HiSeq™, see also Bentley 2006 Current Opinion Genetics & Development 16:545-552; and Bentley, et al., 2008 Nature 456:53-59; and U.S. Pat. No. 7,566,537), pyrophosphate sequencing (e.g., Genome Sequencer FLX™ from 454 Life Sciences, see also U.S. Pat. Nos. 7,211,390, 7,244,559 and 7,264,929454 Life Sciences), ion-sensitive sequencing (e.g., Personal Genome Machine (Ion PGM™) and Ion Proton™ Sequencer, both from Ion Torrent Systems, Inc.) and single molecule sequencing platforms (e.g., Heliscope™ from Helicos). For example, any primer or adaptor can be used to graft a polynucleotide to a support (e.g., bead, flowcell or array of reaction sites) that is used for conducting a sequencing reaction.

In some embodiments, the disclosure relates generally to compositions, as well as related systems, methods, kits, apparatuses and computer-readable media, comprising one or more polymerases. In some embodiments, the compositions (and related methods, systems, kits, apparatuses and computer-readable media) includes one type, or a mixture of different types of polymerases. In some embodiments, the polymerase includes any enzyme, or fragment or subunit of thereof, that can catalyze polymerization of nucleotides and/or nucleotide analogs. In some embodiments, the polymerase requires a nucleic acid having an extendible 3' end. For example, the polymerase can require a terminal 3' OH of a nucleic acid primer to initiate nucleotide polymerization.

The polymerase comprises any enzyme that can catalyze the polymerization of nucleotides (including analogs thereof) into a nucleic acid strand. Typically but not necessarily such nucleotide polymerization can occur in a template-dependent fashion. In some embodiments, the polymerase can be a high fidelity polymerase. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. Typically, the polymerase comprises one or more active sites at which nucleotide binding and/or catalysis of nucleotide polymerization can occur. In some embodiments, the polymerase includes or lacks other enzymatic activities, such as for example, 3' to 5' exonuclease activity or 5' to 3' exonuclease activity. In some embodiments, the polymerase can be isolated from a cell, or generated using recombinant DNA technology or chemical synthesis methods. In some embodiments, the polymerase can be expressed in prokaryote, eukaryote, viral, or phage organisms. In some embodiments, the polymerase can be post-translationally modified proteins or fragments thereof.

In some embodiments, the polymerase can be a DNA polymerase and include without limitation bacterial DNA polymerases, eukaryotic DNA polymerases, archaeal DNA polymerases, viral DNA polymerases and phage DNA polymerases.

In some embodiments, the polymerase can be a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, the polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase. In some embodiments, a reaction mixture that includes a polymerase (e.g., T7 polymerase) can also include thioredoxin.

In some embodiments, the polymerase comprises a heat-stable or heat-labile polymerase. In some embodiments, the polymerase comprises a low fidelity or high fidelity polymerase.

In some embodiment, the polymerase can lack 5'-3' exonuclease activity. In some embodiments, the polymerase can have strand-displacement activity.

In some embodiments, the archaeal DNA polymerase, can be, without limitation, a thermostable or thermophilic DNA polymerase such as, for example: a *Bacillus subtilis* (Bsu) DNA polymerase I large fragment; a *Thermus aquaticus* (Taq) DNA polymerase; a *Thermus filiformis* (Tfi) DNA polymerase; a Phi29 DNA polymerase; a *Bacillus stearothermophilus* (Bst) DNA polymerase; a *Thermococcus* sp. 9° N-7 DNA polymerase; a *Bacillus smithii* (Bsm) DNA polymerase large fragment; a *Thermococcus litoralis* (Tli) DNA polymerase or VENT (exo-) DNA polymerase (from New England Biolabs); or "Deep Vent" (exo-) DNA polymerase (New England Biolabs). In some embodiments, the polymerase comprises *E. coli* large fragment DNA polymerase I (e.g., Klenow).

In some embodiments, the polymerase comprises a polymerase having a fast nucleotide incorporation rate, or a highly processive polymerase, or a polymerase that exhibits tolerance to biological contaminants (e.g., contaminants from a biological fluid such as blood or serum). In some embodiments, the polymerase comprises a *Pyrococcus* or *Pyrococcus*-like enzyme, including a polymerase from *Pyrococcus furiosus* (Pfu). In some embodiments, the polymerase comprises at least a portion of a polymerase from *Pyrococcus* that is fused with a processivity-enhancing domain which increases fidelity and speed. In some embodiments, the polymerase comprises a Phusion polymerase (European patent No. 1463809). In some embodiments, the polymerase comprises a high-fidelity Pfu enzyme which include Q5 enzyme (New England Biolabs).

In some embodiments, the disclosure relates generally to compositions, as well as related systems, methods, kits, apparatuses and computer-readable media, comprising at least one co-factor for polymerase activity. In some embodiments, a co-factor comprises one or more divalent cation. Examples of divalent cations include magnesium, manganese and calcium.

In some embodiments, the disclosure relates generally to compositions, as well as related systems, methods, kits, apparatuses and computer-readable media, comprising one or more nucleotides. In some embodiments, the compositions (and related methods, systems, kits, apparatuses and computer-readable media) includes one type, or a mixture of different types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In some embodiments, one or more phosphorus atoms in the chain can be part of a phosphate group having P and O. In some embodiments, the phosphorus atoms in the chain can be linked together with intervening O, NH, S, methylene, substituted methylene, ethylene, substituted ethylene, $CNH_2$, C(O), $C(CH_2)$, $CH_2CH_2$, or $C(OH)CH_2R$ (where R can be a 4-pyridine or 1-imidazole). In some embodiments, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides that can be used in the disclosed compositions (and related methods, systems, kits, apparatuses and computer-readable media) include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. In some embodiments, a nucleotide can include a purine or pyrimidine base, including adenine, guanine, cytosine, thymine, uracil or inosine. In some embodiments, a nucleotide includes dATP, dGTP, dCTP, dTTP and dUTP.

In some embodiments, the nucleotide is unlabeled. In some embodiments, the nucleotide comprises a label and referred to herein as a "labeled nucleotide". In some embodiments, the label can be in the form of a fluorescent dye attached to any portion of a nucleotide including a base, sugar or any intervening phosphate group or a terminal phosphate group, i.e., the phosphate group most distal from the sugar.

In some embodiments, the nucleotide is a terminator nucleotide. In some embodiments, the terminator nucleotide will, once incorporated, inhibit or block further nucleotide incorporations at the 3' end of the nucleic acid molecule. The terminator nucleotide includes a terminator group (also referred to as a terminator moiety or a blocking moiety or blocking group) that confers the ability to inhibit or block further nucleotide incorporations. In some embodiments, the terminator nucleotides can be operably linked to at least one terminator group or moiety. In some embodiments, at least one terminator group can be operably linked to any portion of the base, sugar (e.g., 2' or 3' position), phosphate group or any phosphate in the phosphate chain. In some embodiments, the terminator group can be neutralized, cleaved, or otherwise removed from the terminator nucleotide via suitable treatments. In some embodiments, neutralization, cleavage or removal of the terminator group can permit subsequent nucleotide incorporations to occur. In some embodiments, the non-extendible end can be converted to an extendible end via cleavage, neutralization or removal of the terminator group. In some embodiments, the terminator group cannot be neutralized, cleaved, or otherwise removed from the terminator nucleotide via suitable treatments (e.g., non-reversible terminator nucleotides). Examples of terminator nucleotide can be found in U.S. Pat. Nos. 7,057,026; 7,566,537; 7,785,796; 8,158,346; 7,541,444; 7,057,026; 7,592,435; 7,414,116; 7,427,673; 8,399,188; 7,713,698; 7,790,869; 8,088,575; 7,635,578; and 7,883,869; and in PCT Application No. PCT/US2016/023139, filed Mar. 18, 2016, which are all expressly incorporated herein by reference as if set forth in full.

In some embodiments, the disclosure relates generally to compositions, as well as related systems, methods, kits, apparatuses and computer-readable media, comprising any one or any combination of oligonucleotide tags, capture primers, reverse solution-phase primers, fusion primers, target polynucleotides and/or nucleotides that are non-labeled or attached to at least one label. In some embodiments, the label comprises a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the disclosure relates generally to compositions, as well as related systems, methods, kits, apparatuses and computer-readable media, comprising at least one member of a binding partner. In some embodiments, a binding partners includes two molecules, or portions thereof, which have a specific binding affinity for one another and typically will bind to each other in preference to binding to other molecules. In some embodiments, binding partners include an “affinity moiety” and a “receptor moiety”. Typically but not necessarily some or all of the structure of one member of a specific binding pair is complementary to some or all of the structure possessed by the other member, with the two members being able to bind together specifically by way of a bond between the complementary structures, optionally by virtue of multiple non-covalent attractions.

In some embodiments, molecules that function as binding partners include: biotin (and its derivatives) and its binding partners avidin, streptavidin and their derivatives; His-tags which bind nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

In some embodiments, an avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products Extravidin™, Captavidin™, Neutravidin™ and Neutralite™ Avidin.

In some embodiments, the disclosure relates generally to compositions, and related methods, systems, kits, apparatuses and computer-readable media, comprising a single reaction mixture which can be a tag-appending reaction mixture that is used for appending a plurality of tags (e.g., randomer tags) to a plurality of polynucleotides, to generate a plurality of tagged polynucleotides, where individual polynucleotides within the plurality are appended with at least one tag. The single reaction mixture can be contained in a single reaction vessel. The single reaction mixture can include any one or any combination of target polynucleotides, enzymes (e.g., polymerases and/or ligases), nucleotides, divalent cations, binding partners, and/or buffer. Optionally, the enzymes comprise polymerases which include recombinant, fusion, mutant, heat-stable or heat labile forms. Optionally, the nucleotides can include compounds having structures the same as or similar to naturally-occurring nucleotides, or nucleotide analogs having derivatized base, sugar and/or phosphate groups, or labeled or non-labeled nucleotides. Optionally, the divalent cations include magnesium, manganese and/or calcium. Optionally, the binding partners include biotin and avidin-like compounds, such as avidin or streptavidin. Optionally, the buffer comprises a source of ions, such as KCl, K-acetate, $NH_4$-acetate, K-glutamate, $NH_4Cl$, or ammonium sulfate. Optionally, the buffer includes Tris, Tricine, HEPES, MOPS, ACES, MES, or inorganic buffers such as phosphate or acetate-based buffers which can provide a pH range of about 4-12. Optionally, the buffer includes chelating agents such as EDTA or EGTA. Optionally, the buffer includes dithiothreitol (DTT), glycerol, spermidine, and/or BSA (bovine serum albumin). Optionally, the buffer includes ATP.

In some embodiments, the disclosure relates generally to compositions, and related methods, systems, kits, apparatuses and computer-readable media, comprising a tag-appending reaction mixture that is distributed into one or more reaction vessels. In some embodiments, a single reaction vessel contains a tag-appending reaction mixture. In some embodiments, a single reaction vessel contains an amplification reaction mixture. Non-limiting examples of a single reaction vessel include a tube, inner wall of a tube, well, microwell, reaction chamber, groove, channel reservoir, flowcell, or similar structures.

In some embodiments, the disclosure relates generally to kits, and related compositions, systems, methods and apparatuses, comprising at least two components or reagents used to generate the tagged nucleic acids as described in the present teachings. For example, the kit contains any combination of at least two of the following reagents: a plurality of randomer tags in the form of double-stranded adaptors or single-stranded tailed primers or both, enzymes (e.g., polymerases and/or ligases), nucleotides, divalent cations, binding partners, and/or buffer(s). Optionally, the kit also contains target nucleic acids to be used as positive or negative control polynucleotides. The kit contains a plurality of randomer tags which comprise oligonucleotides having at least two random sequences alternating with at least two fixed sequences. The polymerases and ligases include recombinant, fusion, mutant, heat-stable or heat labile forms. The nucleotides include compounds having structures the same as or similar to naturally-occurring nucleotides, or nucleotide analogs having derivatized base, sugar and/or phosphate groups, or labeled or non-labeled nucleotides. The divalent cations include magnesium, manganese and/or calcium. The binding partners include biotin and avidin-like compounds, such as avidin or streptavidin. The buffer(s) comprise a source of ions, such as KCl, K-acetate, $NH_4$-acetate, K-glutamate, $NH_4Cl$, or ammonium sulfate. The buffer(s) includes Tris, Tricine, HEPES, MOPS, ACES, MES, or inorganic buffers such as phosphate or acetate-based buffers which can provide a pH range of about 4-12. The buffer(s) include chelating agents such as EDTA or EGTA. The buffer(s) include dithiothreitol (DTT), glycerol, spermidine, and/or BSA (bovine serum albumin). The buffer(s) includes ATP.

In some embodiments, the disclosure relates generally to methods, as well as related systems, compositions, kits, apparatuses and computer-readable media for detecting a genetic variant in a nucleic acid sample having a plurality of polynucleotides, comprising: (a) tagging at least some of the plurality of polynucleotides, with at least one oligonucleotide tag to generate tagged polynucleotides.

In some embodiments, the disclosure relates generally to methods, as well as related systems, compositions, kits, apparatuses and computer-readable media for detecting a genetic variant in a nucleic acid sample having a plurality of polynucleotides, further comprising: (b) amplifying at least some of the tagged polynucleotides to generate tagged amplicons.

In some embodiments, the disclosure relates generally to methods, as well as related systems, compositions, kits, apparatuses and computer-readable media for detecting a genetic variant in a nucleic acid sample having a plurality of polynucleotides, further comprising: (c) sequencing at least some of the tagged amplicons to generate a plurality of candidate sequencing reads, including sequences corresponding to both a portion of the polynucleotide and a portion of the at least one oligonucleotide tag that is appended to the polynucleotide, wherein the candidate sequencing reads are stored in a memory in communication with a processor.

In some embodiments, the disclosure relates generally to methods, as well as related systems, compositions, kits, apparatuses and computer-readable media for detecting a genetic variant in a nucleic acid sample having a plurality of polynucleotides, further comprising: (d) identifying a subset of candidate sequencing reads having errors.

In some embodiments, the disclosure relates generally to methods, as well as related systems, compositions, kits, apparatuses and computer-readable media for detecting a genetic variant in a nucleic acid sample having a plurality of polynucleotides, further comprising: (e) grouping the remaining candidate sequencing reads into families of grouped candidate sequencing reads having a common tag sequence that is unique to a given family of candidate sequencing reads.

In some embodiments, the disclosure relates generally to methods, as well as related systems, compositions, kits, apparatuses and computer-readable media for detecting a genetic variant in a nucleic acid sample having a plurality of polynucleotides, further comprising: (f) removing mistagged sequencing reads from the families of candidate sequencing reads to produce error-corrected families of sequencing reads.

In some embodiments, the disclosure relates generally to methods, as well as related systems, compositions, kits, apparatuses and computer-readable media for detecting a genetic variant in a nucleic acid sample having a plurality of polynucleotides, further comprising: (g) detecting a variant in a plurality of error-corrected families of sequencing reads, wherein the variant is present in the nucleic acid sample at an abundance level of 0.05-5%.

In some embodiments, the identifying of step (d) includes comparing the candidate sequencing read from the plurality of candidate sequencing reads, to a tag-specific reference sequence to determine a number of nucleotides that differ between the candidate sequencing read and the tag-specific reference sequence. In some embodiments, the identifying of step (d) further includes applying a culling threshold to identify a candidate sequencing read having an error. In some embodiments, the identifying of step (d) includes comparing the candidate sequencing read from the plurality of candidate sequencing reads to a polynucleotide-specific reference sequence to determine a number of nucleotides that differ between the candidate sequencing read and the polynucleotide-specific reference sequence. In some embodiments, the identifying of step (d) further includes applying a culling threshold to identify a candidate sequencing read having an error.

In some embodiments, the removing mistagged sequencing reads of step (f) includes comparing the candidate sequencing read in the given family to a polynucleotide-specific reference sequence to determine a number of nucleotides that differ between the candidate sequencing read and the polynucleotide-specific reference sequence. In some embodiments, the removing mistagged sequencing reads of step (f) further includes applying a difference counting threshold to identify a mistagged sequencing read. In some embodiments, the removing mistagged sequencing reads of step (f) includes comparing the candidate sequencing read to one or more other candidate sequencing reads in the given family to identify candidate sequencing reads having a common pattern of variants. In some embodiments, the removing mistagged sequencing reads of step (f) further includes applying a pattern counting threshold to a number of candidate sequencing reads having the common pattern of variants to identify a group of mistagged sequencing reads. In some embodiments, the removing mistagged sequencing reads of step (f) includes comparing the candidate sequencing reads in the given family to a polynucleotide-specific reference sequence to identify a candidate mistagged sequencing read. In some embodiments, the removing mistagged sequencing reads of step (f) further includes comparing the candidate mistagged sequencing read to one or more other candidate mistagged sequencing reads in the family to identify a common pattern of variants. In some embodiments, the removing mistagged sequencing reads of step (f) further includes applying a pattern counting threshold to a number of candidate mistagged sequencing reads having the common pattern of variants to determine a group of mistagged sequencing reads. In some embodiments, the removing mistagged sequencing reads of step (f) includes comparing the candidate sequencing read in the given family to a polynucleotide-specific reference sequence to identify a pattern of differences in a candidate mistagged sequencing read. In some embodiments, the removing mistagged sequencing reads of step (f) further includes determining a number of matches for the pattern of differences in the candidate mistagged sequencing read compared to a pattern of expected differences between the polynucleotide-specific reference sequence and an expected sequence for a non-target polynucleotide. In some embodiments, the removing mistagged sequencing reads of step (f) further includes applying the non-target pattern threshold to the number of matches to identify a mistagged sequencing read.

In some embodiments, the detecting of step (g) includes aligning the sequencing reads for the error-corrected family to a polynucleotide-specific reference sequence. In some embodiments, the detecting of step (g) further includes counting a number of aligned sequences having a particular base difference at a given position in the aligned sequences. In some embodiments, the detecting of step (g) further includes applying a family level threshold to the number to identify a family-based candidate variant. In some embodiments, the detecting of step (g) further includes counting a number of error-corrected families having a particular family-based candidate variant. In some embodiments, the detecting of step (g) further includes applying a multi-family threshold to the number of error-corrected families to identify the variant.

In some embodiments, a value of the multi-family threshold is a nearest integer to a product of a percent factor multiplied by a number of different families corresponding to a given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, the detecting of step (g), the variant detected is present in the nucleic acid sample at an abundance level of 0.05-0.1%.

In some embodiments, the detecting of step (g) includes: (a) aligning the sequencing reads in the error-corrected family to a polynucleotide-specific reference sequence; and (b) for each position in the aligned sequences counting a number of aligned sequences in the family having a particular base at the position.

In some embodiments, the detecting of step (g) includes applying a family level threshold to the number to identify a representative base for the position, wherein a number below the family level threshold at the position indicates a base error in the aligned sequence. In some embodiments, the detecting of step (g) includes generating a family reference sequence having the representative base for each position, wherein the family reference sequence is stored in memory. In some embodiments, the method further comprises removing the sequencing reads of the error-corrected family from memory.

In some embodiments, the detecting of step (g) includes: (a) comparing the family reference sequence to the polynucleotide-specific reference sequence; and (b) identifying a family-based candidate variant at a given position when the representative base at the given position differs from a base at the given position in the polynucleotide-specific reference sequence.

In some embodiments, the detecting of step (g) includes counting a number of error-corrected families having a particular family-based candidate variant. In some embodiments, the detecting of step (g) includes applying a multi-family threshold to the number of error-corrected families to identify the variant.

In some embodiments, a value of the multi-family threshold is a nearest integer to a product of a percent factor multiplied by a number of different families corresponding to given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, the nucleic acid sample comprises cell-free nucleic acids from a biological fluid, nucleic acids from a biopsied tissue, nucleic acids from a needle biopsy, or nucleic acids from cells. In some embodiments, the biological fluid is blood, saliva, sputum, sweat, tears, lavage fluid, amniotic fluid, cerebrospinal fluid, ascites, urine, stool, feces, or semen. In some embodiments, the nucleic acid sample comprises DNA or RNA, or a mixture of DNA and RNA.

In some embodiments, at least two of the plurality of tagged polynucleotides are appended with tags that differ from each other. In some embodiments, the plurality of tagged polynucleotides are appended with a different tag at both ends. In some embodiments, individual oligonucleotide tags in a plurality of oligonucleotide tags include a region comprising different random tag sequences alternating with fixed tag sequences.

In some embodiments, a single reaction mixture contains a plurality of oligonucleotide tags having $10^4$-$10^8$ different random tag sequences.

In some embodiments, the variant is present in the nucleic acid sample as a variant sequence, polymorphic sequence or mutant sequence.

In some embodiments, the sequencing of step (c) comprises using a planar support, a flowcell, a plurality of wells, a particle or a bead. In some embodiments, the support includes an array of $10^4$-$10^9$ sequencing reaction sites. In some embodiments, the sequencing reaction sites are operatively coupled to at least one field effect transistor (FET) sensor. In some embodiments, at least one field effect transistor (FET) sensor detects a byproduct from nucleotide incorporation, wherein the byproduct includes pyrophosphate, hydrogen ions, protons, charge transfer or heat.

In some embodiments, the disclosure relates generally to methods, as well as related systems, compositions, kits, apparatuses and computer-readable media for detecting a variant sequence target polynucleotide which is present in a nucleic acid sample, comprising the steps: (a) forming a single reaction mixture containing: (i) a plurality of polynucleotides from the nucleic acid sample, and (ii) a plurality of oligonucleotide tags; (b) generating within the single reaction mixture a plurality of tagged polynucleotides by appending at least one tag to individual polynucleotides within the plurality of polynucleotides; (c) generating a population of tagged amplicons by amplifying the plurality of tagged polynucleotides; (d) sequencing at least a portion of the population of tagged amplicons to form candidate sequencing reads; and (e) determining that the variant sequence target polynucleotide is present in the nucleic acid sample at an abundance level of 0.05-5%.

The embodiments, the determining of step (e) comprises determining that the variant sequence target polynucleotide is present in the nucleic acid sample at an abundance level of 0.05-0.1%. The embodiments, the determining of step (e) includes comparing the candidate sequencing read to a tag-specific reference sequence to determine a number of nucleotides that differ between the candidate sequencing read and the tag-specific reference sequence. The embodiments, the determining of step (e) further includes applying a culling threshold to identify a candidate sequencing read having an error. The embodiments, the determining of step (e) includes comparing the candidate sequencing read to a polynucleotide-specific reference sequence to determine a number of nucleotides that differ between the candidate sequencing read and the polynucleotide-specific reference sequence. The embodiments, the determining of step (e) includes applying a culling threshold to identify a candidate sequencing read having an error. The embodiments, the determining of step (e) includes grouping the candidate sequencing reads into families of grouped candidate sequencing reads having a common tag sequence that is unique to a given family of candidate sequencing reads. The embodiments, the determining of step (e) includes removing mistagged sequencing reads from the families of candidate sequencing reads to produce error-corrected families of sequencing reads.

The embodiments, the step of removing mistagged sequencing reads includes comparing the candidate sequencing read in the given family to a polynucleotide-specific reference sequence to determine a number of nucleotides that differ between the candidate sequencing read and the polynucleotide-specific reference sequence. The embodiments, the step of removing mistagged sequencing reads further includes applying a difference counting threshold to identify a mistagged sequencing read. The embodiments, the step of removing mistagged sequencing reads includes comparing the candidate sequencing read to one or more other candidate sequencing reads in the given family to identify candidate sequencing reads having a common pattern of variants. The embodiments, the step of removing mistagged sequencing reads further includes applying a pattern counting threshold to a number of candidate sequencing reads having the common pattern of variants to identify a group of mistagged sequencing reads. The embodiments, the step of removing mistagged sequencing reads includes comparing the candidate sequencing reads in the given family to a polynucleotide-specific reference sequence to identify a candidate mistagged sequencing read. The embodiments, the step of removing mistagged sequencing reads further includes comparing the candidate mistagged sequencing read to one or more other candidate mistagged sequencing reads in the family to identify a common pattern of variants. The embodiments, the step of removing mistagged sequencing reads further includes applying a pattern counting threshold to a number of candidate mistagged sequencing reads having the common pattern of variants to determine a group of mistagged sequencing reads. The embodiments, the step of removing mistagged sequencing reads includes comparing the candidate sequencing read in the given family to a polynucleotide-specific reference sequence to identify a pattern of differences in a candidate mistagged sequencing read. The embodiments, the step of removing mistagged sequencing reads further includes determining a number of matches for the pattern of differences in the candidate mistagged sequencing read compared to a pattern of expected differences between the polynucleotide-specific reference sequence and an expected sequence for a non-target polynucleotide. The embodiments, the step of removing mistagged sequencing reads further includes applying the non-target pattern threshold to the number of matches to identify a mistagged sequencing read.

The embodiments, the determining of step (e) includes aligning the sequencing reads for the error-corrected family to a polynucleotide-specific reference sequence. The embodiments, the determining of step (e) further includes counting a number of aligned sequences having a particular base difference at a given position in the aligned sequences. The embodiments, the determining of step (e) further includes applying a family level threshold to the number to identify a family-based candidate variant. The embodiments, the determining of step (e) further includes counting a number of error-corrected families having a particular family-based candidate variant. The embodiments, the determining of step (e) further includes applying a multi-family threshold to the number of error-corrected families to identify a variant in the variant sequence target polynucleotide.

The embodiments, a value of the multi-family threshold is a nearest integer to a product of a percent factor multiplied by a number of different families corresponding to a given target polynucleotide sequence and the value is at least 2 of the number of different families. The embodiments, the percent factor is in a range from 0.001 to 0.1%. The embodiments, the percent factor is in a range from 0.045 to 0.055%.

The embodiments, the determining of step (e) includes: (a) aligning the sequencing reads in the error-corrected family to a polynucleotide-specific reference sequence; and (b) for each position in the aligned sequences counting a number of aligned sequences in the family having a particular base at the position.

The embodiments, the determining of step (e) includes applying a family level threshold to the number to identify a representative base for the position, wherein a number below the family level threshold at the position indicates a base error in the aligned sequence. The embodiments, the determining of step (e) includes generating a family reference sequence having the representative base for each position.

The embodiments, the determining of step (e) includes: (a) comparing the family reference sequence to the polynucleotide-specific reference sequence; and (b) identifying a family-based candidate variant at a given position when the representative base at the given position differs from a base at the given position in the polynucleotide-specific reference sequence.

The embodiments, the determining of step (e) includes counting a number of error-corrected families having a particular family-based candidate variant. The embodiments, the determining of step (e) includes applying a multi-family threshold to the number of error-corrected families to identify a variant in the variant sequence target polynucleotide.

The embodiments, a value of the multi-family threshold is a nearest integer to a product of a percent factor multiplied by a number of different families corresponding to given target polynucleotide sequence and the value is at least 2 of the number of different families. The embodiments, the percent factor is in a range from 0.001 to 0.1%. The embodiments, the percent factor is in a range from 0.045 to 0.055%.

In some embodiments, the disclosure relates generally to methods, as well as related systems, compositions, kits, apparatuses and computer-readable media for the disclosure relates generally to systems, as well as related methods, compositions, kits, apparatuses and computer-readable media, which comprise: a system for detecting a genetic variant in a nucleic acid sample having a plurality of polynucleotides, comprising: (i) a machine-readable memory; and (ii) a processor configured to execute machine-readable instructions, which, when executed by the processor, cause the system to perform steps including: (a) receive a plurality of candidate sequencing reads, wherein the candidate sequencing reads produced from sequencing tagged amplicons generated by amplifying tagged polynucleotides, wherein the tagged polynucleotides are generated by appending at least one oligonucleotide tag to at least some of the plurality of polynucleotides, wherein the plurality of candidate sequencing reads are stored in the memory; (b) identify a subset of candidate sequencing reads having errors; (c) group the remaining candidate sequencing reads into families of grouped candidate sequencing reads having a common tag sequence that is unique to a given family of candidate sequencing reads; (d) remove mistagged sequencing reads from the families of candidate sequencing reads to produce error-corrected families of sequencing reads; and E detect a variant in a plurality of error-corrected families of sequencing reads, wherein the variant is present in the nucleic acid sample at an abundance level of 0.05-5%.

In some embodiments, in the system, the step (b) to identify includes a step to compare the candidate sequencing read from the plurality of candidate sequencing reads, to a tag-specific reference sequence to determine a number of nucleotides that differ between the candidate sequencing read and the tag-specific reference sequence. In some embodiments, the step (b) to identify further includes a step to apply a culling threshold to identify a candidate sequencing read having an error. In some embodiments, the step (b) to identify includes a step to compare the candidate sequencing read from the plurality of candidate sequencing reads to a polynucleotide-specific reference sequence to determine a number of nucleotides that differ between the candidate sequencing read and the polynucleotide-specific reference sequence. In some embodiments, the step (b) to identify further includes a step to apply a culling threshold to identify a candidate sequencing read having an error.

In some embodiments, in the system, the step (d) to remove mistagged sequencing reads includes a step to compare the candidate sequencing read in the given family to a polynucleotide-specific reference sequence to determine a number of nucleotides that differ between the candidate sequencing read and the polynucleotide-specific reference sequence. In some embodiments, the step (d) to remove mistagged sequencing reads further includes a step to apply a difference counting threshold to identify a mistagged sequencing read. In some embodiments, the step (d) to remove mistagged sequencing reads includes a step to compare the candidate sequencing read to one or more other candidate sequencing reads in the given family to identify candidate sequencing reads having a common pattern of variants. In some embodiments, the step (d) to remove mistagged sequencing reads further includes a step to apply a pattern counting threshold to a number of candidate sequencing reads having the common pattern of variants to identify a group of mistagged sequencing reads. In some embodiments, the step (d) to remove mistagged sequencing reads includes a step to compare the candidate sequencing reads in the given family to a polynucleotide-specific reference sequence to identify a candidate mistagged sequencing read. In some embodiments, the step (d) to remove mistagged sequencing reads further includes a step to compare the candidate mistagged sequencing read to one or more other candidate mistagged sequencing reads in the family to identify a common pattern of variants. In some embodiments, the step (d) to remove mistagged sequencing reads further includes a step to apply a pattern counting threshold to a number of candidate mistagged sequencing reads having the common pattern of variants to determine a group of mistagged sequencing reads. In some embodiments, the step (d) to remove mistagged sequencing reads includes a step to compare the candidate sequencing read in the given family to a polynucleotide-specific reference sequence to identify a pattern of differences in a candidate mistagged sequencing read. In some embodiments, the step (d) to remove mistagged sequencing reads further includes a step to determine a number of matches for the pattern of differences in the candidate mistagged sequencing read compared to a pattern of expected differences between the polynucleotide-specific reference sequence and an expected sequence for a non-target polynucleotide. In some embodiments, the step (d) to remove mistagged sequencing reads further includes a step to apply the non-target pattern threshold to the number of matches to identify a mistagged sequencing read.

In some embodiments, in the system, the step (e) to detect includes a step to align the sequencing reads for the error-corrected family to a polynucleotide-specific reference sequence. In some embodiments, the step (e) to detect further includes a step to count a number of aligned sequences having a particular base difference at a given position in the aligned sequences. In some embodiments, the step (e) to detect further includes a step to apply a family level threshold to the number to identify a family-based candidate variant. In some embodiments, the step (e) to detect further includes a step to count a number of error-corrected families having a particular family-based candidate variant. In some embodiments, the step (e) to detect further includes a step to apply a multi-family threshold to the number of error-corrected families to identify the variant.

In some embodiments, in the system, a value of the multi-family threshold is a nearest integer to a product of a percent factor multiplied by a number of different families corresponding to a given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, in the system, in the step (e) to detect, the variant detected is present in the nucleic acid sample at an abundance level of 0.05-0.1%.

In some embodiments, in the system, the step (e) to detect includes steps to: (a) align the sequencing reads in the error-corrected family to a polynucleotide-specific reference sequence; and (b) for each position in the aligned sequences count a number of aligned sequences in the family having a particular base at the position.

In some embodiments, in the system, the step (e) to detect includes a step to apply a family level threshold to the number to identify a representative base for the position, wherein a number below the family level threshold at the position indicates a base error in the aligned sequence. In some embodiments, the step (e) to detect includes a step to generate a family reference sequence having the representative base for each position, wherein the family reference sequence is stored in memory. In some embodiments, the step (e) further comprises a step to remove the sequencing reads of the error-corrected family from memory.

In some embodiments, in the system, the step (e) to detect includes steps to: (a) compare the family reference sequence to the polynucleotide-specific reference sequence; and (b) identify a family-based candidate variant at a given position when the representative base at the given position differs from a base at the given position in the polynucleotide-specific reference sequence.

In some embodiments, in the system, the step (e) to detect includes a step to count a number of error-corrected families having a particular family-based candidate variant. In some embodiments, the step (e) to detect includes a step to apply a multi-family threshold to the number of error-corrected families to identify the variant.

In some embodiments, in the system, a value of the multi-family threshold is a nearest integer to a product of a percent factor multiplied by a number of different families corresponding to given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, in the system, the nucleic acid sample comprises cell-free nucleic acids from a biological fluid, nucleic acids from a biopsied tissue, nucleic acids from a needle biopsy, or nucleic acids from cells. In some embodiments, the biological fluid is blood, saliva, sputum, sweat, tears, lavage fluid, amniotic fluid, cerebrospinal fluid, ascites, urine, stool, feces, or semen. In some embodiments, the nucleic acid sample comprises DNA or RNA, or a mixture of DNA and RNA.

In some embodiments, in the system, at least two of the plurality of tagged polynucleotides are appended with tags that differ from each other. In some embodiments, the plurality of tagged polynucleotides are appended with a different tag at both ends.

In some embodiments, in the system, individual oligonucleotide tags in a plurality of oligonucleotide tags include a region comprising different random tag sequences alternating with fixed tag sequences.

In some embodiments, in the system, a single reaction mixture contains a plurality of oligonucleotide tags having $10^4$-$10^8$ different random tag sequences.

In some embodiments, in the system, the variant is present in the nucleic acid sample as a variant sequence, polymorphic sequence or mutant sequence.

In some embodiments, in the system, the sequencing comprises using a planar support, a flowcell, a plurality of wells, a particle or a bead. In some embodiments, the support includes an array of $10^4$-$10^9$ sequencing reaction sites. In some embodiments, the sequencing reaction sites are operatively coupled to at least one field effect transistor (FET) sensor. In some embodiments, the at least one field effect transistor (FET) sensor detects a byproduct from nucleotide incorporation, wherein the byproduct includes pyrophosphate, hydrogen ions, protons, charge transfer or heat.

In some embodiments, the disclosure relates generally to systems, as well as related methods, compositions, kits, apparatuses and computer-readable media, which comprise a non-transitory machine-readable storage medium comprising instructions which, when executed by a processor, cause the processor to perform the following steps for detecting a genetic variant in a nucleic acid sample having a plurality of polynucleotides: (a) receiving a plurality of candidate sequencing reads, wherein the candidate sequencing reads are produced by sequencing tagged amplicons generated by amplifying tagged polynucleotides, wherein the tagged polynucleotides are generated by appending at least one oligonucleotide tag to at least some of the plurality of polynucleotides; (b) identifying a subset of candidate sequencing reads having errors; (c) grouping the remaining candidate sequencing reads into families of grouped candidate sequencing reads having a common tag sequence that is unique to a given family of candidate sequencing reads; (d) removing mistagged sequencing reads from the families of candidate sequencing reads to produce error-corrected families of sequencing reads; and (e) detecting a variant in a plurality of error-corrected families of sequencing reads, wherein the variant is present in the nucleic acid sample at an abundance level of 0.05-5%. In some embodiments, the at least one oligonucleotide tag is appended to at least some of the plurality of polynucleotides in a single reaction mixture.

In some embodiments, in the non-transitory machine-readable storage medium, the identifying of step (b) includes comparing the candidate sequencing read from the plurality of candidate sequencing reads, to a tag-specific reference sequence to determine a number of nucleotides that differ between the candidate sequencing read and the tag-specific reference sequence.

In some embodiments, in the non-transitory machine-readable storage medium, the identifying of step (b) further includes applying a culling threshold to identify a candidate sequencing read having an error.

In some embodiments, in the non-transitory machine-readable storage medium, the identifying of step (b) includes comparing the candidate sequencing read from the plurality of candidate sequencing reads to a polynucleotide-specific reference sequence to determine a number of nucleotides that differ between the candidate sequencing read and the polynucleotide-specific reference sequence.

In some embodiments, in the non-transitory machine-readable storage medium, the identifying of step (b) further includes applying a culling threshold to identify a candidate sequencing read having an error.

In some embodiments, in the non-transitory machine-readable storage medium, the removing mistagged sequencing reads of step (d) includes comparing the candidate sequencing read in the given family to a polynucleotide-specific reference sequence to determine a number of nucleotides that differ between the candidate sequencing read and the polynucleotide-specific reference sequence.

In some embodiments, in the non-transitory machine-readable storage medium, the removing mistagged sequencing reads of step (d) further includes applying a difference counting threshold to identify a mistagged sequencing read.

In some embodiments, in the non-transitory machine-readable storage medium, the removing mistagged sequencing reads of step (d) includes comparing the candidate sequencing read to one or more other candidate sequencing reads in the given family to identify candidate sequencing reads having a common pattern of variants. In some embodiments, the removing mistagged sequencing reads of step (d) further includes applying a pattern counting threshold to a number of candidate sequencing reads having the common pattern of variants to identify a group of mistagged sequencing reads. In some embodiments, the removing mistagged sequencing reads of step (d) includes comparing the candidate sequencing reads in the given family to a polynucleotide-specific reference sequence to identify a candidate mistagged sequencing read. In some embodiments, the removing mistagged sequencing reads of step (d) further includes comparing the candidate mistagged sequencing read to one or more other candidate mistagged sequencing reads in the family to identify a common pattern of variants. In some embodiments, the removing mistagged sequencing reads of step (d) further includes applying a pattern counting threshold to a number of candidate mistagged sequencing reads having the common pattern of variants to determine a group of mistagged sequencing reads. In some embodiments, the removing mistagged sequencing reads of step (d) includes comparing the candidate sequencing read in the given family to a polynucleotide-specific reference sequence to identify a pattern of differences in a candidate mistagged sequencing read. In some embodiments, the removing mistagged sequencing reads of step (d) further includes determining a number of matches for the pattern of differences in the candidate mistagged sequencing read compared to a pattern of expected differences between the polynucleotide-specific reference sequence and an expected sequence for a non-target polynucleotide. In some embodiments, the removing mistagged sequencing reads of step (d) further includes applying the non-target pattern threshold to the number of matches to identify a mistagged sequencing read.

In some embodiments, in the non-transitory machine-readable storage medium, the detecting of step (e) includes aligning the sequencing reads for the error-corrected family to a polynucleotide-specific reference sequence. In some embodiments, the detecting of step (e) further includes counting a number of aligned sequences having a particular base difference at a given position in the aligned sequences. In some embodiments, the detecting of step (e) further includes applying a family level threshold to the number to identify a family-based candidate variant. In some embodiments, the detecting of step (e) further includes counting a number of error-corrected families having a particular family-based candidate variant. In some embodiments, the detecting of step (e) further includes applying a multi-family threshold to the number of error-corrected families to identify the variant.

In some embodiments, in the non-transitory machine-readable storage medium, a value of the multi-family threshold is a nearest integer to a product of a percent factor multiplied by a number of different families corresponding to a given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, in the non-transitory machine-readable storage medium, the detecting of step (e), the variant detected is present in the nucleic acid sample at an abundance level of 0.05-0.1%.

In some embodiments, in the non-transitory machine-readable storage medium, the detecting of step (e) includes: (i) aligning the sequencing reads in the error-corrected family to a polynucleotide-specific reference sequence; and (ii) for each position in the aligned sequences counting a number of aligned sequences in the family having a particular base at the position.

In some embodiments, in the non-transitory machine-readable storage medium, the detecting of step (e) includes applying a family level threshold to the number to identify a representative base for the position, wherein a number below the family level threshold at the position indicates a base error in the aligned sequence. In some embodiments, the detecting of step (e) includes generating a family reference sequence having the representative base for each position.

In some embodiments, in the non-transitory machine-readable storage medium, further comprises storing the family reference sequence in memory.

In some embodiments, in the non-transitory machine-readable storage medium, further comprises removing the sequencing reads of the error-corrected family from memory.

In some embodiments, in the non-transitory machine-readable storage medium, the detecting of step (e) includes: (i) comparing the family reference sequence to the polynucleotide-specific reference sequence; and (ii) identifying a family-based candidate variant at a given position when the representative base at the given position differs from a base at the given position in the polynucleotide-specific reference sequence.

In some embodiments, in the non-transitory machine-readable storage medium, the detecting of step (e) includes counting a number of error-corrected families having a particular family-based candidate variant. In some embodiments, the detecting of step (e) includes applying a multi-family threshold to the number of error-corrected families to identify the variant.

In some embodiments, in the non-transitory machine-readable storage medium, a value of the multi-family threshold is a nearest integer to a product of a percent factor multiplied by a number of different families corresponding to given target polynucleotide sequence and the value is at least 2 of the number of different families. In some embodiments, the percent factor is in a range from 0.001 to 0.1%. In some embodiments, the percent factor is in a range from 0.045 to 0.055%.

In some embodiments, in the non-transitory machine-readable storage medium, the nucleic acid sample comprises cell-free nucleic acids from a biological fluid, nucleic acids from a biopsied tissue, nucleic acids from a needle biopsy, or nucleic acids from cells. In some embodiments, the biological fluid is blood, saliva, sputum, sweat, tears, lavage fluid, amniotic fluid, cerebrospinal fluid, ascites, urine, stool, feces, or semen. In some embodiments, the nucleic acid sample comprises DNA or RNA, or a mixture of DNA and RNA.

In some embodiments, in the non-transitory machine-readable storage medium, at least two of the plurality of tagged polynucleotides are appended with tags that differ from each other. In some embodiments, the plurality of tagged polynucleotides are appended with a different tag at both ends.

In some embodiments, in the non-transitory machine-readable storage medium, individual oligonucleotide tags in a plurality of oligonucleotide tags include a region comprising different random tag sequences alternating with fixed tag sequences.

In some embodiments, in the non-transitory machine-readable storage medium, the single reaction mixture contains a plurality of oligonucleotide tags having $10^4$-$10^8$ different random tag sequences.

In some embodiments, in the non-transitory machine-readable storage medium, the genetic variant is present in the nucleic acid sample as a variant sequence, polymorphic sequence or mutant sequence.

In some embodiments, in the non-transitory machine-readable storage medium, the sequencing comprises using a planar support, a flowcell, a plurality of wells, a particle or a bead. In some embodiments, the support includes an array of $10^4$-$10^9$ sequencing reaction sites. In some embodiments, the sequencing reaction sites are operatively coupled to at least one field effect transistor (FET) sensor. In some embodiments, at least one field effect transistor (FET) sensor detects a byproduct from nucleotide incorporation, wherein the byproduct includes pyrophosphate, hydrogen ions, protons, charge transfer or heat.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

EXAMPLES

Embodiments of the present teachings can be further understood in light of the following examples, which should not be construed as limiting the scope of the present teachings in any way.

Example 1

Molecule Tagging—A DNA Sample:

The molecular tagging procedure was performed with control DNA and cell-free DNA. A control DNA sample that contains target sequences present at 0.1% (e.g., allelic frequency) was generated by diluting AcroMetrix™ Oncology Hotspot Control (Thermo Fisher Scientific 969056) into genomic DNA background of GM24385 cell line.

Isolating cf DNA:

Cell-free DNA (cfDNA) was extracted from donor blood plasma using the reagents and instructions contained in a MagMAX™ Cell-Free DNA Isolation Kit, alternative protocol B (Thermo Fisher Scientific A29319). Residual blood cells were removed from plasma by centrifugation at 1600×g for 10 minutes at 4° C. The plasma was transferred to a new centrifuge tube and centrifuged at 16000×g for another 10 minutes at 4° C. The plasma volume was measured. The Binding Solution was prepared by mixing together the Lysis/Binding Solution and Magnetic Beads, according to the table provided in the alternative protocol B.

TABLE 1

| Reagents: | Plasma Volume: 1 mL | 2 mL | 4 mL | 10 mL |
|---|---|---|---|---|
| MagMAX ™ Cell Free DNA Lysis/Binding Solution | 1.25 mL | 2.5 mL | 5 mL | 12.5 mL |
| MagMAX ™ Cell Free DNA Magnetic Beads | 15 µL | 30 µL | 60 µL | 150 µL |
| Total Volume: | 1.265 mL | 2.53 mL | 5.06 mL | 12.65 mL |

The Binding Solution was added to the plasma, and the tube was swirled or inverted 10 times. The tube was incubated at room temperature for 10 minutes with rotation. The tube was place on a magnet for 5 minutes, or until the solution appeared clear. While the tube remained on the magnet, the supernatant was carefully removed and discarded. The tube remained on the magnet for 1 additional minute, and the residual supernatant was carefully removed and discarded.

The tube was removed from the magnet. The beads were resuspended in 1 mL of MagMAX™ Cell Free DNA Wash Solution to make a bead slurry. The bead slurry was transferred to a fresh 1.5 mL non-stick microfuge tube, and the lysis/binding tube was saved and set aside. The microfuge tube was placed on a DynaMag™-2 magnet for 20 seconds. The supernatant was removed from the bead slurry, and was used to rinse the lysis/binding tube, then transferred to the bead slurry. The lysis/binding tube was discarded. The tube containing the bead slurry remained on the magnet for an additional 2 minutes. The supernatant was removed with a 1 mL pipette. While the tube remained on the magnet, the DynaMag™-2 magnet stand was tapped on the benchtop 5 times. Any residual liquid was removed from the tube using a 200 uL pipette. The tube was removed from the magnet. 1 mL of freshly-prepared 80% ethanol was added to the tube, and the tube was vortexed for 30 seconds. The tube was placed on the magnet for 2 minutes. The supernatant was removed using a 1 mL pipette. The tube remained on the magnet, while the beads were air-dried for 3-5 minutes. While the tube remained on the magnet, the DynaMag™-2 magnet stand was tapped on the benchtop 5 times. Any residual liquid was removed from the tube using a 200 uL pipette.

400 uL of 0.1×TAE was added to the tube, followed by vortexing for 5 minutes. The tube was placed on the magnet for 2 minutes. The supernatant was removed and transferred to a fresh 1.5 mL tube. 5 uL of MagMAX™ Cell free DNA Magnetic Beads and 500 uL of MagMAX™ Cell Free Lysis/Binding Solution was added to the supernatant (in the fresh tube), and mixed thoroughly. The tube was shaken for 5 minutes to bind the cfDNA to the beads. The tube was placed on the magnet for 5 minutes. The supernatant was removed using a 1 mL pipette. The tube was removed from the magnet, and 1 mL of MagMAX™ Cell Free DNA Wash Solution was added, and the tube was vortexed for 30 seconds. The tube was placed on the magnet for 2 minutes. The supernatant was removed using a 1 mL pipette. While the tube remained on the magnet, the DynaMag™-2 magnet stand was tapped on the benchtop 5 times. Any residual liquid was removed from the tube using a 200 uL pipette.

The tube was removed from the magnet for the 80% ethanol wash steps. 1 mL of freshly-prepared 80% ethanol was added, and the tube was vortexed for 30 seconds. The tube was place on the magnet for 2 minutes. The supernatant was removed using a 1 mL pipette. While the tube remained on the magnet, the DynaMag™-2 magnet stand was tapped on the benchtop 5 times. Any residual liquid was removed from the tube using a 200 uL pipette. The tube was removed from the magnet. 1 mL of freshly-prepared 80% ethanol was added, and the tube was vortexed for 30 seconds. The tube was place on the magnet for 2 minutes. The supernatant was removed using a 1 mL pipette. While the tube remained on the magnet, the DynaMag™-2 magnet stand was tapped on the benchtop 5 times. Any residual liquid was removed from the tube using a 200 uL pipette. While the tube remained on the magnet, the beads were air dried for 3-5 minutes. While the tube remained on the magnet, the DynaMag™-2 magnet stand was tapped on the benchtop 5 times. Any residual liquid was removed from the tube using a 200 uL pipette.

The cfDNA was eluted from the beads by adding 10-15 uL of MagMAX™ Cell Free DNA Elution Solution to the tube. The tube was vortexed for 5 minutes using a vortex adapter. The tube was placed on the magnet for 2 minutes. The supernatant contains the purified cfDNA. The cfDNA was used to generate molecular tagged libraries, or was stored at 4° C. for 24 hours or at −20° C. for long-term storage.

Figure 3A:
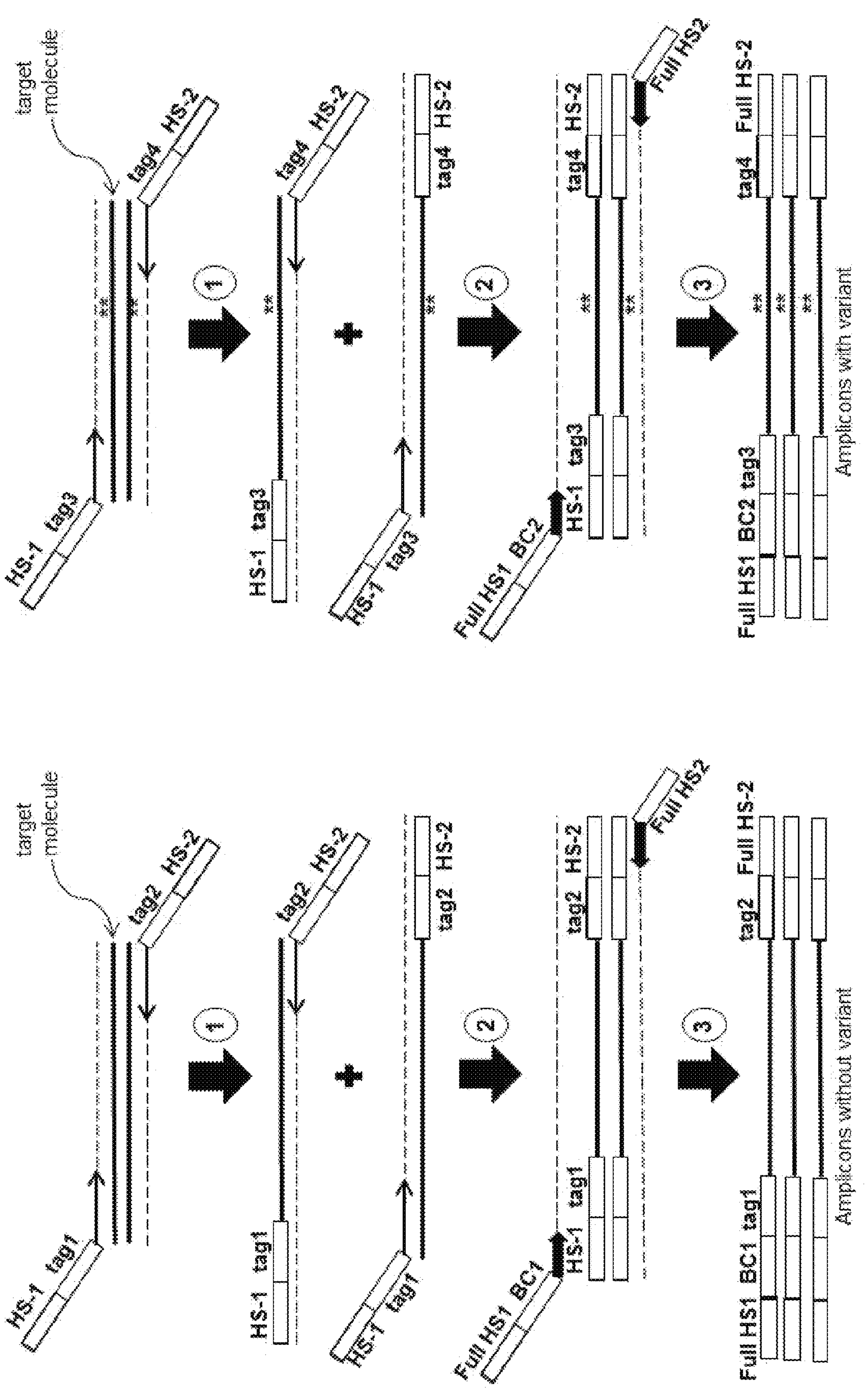
FIG. 3A is a schematic that depicts a non-limiting embodiment of a molecular tagging method.
Figure 3B:
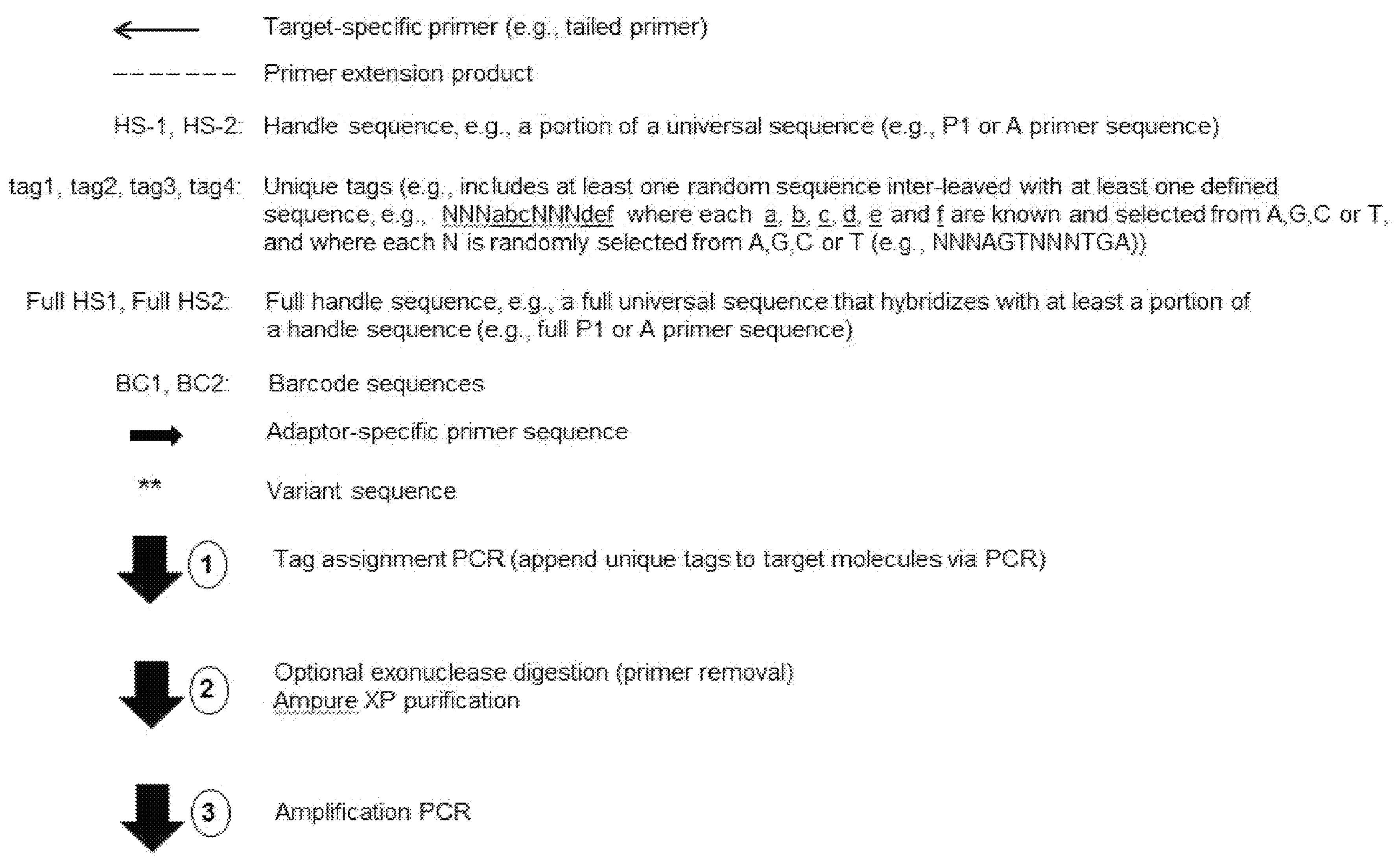
FIG. 3B is a figure legend for FIG. 3A.

Molecular Tagging Procedure:

Molecular tagged libraries were generated from the cfDNA using PCR molecular tagging assignment (approximately 2-4 PCR cycles) followed by PCR amplification (approximately 16-18 PCR cycles) (see FIG. 3 and legend for FIG. 3).

Forward and reverse gene-specific primers were designed to contain unique molecular tags consisting of a total of 6 "N" degenerate bases interspersed with spacer sequences (fixed sequences) located 5' of the gene-specific sequences (FIG. 3 and legend for FIG. 3). For example, the forward and reverse gene-specific primers contained a random tagging sequence located 5' to the gene-specific sequence: 5' NNNACTNNNTGA-3' (SEQ ID NO:1). The forward gene-specific primers also included a portion of a universal A-primer sequence located 5' of the random tagging sequence and an IonXpress barcode sequence. The reverse gene-specific primers included a portion of a universal P1-primer sequence located 5' of the random tagging sequence but lacked a barcode sequence. The forward and reverse gene-specific primers contained a portion of a universal A-primer sequence, or a portion of a universal P1 primer sequence, to be used for subsequent PCR amplification in which the remainder of the universal A or P1 sequences were added using tailed primers, for compatibility for Ion Torrent sequencing. Thus, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. Also, forward and reverse tailed gene-specific primers that lacked the random tag sequence were tested.

Two or four molecular tagging PCR cycles were performed in a 25 µL reaction containing 20 ng of cfDNA, 1× Phusion™ U Multiplex PCR Master Mix (Thermo Fisher Scientific F-562S), and 10 to 50 nM of each primer depending on the total number of amplicons with cycling conditions as follows: 1 cycle of 98° C. for 2 minutes, 2 or 4 cycles of 98° C. for 15 seconds, 60° C. for 4 minutes, 72° C. for 2 minutes, an hold at 4° C. Alternatively, the 20 ng of cf DNA was split into 2 or 4 aliquots, and each aliquot was subjected to the molecular tagging PCR cycles as described above.

Excess primers were removed by $RecJ_f$ exonuclease (New England Biolabs, M0264S), by diluting $RecJ_f$ exonuclease (30 U/uL) 1:10 in 1×NEB Buffer 2, and adding 2 uL of the diluted enzyme to the PCR reaction, and digesting at 37° C. for 15 minutes (optional for primer pools <40 amplicons), and subsequent AMPure™ XP purification.

Purification: First Round:

For the AMPure™ XP purification steps, 25 uL of the PCR reaction was transferred to a fresh 1.5 mL tube. The PCR tube was washed with an additional 25 uL of water to collect all the contents, which was transferred to the 1.5 mL tube. 75 uL of the 1.5× AMPure™ XP Reagent (Beckman Coulter, A63880) was added to the 1.5 mL tube, and the tube was incubated for 10 minutes at room temperature on a rotor. Fresh 80% ethanol was prepared. The sample was washed with the fresh 80% ethanol twice, by following the manufacturer's instructions. The final washed sample was eluted in 25 μL of low TE Buffer (10 mM Tris-HCl, pH 8.0, 0.1 mM EDTA).

PCR Amplification:

For the PCR amplification part of the workflow, approximately 16-18 PCR cycles were performed using forward primers that contained a portion of the universal A primer sequence and an IonXpress barcode sequence, and using reverse primers that contained a portion of the universal P1 primer sequences. The PCR amplification reactions were conducted in a 50 uL reaction containing the previously eluted DNA, 1× Phusion™ HiFi Buffer, 200 μM dNTPs, 0.4 μM forward primer, 0.4 μM reverse primer and 2 U Phusion™ HiFi DNA Polymerase with the following cycling conditions: 1 cycle of 98° C. for 2 minutes, 16 to 18 cycles of 98° C. for 15 seconds, 63° C. for 15 seconds, 72° C. for 15 seconds, and hold at 4° C.

Purification: Second Round:

The reaction was purified with AMPure™ XP Reagent. The amplicons were transferred to a fresh 1.5 mL tube. The PCR tube was washed with an additional 20 uL of water to collect all the contents, which was transferred to the 1.5 mL tube, which contains approximately 70 uL. Double size selection was performed with 0.5× and 0.95× AMPure™ XP Reagent. Alternatively Pippin Prep could be used for size selection. For the AMPure™ method, 77 uL of the 1.5× AMPure™ XP Reagent was added to the 1.5 mL tube, and the tube was incubated for 10 minutes at room temperature on a rotor. The sample was washed with the fresh 80% ethanol twice, by following the manufacturer's instructions. The final washed sample was eluted in 25 μL of low TE Buffer (10 mM Tris-HCl, pH 8.0, 0.1 mM EDTA).

The final library was eluted in 25 uL low TE Buffer and quantified using High Sensitivity DNA Kit on the Agilent 2100 Bioanalyzer. 40 pM of library was used for template amplification and attaching to Ion sphere beads, using an Ion PGM™ Hi-Q™ Chef 400 Supplies kit (Thermo Fisher Scientific A25948 and A27293 kits) and 318 v2 chip loading procedures. Sequencing was performed on Ion PGM apparatus. The sequencing data was analyzed using various culling, sorting and counting methodologies with applied thresholds and demonstrated that 0.05-0.1% limit of detection was achieved. In one tagging experiment, the results showed: 45/163 true variants were detected (requirement >2 families and >0.8 members carrying a variant); 6/45 detected variants have coverage below 20,000; 5/45 detected variants observed at frequency below 0.1%; and the observed allelic frequencies varied 0.1%±0.1%.

Example 2

Molecular Tagging—Cell Free DNA:

Cell-free DNA was isolated from a single tube of blood (approximately 7.5 mL blood) and processed as described in Example 1 above.

In a 96-well plate, the molecular tagging PCR assignment was set-up as follows. Individual wells contained: 20 ng cfDNA, 1× Phusion™ U Multiplex PCR Master Mix (Thermo Fisher Scientific F-562S or F-562L), 3.5 uL lung gene-specific primer panel, and water to make a final volume of 25 uL. Different panels of the lung gene-specific primers were tested. The panels of lung-specific primers contained a repertoire of forward and reverse primers. For example, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. The sequence 5'-NNNACTNNNTGA-3' is SEQ ID NO:1. The lung gene-specific primer panel is a multiplex panel that contained 38-46 different pairs of lung-specific primers, where each pair contained a forward and reverse primer. The gene-specific primer pairs in the panel also contained the random tagging sequence, and either the universal A or P1 primer sequences (see description in Example 1 above). The 96-well plate was sealed with an adhesive film. The plate was vortexed to mix the contents wells, and the plate was spun. The plate was loaded into a thermocycler, and the following program was run:

TABLE 2

| Stage: | Temperature: | Time: |
|---|---|---|
| Hold | 98° C. | 2 minutes |
| Cycle: 2 | 98° C. | 15 seconds |
| | 60° C. | 4 minutes |
| | 72° C. | 2 minutes |
| Hold | 72° C. | 2 minutes |
| Hold | 4° C. | ∞ |

Alternatively, the 20 ng of cf DNA was split into 2 or 4 aliquots, and each aliquot was subjected to the molecular tagging PCR cycles as described above.

AMPure™ XP Reagent was incubated at room temperature for at least 30 minutes, and vortexed to disperse the beads. A solution of 80% ethanol was freshly prepared. 260 uL of the 80% ethanol was mixed with 65 uL water.

The adhesive film was removed from the plate. 25 uL of nuclease-free water was added to each well containing a sample. 75 uL (e.g., 1.5× of the sample volume) of Agencourt AMPure™ XP Reagent was added. The plate was re-sealed with film, and vortexed to mix, then incubated at room temperature for 5 minutes. The plate was vortexed again, and incubated again at room temperature for 5 minutes. The plate was spun briefly. The plate was placed on a 96-well plate rack, the film was removed, and the plate was place on a magnetic stand and incubated for 5 minutes or until the solution turned clear. The supernatant was removed and discarded, from individual wells without disturbing the pellet. 150 uL of the 80% ethanol was added. The plate was moved side-to-side to two or four positions on the magnet t wash the beads. The supernatant was removed and discarded, from individual wells without disturbing the pellet. The 80% ethanol wash was repeated once. The supernatant was removed and discarded, from individual wells without disturbing the pellet. A smaller pipette was used to remove the ethanol drops from the side of the wells. The beads in the wells were air-dried on the magnet at room temperature for 5 minutes. The plate was removed from the magnet. 23 uL of TE was added to individual wells to disperse the beads. The plate was re-sealed with adhesive film, vortexed thoroughly, and incubated at room temperature for 5 minutes. The plate was spun to collect the droplets. The plate was placed on a 96-well plate rack, and the film was removed. The plate was placed on a magnet for at least 2 minutes. 23 uL of the supernatant was transferred to new wells on the same plate.

The PCR amplification procedure was set-up as follows: to the wells containing the 23 uL of sample from the previous step, the following was added: 1 uL universal primer-A (contains an IonXpress barcode sequence), 1 uL universal primer P1, 25 uL 2× Phusion™ U Multiplex PCR Master Mix (Thermo Fisher Scientific F-562S or F-562L). The wells contained about 50 uL of liquid. The contents of the wells were mixed by pipetting up and down 5 times. The plate was spun down briefly. Optional: if there were any carry over beads, the plate was placed on the magnet stand for 3 minutes, and 50 uL of the reaction was transferred to new wells on the same plate. The plate was re-sealed. The plate was loaded onto a thermo-cycler and the following program was run:

TABLE 3

| Stage: | Temperature: | Time: |
|---|---|---|
| Hold | 98° C. | 2 minutes |
| Cycle 2: | 98° C. | 15 seconds |
| | 60° C. | 30 seconds |
| | 72° C. | 30 seconds |
| Cycle 16: | 98° C. | 15 seconds |
| | 63° C. | 15 seconds |
| | 72° C. | 15 seconds |
| Hold: | 4° C. | ∞ |

520 uL of the freshly-prepared 80% ethanol was mixed with 130 uL of nuclease-free water, per sample. The film was removed from the plate. 57.5 uL (e.g., 1.15× of the sample volume) of Agencourt AMPure™ XP Reagent was added to each sample, and pipetted up and down 5 times. The plate was incubated at room temperature for 10 minutes. The plate was placed on a magnet and incubated at room temperature for 5 minutes, or until the solution cleared. The supernatant was carefully removed without disturbing the pellet. 150 uL of the 80% ethanol was added to the samples, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 50 uL of Low TE was added to the pellets to disperse the beads. The samples were pipetted up and down 5 times to resuspend the beads. Alternatively, the plate was sealed with adhesive film, and vortexed thoroughly, and spun down to collect the droplets. The plate was placed on the magnet for at least 2 minutes. 50 uL of the supernatant was transferred to new wells on the same plate. The plate was removed from the magnet. 50 uL (e.g., 1× of the sample volume) of Agencourt AMPure™ XP Reagent was added to each sample. The sample was pipetted up and down 5 times. The plate was incubated at room temperature for 10 minutes. The plate was place on a magnet and incubated for 5 minutes, or until the solution cleared. The supernatant was carefully removed and discarded, without disturbing the pellet. 150 uL of the 80% ethanol was added, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 30 uL of Low TE was added to the pellets to disperse the beads. The samples were pipetted up and down 10 times to resuspend the beads. Alternatively, the plate was sealed with adhesive film, and vortexed thoroughly, and spun down to collect the droplets. The plate was placed on the magnet for at least 2 minutes. 28 uL of the supernatant was transferred to new wells on the same plate.

To quantitate the library, 5 dilution sample points were prepared from standard *E. coli* library (*E. coli* DH10B library at approximately 68 pM stock solution). For example, dilution samples were prepared at: 6.8 pM, 0.68 pM, 0.068 pM, 0.0068 pM and 0.00068 pM. Dilution samples of the library prepared from the cfDNA was prepared by mixing 2 uL of the cfDNA library with 198 uL water, mixed and spun down briefly (this is the 1:100 dilution sample). 3 uL of the 1:100 dilution sample was mixed with 27 uL of water, mixed and spun down briefly (this is the 1:1000 dilution sample). For each sample, 3 wells were set up for: sample, standard, and NTC. A master mix was prepared using the following formula for a 384 well plate:

TABLE 4

| Component: | Volume: |
|---|---|
| 2X TaqMan Master Mix | 5 uL |
| 20X Ion TaqMan Assay | 0.5 uL |
| Total volume: | 5.5 uL |

5.5 uL of the master mix was dispensed into each well, and 4.5 uL of the 1:1000 diluted library and standard was added to these wells.

A PCR reaction on a 7900 HT thermo-cycler (qPCR system) was set up as follows:

TABLE 5

| Stage: | Temperature: | Time: |
|---|---|---|
| Hold | 50° C. | 2 minutes |
| Hold | 95° C. | 20 seconds |
| 40 cycles | 95° C. | 1 second |
| | 60° C. | 20 seconds |

The average concentration of the undiluted cfDNA library was calculated by multiplying the concentration determined with qPCR by the library dilution used in this assay.

The final library was eluted in 25 uL low TE Buffer and quantified using High Sensitivity DNA Kit on the Agilent 2100 Bioanalyzer. 40 pM of library was used for template amplification and attaching to Ion sphere beads, using an Ion PGM™ Hi-Q™ Chef 400 Supplies kit (Thermo Fisher Scientific A25948 and A27293 kits) and 318 v2 chip loading procedures. Sequencing was performed on Ion PGM apparatus. The sequencing data was analyzed using various culling, sorting and counting methodologies with applied thresholds (e.g., see Appendix 2 and 3), and demonstrated that 0.05-0.1% limit of detection was achieved (see all the data in Appendix 1).

The molecular tagging PCR assignment was also conducted using 20 ng of a 0.1% dilution of MegaMix Control DNA (from AcroMetrix) which contains synthetic and genomic DNA including cancer-relevant mutations. Each molecular tagging reaction was conducted with 2 PCR cycles using Phusion U Multiplex PCR Master Mix (Thermo Fisher Scientific F-562S or F-562L) and a multiplex primer panel that contained BRAF, and the amplification products were purified with 1.5× AMPure™ XP Reagent. The second PCR amplification was conducted with 22 PCR cycles using Phusion HiFi DNA polymerase and buffer, and universal primer-A1 and universal primer-P1, and the amplification products were purified with 1.4× AMPure™ XP Reagent. The results are shown in the Table below. 6700 of the reads had more than 1000× coverage. There were no reverse reads because universal primer-A1 was always on the 5' primer.

Enzyme mix, and nuclease-free water to make 10 uL total volume. The 96-well plate was sealed with an adhesive film. The plate was vortexed to mix the contents wells, and the plate was spun. The plate was loaded into a Thermocycler, and the following program was run:

TABLE 7

| Stage: | Temperature: | Time: |
|---|---|---|
| Stage 1 | 42° C. | 30 minutes |
| Stage 2 | 85° C. | 5 minutes |
| Hold | 10° C. | ∞ |

Tagging: First Round PCR:

Reagents for the molecular tagging PCR assignment were set up in new wells in the same 96-well plate as follows. A

TABLE

| 1 | contig_id | contig_srt | contig_end | region_id | gc_count | overlaps | fwd_e2e | rev_e2e |
|---|---|---|---|---|---|---|---|---|
| 184 | chr3 | 178936024 | 178936105 | CHP2_PIK3CA_7 | 32 | 16491 | 15341 | 0 |
| 185 | chr13 | 49027106 | 49027178 | CHP2_RB1_7 | 23 | 16713 | 15889 | 0 |
| 186 | chr11 | 108200916 | 108200993 | CHP2_ATM_10 | 32 | 17239 | 16787 | 0 |
| 187 | chr7 | 55232963 | 55233053 | CHP2_EFGR_3 | 55 | 17617 | 14341 | 0 |
| 188 | chr2 | 212652720 | 212652806 | CHP2_ERBB4_2 | 32 | 18224 | 15381 | 0 |
| 189 | chr13 | 49039150 | 49039232 | CHP2_RB1_10 | 27 | 18239 | 16790 | 0 |
| 190 | chr4 | 153250853 | 153250926 | CHP2_FBXW7_2 | 28 | 18525 | 17485 | 0 |
| 191 | chr5 | 112173872 | 112173962 | CHP2_APC_1 | 45 | 18536 | 15019 | 0 |
| 192 | chr4 | 1808312 | 1808399 | CHP2_FGFR3_4 | 60 | 18912 | 16711 | 0 |
| 193 | chr7 | 55241636 | 55241729 | CHP2_EFGR_4 | 48 | 19886 | 18383 | 0 |
| 194 | chr18 | 48603029 | 48603119 | CHP2_SMAD4_8 | 58 | 20342 | 10273 | 0 |
| 195 | chr7 | 116423408 | 116423492 | CHP2_MET_6 | 34 | 21720 | 19592 | 0 |
| 196 | chr4 | 153245411 | 153245492 | CHP2_FBXW7_5 | 36 | 21816 | 17014 | 0 |
| 197 | chr1 | 115258690 | 115258774 | CHP2_NRAS_1 | 41 | 22292 | 7102 | 0 |
| 198 | chr11 | 108137932 | 108138025 | CHP2_ATM_4 | 34 | 24315 | 20446 | 0 |
| 199 | chr7 | 55211045 | 5521126 | CHP2_EFGR_1 | 33 | 25437 | 21672 | 0 |
| 200 | chr4 | 55960977 | 55961059 | CHP2_KDR_5 | 46 | 25493 | 23750 | 0 |
| 201 | chr2 | 212288905 | 212288990 | CHP2_ERBB4_8 | 38 | 25891 | 5967 | 0 |
| 202 | chr4 | 55955079 | 55955168 | CHP2_KDR_6 | 46 | 27323 | 25295 | 0 |
| 203 | chr17 | 7578517 | 7578601 | CHP2_TP53_3 | 43 | 27366 | 25451 | 0 |
| 204 | chr4 | 55597437 | 55597524 | CHP2_KIT_7 | 40 | 28103 | 26228 | 0 |
| 205 | chr4 | 55953776 | 55953860 | CHP2_KDR_7 | 41 | 30929 | 29379 | 0 |
| 206 | chr7 | 116339616 | 116339701 | CHP2_MET_1 | 47 | 32261 | 29832 | 0 |
| 207 | chr4 | 153247278 | 153247369 | CHP2_FBXW7_4 | 44 | 42625 | 38789 | 0 |
| 208 | chr12 | 121432011 | 121432099 | CHP2_HNF1A_2 | 55 | 45780 | 39559 | 0 |

Example 3

Molecular Tagging—Fusion RNA:

Cell-free DNA was isolated from a single tube of blood (approximately 7.5 mL blood) and processed as described in Example 1 above.

Two nucleic acid samples containing a mixture of DNA and RNA were prepared as follows. An RNA cocktail, which contained known fusion RNA species, was spiked into the cfDNA to a final concentration of 25% or 50% RNA. A third nucleic acid sample containing only the RNA cocktail was also used for the molecular tagging procedure. Other samples were prepared and tested in which the RNA cocktail was spiked into the cfDNA to a final concentration of 2%, 1%, 0.5%, and 0.1% RNA. The RNA cocktail was prepared from fusion-positive lung NCI cell lines H2228 and HCC78.

Reverse Transcription Reaction:

The 5× VILO™ RT Reaction Mix and 10× Superscript™ III Enzyme Mix were from a Superscript™ IV VILO™ cDNA Synthesis Kit (Thermo Fisher Scientific, catalog No. 11754-050). In a 96-well plate, a reverse transcription reaction was set-up as follows. Individual wells contained: 20 ng nucleic acid sample (cfDNA plus spiked-in RNA), 2 uL of 5× VILO Reaction Mix, 1 uL of 10× Superscript™ III total volume of 25 uL reaction volume contained: 10 uL of the cDNA from the reverse transcription reaction described above, 12.5 uL of 2× Phusion™ U Multiplex PCR Master Mix (Thermo Fisher Scientific F-562S or F-562L), 2.5 uL of tagged primer panel. The tagged primer panel contains a multiplex set paired forward and reverse gene-specific primers that are designed to produce amplicons having a fusion sequence. The tagged primers in the panel also contained the random tagging sequence, and either the universal A or P1 primer sequences (see the description of the forward and reverse gene-specific primers in Example 1 above). For example, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. The sequence 5'-NNNACTNNNTGA-3' is SEQ ID NO:1. The 96-well plate was sealed with an adhesive film. The plate was vortexed to mix the contents wells, and the plate was spun. The plate was loaded into a thermocycler, and the following program was run:

TABLE 8

| Stage: | Temperature: | Time: |
|---|---|---|
| Hold | 98° C. | 2 minutes |
| Cycle: 2 | 98° C. | 15 seconds |
| | 60° C. | 4 minutes |
| | 72° C. | 2 minutes |
| Hold | 72° C. | 2 minutes |
| Hold | 4° C. | ∞ |

Purification: First Round:

AMPure™ XP Reagent was incubated at room temperature for at least 30 minutes, and vortexed to disperse the beads. A solution of 80% ethanol was freshly prepared. 260 uL of the 80% ethanol was mixed with 65 uL water.

The adhesive film was removed from the plate. 25 uL of nuclease-free water was added to each well containing a sample. 75 uL (e.g., 1.5× of the sample volume) of Agencourt AMPure™ XP Reagent was added. The plate was re-sealed with film, and vortexed to mix, then incubated at room temperature for 5 minutes. The plate was vortexed again, and incubated again at room temperature for 5 minutes. The plate was spun briefly. The plate was placed on a 96-well plate rack, the film was removed, and the plate was place on a magnetic stand and incubated for 5 minutes or until the solution turned clear. The supernatant was removed and discarded, from individual wells without disturbing the pellet. 150 uL of the 80% ethanol was added. The plate was moved side-to-side to two or four positions on the magnet t wash the beads. The supernatant was removed and discarded, from individual wells without disturbing the pellet. The 80% ethanol wash was repeated once. The supernatant was removed and discarded, from individual wells without disturbing the pellet. A smaller pipette was used to remove the ethanol drops from the side of the wells. The beads in the wells were air-dried on the magnet at room temperature for 5 minutes. The plate was removed from the magnet. 23 uL of TE was added to individual wells to disperse the beads. The plate was re-sealed with adhesive film, vortexed thoroughly, and incubated at room temperature for 5 minutes. The plate was spun to collect the droplets. The plate was placed on a 96-well plate rack, and the film was removed. The plate was placed on a magnet for at least 2 minutes. 23 uL of the supernatant was transferred to new wells on the same plate.

Second Round PCR:

The PCR amplification procedure was set-up as follows: to the wells containing the 23 uL of sample from the previous step, the following was added: 1 uL universal primer-A (contains an IonXpress barcode sequence), 1 uL universal primer P1, 25 uL 2× Phusion™ U Multiplex PCR Master Mix (Thermo Fisher Scientific F-562S or F-562L). The wells should contain about 50 uL of liquid. The contents of the wells were mixed by pipetting up and down 5 times. The plate was spun down briefly. Optional: if there were any carry over beads, the plate was placed on the magnet stand for 3 minutes, and 50 uL of the reaction was transferred to new wells on the same plate. The plate was re-sealed. The plate was loaded onto a thermo-cycler and the following program was run:

TABLE 9

| Stage: | Temperature: | Time: |
|---|---|---|
| Hold | 98° C. | 2 minutes |
| Cycle 2: | 98° C. | 15 seconds |

TABLE 9-continued

| Stage: | Temperature: | Time: |
|---|---|---|
| | 60° C. | 30 seconds |
| | 72° C. | 30 seconds |
| Cycle 16: | 98° C. | 15 seconds |
| | 63° C. | 15 seconds |
| | 72° C. | 15 seconds |
| Hold: | 4° C. | ∞ |

Purification—Second Round:

520 uL of the freshly-prepared 80% ethanol was mixed with 130 uL of nuclease-free water, per sample. The film was removed from the plate. 57.5 uL (e.g., 1.15× of the sample volume) of Agencourt AMPure™ XP Reagent was added to each sample, and pipetted up and down 5 times. The plate was incubated at room temperature for 10 minutes. The plate was placed on a magnet and incubated at room temperature for 5 minutes, or until the solution cleared. The supernatant was carefully removed without disturbing the pellet. 150 uL of the 80% ethanol was added to the samples, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 50 uL of Low TE was added to the pellets to disperse the beads. The samples were pipetted up and down 5 times to resuspend the beads. Alternatively, the plate was sealed with adhesive film, and vortexed thoroughly, and spun down to collect the droplets. The plate was placed on the magnet for at least 2 minutes. 50 uL of the supernatant was transferred to new wells on the same plate. The plate was removed from the magnet. 50 uL (e.g., 1× of the sample volume) of Agencourt AMPure™ XP Reagent was added to each sample. The sample was pipetted up and down 5 times. The plate was incubated at room temperature for 10 minutes. The plate was place on a magnet and incubated for 5 minutes, or until the solution cleared. The supernatant was carefully removed and discarded, without disturbing the pellet. 150 uL of the 80% ethanol was added, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 30 uL of Low TE was added to the pellets to disperse the beads. The samples were pipetted up and down 10 times to resuspend the beads. Alternatively, the plate was sealed with adhesive film, and vortexed thoroughly, and spun down to collect the droplets. The plate was placed on the magnet for at least 2 minutes. 28 uL of the supernatant was transferred to new wells on the same plate.

To quantitate the library, 5 dilution sample points were prepared from standard *E. coli* library (*E. coli* DH10B library at approximately 68 pM stock solution). For example, dilution samples were prepared at: 6.8 pM, 0.68 pM, 0.068 pM, 0.0068 pM and 0.00068 pM. Dilution samples of the library prepared from the cfDNA was prepared by mixing 2 uL of the cfDNA library with 198 uL water, mixed and spun down briefly (this is the 1:100 dilution sample). 3 uL of the 1:100 dilution sample was mixed with 27 uL of water, mixed and spun down briefly (this is the 1:1000 dilution sample). For each sample, 3 wells were set up for: sample, standard, and NTC. A master mix was prepared using the following formula for a 384 well plate:

TABLE 10

| Component: | Volume: |
|---|---|
| 2X TaqMan Master Mix | 5 uL |
| 20X Ion TaqMan Assay | 0.5 uL |
| Total volume: | 5.5 uL |

5.5 uL of the master mix was dispensed into each well, and 4.5 uL of the 1:1000 diluted library and standard was added to these wells.

A PCR reaction on a 7900 HT thermo-cycler (qPCR system) was set up as follows:

TABLE 11

| Stage: | Temperature: | Time: |
|---|---|---|
| Hold | 50° C. | 2 minutes |
| Hold | 95° C. | 20 seconds |
| 40 cycles | 95° C. | 1 second |
| | 60° C. | 20 seconds |

The average concentration of the undiluted cfDNA library was calculated by multiplying the concentration determined with qPCR by the library dilution used in this assay.

The final library was eluted in 25 uL low TE Buffer and quantified using High Sensitivity DNA Kit on the Agilent 2100 Bioanalyzer. 40 pM of library was used for template amplification and attaching to Ion sphere beads, using an Ion PGM™ Hi-Q™ Chef 400 Supplies kit (Thermo Fisher Scientific A25948 and A27293 kits) and 318 v2 chip loading procedures. Sequencing was performed on Ion PGM apparatus. The sequencing data was analyzed using various culling, sorting and counting methodologies with applied thresholds, and demonstrated that EML4-ALK and SLC34A2-ROS1 fusion transcripts were detected.

Example 4

Molecular Tagging with Lung Primer Panel—cfDNA, MegaMix Control DNA, and Horizon Control DNA Samples.

Cell-free DNA was isolated from a single tube of blood (approximately 7.5 mL blood, 4-5 mL plasma) from human lung cancer subjects (e.g., late stage lung cancer) and processed as described in Example 1 above. The blood was collected in EDTA blood collection tubes or Streck DNA blood collection tubes. Generally, approximately 20-50 ng of cfDNA was isolated from about 7.5 mL blood. Also, matched FFPE samples were obtained from the same human lung cancer subjects.

Tagging cfDNA, MegaMix Control DNA or Horizon Control DNA:

The components from an Oncomine® Lung cfDNA Kit were thawed on ice, including: the Lung cfDNA Panel of primers, and the cfDNA Library PCR Master Mix. The Lung cfDNA Panel of primers included primer pairs for generating 35 different amplicons that covers mutations in 11 genes, including 157 hotspot mutations. For example, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. The sequence 5'-NNNACTNNNTGA-3' is SEQ ID NO:1.

The MegaMix Control DNA is a control DNA mixture from AcroMetrix™ containing synthetic and genomic DNA which includes cancer-relevant mutations.

The Horizon cfDNA Control DNA is a reference standard made from engineered cell lines and contains cancer-relevant mutations.

In a 96-well plate, the molecular tagging PCR assignment was set-up in individual wells as follows:

TABLE 12

| Component: | Volume: |
|---|---|
| cfDNA or MegaMix or Horizon Control DNA | X μL |
| Nuclease-free water | 12.6 minus X μL |
| Lung cfDNA Panel | 2.4 μL |
| cfDNA Library PCR Master Mix | 15 μL |
| Total volume: | 30 μL |

The cfDNA PCR Master Mix was added last to minimize the amount of time the reaction mixture spent at room temperature. Alternatively, the Master Mix was set up on ice.

The plate was sealed with MicroAmp® Clear adhesive film. The plate was vortexed to mix well. The plate was spun at 300×g for 30 seconds.

A thermal cycler was pre-heated to 90° C. The plate was loaded into the thermal cycler and run under the following program:

TABLE 13

| Stage: | Temperature: | Time: |
|---|---|---|
| Hold | 98° C. | 2 min. |
| Cycle: 2 | 98° C. | 30 sec. |
| | 64° C. | 2 min. |
| | 62° C. | 2 min. |
| | 60° C. | 4 min. |
| | 58° C. | 2 min. |
| | 72° C. | 30 sec. |
| Hold | 72° C. | 2 min. |
| Hold | 4° C. | ∞ |

To minimize sample evaporation, a MicroAmp® Optical Film Compression Pad was used during PCR.

First Round Purification:

AMPure™ XP Reagent was incubated at room temperature for at least 30 minutes, and vortexed thoroughly to disperse the beads. Low retention pipet tips were used for the AMPure™ purification steps. A solution of 80% ethanol was freshly prepared. 260 uL of the 80% ethanol was mixed with 65 uL nuclease-free water per sample.

The plate was briefly spun to collect the samples at the bottom of the wells. The adhesive film was carefully removed from the plate. 30 μL of nuclease-free water was added to each sample. 96 μL (1.6× sample volume) of Agencourt AMPure™ XP Reagent was added to each sample. The plate was re-sealed with film, and vortexed to mix, and incubated at room temperature for 5 minutes. The plate was vortexed again and incubated at room temperature for another 5 minutes. The color of the sample was checked after each vortexing to ensure thorough mixing of the beads. The plate was spun at 300×g for 1 minute. The plate was placed on a 96-well plate rack, and the film was removed. The plate was placed on a magnetic stand and incubated for 5 minutes or until the solution turned clear. The supernatant was removed, without disturbing the pellet, and the supernatant was discarded. 150 μL of freshly prepared 80% ethanol was added to each well, and incubated at room temperature for 30 seconds. The supernatant was removed, without disturbing the pellet, and the supernatant was discarded. The plate was not moved while resting on the magnet. The wash was repeated with 150 μL of freshly prepared 80% ethanol was added to each well, and incubated at room temperature for 30 seconds. The supernatant was removed, without disturbing the pellet, and the supernatant was discarded. A smaller pipette (e.g., 10 or 20 μL) was used to remove all the ethanol droplets from the wells. The beads in the wells were air-dried on the magnet at room temperature for 5 minutes. The plate was removed from the magnet. 24 μL of Low TE was added to the pellet to disperse the beads. The plate was re-sealed with fresh MicroAmp® adhesive film, and vortexed thoroughly, and incubated at room temperature for 5 minutes. The plate was spun at 300×g for 30 seconds to collect the droplets. The plate was placed on a 96-well plate rack, and the film was removed. The plate was placed on a magnetic stand and incubated for at least 2 minutes. 23 μL of the supernatant was transferred to new wells on the same plate, using low retention tips to reduce sample loss.

Appending the Universal P1 and Barcoded A Adaptors:

A second PCR reaction was set-up as follows: to the wells containing the 23 μL sample from the previous step, the following was added: 1 μL cfDNA Library Primer A/BC X (barcodes 1-16); 1 μL cfDNA Library Primer P1; 25 μL cfDNA Library Master Mix (for a total of 50 μL volume). The cfDNA Library Master Mix was added last to minimize the amount of time the reaction spent at room temperature. The plate was sealed with new MicroAmp® adhesive film, and vortexed thoroughly. The plate was spun at 300×g for 30 seconds to collect the droplets.

A thermal cycler was pre-heated to 90° C. The plate was loaded into the thermal cycler and run under the following program:

TABLE 14

| Stage: | Temperature: | Time: |
|---|---|---|
| Hold: | 98° C. | 2 min. |
| Cycle: 18 | 98° C. | 15 sec. |
| | 64° C. | 15 sec. |
| | 72° C. | 15 sec. |
| Hold: | 72° C. | 5 min. |
| Hold: | 4° C. | ∞ |

To minimize sample evaporation, a MicroAmp® Optical Film Compression Pad was used during PCR.

Second Round Purification:

520 μL of freshly-prepared 80% ethanol was mixed with 130 μL of nuclease-free water, per sample. 115 μL (1.15× sample volume) of Agencourt AMPure™ XP Reagent was added to each sample. The plate was re-sealed, vortexed to mix, and incubated at room temperature for 5 minutes. The color of the sample was checked after vortexing to ensure thorough mixing of the beads. The plate was spun at 300×g for 1 minute. The plate was placed on a 96-well plate rack, and the film was removed. The plate was placed on a magnetic stand and incubated for 5 minutes or until the solution turned clear. The supernatant was removed, without disturbing the pellet, and the supernatant was discarded. 150 μL of freshly prepared 80% ethanol was added to each well, and incubated at room temperature for 30 seconds. The supernatant was removed, without disturbing the pellet, and the supernatant was discarded. The plate was not moved while resting on the magnet. The wash was repeated with 150 μL of freshly prepared 80% ethanol was added to each well, and incubated at room temperature for 30 seconds. The supernatant was removed, without disturbing the pellet, and the supernatant was discarded. A smaller pipette (e.g., 10 or 20 μL) was used to remove all the ethanol droplets from the wells. The beads in the wells were air-dried on the magnet at room temperature for 5 minutes. The plate was removed from the magnet. 50 μL of Low TE was added to the pellet to disperse the beads. The plate was re-sealed with fresh MicroAmp® adhesive film, and vortexed thoroughly, and incubated at room temperature for 5 minutes. The plate was spun at 300×g for 30 seconds to collect the droplets. The plate was placed on a 96-well plate rack, and the film was removed. The plate was placed on a magnetic stand and incubated for at least 2 minutes. 50 L of the supernatant was transferred to new wells on the same plate, using low retention tips to reduce sample loss.

Size-Selection:

Size-selection was performed as follows. The plate was removed from the magnet. 45 μL (0.9× sample volume) of Agencourt AMPure™ XP Reagent was added to each sample. The plate was re-sealed, vortexed to mix, and incubated at room temperature for 5 minutes. The color of the sample was checked after vortexing to ensure thorough mixing of the beads. The plate was spun at 300×g for 1 minute. The plate was placed on a 96-well plate rack, and the film was removed. The plate was placed on a magnetic stand and incubated for 5 minutes or until the solution turned clear. The supernatant was removed, without disturbing the pellet, and the supernatant was discarded. 150 μL of freshly prepared 80% ethanol was added to each well, and incubated at room temperature for 30 seconds. The supernatant was removed, without disturbing the pellet, and the supernatant was discarded. The plate was not moved while resting on the magnet. The wash was repeated with 150 μL of freshly prepared 80% ethanol was added to each well, and incubated at room temperature for 30 seconds. The supernatant was removed, without disturbing the pellet, and the supernatant was discarded. A smaller pipette (e.g., 10 or 20 μL) was used to remove all the ethanol droplets from the wells. The beads in the wells were air-dried on the magnet at room temperature for 5 minutes. The plate was removed from the magnet. 30 μL of Low TE was added to the pellet to disperse the beads. The plate was re-sealed with fresh MicroAmp® adhesive film, and vortexed thoroughly, and incubated at room temperature for 5 minutes. The plate was spun at 300×g for 30 seconds to collect the droplets. The plate was placed on a 96-well plate rack, and the film was removed. The plate was placed on a magnetic stand and incubated for at least 2 minutes. 28 μL of the supernatant was transferred to new wells on the same plate, using low retention tips to reduce sample loss.

Library Quantification and Preparing Dilution Standards:

A dilution series was prepared using *E. coli* DH10B Control DNA (~68 pM stock), which included 6.8 pM, 0.68 pM, 0.068 pM, 0.0068 pM and 0.00068 pM. These dilutions were used as dilution standards in a qPCR instrument.

A 1:100 dilution of the tagged library was prepared by combining 2 μL of a tagged library with 198 μL of nuclease-free water, the mixture was vortexed well, and spun briefly. A 1:1000 dilution of the tagged library was prepared by combining 3 μL of the 1:100 dilution with 27 μL of nuclease-free water, the mixture was vortexed, and spun briefly.

Three wells each were set up for each tagged library, dilution standard and no template control (NTC). The volume of Master Mix for each sample was prepared using the following table:

TABLE 15

| Component: | Volume: |
| --- | --- |
| 2X TaqMan Master Mix | 5 μL |
| 20X Ion TaqMan assay | 0.5 μL |
| Total volume: | 5.5 μL |

5.5 μL of Master Mix was dispensed into each well, and 4.5 μL of the 1:1000 dilution standard or the 1:1000 diluted tagged library.

A 7900 HT systems thermal cycler was run as follows:

TABLE 16

| Stage: | Temperature: | Time: |
| --- | --- | --- |
| Hold | 50° C. | 2 min. |
| Hold | 95° C. | 20 sec. |
| Cycle: 40 | 95° C. | 1 sec. |
| | 60° C. | 20 sec. |

The average concentration of the undiluted tagged library was calculated by multiplying the concentration determined by qPCR by the library dilution used in this assay.

Figure 4:
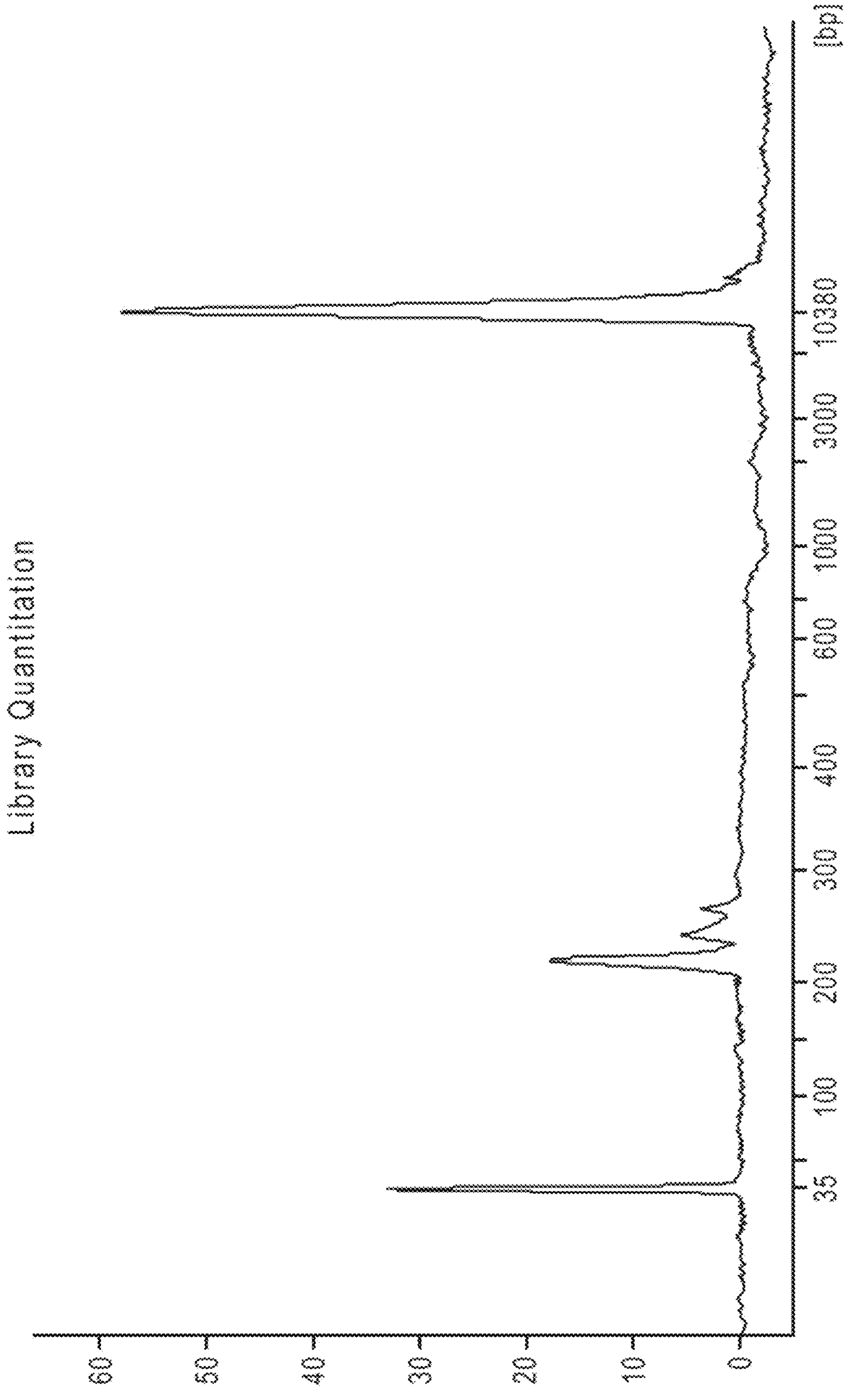
FIG. 4 is a graph showing library quantitation.

Results:

The results of a library quantitation procedure of a tagged library generated from cfDNA, and using the molecular tagging method described in Example 4, is shown in FIG. 4.

Figure 5:
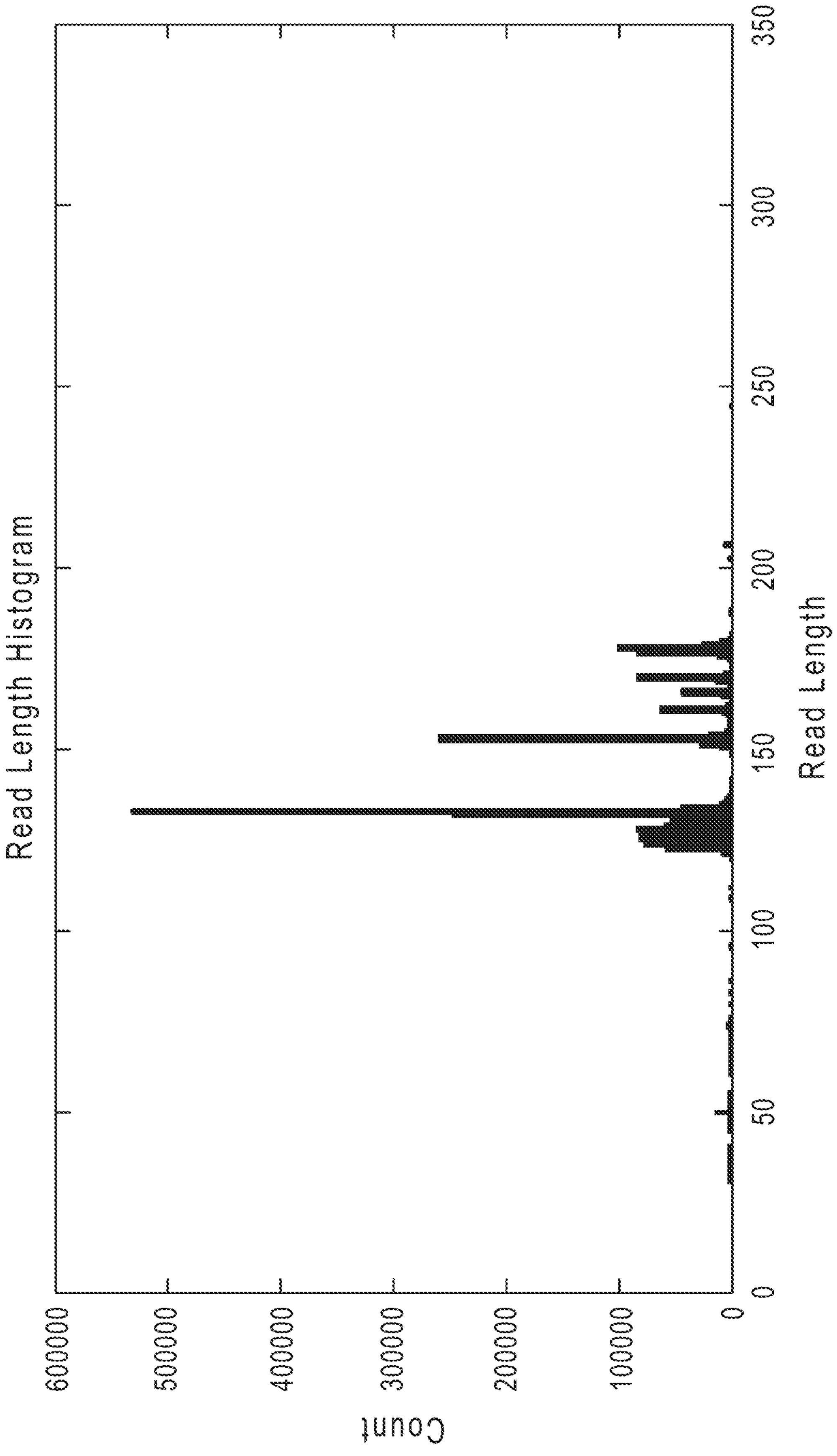
FIG. 5 is a read length histogram.

The results of a read length analysis of a tagged library generated from cfDNA, and using the molecular tagging method described in Example 4, and then sequenced on an Ion Torrent semiconductor sequencing chip is shown in FIG. 5.

The results of a true positive count and a sensitivity analysis of several tagged libraries generated from different dilution standards of control DNA (e.g., 0.5% or 0.1%), and using the molecular tagging method described in Example 4, and then sequenced on an Ion Torrent semiconductor sequencing chip is shown in FIG. 6.

Figure 7A:
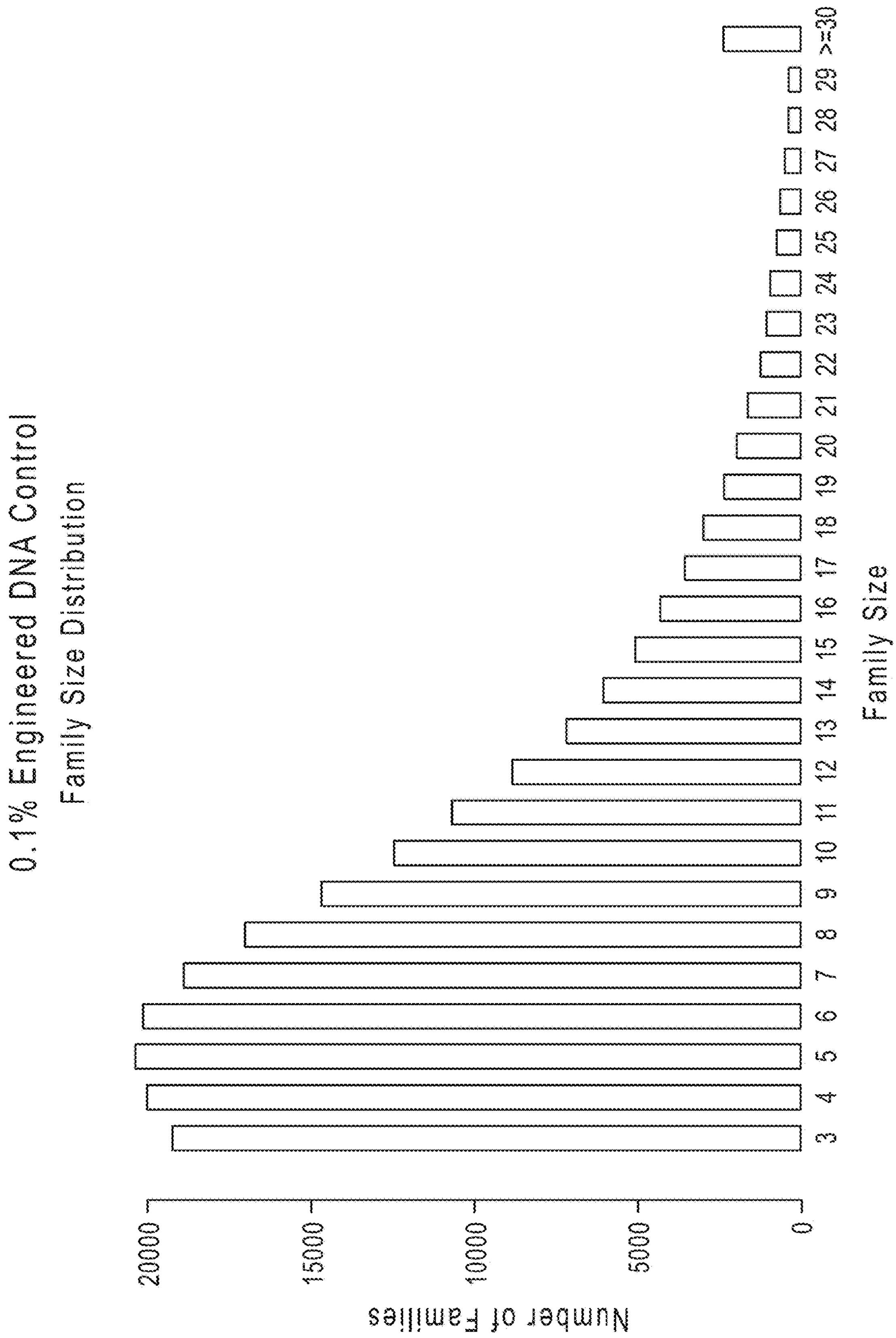
FIG. 7A is a histogram showing family size distribution of a tagged library generated from a 0.1% dilution standard from an engineered control sample.

The results of a family size distribution analysis of a tagged library generated from a 0.1% dilution standard of engineered control DNA, and using the molecular tagging method described in Example 4, and then sequenced on an Ion Torrent semiconductor sequencing chip is shown in FIG. 7A.

Figure 7B:
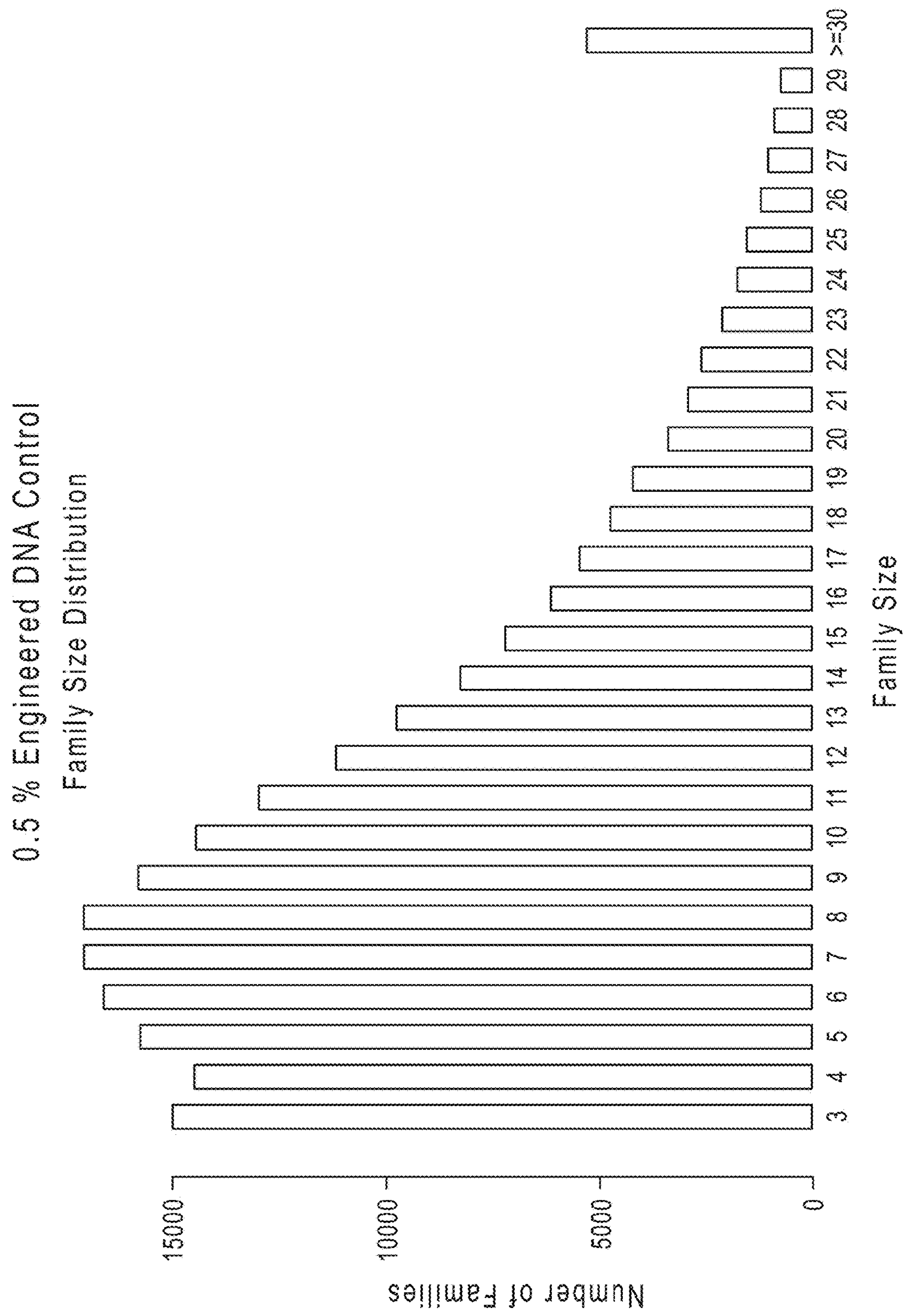
FIG. 7B is a histogram showing family size distribution of a tagged library generated from a 0.5% dilution standard from an engineered control sample.

The results of a family size distribution analysis of a tagged library generated from a 0.5% dilution standard of engineered control DNA, and using the molecular tagging method described in Example 4, and then sequenced on an Ion Torrent semiconductor sequencing chip is shown in FIG. 7B.

Figure 8A:
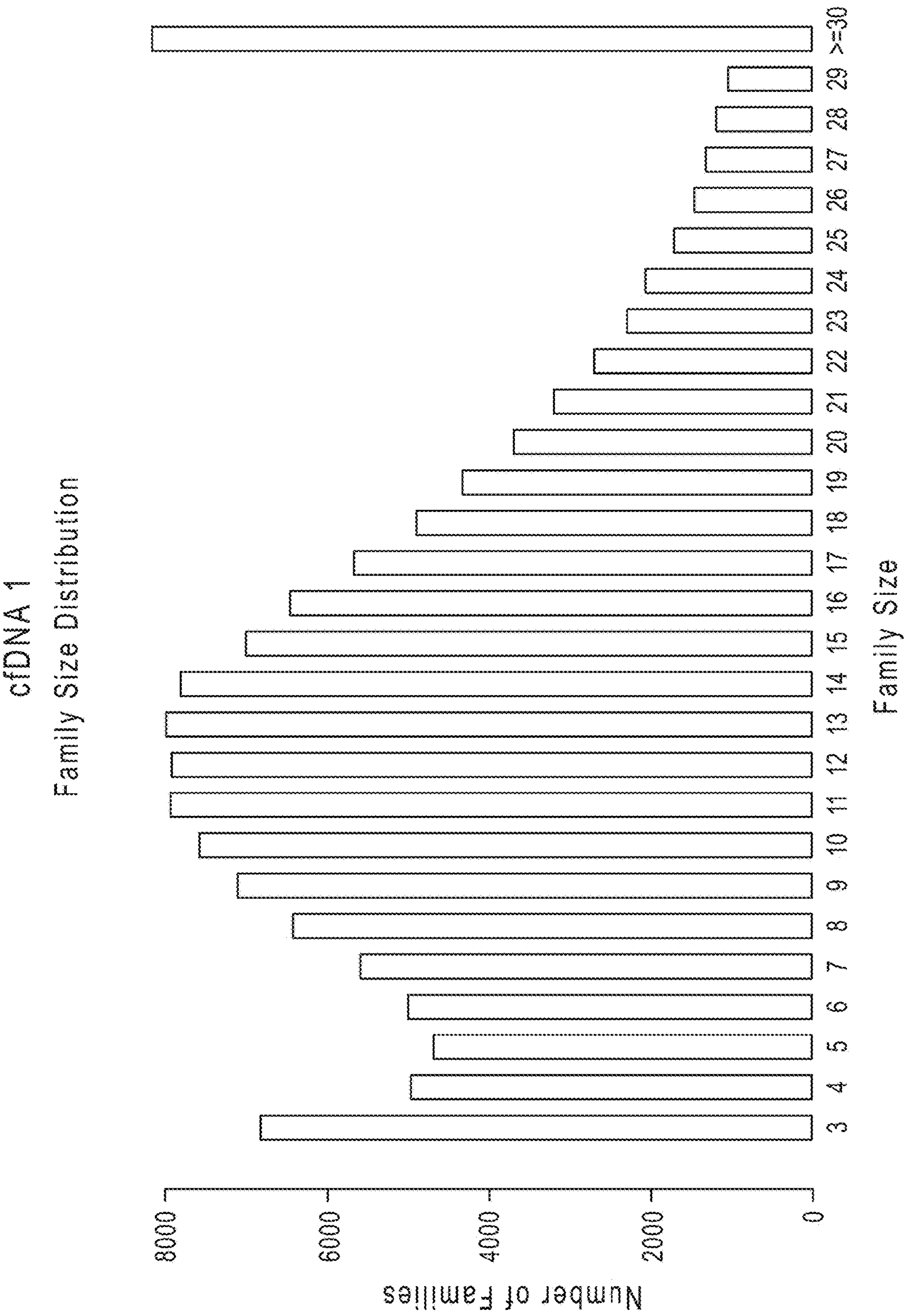
FIG. 8A is a histogram showing family size distribution of a tagged library generated from cfDNA.

The results of a family size distribution analysis of a tagged library generated from a cfDNA-1 sample, and using the molecular tagging method described in Example 4, and then sequenced on an Ion Torrent semiconductor sequencing chip is shown in FIG. 8A.

Figure 8B:
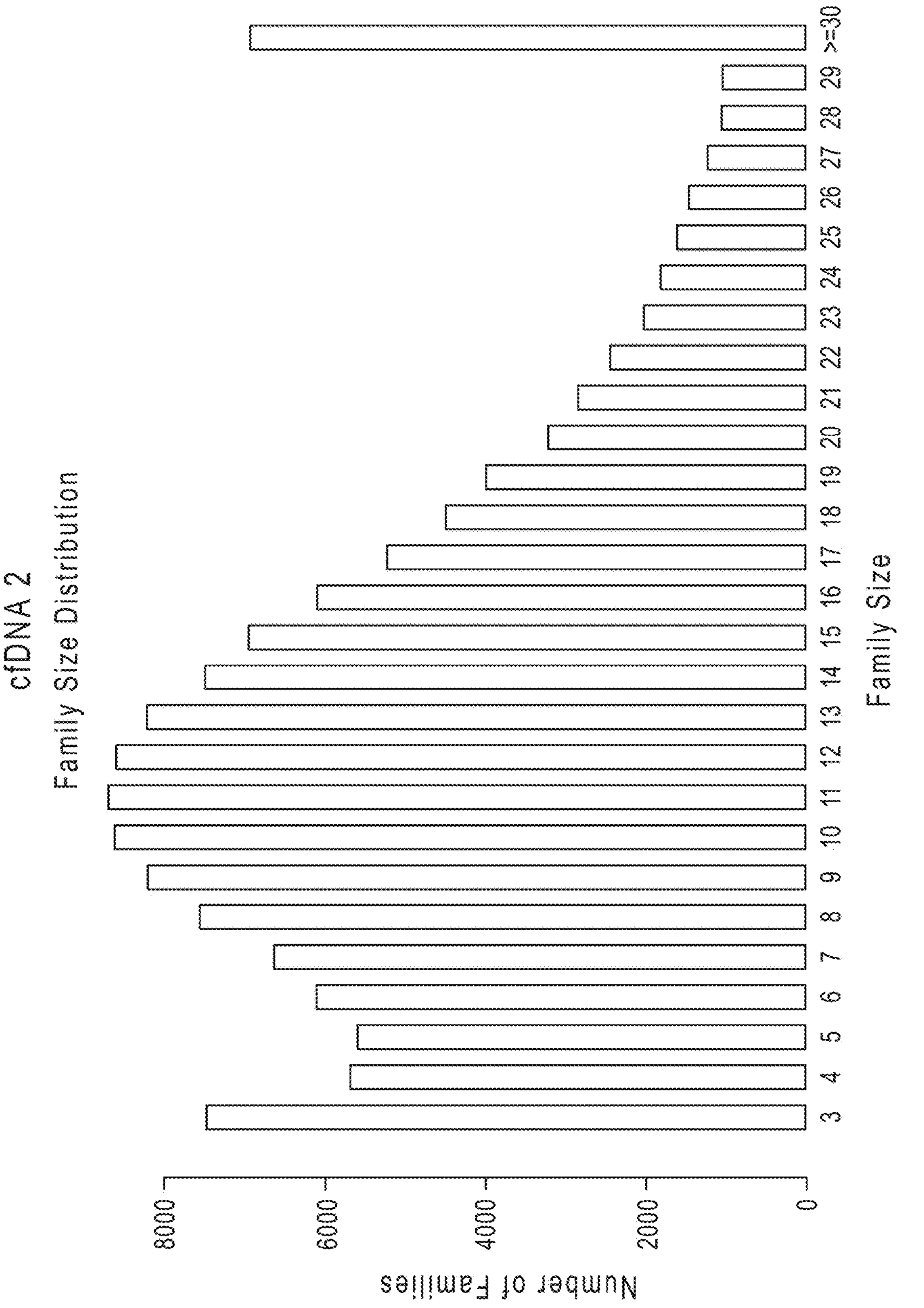
FIG. 8B is a histogram showing family size distribution of a tagged library generated from cfDNA.

The results of another family size distribution analysis of a different tagged library generated from a cfDNA-2 sample, and using the molecular tagging method described in Example 4, and then sequenced on an Ion Torrent semiconductor sequencing chip is shown in FIG. 8B.

Figure 9A:
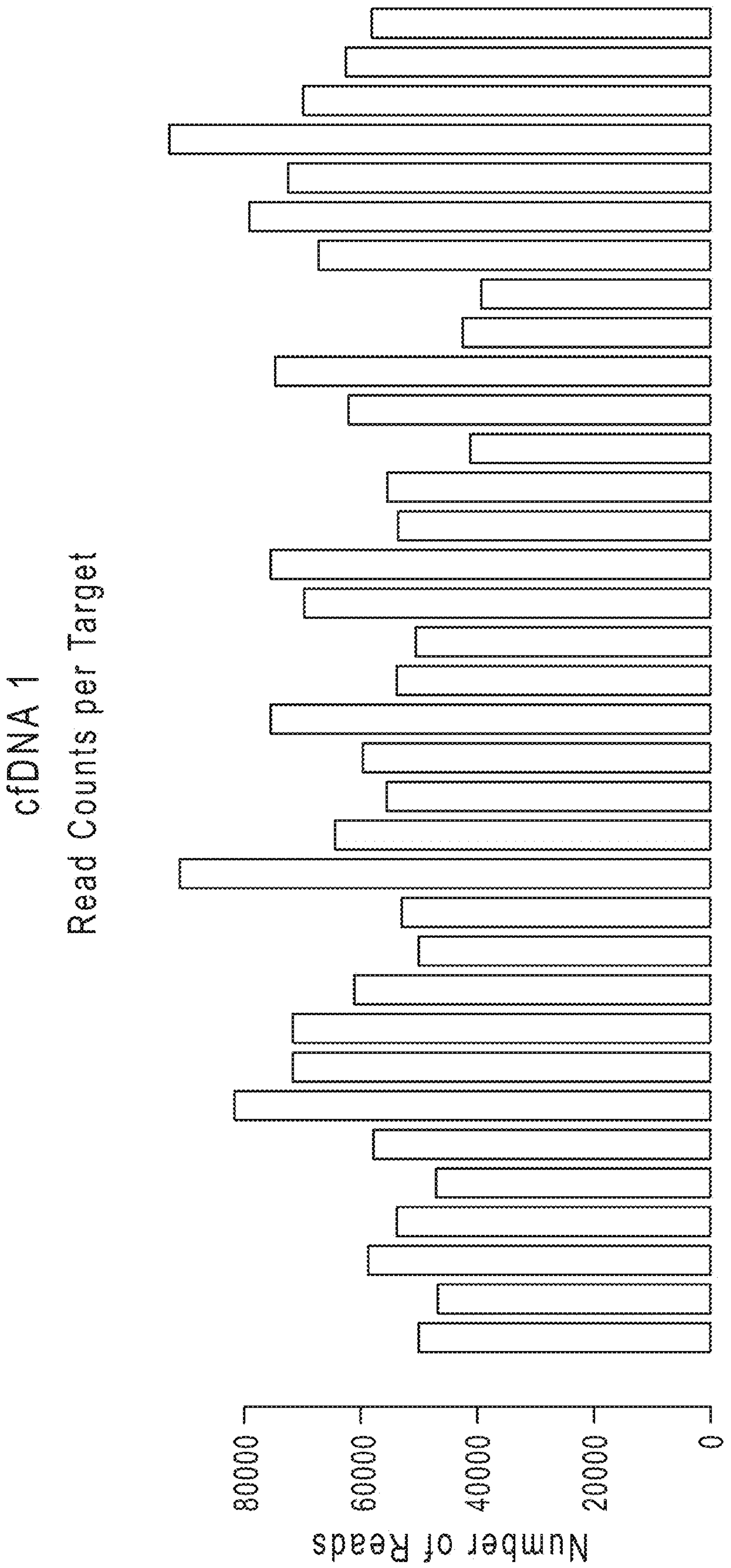
FIG. 9A is a histogram showing read counts per target sequence of a tagged library generated from cfDNA.

The results of a reads count per target sequence of a tagged library generated from a cfDNA-1 sample, and using the molecular tagging method described in Example 4, and then sequenced on an Ion Torrent semiconductor sequencing chip is shown in FIG. 9A.

Figure 9B:
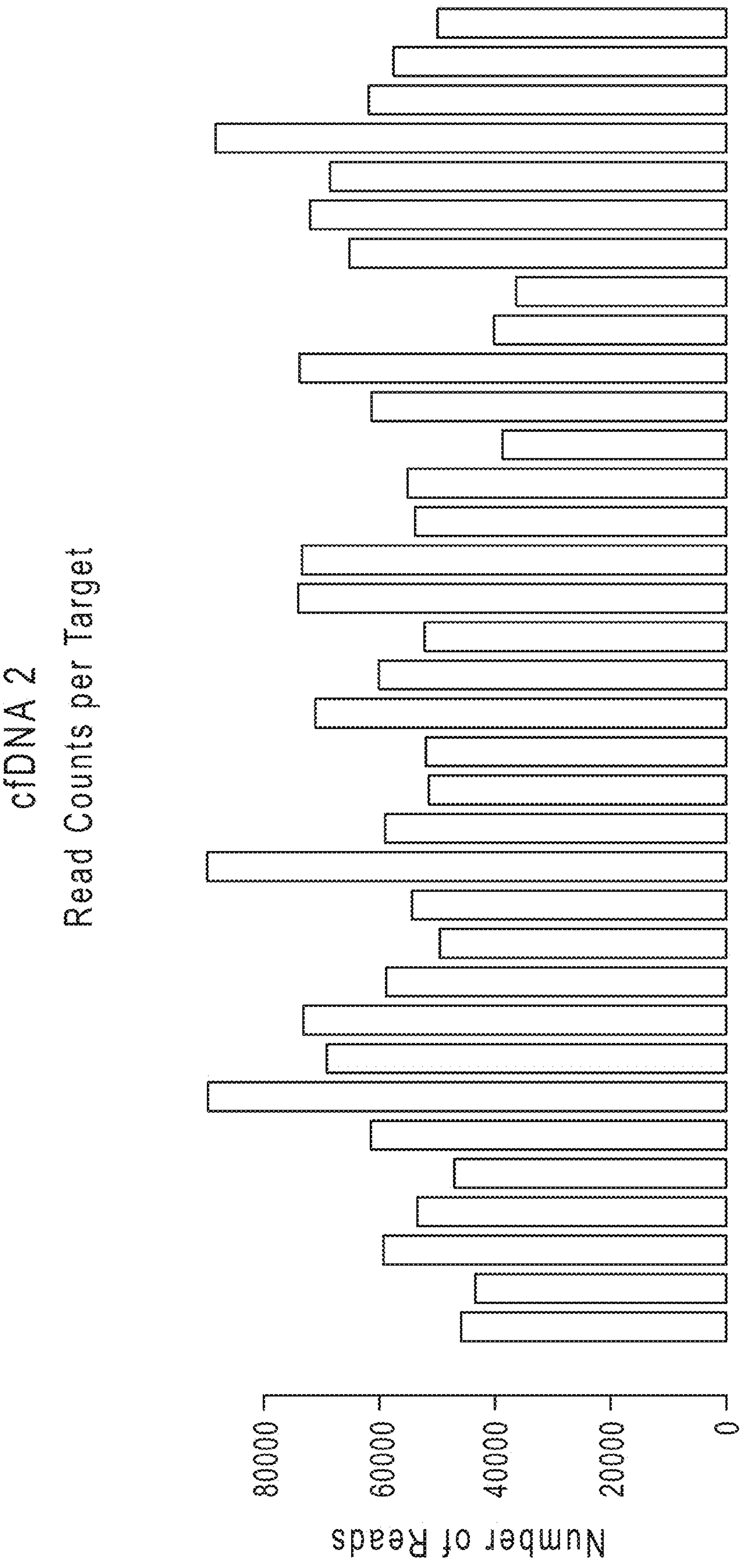
FIG. 9B is a histogram showing read counts per target sequence of a tagged library generated from cfDNA.

The results of a reads count per target sequence of a tagged library generated from a cfDNA-2 sample, and using the molecular tagging method described in Example 4, and then sequenced on an Ion Torrent semiconductor sequencing chip is shown in FIG. 9B.

Figure 10A:
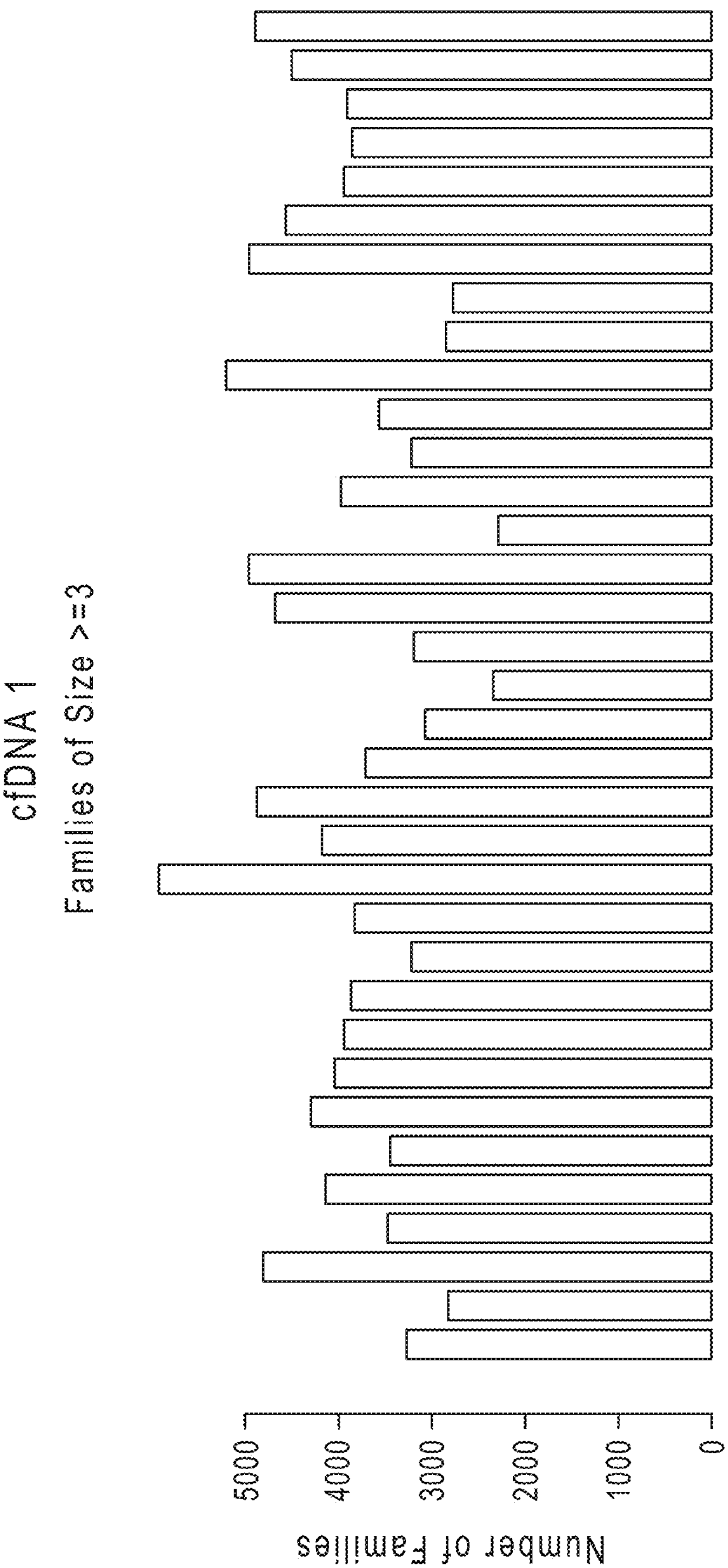
FIG. 10A is a histogram showing the number of different families of size at least 3, of a tagged library generated from cfDNA.

The results of a family size analysis (e.g., size ≥3) of a tagged library generated from a cfDNA-1 sample, and using the molecular tagging method described in Example 4, and then sequenced on an Ion Torrent semiconductor sequencing chip is shown in FIG. 10A.

Figure 10B:
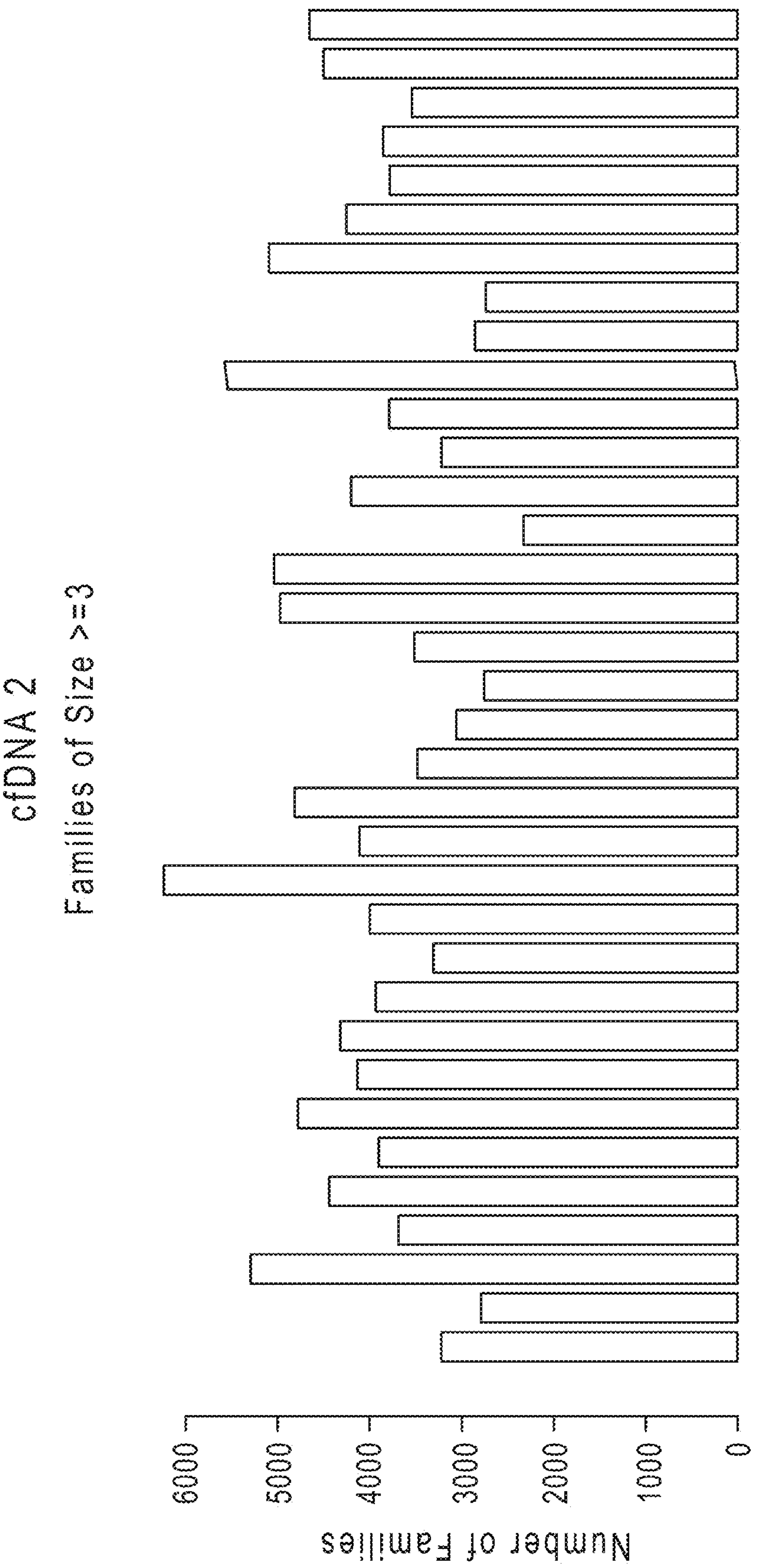
FIG. 10B is a histogram showing the number of different families of size at least 3, of a tagged library generated from cfDNA.

The results of a family size analysis (e.g., size ≥3) of a tagged library generated from a cfDNA-2 sample, and using the molecular tagging method described in Example 4, and then sequenced on an Ion Torrent semiconductor sequencing chip is shown in FIG. 10B.

Tagged libraries were generated from eight different cfDNA samples, using the molecular tagging method described in Example 4, and then sequenced on an Ion Torrent semiconductor sequencing chip. The results of median read coverage, median functional families, targets >0.8 MM coverage, and hotspot variants called for false-positives are shown in the Table 17 below:

TABLE 17

| Sample Name | Median Read Cov | Median Functional Families | Targets >0.8 MM Cov | Hotspot Variants Called (FPs) |
| --- | --- | --- | --- | --- |
| cfDNA1 | 63767 | 3912 | 88.57% | 0 |
| cfDNA2 | 64373 | 3771 | 82.86% | 0 |
| cfDNA3 | 57282 | 5092 | 82.86% | 0 |
| cfDNA4 | 57008 | 5229 | 80% | 0 |
| cfDNA5 | 62452 | 5006 | 65.71% | 0 |
| cfDNA6 | 57867 | 4992 | 65.71% | 0 |
| cfDNA7 | 55599 | 4375 | 80% | 1 |
| cfDNA8 | 57279 | 4137 | 74.29% | 1 |

Example 5

Molecular Tagging with Lung Primer Panel

Cell-free DNA was isolated from a single tube of blood (approximately 7.5 mL blood, 4-5 mL plasma) from human lung cancer subjects (e.g., late stage lung cancer) and processed as described in Example 1 above. The blood was collected in EDTA blood collection tubes or Streck DNA blood collection tubes. Also, matched FFPE samples were obtained from the same human lung cancer subjects.

cfDNA was isolated from blood plasma, using the MagMAX™ Cell-Free DNA isolation procedure described in Example 4 above. DNA from the FFPE samples were isolated using the RecoverAll™ Multi-Sample RNA/DNA isolation kit according the manufacturer's instructions (Thermo Fisher Scientific catalog No. A26069).

A control dilution series was prepared by diluting engineered plasmid control DNA (AcroMetrix™ Oncology Hotspot Control) in a background of GM24385 genomic DNA down to 0.1% or 0.5% frequency, and then fragmented the DNA mix to generate fragments with an average size of 170 bp. The AcroMetrix™ sample contained 40 common tumor mutations interrogated by the molecular tagging procedure.

Figure 11:
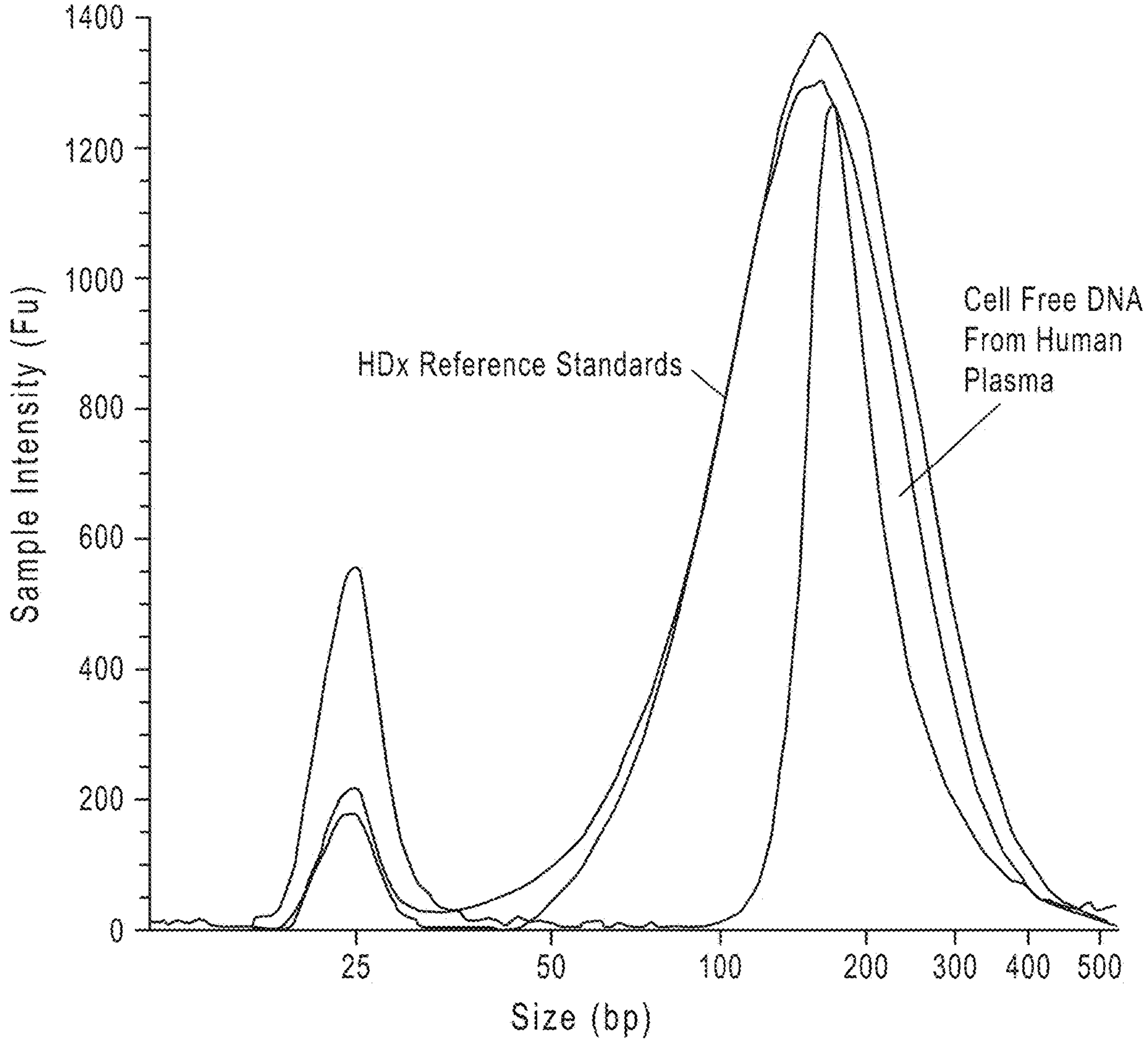
FIG. 11 is a graph showing size distribution of reference DNA and cfDNA from human blood.

The size distribution looked similar to Horizon's cfDNA reference sample (FIG. 11). The amount of input reference was doubled in order to match the number of DNA fragments longer than 110 bp in human cfDNA.

Dilution series of the Horizon standard reference HD780 (0.1%, 1%, and 5%) was also tested, The Horizon sample contained 8 low frequency mutations in our hotspot positions, including two large insertion and deletion variants of size >10 bp.

An analytical verification of variant detection performance in normal cfDNA samples and FF/FFPE tumor samples.

Tagged libraries were generated from the cfDNA (from blood plasma), DNA (from FFPE samples), Horizon Multiplex I cfDNA reference standard (5, 10, 30, 40, 50 or 60 ng input DNA), and AcroMetrix™ Oncology Hotspot Control, using the lung cfDNA primer panel as described in Example 4 above. For example, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. The sequence 5'-NNNACTNNNTGA-3' is SEQ ID NO:1. The lung cfDNA primer panel targeted: ALK, BRAF, EGFR, ERBB2, KRAS, MAP2K1, MET, NRAS, PIK3CA, ROS1 and TP53. The lung cfDNA primer panel targets 35 amplicons, covering 157 or 169 hotspot mutations in 11 genes. The forward and reverse primers were placed 40-60 bp apart to accommodate the size distribution of the cfDNA and FFPE DNA. The tagged libraries were sequenced on an Ion Torrent semiconductor sequencing chip.

The Horizon reference standard was used to demonstrate detection sensitivity and specificity of the molecular tagging procedure. The results indicate that, for the Horizon reference standard, >80% sensitivity was achieved with 5 ng input of the 1% Horizon standard and 50 ng of the 0.1% Horizon standard (see Table 18 below). 20 ng input cfDNA was also tested.

TABLE 18

| Horizon control | Input | Sensitivity | Specificity |
|---|---|---|---|
| 5% | 5 ng | 100% | 100% |
| 5% | 10 ng | 100% | 100% |
| 1% | 5 ng | 81.25% | 100% |
| 1% | 10 ng | 100% | 100% |
| 0.1% | 30 ng | 75% | 99% |
| 0.1% | 40 ng | 75% | 100% |
| 0.1% | 50 ng | 94% | 100% |
| 0.1% | 60 ng | 94% | 100% |

The molecular tagging procedure achieved >95% sensitivity with >20 ng input DNA and >85% sensitivity with 20 ng input DNA, and, <1 false (FP=false positive) call per sample for allelic variants in hotspot positions present in the sample at 0.1% (see Table 19 below).

TABLE 19

| Sample Input | cfDNA 20 ng | FFPE/cfDNA 10 ng |
|---|---|---|
| LOD | 0.1% | 0.50% |
| Sensitivity (%) | 89.6 ± 5.8 | 100% |
| Specificity (%) | 99.4 ± 0.3 | 100% |
| FP/sample | 0.25 | 0 |

Figure 12:
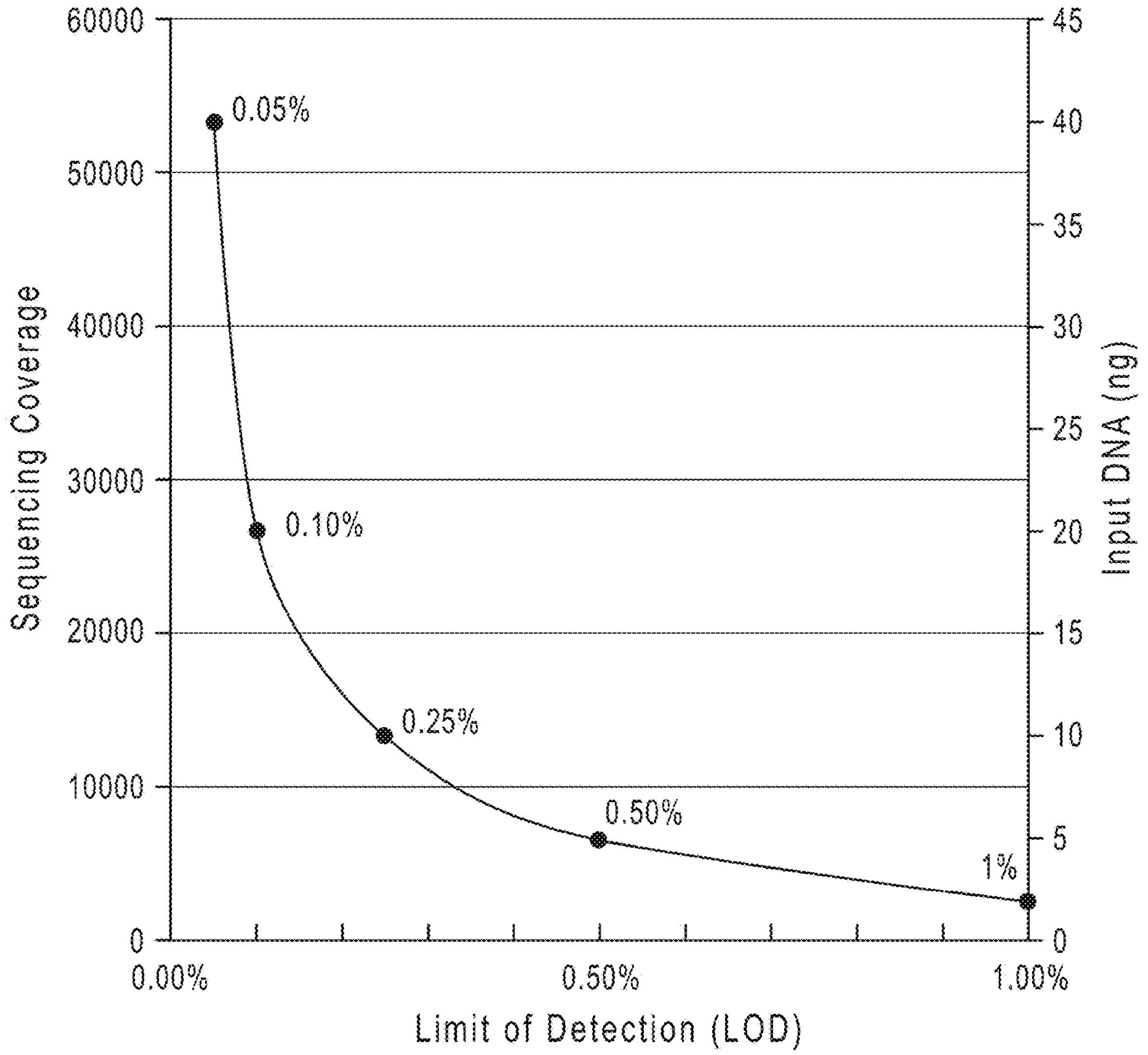
FIG. 12 is a graph showing the sequencing and input requirements for level of detection (LOD) levels.

The molecular tagging procedure requires only ~20 ng of input DNA for 0.1% level of detection (FIG. 12).

Figure 13:
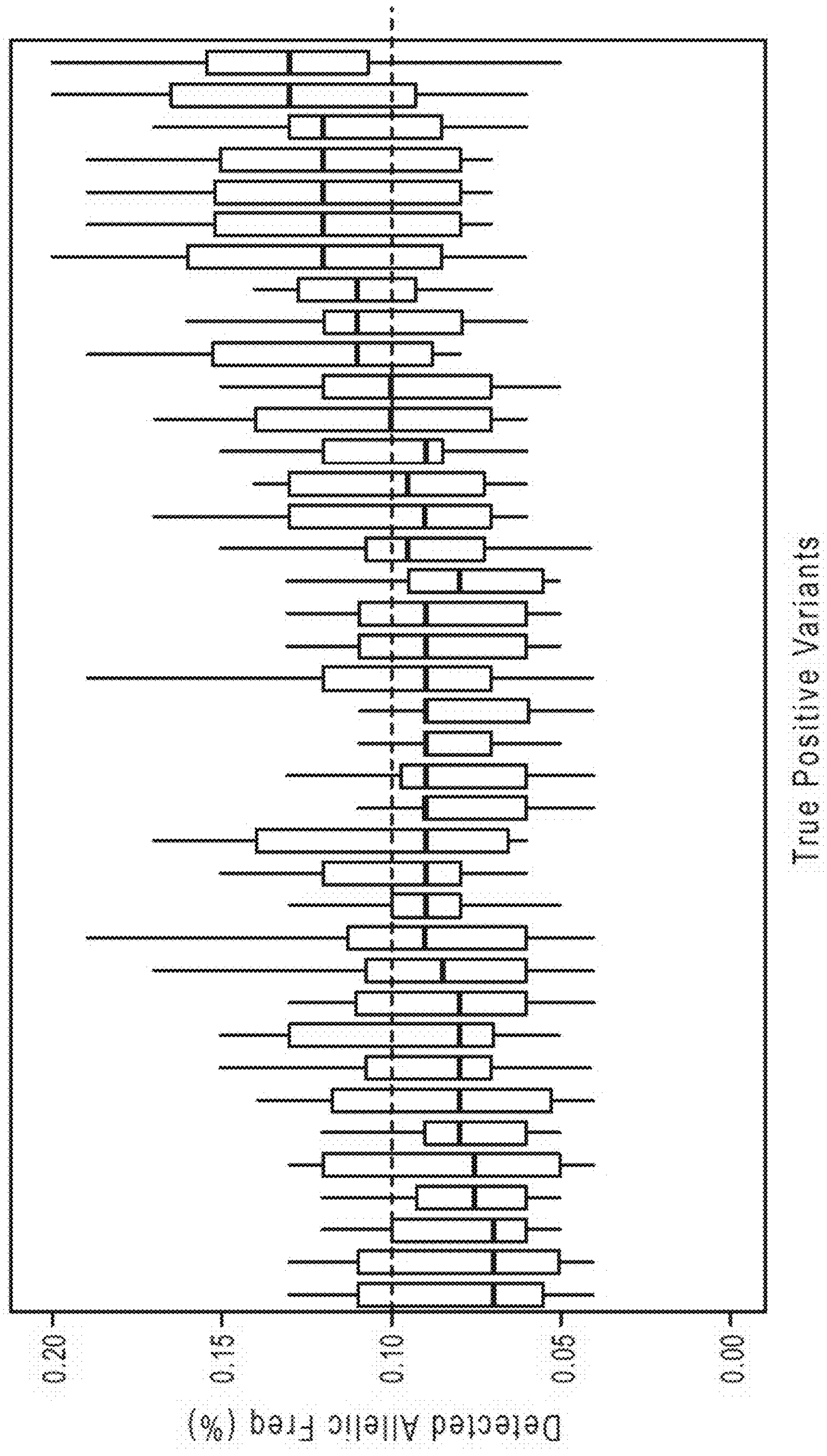
FIG. 13 is a graph showing the detected frequency of allelic variants.

The AcroMetrix™ Oncology Hotspot reference control contains fragmented DNA representing 39 variants at ~0.1% allelic frequency, and was used to test the sensitivity of the molecular tagging procedure. The results show that >80% sensitivity and >95% specificity was achieved. The allelic frequencies of 39 variants were observed at range of about 0.05%-0.15% (FIG. 13).

Figure 14A:
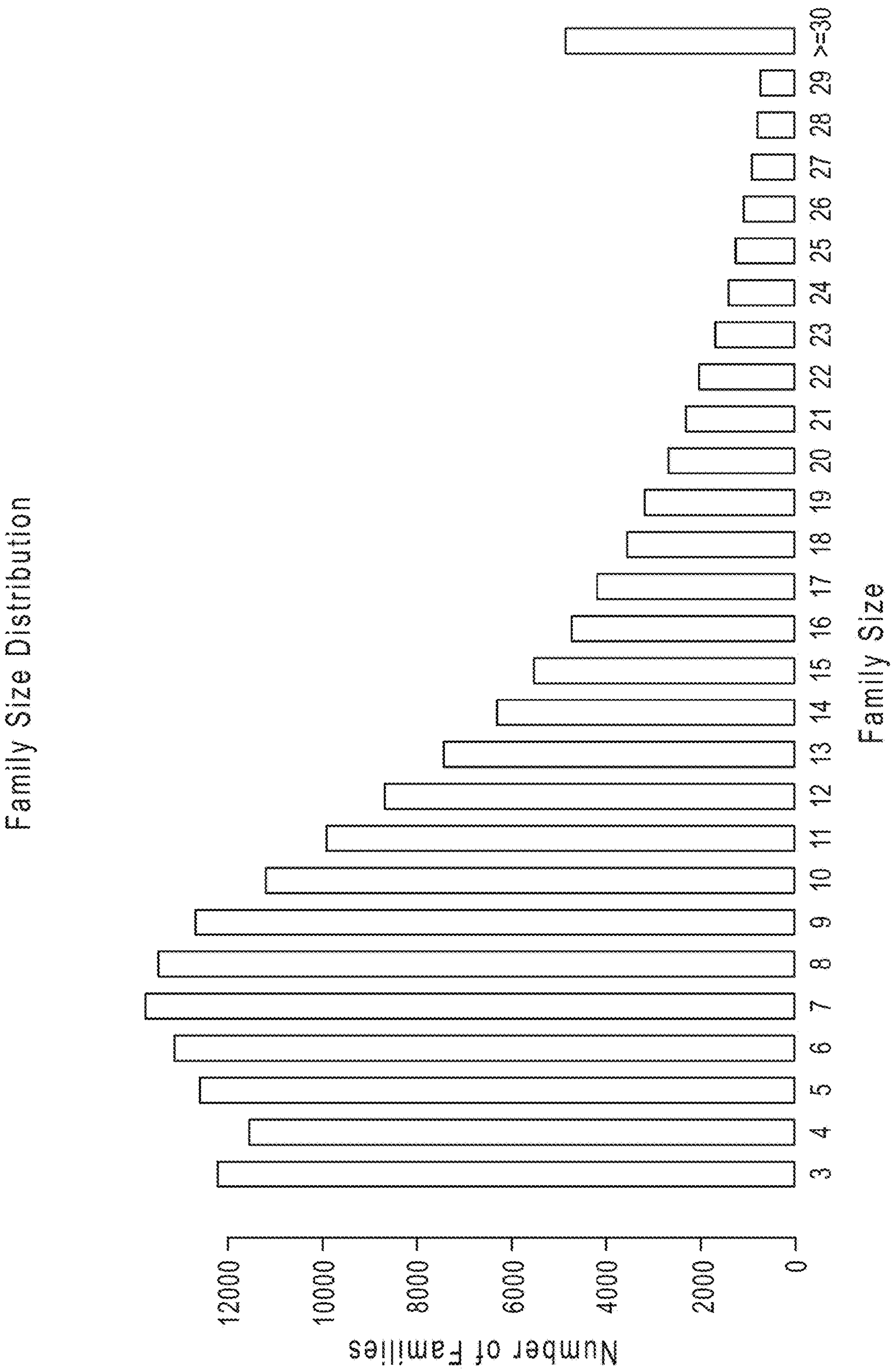
FIG. 14A is a histogram showing family size distribution.
Figure 14B:
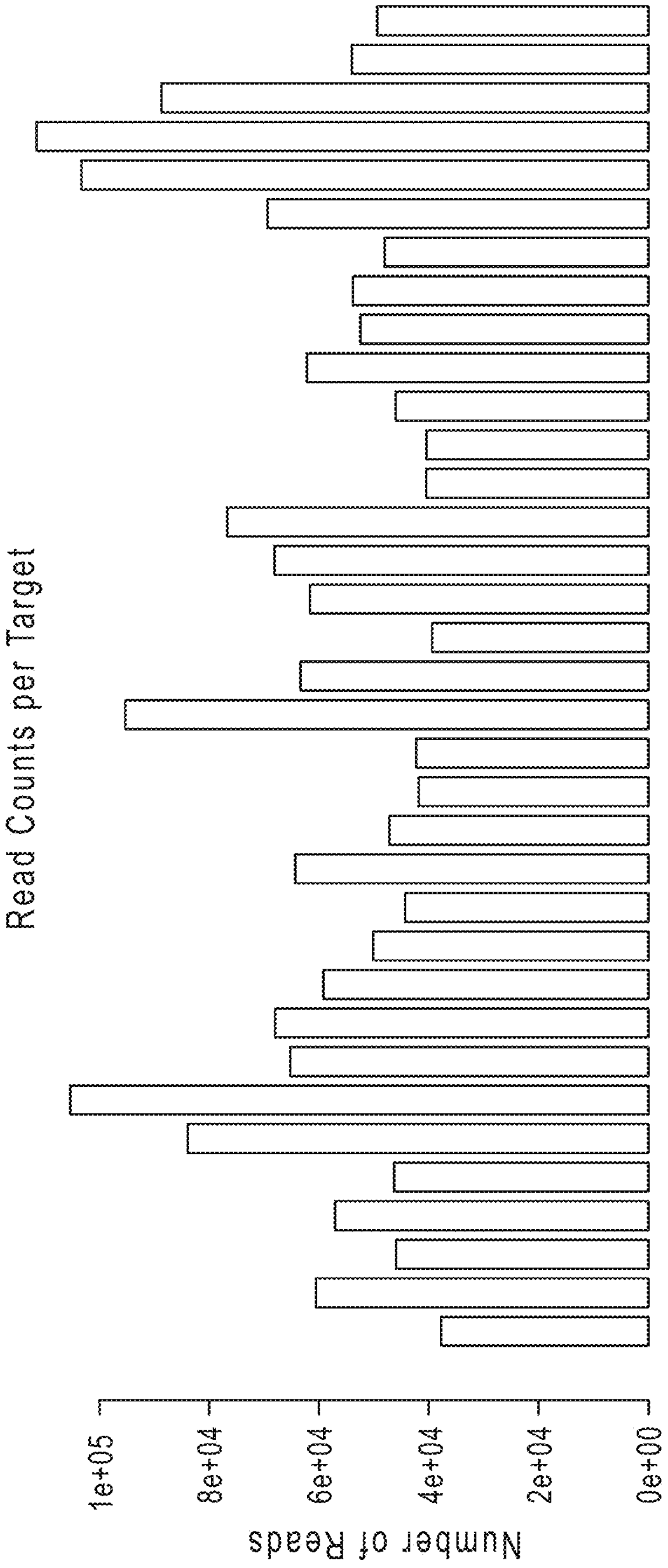
FIG. 14B is a histogram showing amplicon read coverage.
Figure 14C:
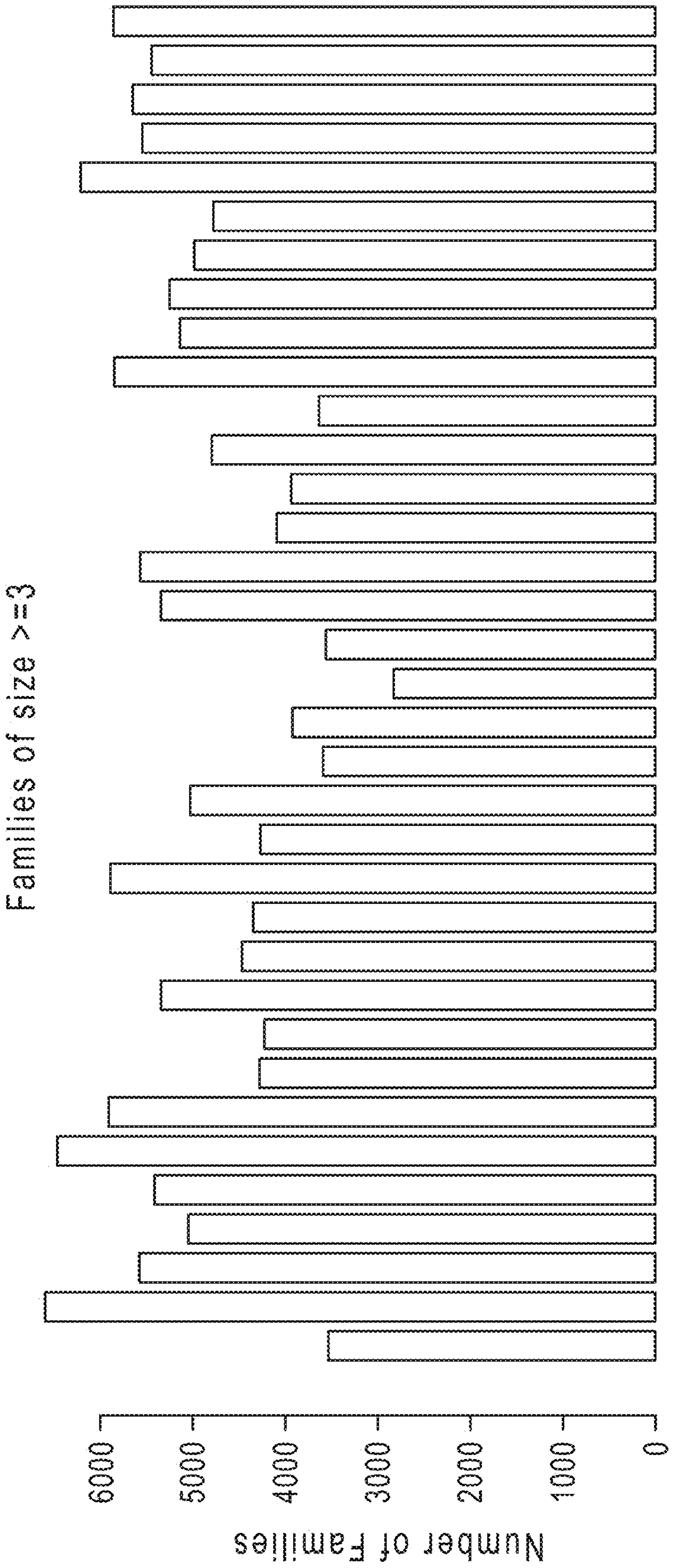
FIG. 14C is a histogram showing amplicon molecular coverage.

The molecular tagging procedure permitted interrogation of 171 biomarkers relevant in lung from COSMIC and Oncomine® databases, and de novo variant detection at ~1,700 genomic positions in 11 genes implicated in non-small cell lung cancer. The molecular tagging procedure achieved >95% on-target reads and highly uniform amplification across targeted cfDNA molecules from 20 ng input human cfDNA (FIGS. 14A, B and C).

High concordance in variant detection was observed between the cfDNA from blood and matched FFPE samples (see Table 20 below which shows the observed frequencies of variants detected from matched plasma and FFPE samples).

TABLE 20

| Sample | Variant | FFPE | Plasma |
|---|---|---|---|
| 1 | EGFR-L858R | 71.42% | 2.62% |
| 2 | TP53-R158L | 51.89% | 4.32% |
| 3 | MET-T1010I | 43.87% | 51.75% |
| | KRAS-G12C | 34.62% | 0.28% |
| 4 | N/A | No detection | No detection |
| 5 | EGFR-L858R | 58.44% | 7.28% |
| | MET-T1010I | 41.93% | 48.72% |
| | TP53-Y220C | 35.54% | 1.93% |
| 6 | TP53-R158L | 10.19% | 1.26% |

Figure 17:
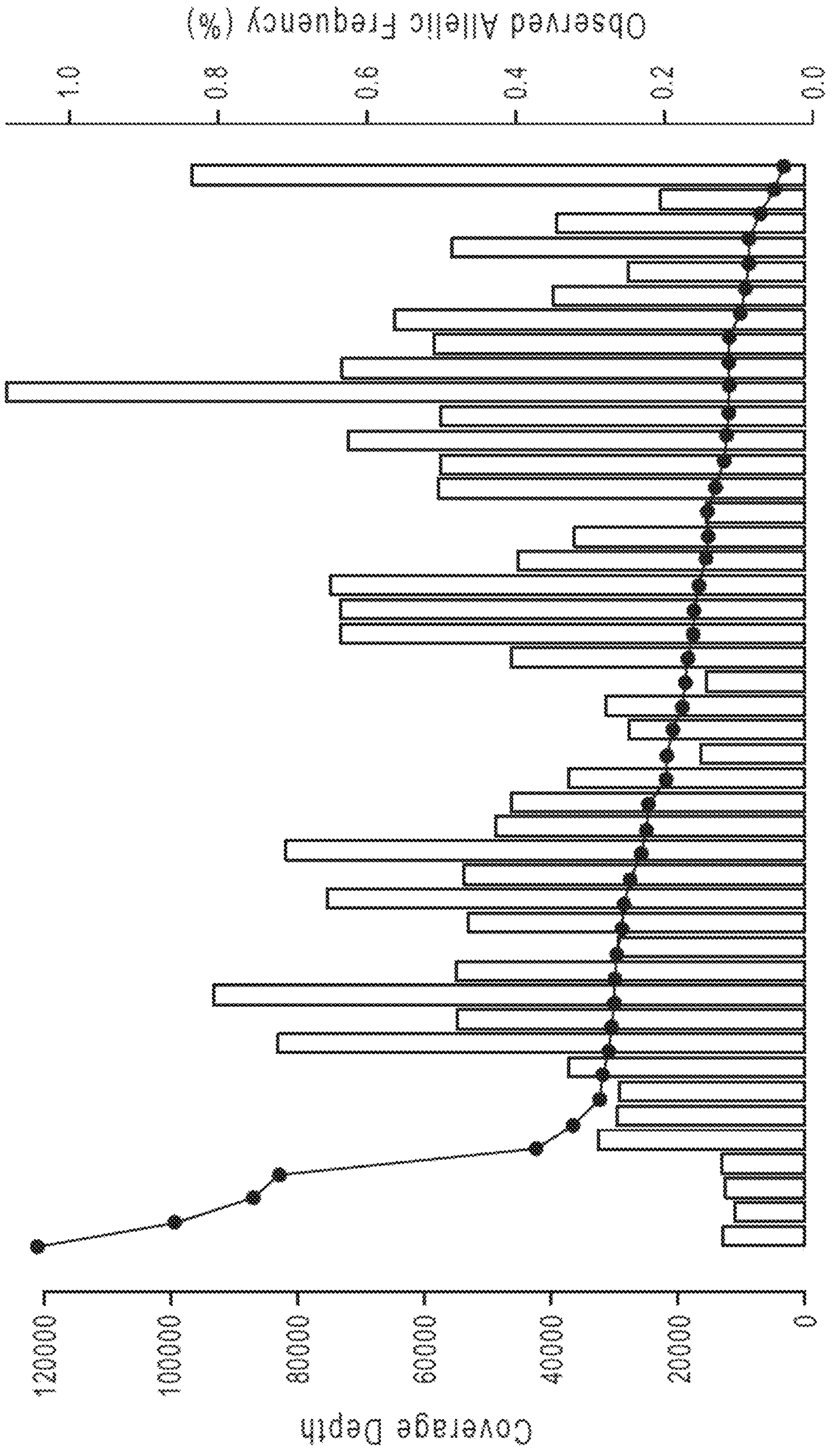
FIG. 17 is a graph showing the coverage depth and the detected frequency of allelic variants.

Data analysis: sequencing reads with the same unique tag sequence were grouped together in a family. A family containing at least 3 read was called a functional family, which enabled accurate reconstruction of the sequence of the original DNA fragment. For 0.1% LOD, 20 ng of input DNA was required and >25,000× read coverage (FIG. 12). This generated more than 2,500 functional families (molecular coverage) on each target (FIGS. 14A, B and C). See also FIG. 17 which shows a range of coverage depth for some target sequences having observed allelic frequencies of about 0.1-1%.

Figure 20B:
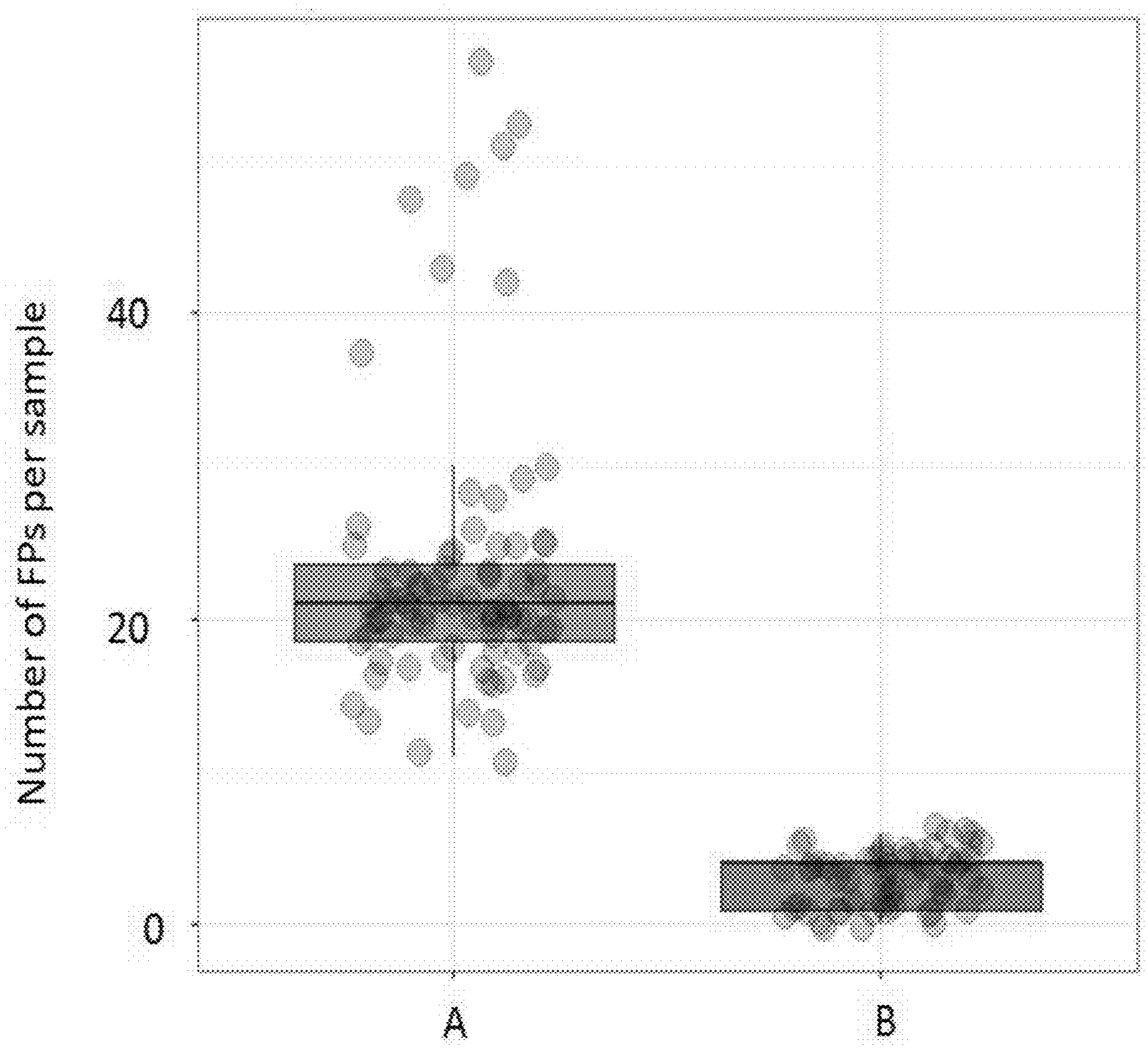
FIG. 20B is a histogram showing the number of hotspot false positive (FP) called for 0.1% allelic frequency in a positive control AcroMetrix™ sample.
Figure 21A:
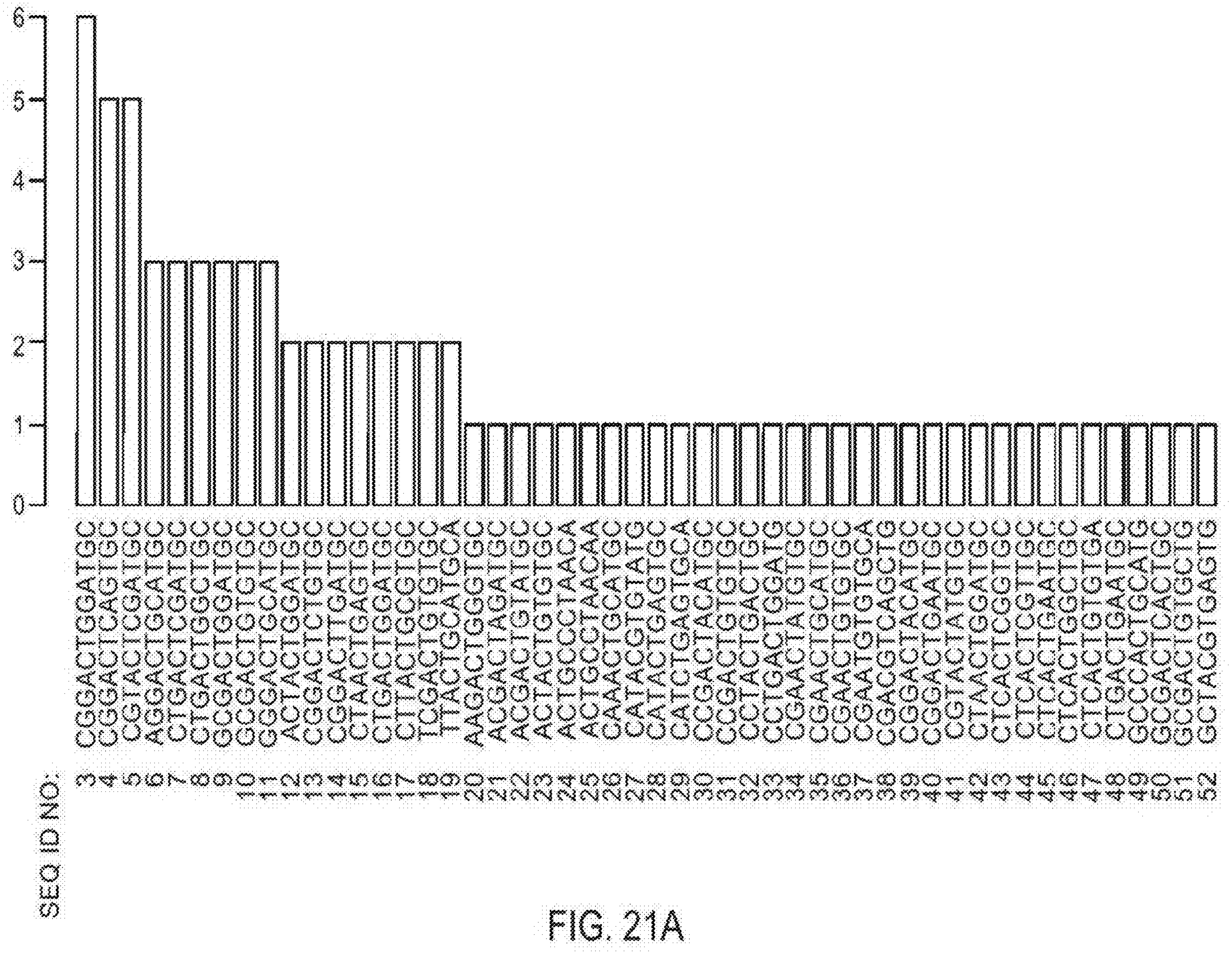
FIG. 21A is histogram showing the number of reads carrying the variant in each tagged family. The various unique tag sequences are listed along the x-axis (SEQ ID NOS: 3-52) and the number of reads per tagged family is shown along the y-axis.
Figure 21B:
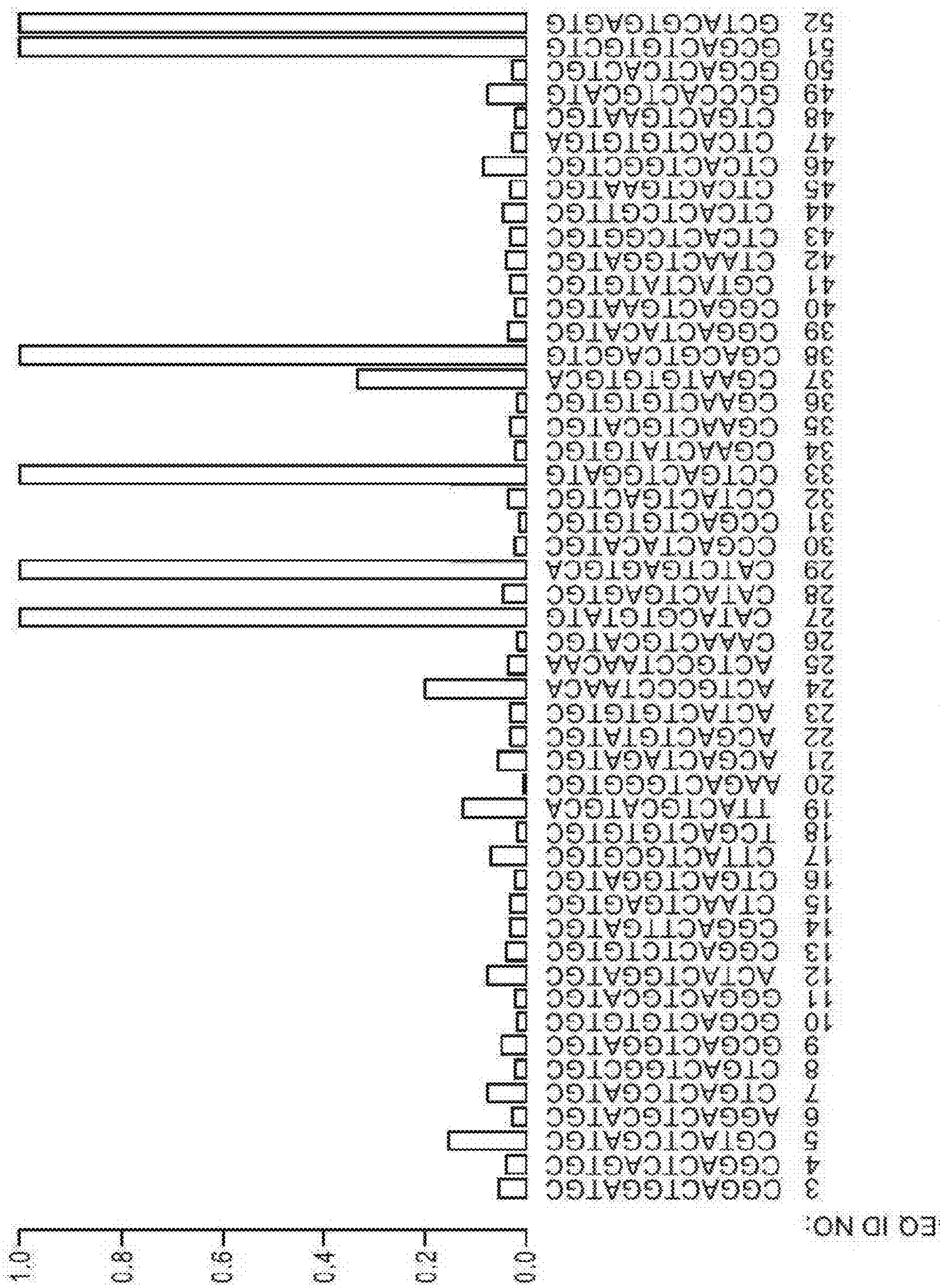
FIG. 21B is a histogram of the data from FIG. 21A showing the fraction of reads carrying the variant in each tagged family. The various unique tag sequences are listed along the x-axis (SEQ ID NOS: 3-52) and the % reads containing variants is shown along the y-axis.
Figure 22A:
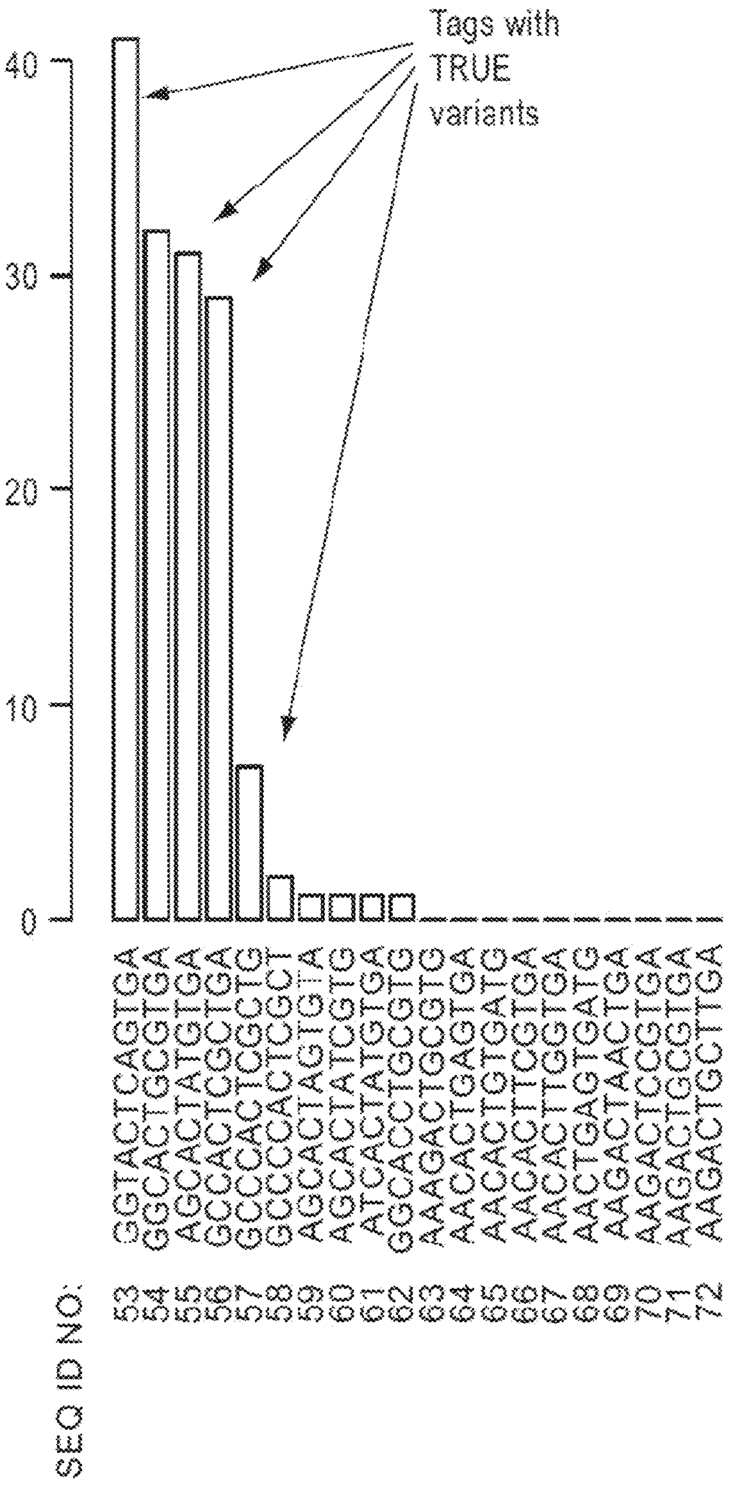
FIG. 22A is a histogram showing the number of reads carrying the variant in each tagged family. The various unique tag sequences are listed along the x-axis (SEQ ID NOS:53-72) and the number of reads per tagged family is shown along the y-axis. There are 45,780 reads covering this amplicon (HNF1A2). These reads span 1,532 unique 5' tags. The true variants are carried by 4 tagged families, each containing >90% allelic frequency. The bar graph shows that if a barcode family contains a true variant, the variant should be carried by the majority of read members in that family.
Figure 22B:
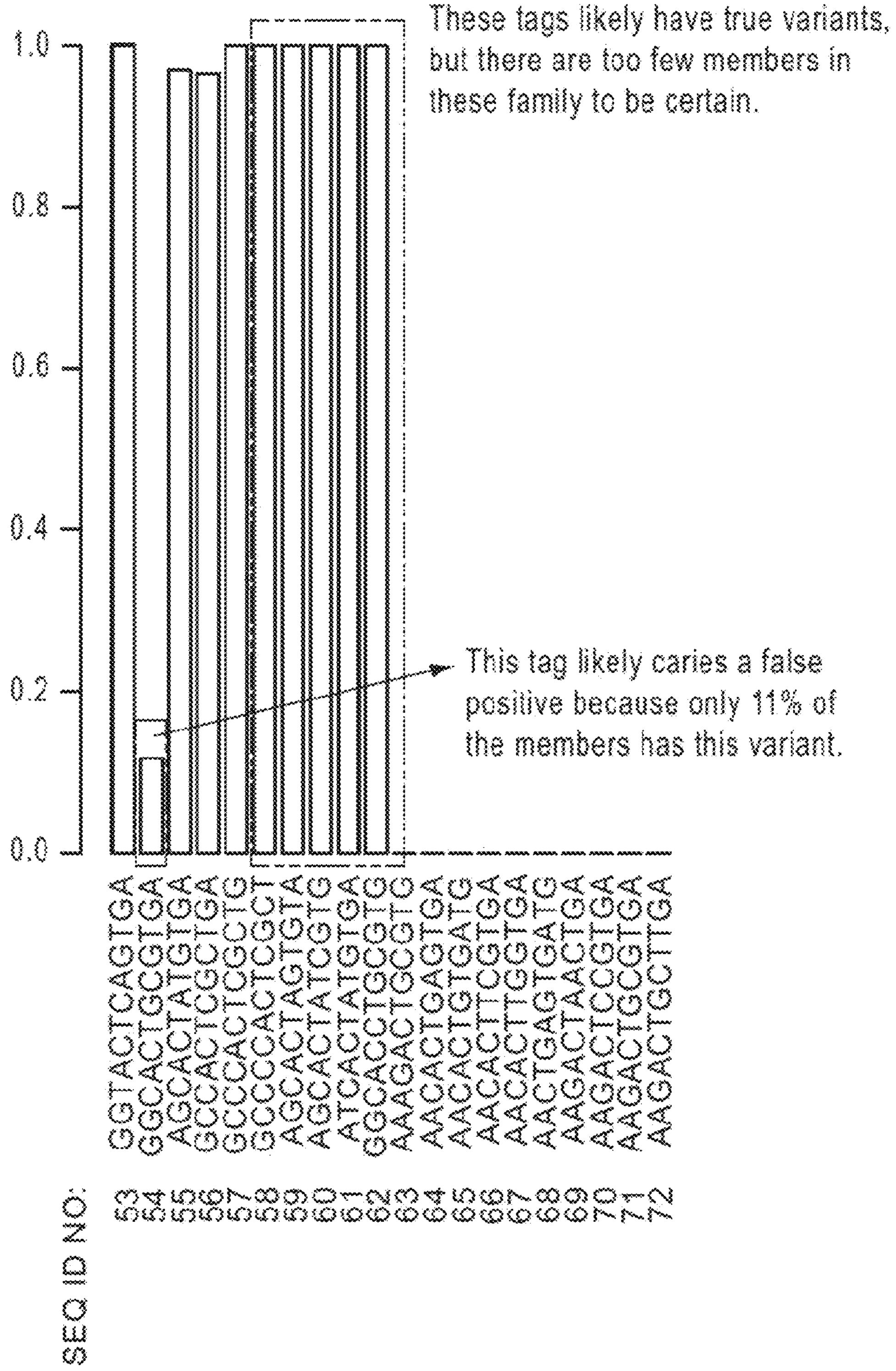
FIG. 22B is a histogram of the data from FIG. 22A showing the fraction of reads carrying the variant in each tagged family. The various unique tag sequences are listed along the x-axis (SEQ ID NOS:53-72) and the fraction of reads carrying the variant in each tagged family is shown along the y-axis.
Figure 23A:
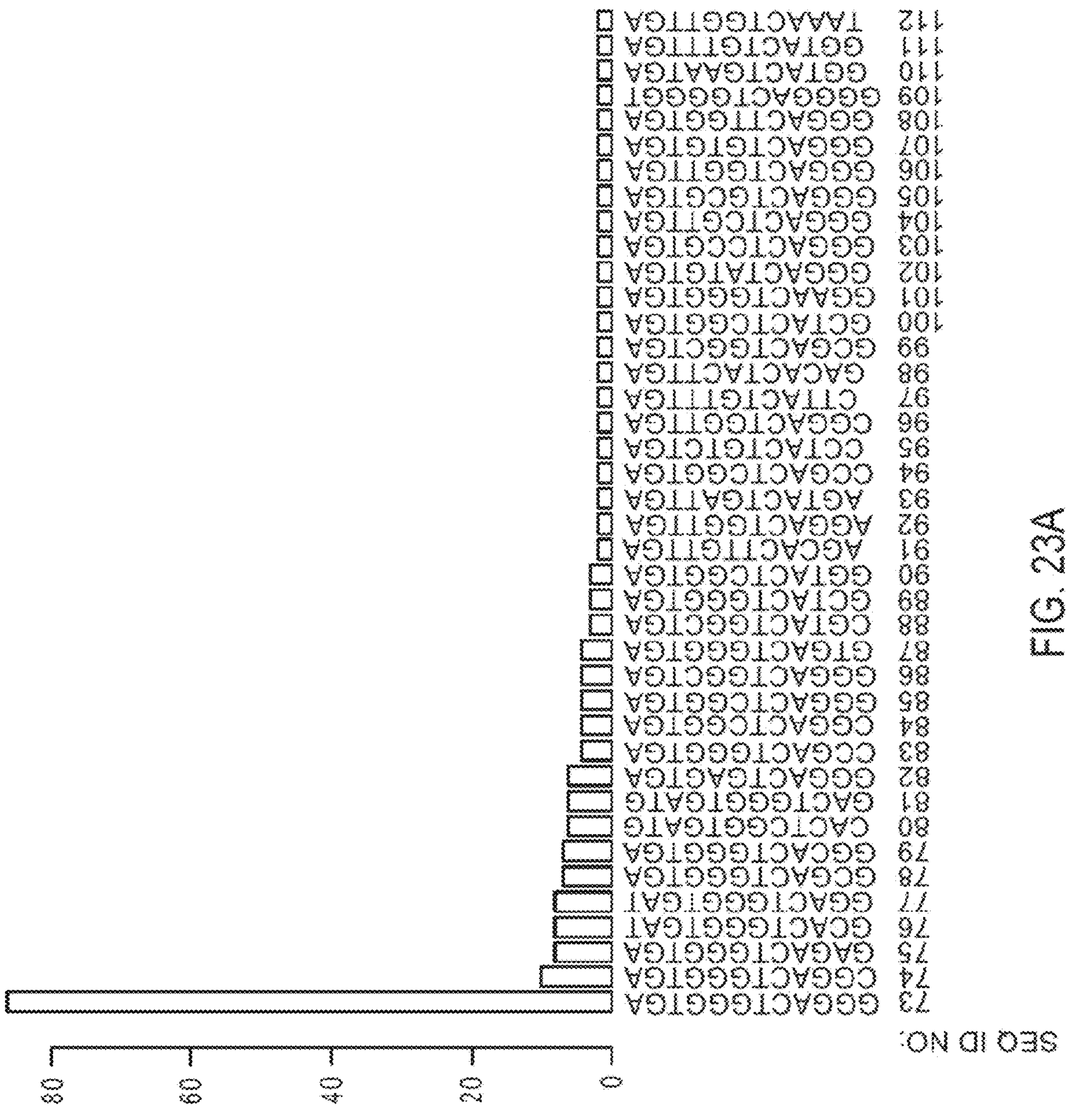
FIG. 23A is a histogram showing the number of reads carrying the variant in each tagged family. The various unique tag sequences are listed along the x-axis (SEQ ID NOS:73-112) and the number of reads per tagged family is shown along the y-axis.
Figure 23B:
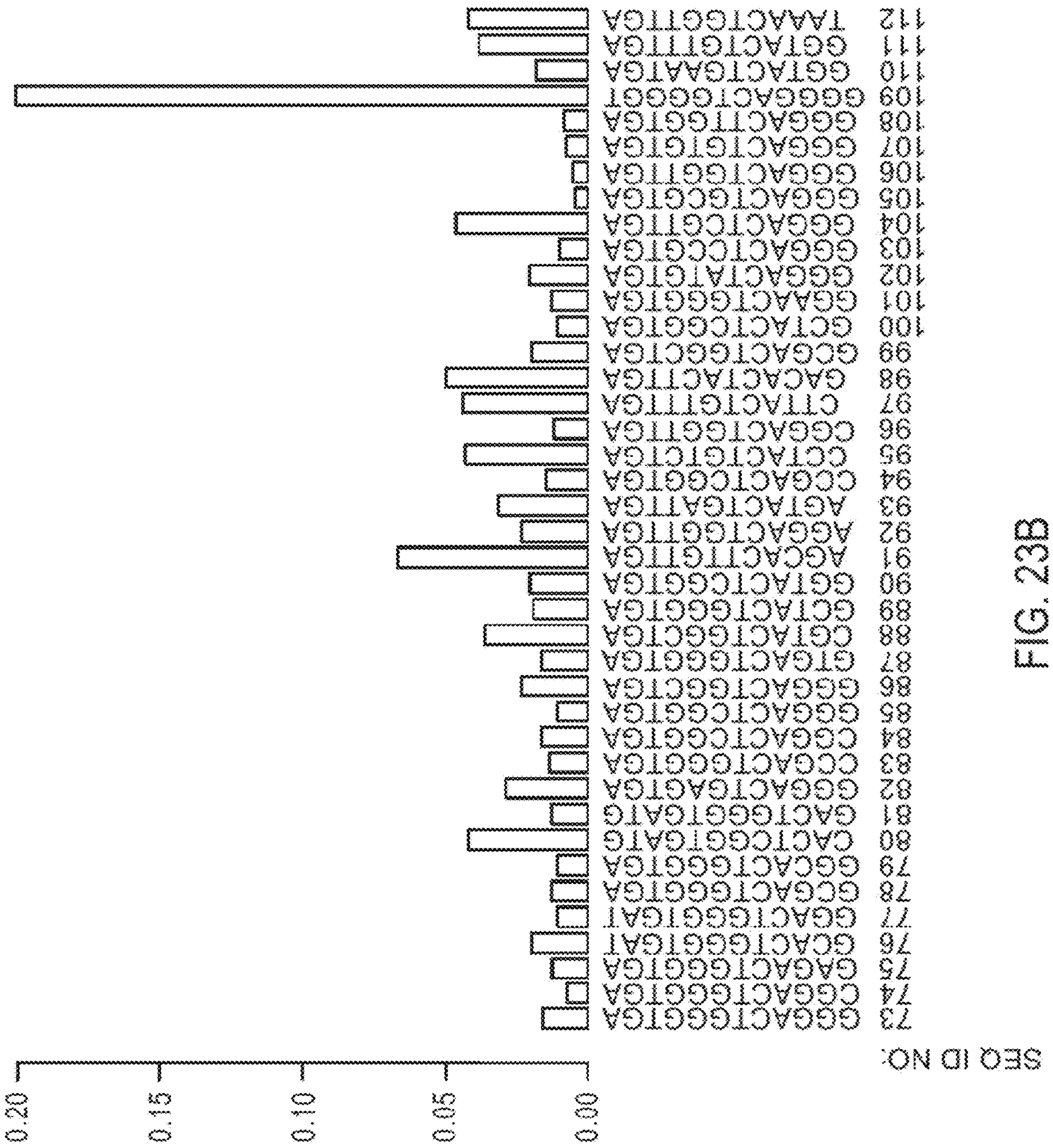
FIG. 23B is a histogram of the data from FIG. 23A showing the fraction of reads carrying the variant in each tagged family. The various unique tag sequences are listed along the x-axis (SEQ ID NOS:73-112) and the fraction of reads containing variants is shown along the y-axis.
Figure 24A:
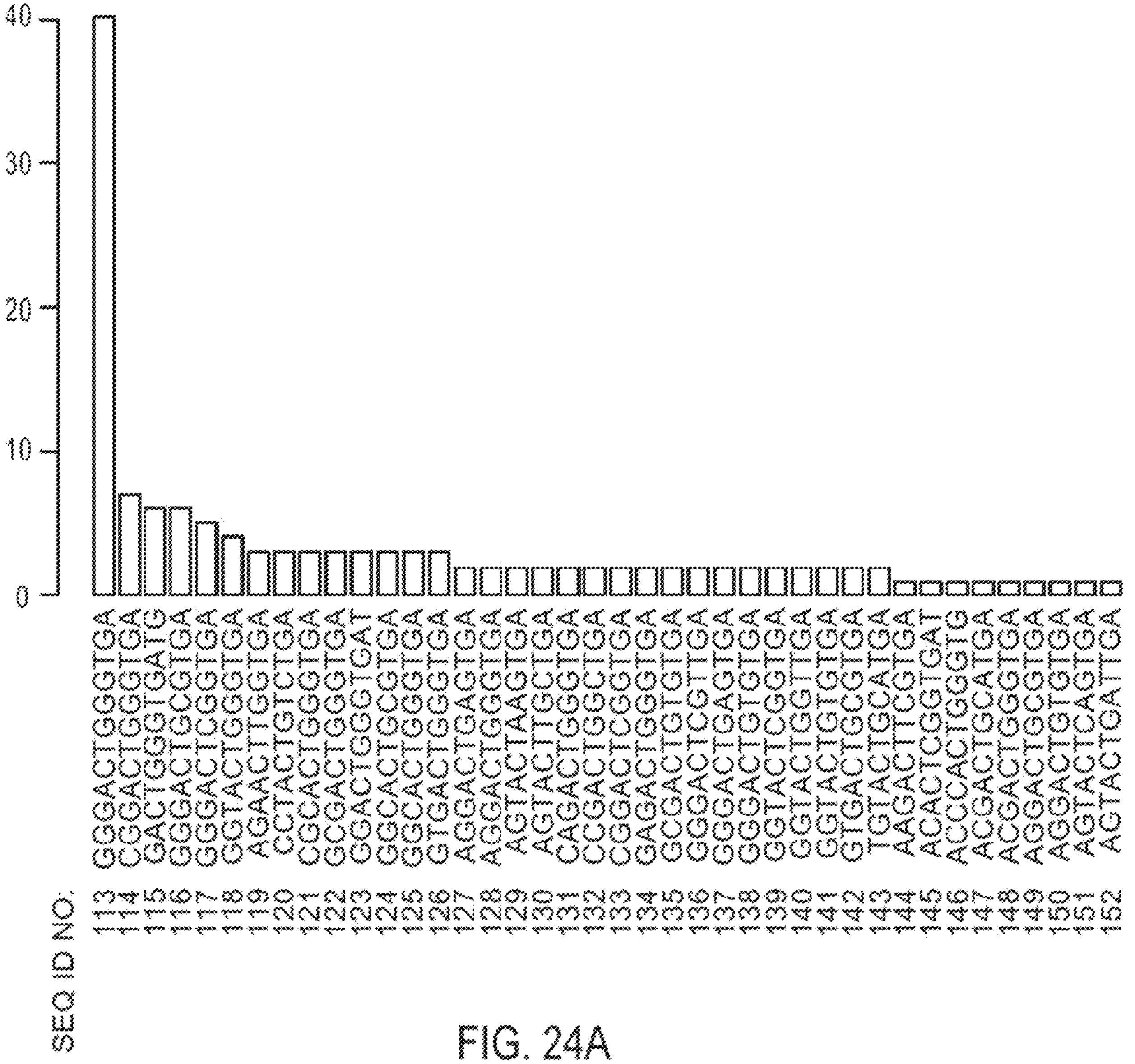
FIG. 24A is a histogram showing the number of reads carrying the variant in each tagged family. The various unique tag sequences are listed along the x-axis (SEQ ID NOS:113-152) and the number of reads per tagged family is shown along the y-axis.
Figure 24B:
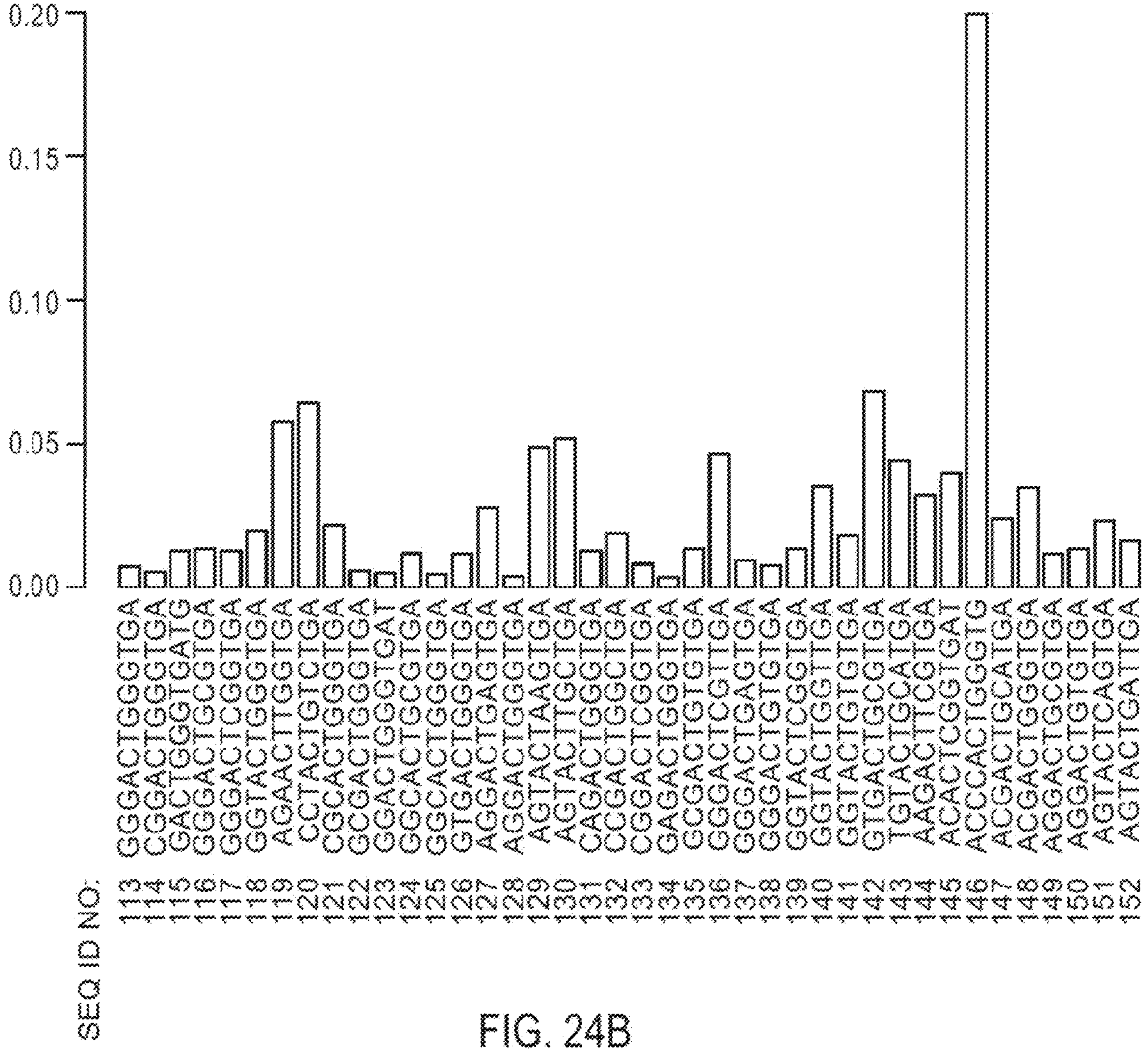
FIG. 24B is a histogram of the data from FIG. 24A showing the fraction of reads carrying the variant in each tagged family. The various unique tag sequences are listed along the x-axis (SEQ ID NOS:113-152) and the fraction of reads containing variants is shown along the y-axis.
Figure 25:
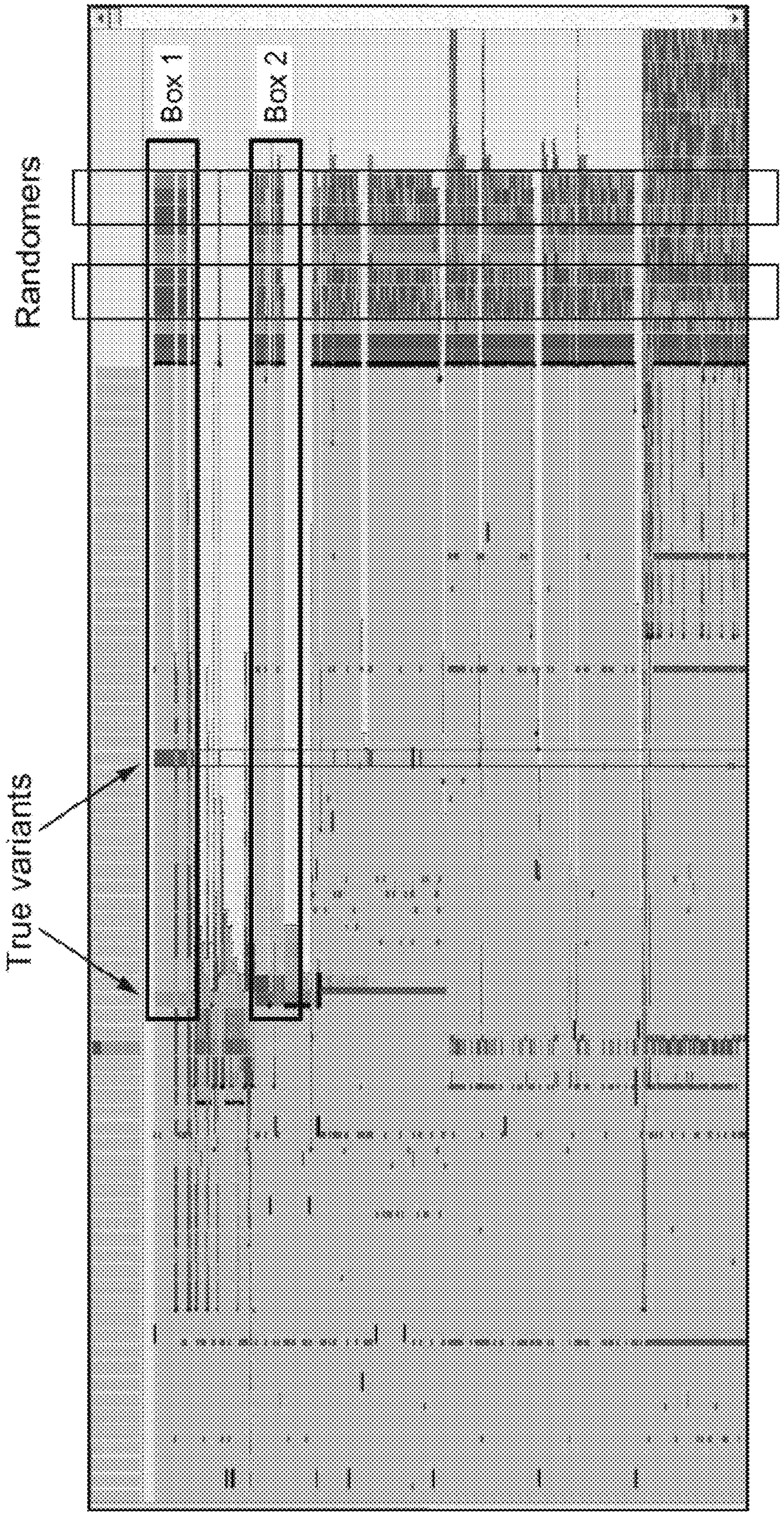
FIG. 25 is a visualization of true variants. Box 1: these reads contain true variants because the randomers between the spacers are the same. Also, the reads contain both of the true variants. Box 2: these reads contains false positive because reads carrying the variant come from a mixture of all different barcodes.
Figure 26A:
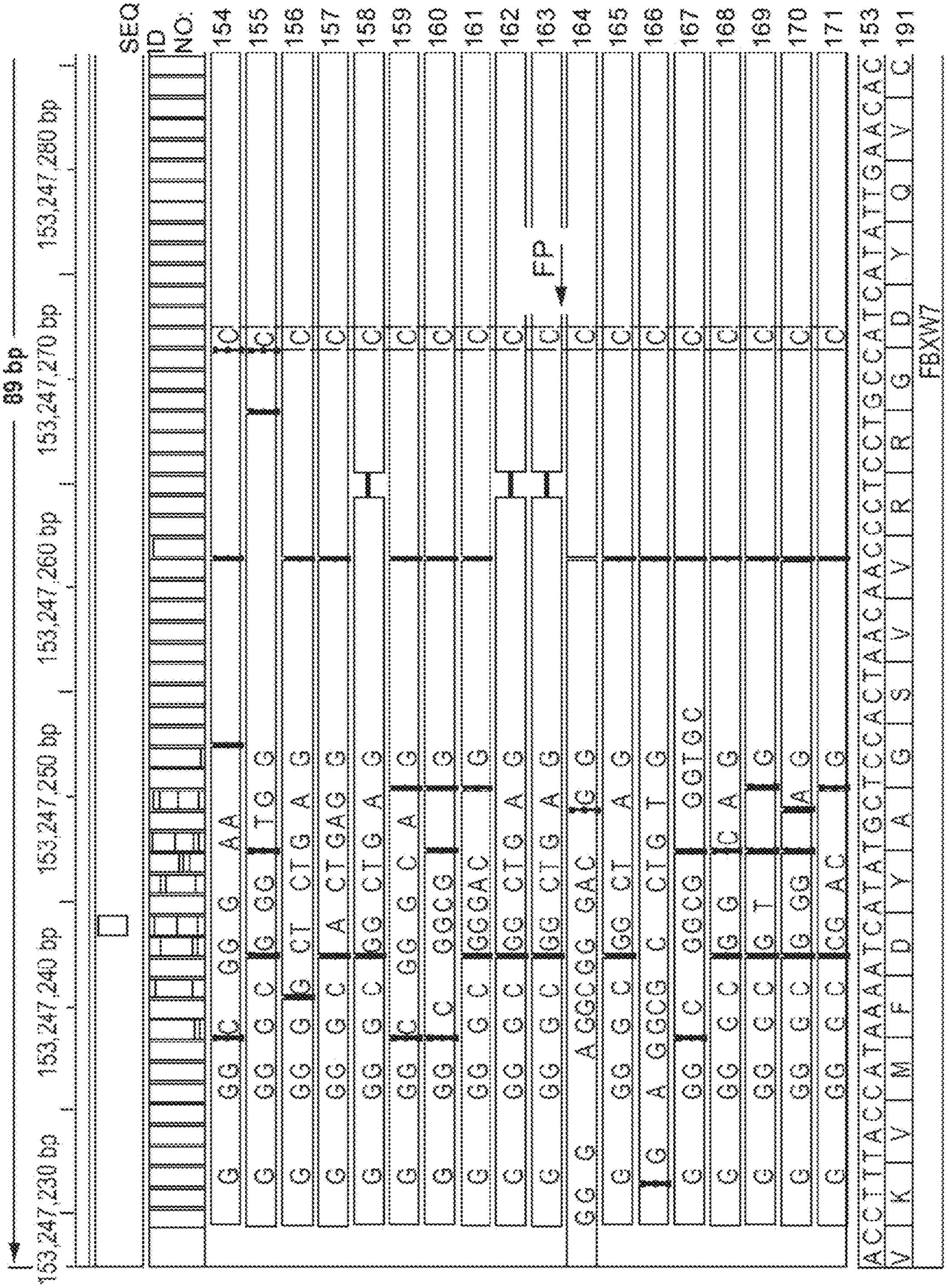
FIG. 26A is a detection of false positives (FP) the first 18 aligned sequencing reads. FP example: there are 40,886 reads covering this amplicon; these reads span 1,808 unique 5' barcodes; there are 96 reads carrying the variant. Shown in FIG. 21A, the top 50 families whose members contain the FP variant. Shown in FIG. 21B, the fraction of reads carrying the variant in each family. The first barcode family contains 6 reads carrying the variant, but these 6 reads represent only 5% of total reads in this family.
Figure 26B:
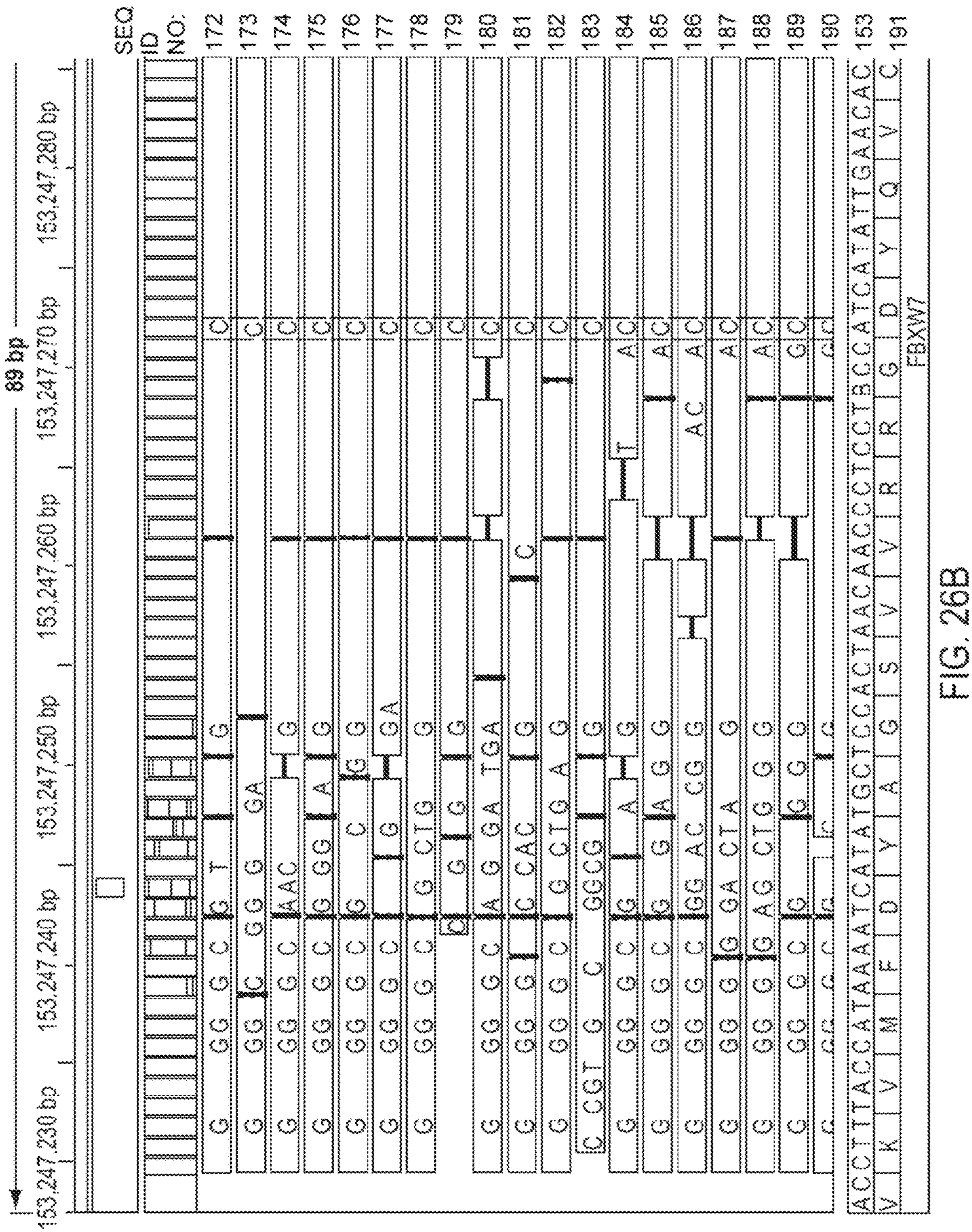
FIG. 26B is a continuation of FIG. 26A showing the next 19 aligned sequencing reads.
Figure 27A:
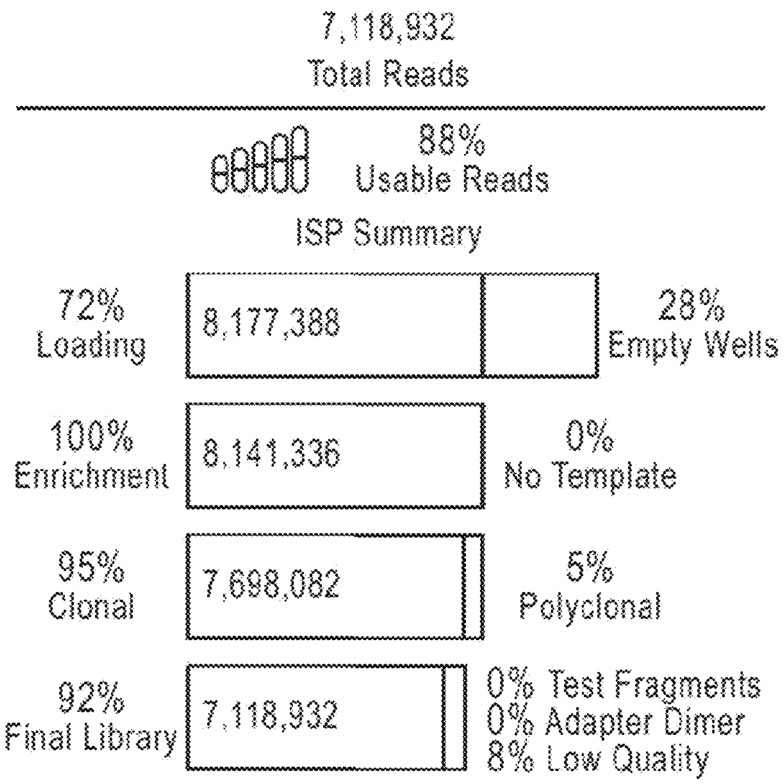
FIG. 27A is an ISP summary showing the number of total reads and usable reads of a sequencing run having 4.4 million mapped reads and 40,000× mean depth.
Figure 27B:
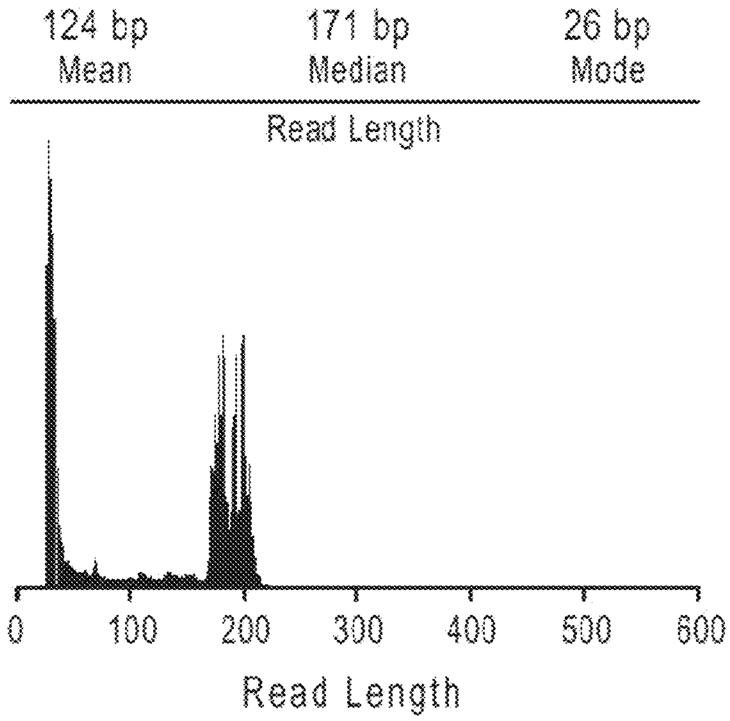
FIG. 27B is a graph showing read length from a sequencing run shown in FIG. 27A.
Figure 28:
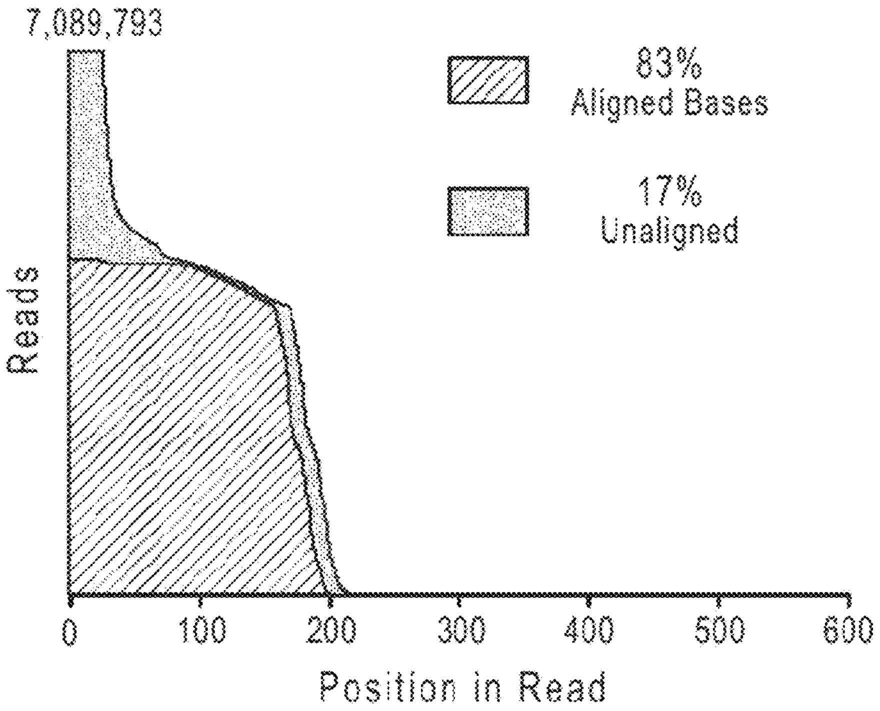
FIG. 28 is a graph showing total aligned bases and reference coverage and position in the read of a sequencing run corresponding to FIGS. 27A and B.
Figure 29:
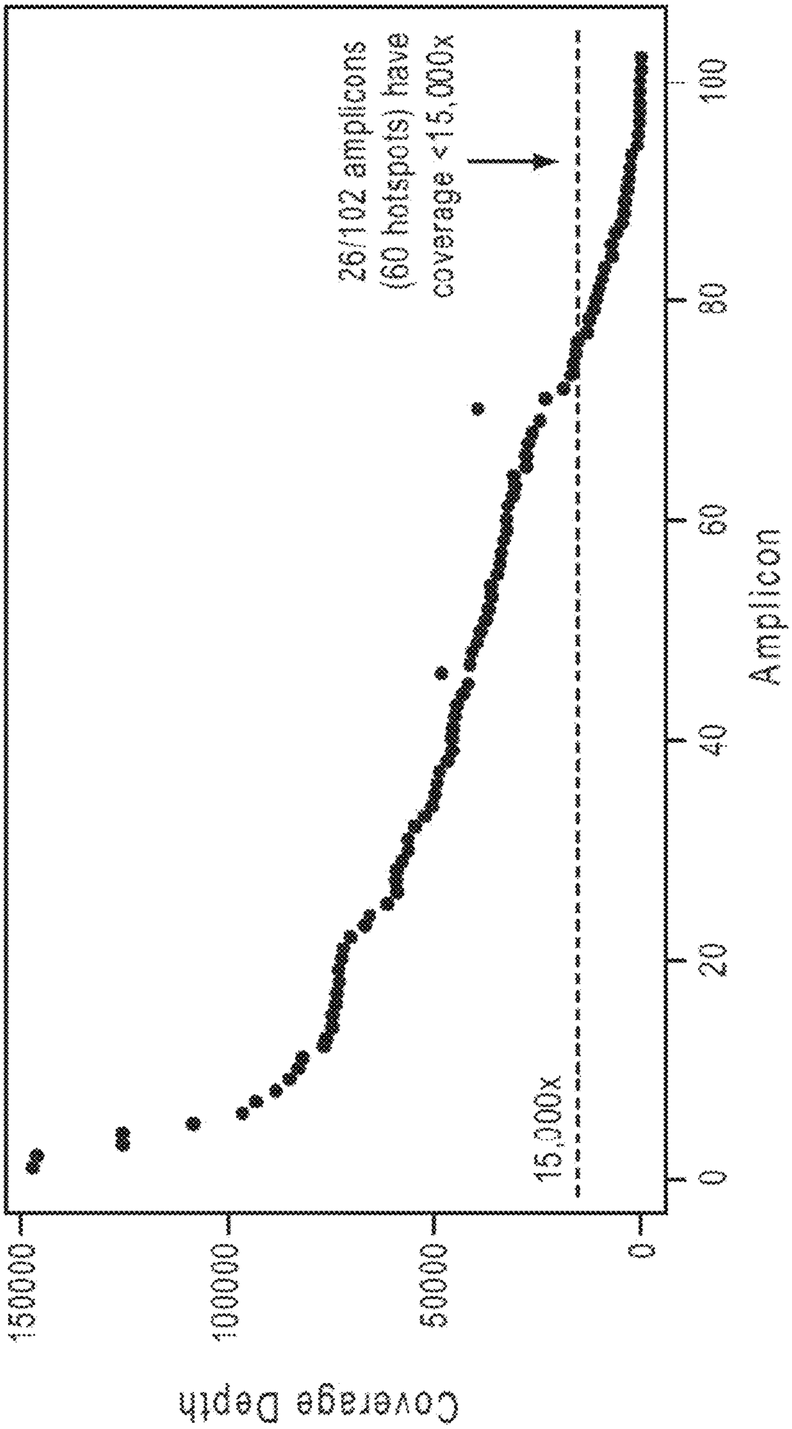
FIG. 29 is a graph showing the coverage depth of tagged amplicons of a sequencing run corresponding to FIGS. 27A and B.
Figure 30A:
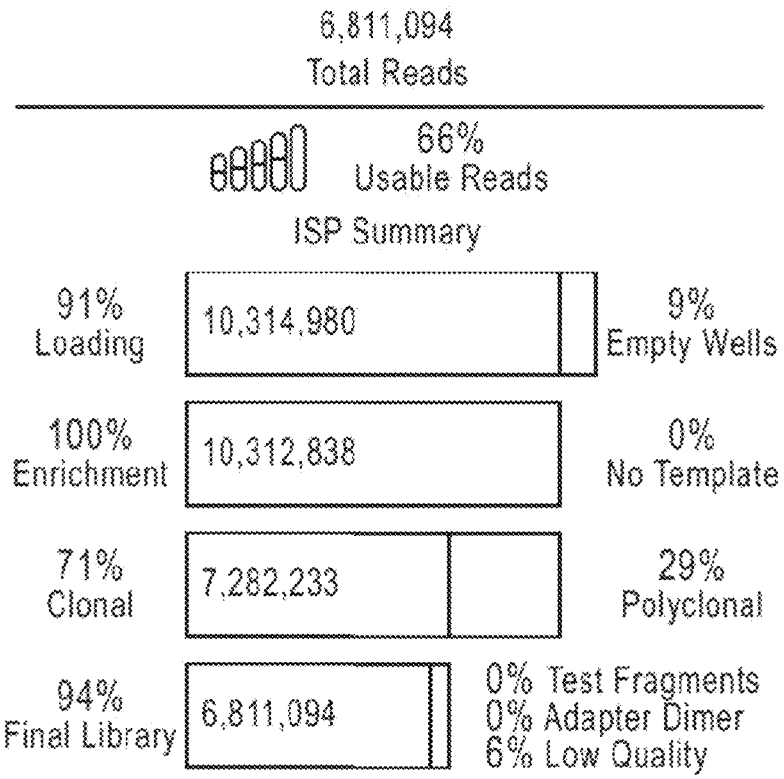
FIG. 30A is an ISP summary showing the number of total reads and usable reads of a sequencing run.
Figure 30B:
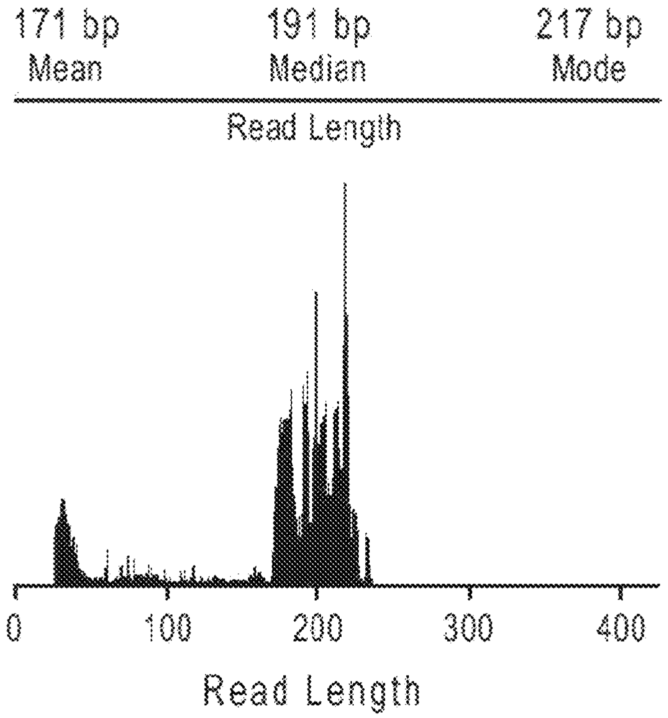
FIG. 30B is a graph showing read length from a sequencing run.
Figure 31:
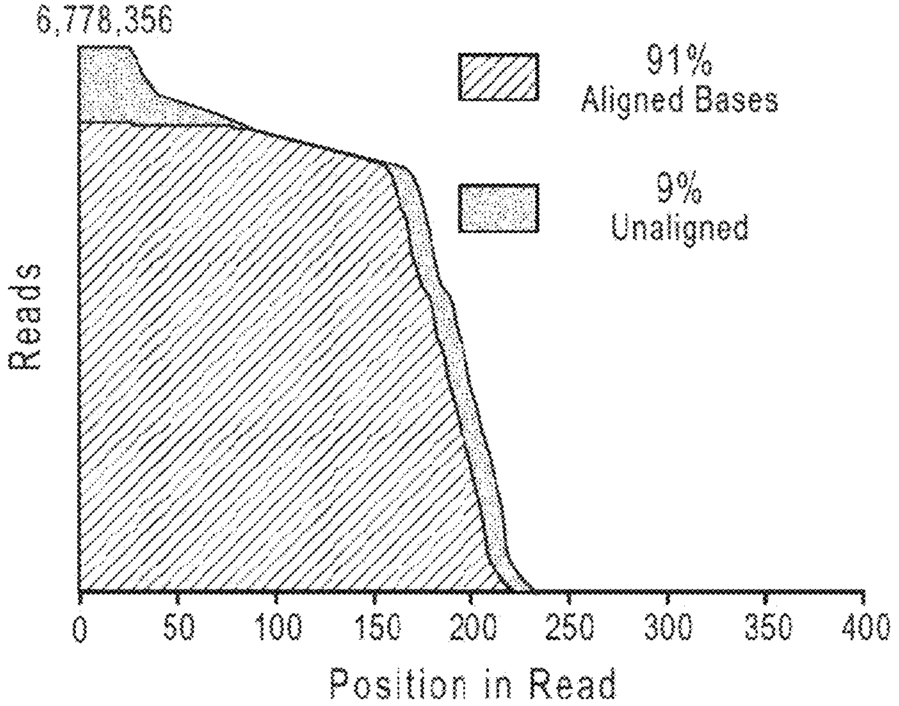
FIG. 31 is a graph showing total aligned reads and reference coverage and position in the read of a sequencing run corresponding to FIGS. 30A and B.
Figure 32A:
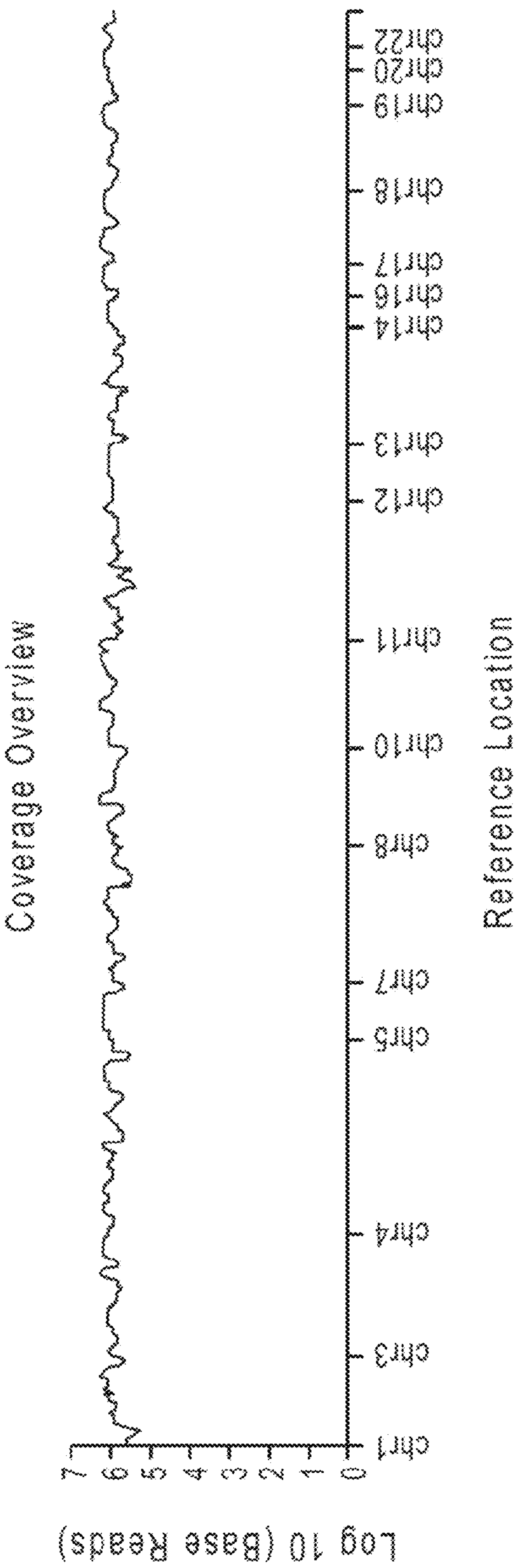
FIG. 32A is a graph showing coverage overview of a sequencing run corresponding to FIGS. 30A and B.
Figure 33:
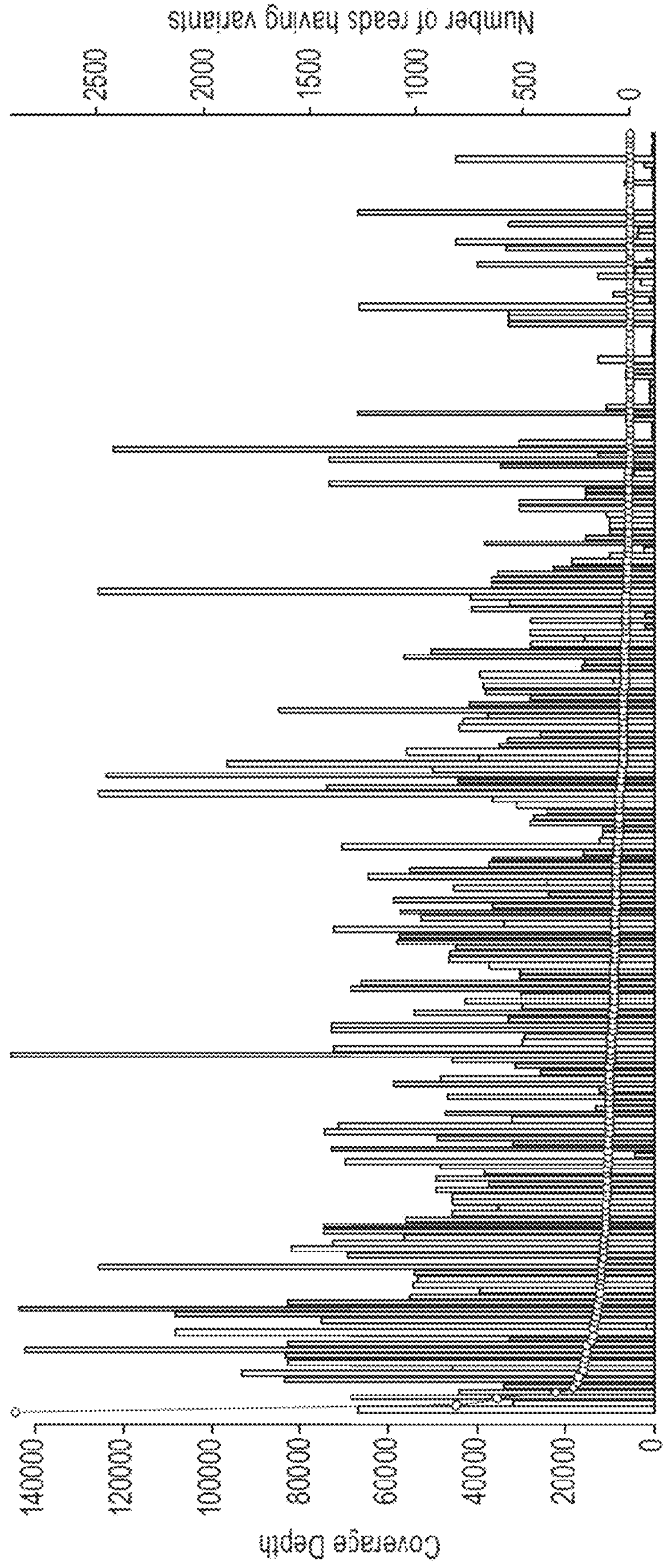
FIG. 33 is a histogram showing coverage depth (left y-axis) or number of reads having variants (right x-axis, solid dots) for sequencing reads of various target sequences (x-axis) corresponding to the data shown in FIGS. 27A and B. Undetectable hotspots. 25% of hotspots will not be detectable because too few reads carry them (they are likely not all from the same family). Coverage for these hotspots: 80-120,000×. For hotspots with low coverage, it is likely that the amplicon has poor performance. For hotspots with high coverage, it is possible that the variant was either not present in the sample due to non-uniform sample preparation or reads with variants were not sequenced.

The data analysis also included applying various thresholds to the candidate sequencing reads, including the culling threshold, grouping threshold, counting grouped reads threshold counting family threshold, difference counting threshold, pattern counting threshold and non-target pattern threshold, which yielded a high percentage of true positives while reducing the percentage of false positives (FIGS. 20A and B) when compared to data analysis that did not include these various thresholds. FIG. 20A is a histogram showing the number of whole target false positive (FP) called when applying a default set of thresholds (A) compared to the number of false positive called when applying the various thresholds described according the present teachings (B) for 0.1% allelic frequency in a 0.1% AcroMetrix™ sample. FIG. 20B is a histogram showing the number of hotspot false positive (FP) called when applying a default set of thresholds (A) compared to the number of false positive called when applying the various thresholds described according the present teachings (B) for 0.1% allelic frequency in a positive control AcroMetrix™ sample.

A summary of the data is shown in Table 21 below:

TABLE 21

| Input Type: | cfDNA | cfDNA | 0.1% AcroMetrix ™ | 0.1% AcroMetrix ™ |
|---|---|---|---|---|
| Input Amount: | 20 ng | 20 ng | 6000 copies | 6000 copies |
| # Mapped Reads: | 2,604,630 | 1,909,181 | 1,897,828 | 2,248,694 |
| % On Target Reads: | 78.63% | 85.59% | 91.21% | 92.59% |
| Median Read Coverage: | 59,047 | 46,246 | 48,040 | 58,473 |
| Median Molecular Coverage: | 5231 | 5300 | 7328 | 7773 |
| % of amplicons >0.8 of MMC: | 77.14% | 74.29% | 89.18% | 86.44% |
| # True Positives: | N/A | N/A | 35 | 37 |
| # False Positives: | 0 | 0 | 0 | 0 |
| Sensitivity: | N/A | N/A | 87.18% | 92.5% |
| PPV: | 100% | 100% | 100% | 100% |

The data demonstrates that the molecular tagging procedure is sensitive enough to detect low abundance nucleic acid molecules carrying allelic variants, which are present in a sample at about 0.1%, and the molecular tagging procedure can be used to achieve that same level of detection in cfDNA from a biological fluid (e.g., blood).

This data also demonstrates that the molecular tagging procedure detects overlapping mutations in cfDNA and matched FFPE samples, and the molecular tagging procedure can be used to monitor tumor dynamics (e.g., monitor non-small cell lung cancer and other cancers).

Example 6

Molecular Tagging—Fusion RNA:

Cell-free DNA was isolated from a single tube of blood (approximately 7.5 mL blood) and processed as described in Example 1 above.

Mixtures of RNA spiked into cfDNA was prepared as described in Example 3 above.

The reverse transcription reaction was conducted as described in Example 3 above.

Tagging: First Round PCR:

Reagents for the molecular tagging PCR assignment were set up in new wells in the same 96-well plate as follows. A total volume of 30 uL reaction volume contained: 10 uL of the cDNA from the reverse transcription reaction described above, 15 uL of cfDNA Library PCR Master Mix, 2.5 uL of tagged primer panel, and 2.5 uL of lung cfDNA primer panel. For example, the forward gene-specific primers contained the following sequences: 5'-[portion of Universal A]-[NNNACTNNNTGA]-[gene specific sequence]-3'. The reverse gene-specific primers contained the following sequences: 5'-[portion of Universal P1]-[NNNACTNNNTGA]-[gene specific sequence]-3'. The sequence 5'-NNNACTNNNTGA-3' is SEQ ID NO:1. The 96-well plate was sealed with an adhesive film. The plate was vortexed to mix the contents wells, and the plate was spun. The plate was loaded into a thermocycler, and the following program was run:

TABLE 22

| Stage: | Temperature: | Time: |
|---|---|---|
| Hold | 98° C. | 2 min. |
| Cycles: 2 | 98° C. | 30 sec. |
| | 64° C. | 2 min. |

TABLE 22-continued

| Stage: | Temperature: | Time: |
|---|---|---|
| | 62° C. | 2 min. |
| | 60° C. | 4 min. |
| | 58° C. | 2 min. |
| | 72° C. | 30 sec. |
| Hold | 72° C. | 2 min. |
| Hold | 4° C. | ∞ |

Purification: First Round:

AMPure™ XP Reagent was incubated at room temperature for at least 30 minutes, and vortexed to disperse the beads. A solution of 80% ethanol was freshly prepared. 260 uL of the 80% ethanol was mixed with 65 uL water.

The adhesive film was removed from the plate. 30 uL of nuclease-free water was added to each well containing a sample. 96 uL (e.g., 1.6× of the sample volume) of Agencourt AMPure™ XP Reagent was added. The plate was re-sealed with film, and vortexed to mix, then incubated at room temperature for 5 minutes. The plate was vortexed again, and incubated again at room temperature for 5 minutes. The plate was spun briefly. The plate was placed on a 96-well plate rack, the film was removed, and the plate was place on a magnetic stand and incubated for 5 minutes or until the solution turned clear. The supernatant was removed and discarded, from individual wells without disturbing the pellet. 150 uL of the 80% ethanol was added. The plate was moved side-to-side to two or four positions on the magnet t wash the beads. The supernatant was removed and discarded, from individual wells without disturbing the pellet. The 80% ethanol wash was repeated once. The supernatant was removed and discarded, from individual wells without disturbing the pellet. A smaller pipette was used to remove the ethanol drops from the side of the wells. The beads in the wells were air-dried on the magnet at room temperature for 5 minutes. The plate was removed from the magnet. 24 uL of TE was added to individual wells to disperse the beads. The plate was re-sealed with adhesive film, vortexed thoroughly, and incubated at room temperature for 5 minutes. The plate was spun to collect the droplets. The plate was placed on a 96-well plate rack, and the film was removed. The plate was placed on a magnet for at least 2 minutes. 23 uL of the supernatant was transferred to new wells on the same plate.

Second Round PCR:

The PCR amplification procedure was set-up as follows: to the wells containing the 23 uL of sample from the previous step, the following was added: 1 uL universal primer-A (contains an IonXpress barcode sequence), 1 uL universal primer P1, 25 uL 2× Phusion™ U Multiplex PCR Master Mix (Thermo Fisher Scientific F-562S or F-562L). The wells should contain about 50 uL of liquid. The contents of the wells were mixed by pipetting up and down 5 times. The plate was spun down briefly. Optional: if there were any carry over beads, the plate was placed on the magnet stand for 3 minutes, and 50 uL of the reaction was transferred to new wells on the same plate. The plate was re-sealed. The plate was loaded onto a thermo-cycler and the following program was run:

TABLE 23

| Stage: | Temperature: | Time: |
|---|---|---|
| Hold | 98° C. | 2 min. |
| Cycles: 18 | 98° C. | 15 sec. |

TABLE 23-continued

| Stage: | Temperature: | Time: |
|---|---|---|
| | 64° C. | 15 sec. |
| | 72° C. | 15 sec. |
| Hold | 72° C. | 5 min. |
| Hold | 4° C. | ∞ |

Purification—Second Round:

520 uL of the freshly-prepared 80% ethanol was mixed with 130 uL of nuclease-free water, per sample. The film was removed from the plate. 50 uL of nuclease-free water was added to each sample. 115 uL (e.g., 1.15× of the sample volume) of Agencourt AMPure™ XP Reagent was added to each sample, and pipetted up and down 5 times. The plate was incubated at room temperature for 10 minutes. The plate was placed on a magnet and incubated at room temperature for 5 minutes, or until the solution cleared. The supernatant was carefully removed without disturbing the pellet. 150 uL of the 80% ethanol was added to the samples, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 50 uL of Low TE was added to the pellets to disperse the beads. The samples were pipetted up and down 5 times to resuspend the beads. Alternatively, the plate was sealed with adhesive film, and vortexed thoroughly, and spun down to collect the droplets. The plate was placed on the magnet for at least 2 minutes. 50 uL of the supernatant was transferred to new wells on the same plate. The plate was removed from the magnet. 45 uL (e.g., 0.9× of the sample volume) of Agencourt AMPure™ XP Reagent was added to each sample. The sample was pipetted up and down 5 times. The plate was incubated at room temperature for 10 minutes. The plate was place on a magnet and incubated for 5 minutes, or until the solution cleared. The supernatant was carefully removed and discarded, without disturbing the pellet. 150 uL of the 80% ethanol was added, and the plate was moved side-to-side in two or four positions on the magnet to wash the beads. The supernatant was removed and discarded, without disturbing the pellet. The wash was repeated with 150 uL of the 80% ethanol. The supernatant was removed and discarded. Using a smaller pipetted (e.g., 10 to 20 uL pipette), ethanol droplets remaining in the wells were removed. The plate was left on the magnet, at room temperature for 5 minutes, to air-dry the beads. The plate was removed from the magnet. 30 uL of Low TE was added to the pellets to disperse the beads. The samples were pipetted up and down 10 times to resuspend the beads. Alternatively, the plate was sealed with adhesive film, and vortexed thoroughly, and spun down to collect the droplets. The plate was placed on the magnet for at least 2 minutes. 28 uL of the supernatant was transferred to new wells on the same plate.

To quantitate the library, 5 dilution sample points were prepared from standard *E. coli* library (*E. coli* DH10B library at approximately 68 pM stock solution). For example, dilution samples were prepared at: 6.8 pM, 0.68 pM, 0.068 pM, 0.0068 pM and 0.00068 pM. Dilution samples of the library prepared from the cfDNA was prepared by mixing 2 uL of the cfDNA library with 198 uL water, mixed and spun down briefly (this is the 1:100 dilution sample). 3 uL of the 1:100 dilution sample was mixed with 27 uL of water, mixed and spun down briefly (this is the 1:1000 dilution sample). For each sample, 3 wells were set up for: sample, standard, and NTC. A master mix was prepared using the following formula for a 384 well plate:

TABLE 24

| Component: | Volume: |
|---|---|
| 2X TaqMan Master Mix | 5 uL |
| 20X Ion TaqMan Assay | 0.5 uL |
| Total volume: | 5.5 uL |

5.5 uL of the master mix was dispensed into each well, and 4.5 uL of the 1:1000 diluted library and standard was added to these wells.

A PCR reaction on a 7900 HT thermo-cycler (qPCR system) was set up as follows:

TABLE 25

| Stage: | Temperature: | Time: |
|---|---|---|
| Hold | 50° C. | 2 minutes |
| Hold | 95° C. | 20 seconds |
| 40 cycles | 95° C. | 1 second |
| | 60° C. | 20 seconds |

The average concentration of the undiluted cfDNA library was calculated by multiplying the concentration determined with qPCR by the library dilution used in this assay.

Figure 15A:
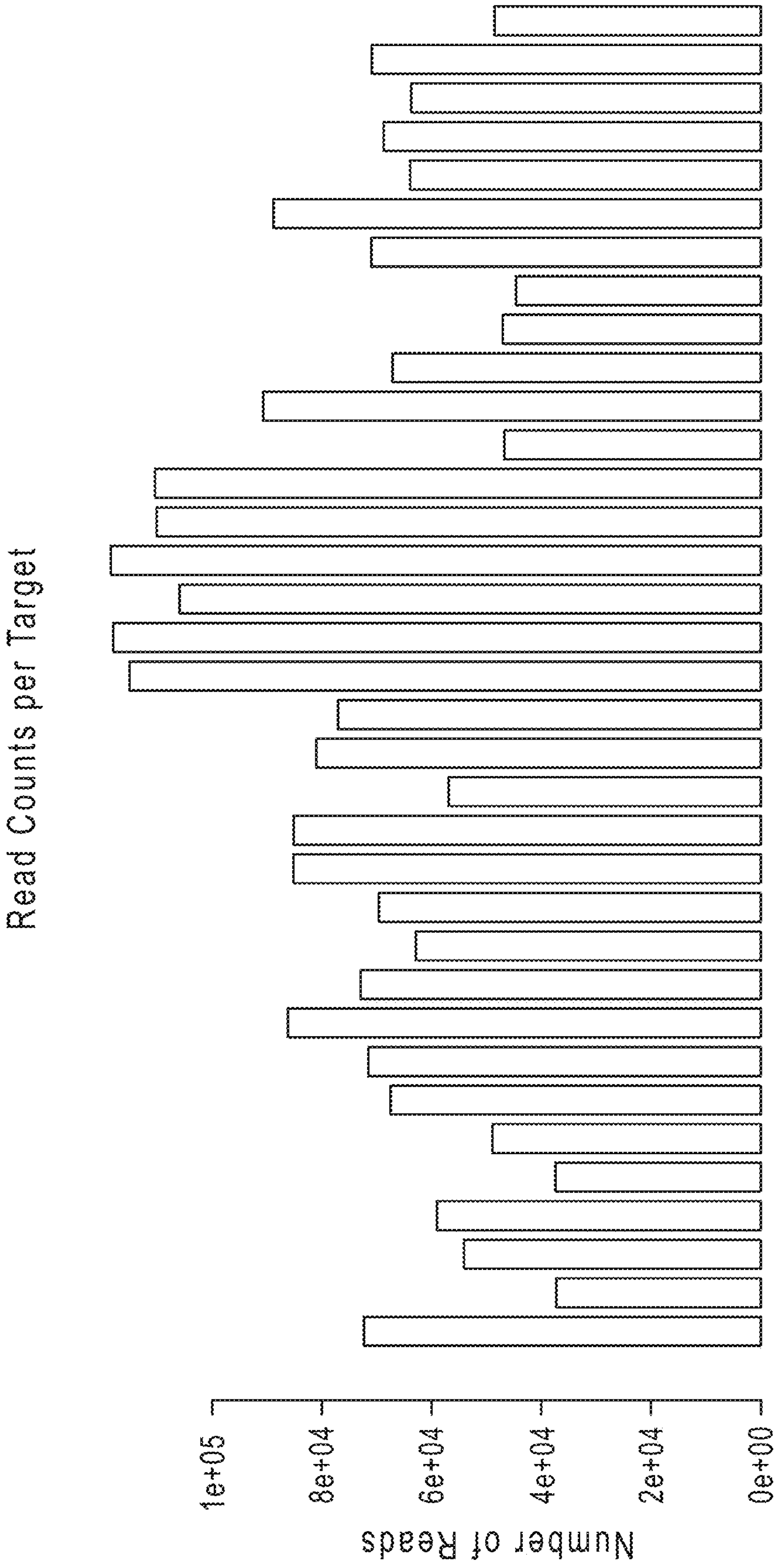
FIG. 15A is a histogram showing the on-target amplicon coverage for samples containing RNA spiked into DNA.
Figure 15B:
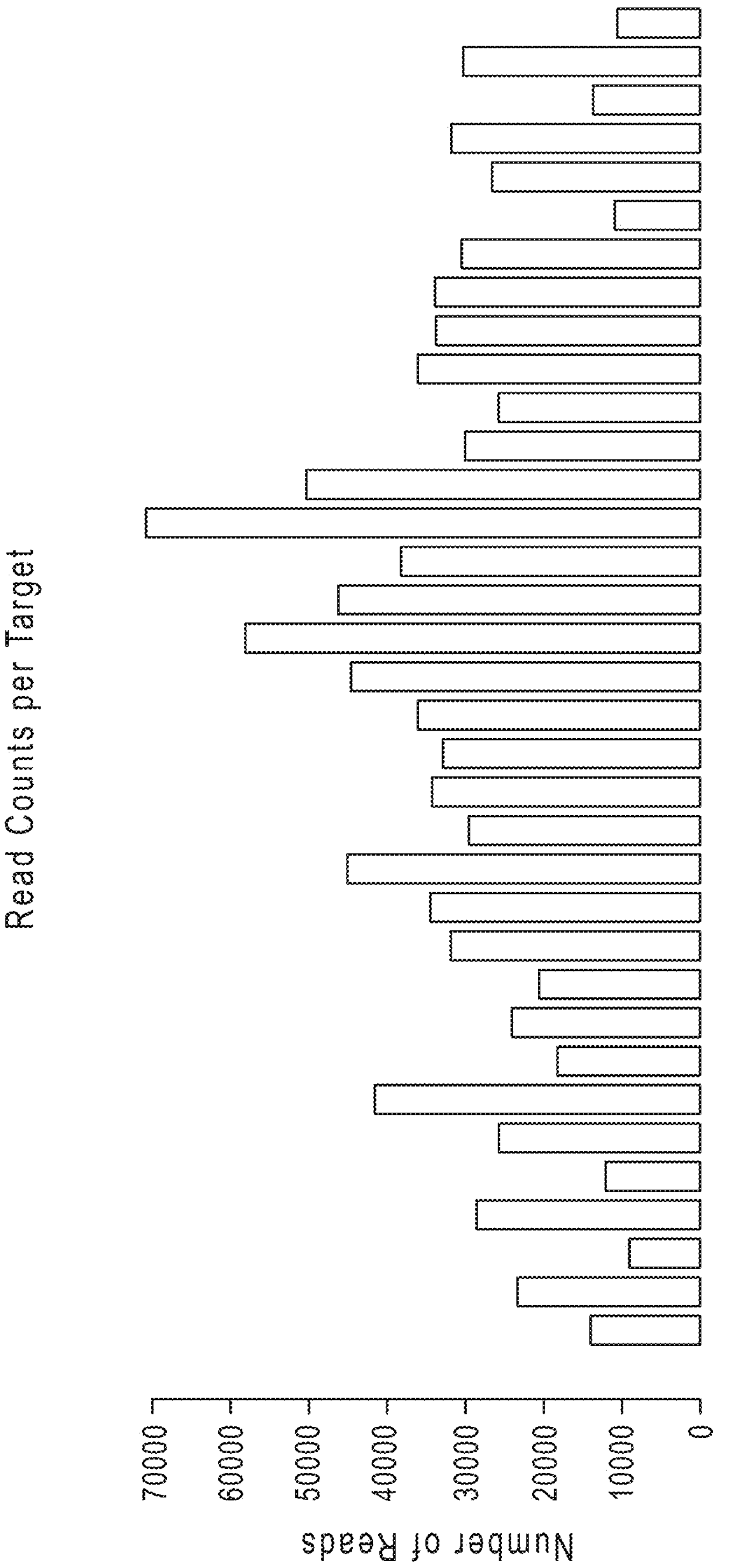
FIG. 15B is a histogram showing the on-target amplicon coverage for samples containing RNA spiked into DNA.

The final library was eluted in 25 uL low TE Buffer and quantified using High Sensitivity DNA Kit on the Agilent 2100 Bioanalyzer. The tagged library was used for template amplification and attaching to Ion sphere beads, and Ion S5 and 530 chip loading procedures. Sequencing was performed on Ion Proton apparatus. The sequencing data was analyzed using various culling, sorting and counting methodologies with applied thresholds, and demonstrated that EML4-ALK and SLC34A2-ROS1 fusion transcripts were detected. FIGS. 15A and B show the on-target amplicon coverage for the RNA-spiked DNA samples. Table 26 below shows the specific detection of all eight Horizon hotspot sequences.

TABLE 26

| Frequency: | Allele Name: | Gene ID | Coverage: | Allele Read Coverage: |
|---|---|---|---|---|
| 0.74% | A59T | NRAS | 10,388 | 59 |
| 1.03% | E545K | PIK3CA | 10,261 | 57 |
| 1.43% | G12D | KRAS | 17,091 | 228 |
| 0.42% | L858R | EGFR | 27,585 | 170 |
| 0.13% | P848L | EGFR | 24,000 | 45 |
| 0.42% | Q61K | NRAS | 33,395 | 30 |
| 0.21% | T790M | EGFR | 20,880 | 169 |
| 0.45% | V69_D770insASV | EGFR | 23,077 | 299 |

Table 27 below shows the coverage for fusion target sequences achieved using random priming or gene-specific priming for the for reverse transcription step.

TABLE 27

| | 1% cocktail RNA + cfDNA Control Random RT | 1% cocktail RNA + cfDNA Control Random RT | 1% cocktail RNA + cfDNA Control Gene-specific RT | 1% cocktail RNA + cfDNA Control Gene-specific RT |
|---|---|---|---|---|
| EML4-ALK E6aA20.AB374361 | 81 | 134 | 186 | 26 |
| EML4-ALK E6bA20.AB374362 | 29 | 0 | 43 | 48 |
| SLC34A2-ROS1 S4R32.COSF1197 | 272 | 230 | 93 | 186 |
| SLC34A2-ROS1 S4R34.COSF1198 | 206 | 273 | 152 | 169 |

The molecular tagging procedure achieved detection at ~1% of RNA fusion and DNA variants, in a sample containing a mixture of RNA and DNA.

Example 7

Molecular Tagging Via Adaptor Ligation-MegaMix Control DNA

The MegaMix Control DNA is a control DNA mixture from AcroMetrix™ containing synthetic and genomic DNA which includes cancer-relevant mutations. The input sample included MegaMix diluted to 0.1%. The workflow included: dephosphorylation of input DNA, gene-specific amplification using AMPLISEQ (Thermo Fisher Scientific, catalog No. 4475345) using non-tagged gene-specific primers, amplicon-end clean-up, tagged adaptor ligation, PCR amplification, and sequencing.

Dephosphorylation:

All reactions were conducted in a multiwall plate. The dephosphorylation reaction included: 3.5 uL (20 ng) of MegaMix DNA, 0.5 uL of 10× FastAP Buffer, and 1 uL of FastAP Thermosensitive alkaline phosphatase (Thermo Fisher Scientific, catalog No. EF0654. The dephosphorylation reaction was incubated at 37° C. for 60 minutes, then at 75° C. for 5 minutes to deactivate the enzyme, and cooled at 4° C.

Gene-Specific Amplification:

The gene-specific amplification reaction included: 10 uL of 2× Phusion™ U Multiplex MasterMix (Thermo Fisher Scientific catalog No. F562S), 4 uL AmpliSeq DNA panel (colon and lung primer panel, Thermo Fisher Scientific catalog No. 4475345), and 1 uL of nuclease-free water. The amplification reaction was mixed well, then 5 uL of the dephosphorylated input DNA was added. The thermocycler was programmed as follows:

TABLE 28

| Stage: | Temperature: | Time: |
|---|---|---|
| Hold | 98° C. | 2 min. |
| Cycles: 12 or 14 | 98° C. | 15 sec. |
| | 60° C. | 4 min. |
| Hold | 10° C. | ∞ |

Then 2 uL of the FuPa reagent from the AmpliSeq kit was added, and the reaction was incubated at 50° C. for 10 minutes, 55° C. for 10 minutes, 60° C. for 20 minutes, and then the reaction was held at 10° C. for no longer than 1 hour. The volume of this amplicon reaction now contains 22 uL.

Tagging Via Adaptor Ligation:

The tagging adaptors contained a mixture of different 14-mer random/degenerate sequences, so that potentially $4^{14}$=2.68×10$^{8}$ different tags sequences were present. The 14-mer random tag adaptors did not contain interspersed random and fixed sequences. The tagging adaptors also contained either a universal A or P1 adaptor sequence. For example, the A-tagging adaptors contained 5'-[A adaptor]-[14-mer random tag]-3' and the P1-tagging adaptors contained 5'-[14-mer]-[P1 adaptor]-3'. The ligation reaction contained: 4 uL of the Switch solution from the AmpliSeq kit, 2 uL of the tagged adaptors, 22 uL of the amplicons, and 2 uL of DNA ligase. The ligation reaction was incubated at 22° C. for 30 minutes, 72° C. for 10 minutes, and hold at 10° C.

First Round Purification:

AMPure™ XP Reagent was incubated at room temperature for at least 30 minutes, and vortexed thoroughly to disperse the beads. Low retention pipet tips were used for the AMPure™ purification steps. A solution of 70% ethanol was freshly prepared by mixing 230 uL of ethanol with 100 uL nuclease-free water per sample.

45 uL (1.5× sample volume) of Agencourt AMPure™ XP Reagent was added to each ligation reaction, and mixed by pipetting 5 times, and incubated at room temperature for 5 minutes. The plate was placed on a magnetic rack for 2 minutes or until the solution appeared clear. The supernatant was carefully removed, without disturbing the pellet, and the supernatant was discarded. 150 uL of the freshly-prepared 70% ethanol was added to the pellet, and the plate was moved side-to-side between the two magnets to wash the pellet. The supernatant was carefully removed, without disturbing the pellet, and the supernatant was discarded. The washing step was repeated by adding 150 uL of the freshly-prepared 70% ethanol was added to the pellet, and the plate was moved side-to-side between the two magnets to wash the pellet. The supernatant was carefully removed, without disturbing the pellet, and the supernatant was discarded. The plate was placed back on the magnet, and the bead/pellet was air-dried at room temperature for 5 minutes.

The plate was removed from the magnet. 23 uL of Low TE was added to the pellet to disperse the beads. The plate was sealed, vortexed, and spun to collect the droplets. The plate was placed on the magnet for at least 2 minutes. The supernatant (~23 uL) was removed to a new tube.

Amplification Via PCR:

The PCR amplification reaction was conducted by mixing: 25 uL of 2× Phusion™ U Multiplex Master Mix (Thermo Fisher Scientific catalog No. F562S), 2 uL of universal A and P1 amplification primers, and 23 uL of the AMPure™-purified supernatant

TABLE 29

| Stage: | Temperature: | Time: |
|---|---|---|
| Hold | 98° C. | 2 min. |
| Cycles: 5 or 3 | 98° C. | 15 sec. |
| | 64° C. | 1 min. |
| Hold | 10° C. | ∞ |

Second Round Purification:

AMPure™ XP Reagent was incubated at room temperature for at least 30 minutes, and vortexed thoroughly to disperse the beads. Low retention pipet tips were used for the AMPure™ purification steps. A solution of 70% ethanol was freshly prepared by mixing 230 uL of ethanol with 100 uL nuclease-free water per sample.

75 uL (1.5× sample volume) of Agencourt AMPure™ XP Reagent was added to each ligation reaction, and mixed by pipetting 5 times, and incubated at room temperature for 5 minutes. The plate was placed on a magnetic rack for 2 minutes or until the solution appeared clear. The supernatant was carefully removed, without disturbing the pellet, and the supernatant was discarded. 150 uL of the freshly-prepared 70% ethanol was added to the pellet, and the plate was moved side-to-side between the two magnets to wash the pellet. The supernatant was carefully removed, without disturbing the pellet, and the supernatant was discarded. The washing step was repeated by adding 150 uL of the freshly-prepared 70% ethanol was added to the pellet, and the plate was moved side-to-side between the two magnets to wash the pellet. The supernatant was carefully removed, without disturbing the pellet, and the supernatant was discarded. The plate was placed back on the magnet, and the bead/pellet was air-dried at room temperature for 5 minutes.

The plate was removed from the magnet. 50 uL of Low TE was added to the pellet to disperse the beads. The plate was sealed, vortexed, and spun to collect the droplets. The plate was placed on the magnet for at least 2 minutes. The supernatant (~23 uL) was removed to a new tube.

Library Quantification and Preparing Dilution Standards:

A dilution series was prepared using *E. coli* DH10B Control DNA (~68 pM stock), which included 6.8 pM, 0.68 pM, 0.068 pM, 0.0068 pM and 0.00068 pM. These dilutions were used as dilution standards in a qPCR instrument.

A 1:1,000 and 1:10,000 dilution of the tagged library were prepared.

Three wells each were set up for each tagged library, dilution standard and no template control (NTC). The volume of Master Mix for each sample was prepared using the following table:

TABLE 30

| Component: | Volume: |
|---|---|
| 2X TaqMan Master Mix | 5 µL |
| 20X Ion TaqMan assay | 0.5 µL |
| Total volume: | 5.5 µL |

5.5 µL of Master Mix was dispensed into each well, and 4.5 µL of the 1:1,000 or 1:10,000 diluted tagged library.

The thermal cycler was programmed as follows:

TABLE 31

| Stage: | Temperature: | Time: |
|---|---|---|
| Hold | 50° C. | 2 min. |
| Hold | 95° C. | 20 sec. |
| Cycle: 40 | 95° C. | 1 sec. |
| | 60° C. | 20 sec. |

The average concentration of the undiluted tagged library was calculated by multiplying the concentration determined by qPCR by the library dilution used in this assay.

The average concentration of the undiluted DNA library was calculated by multiplying the concentration determined with qPCR by the library dilution used in this assay.

The final library was eluted in 25 uL low TE Buffer and quantified using High Sensitivity DNA Kit on the Agilent 2100 Bioanalyzer. The tagged library was used for template amplification and attaching to Ion sphere beads, and Ion PGM/318 or Proton P1 chip loading procedures. Sequencing was performed on an Ion PGM or Proton I sequencing apparatus. The sequencing data was analyzed using various culling, sorting and counting methodologies with applied thresholds. Table 32 below shows that the tag-ligation workflow yielded about 54-89% on-target reads. Some of the variant sequences were detected at 0.1% LOD, with a high percentage of false positives.

TABLE 32

| Input DNA | Cycles: AmpliSeq PCR/2$^{nd}$ PCR | Reads | On-target reads | MRL | Uniformity |
|---|---|---|---|---|---|
| Ion Torrent PGM/318 sequencing chip | | | | | |
| 20 ng | 12 + 5 | 1,371,381 | 54.49% | 129 | 85.78% |
| 20 ng | 14 + 3 | 1,415,096 | 86.80% | 119 | 96.55% |
| Ion Torrent Proton I sequencing chip | | | | | |
| 20 ng | 12 + 5 | 19,271,454 | 64.21% | 121 | 77.86% |
| 20 ng | 14 + 3 | 21,292,642 | 89.79% | 118 | 94.72% |

What is claimed:

1. A method for detecting a genetic variant in a nucleic acid sample, comprising:

a) appending individual polynucleotides of a plurality of polynucleotides of the nucleic acid sample with at least one oligonucleotide tag of a plurality of oligonucleotide tags to generate tagged polynucleotides, wherein the at least one oligonucleotide tag comprises a structure, $N_1N_2N_3X_1X_2X_3M_4M_5M_6Y_4Y_5Y_6$ (i) wherein N represents a random tag sequence wherein each base position in the random tag sequence is independently selected from A, G, C or T;

(ii) wherein $X_1X_2X_3$ represents a first fixed tag sequence that is the same in all of the plurality of tags;

wherein M represents a random tag sequence wherein each base position in the random tag sequence is independently selected from A, G, C or T, wherein the random tag sequence M differs from the random tag sequence N; and (iv) wherein $Y_4Y_5Y_6$ represents a second fixed tag sequence that is the same in all of the plurality of tags, and the second fixed tag sequence of $Y_4Y_5Y_6$ differs from the first fixed tag sequence of $X_1X_2X_3$;

b) amplifying the tagged polynucleotides to generate tagged amplicons;

c) sequencing the tagged amplicons to generate a plurality of candidate sequencing reads, wherein each candidate sequencing read includes at least a portion of a sequence corresponding to the polynucleotide and at least a portion of a sequence corresponding to the at least one oligonucleotide tag that is appended to the polynucleotide, wherein the candidate sequencing reads are stored in a memory in communication with a processor;

d) grouping the candidate sequencing reads into families of grouped candidate sequencing reads having a common tag sequence that is unique to a given family of candidate sequencing reads;

e) removing mistagged sequencing reads from the families of candidate sequencing reads to produce error-corrected families of sequencing reads, wherein a mistagged sequencing read has the common tag sequence for the given family but corresponds to a different polynucleotide than other candidate sequencing reads in the given family due to errors in the appending of step a); and f) detecting a variant in a plurality of error-corrected families of sequencing reads.

2. The method of claim 1, further comprising identifying an error in one or more of the candidate sequencing reads.

3. The method of claim 2, wherein the step of identifying an error further includes applying a culling threshold to a number of nucleotides that differ between the candidate sequencing read and a reference sequence to identify a candidate sequencing read having an error.

4. The method of claim 3, wherein the reference sequence is a tag-specific reference sequence.

5. The method of claim 3, wherein the reference sequence is a polynucleotide-specific reference sequence.

6. The method of claim 1, wherein the removing mistagged sequencing reads of step e) further includes comparing the candidate sequencing read in the given family to a polynucleotide-specific reference sequence to determine a number of nucleotides that differ between the candidate sequencing read and the polynucleotide-specific reference sequence.

7. The method of claim 6, wherein the removing mistagged sequencing reads of step e) further includes applying a difference counting threshold to identify a mistagged sequencing read.

8. The method of claim 1, wherein the removing mistagged sequencing reads of step e) includes comparing the candidate sequencing read to one or more other candidate sequencing reads in the given family to identify candidate sequencing reads having a common pattern of variants.

9. The method of claim 8, wherein the removing mistagged sequencing reads of step e) further includes applying a pattern counting threshold to a number of candidate sequencing reads having the common pattern of variants to identify a group of mistagged sequencing reads.

10. The method of claim 1, wherein the removing mistagged sequencing reads of step e) includes comparing the candidate sequencing reads in the given family to a polynucleotide-specific reference sequence to identify a candidate mistagged sequencing read.

11. The method of claim 10, wherein the removing mistagged sequencing reads of step e) further includes comparing the candidate mistagged sequencing read to one or more other candidate mistagged sequencing reads in the given family to identify a common pattern of variants.

12. The method of claim 11, wherein the removing mistagged sequencing reads of step e) further includes applying a pattern counting threshold to a number of candidate mistagged sequencing reads having the common pattern of variants to determine a group of mistagged sequencing reads.

13. The method of claim 1, wherein the removing mistagged sequencing reads of step e) includes comparing the candidate sequencing read in the given family to a polynucleotide-specific reference sequence to identify a pattern of differences in a candidate mistagged sequencing read.

14. The method of claim 13, wherein the removing mistagged sequencing reads of step e) further includes determining a number of matches for the pattern of differences in the candidate mistagged sequencing read compared to a pattern of expected differences between the polynucleotide-specific reference sequence and an expected sequence for a non-target polynucleotide.

15. The method of claim 14, wherein the removing mistagged sequencing reads of step e) further includes applying a non-target pattern threshold to the number of matches to identify a mistagged sequencing read.

16. The method of claim 1, wherein the detecting of step f) includes aligning the sequencing reads for the error-corrected family to a polynucleotide-specific reference sequence.

17. The method of claim 16, wherein the detecting of step f) further includes counting a number of aligned sequencing reads having a particular base difference at a given position with respect to the polynucleotide-specific reference sequence.

18. The method of claim 17, wherein the detecting of step f) further includes applying a family level threshold to the number of aligned sequencing reads to identify a family-based candidate variant.

19. The method of claim 1, the detecting of step f) further includes counting a number of error-corrected families having a particular family-based candidate variant.

20. The method of claim 19, the detecting of step f) further includes applying a multi-family threshold to the number of error-corrected families to identify the variant.

* * * * *

UNITED STATES PATENT AND TRADEMARK OFFICE

CERTIFICATE OF CORRECTION

PATENT NO. : 12,338,496 B2
APPLICATION NO. : 17/389009
DATED : June 24, 2025
INVENTOR(S) : Kelli Bramlett et al.

It is certified that error appears in the above-identified patent and that said Letters Patent is hereby corrected as shown below:

In the Claims

In Column 249, Claim 1, Lines 3-7, delete "wherein M represents a random tag sequence wherein each base position in the random tag sequence is independently selected from A, G, C or T, wherein the random tag sequence M differs from the random tag sequence N; and" and insert -- (iii) wherein M represents a random tag sequence wherein each base position in the random tag sequence is independently selected from A, G, C or T. --, therefor.

Signed and Sealed this
Twenty-eighth Day of October, 2025

John A. Squires
*Director of the United States Patent and Trademark Office*

SEQUENCE LISTING

```
<160> NUMBER OF SEQ ID NOS: 191

<210> SEQ ID NO 1
<211> LENGTH: 12
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(9)
<223> OTHER INFORMATION: where "N" represents any of A, T, C or G

<400> SEQUENCE: 1

nnnactnnnt ga                                                    12


<210> SEQ ID NO 2
<211> LENGTH: 12
<212> TYPE: DNA
<213> ORGANISM: Artificial Sequence
```

<220> FEATURE:
<223> OTHER INFORMATION: Synthetic DNA
<220> FEATURE:
<221> NAME/KEY: misc_feature
<222> LOCATION: (1)..(9)
<223> OTHER INFORMATION: where "N" represents any of A, T, C or G

<400> SEQUENCE: 2
nnnactnnnt gc 12

<210> SEQ ID NO 3
<211> LENGTH: 12
<212> TYPE: DNA
<213> ORGANISM: Artificial Sequence
<220> FEATURE:
<223> OTHER INFORMATION: Synthetic

<400> SEQUENCE: 3
cggactggat gc 12

<210> SEQ ID NO 4
<211> LENGTH: 12
<212> TYPE: DNA
<213> ORGANISM: Artificial Sequence
<220> FEATURE:
<223> OTHER INFORMATION: Synthetic

<400> SEQUENCE: 4
cggactcagt gc 12

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
cgtactcgat gc 12

<210> SEQ ID NO 6
<211> LENGTH: 12
<212> TYPE: DNA
<213> ORGANISM: Artificial Sequence
<220> FEATURE:
<223> OTHER INFORMATION: Synthetic

<400> SEQUENCE: 6
aggactgcat gc 12

<210> SEQ ID NO 7
<211> LENGTH: 12
<212> TYPE: DNA
<213> ORGANISM: Artificial Sequence
<220> FEATURE:
<223> OTHER INFORMATION: Synthetic

<400> SEQUENCE: 7
ctgactcgat gc 12

<210> SEQ ID NO 8
<211> LENGTH: 12
<212> TYPE: DNA
<213> ORGANISM: Artificial Sequence
<220> FEATURE:
<223> OTHER INFORMATION: Synthetic

<400> SEQUENCE: 8
ctgactggct gc 12

<210> SEQ ID NO 9
<211> LENGTH: 12
<212> TYPE: DNA
<213> ORGANISM: Artificial Sequence
<220> FEATURE:
<223> OTHER INFORMATION: Synthetic

<400> SEQUENCE: 9
gcgactggat gc 12

<210> SEQ ID NO 10
<211> LENGTH: 12
<212> TYPE: DNA
<213> ORGANISM: Artificial Sequence
<220> FEATURE:
<223> OTHER INFORMATION: Synthetic

<400> SEQUENCE: 10
gcgactgtgt gc 12

<210> SEQ ID NO 11
<211> LENGTH: 12
<212> TYPE: DNA
<213> ORGANISM: Artificial Sequence
<220> FEATURE:
<223> OTHER INFORMATION: Synthetic

<400> SEQUENCE: 11
gggactgcat gc 12

<210> SEQ ID NO 12
<211> LENGTH: 12
<212> TYPE: DNA
<213> ORGANISM: Artificial Sequence
<220> FEATURE:
<223> OTHER INFORMATION: Synthetic

<400> SEQUENCE: 12
actactggat gc 12

<210> SEQ ID NO 13
<211> LENGTH: 12
<212> TYPE: DNA
<213> ORGANISM: Artificial Sequence
<220> FEATURE:
<223> OTHER INFORMATION: Synthetic

<400> SEQUENCE: 13
cggactctgt gc 12

<210> SEQ ID NO 14
<211> LENGTH: 12
<212> TYPE: DNA
<213> ORGANISM: Artificial Sequence
<220> FEATURE:
<223> OTHER INFORMATION: Synthetic

<400> SEQUENCE: 14
cggacttgat gc 12

<210> SEQ ID NO 15
<211> LENGTH: 12

<212> TYPE: DNA
<213> ORGANISM: Artificial Sequence
<220> FEATURE:
<223> OTHER INFORMATION: Synthetic

<400> SEQUENCE: 15
ctaactgagt gc 12

<210> SEQ ID NO 16
<211> LENGTH: 12
<212> TYPE: DNA
<213> ORGANISM: Artificial Sequence
<220> FEATURE:
<223> OTHER INFORMATION: Synthetic

<400> SEQUENCE: 16
ctgactggat gc 12

<210> SEQ ID NO 17
<211> LENGTH: 12
<212> TYPE: DNA
<213> ORGANISM: Artificial Sequence
<220> FEATURE:
<223> OTHER INFORMATION: Synthetic

<400> SEQUENCE: 17
cttactgcgt gc 12

<210> SEQ ID NO 18
<211> LENGTH: 12
<212> TYPE: DNA
<213> ORGANISM: Artificial Sequence
<220> FEATURE:
<223> OTHER INFORMATION: Synthetic

<400> SEQUENCE: 18
tcgactgtgt gc 12

<210> SEQ ID NO 19
<211> LENGTH: 12
<212> TYPE: DNA
<213> ORGANISM: Artificial Sequence
<220> FEATURE:
<223> OTHER INFORMATION: Synthetic

<400> SEQUENCE: 19
ttactgcatg ca 12

<210> SEQ ID NO 20
<211> LENGTH: 12
<212> TYPE: DNA
<213> ORGANISM: Artificial Sequence
<220> FEATURE:
<223> OTHER INFORMATION: Synthetic

<400> SEQUENCE: 20
aagactgggt gc 12

<210> SEQ ID NO 21
<211> LENGTH: 12
<212> TYPE: DNA
<213> ORGANISM: Artificial Sequence
<220> FEATURE:
<223> OTHER INFORMATION: Synthetic

<400> SEQUENCE: 21
acgactagat gc 12

<210> SEQ ID NO 22
<211> LENGTH: 12
<212> TYPE: DNA
<213> ORGANISM: Artificial Sequence
<220> FEATURE:
<223> OTHER INFORMATION: Synthetic

<400> SEQUENCE: 22
acgactgtat gc 12

<210> SEQ ID NO 23
<211> LENGTH: 12
<212> TYPE: DNA
<213> ORGANISM: Artificial Sequence
<220> FEATURE:
<223> OTHER INFORMATION: Synthetic

<400> SEQUENCE: 23
actactgtgt gc 12

<210> SEQ ID NO 24
<211> LENGTH: 12
<212> TYPE: DNA
<213> ORGANISM: Artificial Sequence
<220> FEATURE:
<223> OTHER INFORMATION: Synthetic

<400> SEQUENCE: 24
actgccctaa ca 12

<210> SEQ ID NO 25
<211> LENGTH: 12
<212> TYPE: DNA
<213> ORGANISM: Artificial Sequence
<220> FEATURE:
<223> OTHER INFORMATION: Synthetic

<400> SEQUENCE: 25
actgcctaac aa 12

<210> SEQ ID NO 26
<211> LENGTH: 12
<212> TYPE: DNA
<213> ORGANISM: Artificial Sequence
<220> FEATURE:
<223> OTHER INFORMATION: Synthetic

<400> SEQUENCE: 26
caaactgcat gc 12

<210> SEQ ID NO 27
<211> LENGTH: 12
<212> TYPE: DNA
<213> ORGANISM: Artificial Sequence
<220> FEATURE:
<223> OTHER INFORMATION: Synthetic

<400> SEQUENCE: 27
catacgtgta tg 12

<210> SEQ ID NO 28
<211> LENGTH: 12
<212> TYPE: DNA
<213> ORGANISM: Artificial Sequence

```
<220> FEATURE:
<223> OTHER INFORMATION: Synthetic

<400> SEQUENCE: 28

catactgagt gc                                                           12


<210> SEQ ID NO 29
<211> LENGTH: 12
<212> TYPE: DNA
<213> ORGANISM: Artificial Sequence
<220> FEATURE:
<223> OTHER INFORMATION: Synthetic

<400> SEQUENCE: 29

catctgagtg ca                                                           12


<210> SEQ ID NO 30
<211> LENGTH: 12
<212> TYPE: DNA
<213> ORGANISM: Artificial Sequence
<220> FEATURE:
<223> OTHER INFORMATION: Synthetic

<400> SEQUENCE: 30

ccgactacat gc                                                           12


<210> SEQ ID NO 31
<211> LENGTH: 12
<212> TYPE: DNA
<213> ORGANISM: Artificial Sequence
<220> FEATURE:
<223> OTHER INFORMATION: Synthetic

<400> SEQUENCE: 31

ccgactgtgt gc                                                           12


<210> SEQ ID NO 32
<211> LENGTH: 12
<212> TYPE: DNA
<213> ORGANISM: Artificial Sequence
<220> FEATURE:
<223> OTHER INFORMATION: Synthetic

<400> SEQUENCE: 32

cctactgact gc                                                           12


<210> SEQ ID NO 33
<211> LENGTH: 12
<212> TYPE: DNA
<213> ORGANISM: Artificial Sequence
<220> FEATURE:
<223> OTHER INFORMATION: Synthetic

<400> SEQUENCE: 33

cctgactgga tg                                                           12


<210> SEQ ID NO 34
<211> LENGTH: 12
<212> TYPE: DNA
<213> ORGANISM: Artificial Sequence
<220> FEATURE:
<223> OTHER INFORMATION: Synthetic

<400> SEQUENCE: 34

cgaactatgt gc                                                           12
```

<210> SEQ ID NO 35
<211> LENGTH: 12
<212> TYPE: DNA
<213> ORGANISM: Artificial Sequence
<220> FEATURE:
<223> OTHER INFORMATION: Synthetic

<400> SEQUENCE: 35
cgaactgcat gc 12

<210> SEQ ID NO 36
<211> LENGTH: 12
<212> TYPE: DNA
<213> ORGANISM: Artificial Sequence
<220> FEATURE:
<223> OTHER INFORMATION: Synthetic

<400> SEQUENCE: 36
cgaactgtgt gc 12

<210> SEQ ID NO 37
<211> LENGTH: 12
<212> TYPE: DNA
<213> ORGANISM: Artificial Sequence
<220> FEATURE:
<223> OTHER INFORMATION: Synthetic

<400> SEQUENCE: 37
cgaatgtgtg ca 12

<210> SEQ ID NO 38
<211> LENGTH: 12
<212> TYPE: DNA
<213> ORGANISM: Artificial Sequence
<220> FEATURE:
<223> OTHER INFORMATION: Synthetic

<400> SEQUENCE: 38
cgacgtcagc tg 12

<210> SEQ ID NO 39
<211> LENGTH: 12
<212> TYPE: DNA
<213> ORGANISM: Artificial Sequence
<220> FEATURE:
<223> OTHER INFORMATION: Synthetic

<400> SEQUENCE: 39
cggactacat gc 12

<210> SEQ ID NO 40
<211> LENGTH: 12
<212> TYPE: DNA
<213> ORGANISM: Artificial Sequence
<220> FEATURE:
<223> OTHER INFORMATION: Synthetic

<400> SEQUENCE: 40
cggactgaat gc 12

<210> SEQ ID NO 41
<211> LENGTH: 12
<212> TYPE: DNA
<213> ORGANISM: Artificial Sequence
<220> FEATURE:
<223> OTHER INFORMATION: Synthetic

<400> SEQUENCE: 41
cgtactatgt gc 12

<210> SEQ ID NO 42
<211> LENGTH: 12
<212> TYPE: DNA
<213> ORGANISM: Artificial Sequence
<220> FEATURE:
<223> OTHER INFORMATION: Synthetic

<400> SEQUENCE: 42
ctaactggat gc 12

<210> SEQ ID NO 43
<211> LENGTH: 12
<212> TYPE: DNA
<213> ORGANISM: Artificial Sequence
<220> FEATURE:
<223> OTHER INFORMATION: Synthetic

<400> SEQUENCE: 43
ctcactcggt gc 12

<210> SEQ ID NO 44
<211> LENGTH: 12
<212> TYPE: DNA
<213> ORGANISM: Artificial Sequence
<220> FEATURE:
<223> OTHER INFORMATION: Synthetic

<400> SEQUENCE: 44
ctcactcgtt gc 12

<210> SEQ ID NO 45
<211> LENGTH: 12
<212> TYPE: DNA
<213> ORGANISM: Artificial Sequence
<220> FEATURE:
<223> OTHER INFORMATION: Synthetic

<400> SEQUENCE: 45
ctcactgaat gc 12

<210> SEQ ID NO 46
<211> LENGTH: 12
<212> TYPE: DNA
<213> ORGANISM: Artificial Sequence
<220> FEATURE:
<223> OTHER INFORMATION: Synthetic

<400> SEQUENCE: 46
ctcactggct gc 12

<210> SEQ ID NO 47
<211> LENGTH: 12
<212> TYPE: DNA
<213> ORGANISM: Artificial Sequence
<220> FEATURE:
<223> OTHER INFORMATION: Synthetic

<400> SEQUENCE: 47
ctcactgtgt ga 12

<210> SEQ ID NO 48

<211> LENGTH: 12
<212> TYPE: DNA
<213> ORGANISM: Artificial Sequence
<220> FEATURE:
<223> OTHER INFORMATION: Synthetic

<400> SEQUENCE: 48
ctgactgaat gc 12

<210> SEQ ID NO 49
<211> LENGTH: 12
<212> TYPE: DNA
<213> ORGANISM: Artificial Sequence
<220> FEATURE:
<223> OTHER INFORMATION: Synthetic

<400> SEQUENCE: 49
ctgactgaat gc 12

<210> SEQ ID NO 50
<211> LENGTH: 12
<212> TYPE: DNA
<213> ORGANISM: Artificial Sequence
<220> FEATURE:
<223> OTHER INFORMATION: Synthetic

<400> SEQUENCE: 50
gcgactcact gc 12

<210> SEQ ID NO 51
<211> LENGTH: 12
<212> TYPE: DNA
<213> ORGANISM: Artificial Sequence
<220> FEATURE:
<223> OTHER INFORMATION: Synthetic

<400> SEQUENCE: 51
gcgactgtgc tg 12

<210> SEQ ID NO 52
<211> LENGTH: 12
<212> TYPE: DNA
<213> ORGANISM: Artificial Sequence
<220> FEATURE:
<223> OTHER INFORMATION: Synthetic

<400> SEQUENCE: 52
gctacgtgag tg 12

<210> SEQ ID NO 53
<211> LENGTH: 12
<212> TYPE: DNA
<213> ORGANISM: Artificial Sequence
<220> FEATURE:
<223> OTHER INFORMATION: Synthetic

<400> SEQUENCE: 53
ggtactcagt ga 12

<210> SEQ ID NO 54
<211> LENGTH: 12
<212> TYPE: DNA
<213> ORGANISM: Artificial Sequence
<220> FEATURE:
<223> OTHER INFORMATION: Synthetic

<400> SEQUENCE: 54
ggcactgcgt ga 12

<210> SEQ ID NO 55
<211> LENGTH: 12
<212> TYPE: DNA
<213> ORGANISM: Artificial Sequence
<220> FEATURE:
<223> OTHER INFORMATION: Synthetic

<400> SEQUENCE: 55
agcactatgt ga 12

<210> SEQ ID NO 56
<211> LENGTH: 12
<212> TYPE: DNA
<213> ORGANISM: Artificial Sequence
<220> FEATURE:
<223> OTHER INFORMATION: Synthetic

<400> SEQUENCE: 56
gccactcgct ga 12

<210> SEQ ID NO 57
<211> LENGTH: 12
<212> TYPE: DNA
<213> ORGANISM: Artificial Sequence
<220> FEATURE:
<223> OTHER INFORMATION: Synthetic

<400> SEQUENCE: 57
gcccactcgc tg 12

<210> SEQ ID NO 58
<211> LENGTH: 12
<212> TYPE: DNA
<213> ORGANISM: Artificial Sequence
<220> FEATURE:
<223> OTHER INFORMATION: Synthetic

<400> SEQUENCE: 58
gccccactcg ct 12

<210> SEQ ID NO 59
<211> LENGTH: 12
<212> TYPE: DNA
<213> ORGANISM: Artificial Sequence
<220> FEATURE:
<223> OTHER INFORMATION: Synthetic

<400> SEQUENCE: 59
agcactagtg ta 12

<210> SEQ ID NO 60
<211> LENGTH: 12
<212> TYPE: DNA
<213> ORGANISM: Artificial Sequence
<220> FEATURE:
<223> OTHER INFORMATION: Synthetic

<400> SEQUENCE: 60
agcactatcg tg 12

<210> SEQ ID NO 61
<211> LENGTH: 12
<212> TYPE: DNA

<213> ORGANISM: Artificial Sequence
<220> FEATURE:
<223> OTHER INFORMATION: Synthetic

<400> SEQUENCE: 61
atcactatgt ga 12

<210> SEQ ID NO 62
<211> LENGTH: 12
<212> TYPE: DNA
<213> ORGANISM: Artificial Sequence
<220> FEATURE:
<223> OTHER INFORMATION: Synthetic

<400> SEQUENCE: 62
ggcacctgcg tg 12

<210> SEQ ID NO 63
<211> LENGTH: 12
<212> TYPE: DNA
<213> ORGANISM: Artificial Sequence
<220> FEATURE:
<223> OTHER INFORMATION: Synthetic

<400> SEQUENCE: 63
aaagactgcg tg 12

<210> SEQ ID NO 64
<211> LENGTH: 12
<212> TYPE: DNA
<213> ORGANISM: Artificial Sequence
<220> FEATURE:
<223> OTHER INFORMATION: Synthetic

<400> SEQUENCE: 64
aacactgagt ga 12

<210> SEQ ID NO 65
<211> LENGTH: 12
<212> TYPE: DNA
<213> ORGANISM: Artificial Sequence
<220> FEATURE:
<223> OTHER INFORMATION: Synthetic

<400> SEQUENCE: 65
aacactgtga tg 12

<210> SEQ ID NO 66
<211> LENGTH: 12
<212> TYPE: DNA
<213> ORGANISM: Artificial Sequence
<220> FEATURE:
<223> OTHER INFORMATION: Synthetic

<400> SEQUENCE: 66
aacacttcgt ga 12

<210> SEQ ID NO 67
<211> LENGTH: 12
<212> TYPE: DNA
<213> ORGANISM: Artificial Sequence
<220> FEATURE:
<223> OTHER INFORMATION: Synthetic

<400> SEQUENCE: 67
aacacttggt ga 12

<210> SEQ ID NO 68
<211> LENGTH: 12
<212> TYPE: DNA
<213> ORGANISM: Artificial Sequence
<220> FEATURE:
<223> OTHER INFORMATION: Synthetic

<400> SEQUENCE: 68
aactgagtga tg 12

<210> SEQ ID NO 69
<211> LENGTH: 12
<212> TYPE: DNA
<213> ORGANISM: Artificial Sequence
<220> FEATURE:
<223> OTHER INFORMATION: Synthetic

<400> SEQUENCE: 69
aagactaact ga 12

<210> SEQ ID NO 70
<211> LENGTH: 12
<212> TYPE: DNA
<213> ORGANISM: Artificial Sequence
<220> FEATURE:
<223> OTHER INFORMATION: Synthetic

<400> SEQUENCE: 70
aagactccgt ga 12

<210> SEQ ID NO 71
<211> LENGTH: 12
<212> TYPE: DNA
<213> ORGANISM: Artificial Sequence
<220> FEATURE:
<223> OTHER INFORMATION: Synthetic

<400> SEQUENCE: 71
aagactgcgt ga 12

<210> SEQ ID NO 72
<211> LENGTH: 12
<212> TYPE: DNA
<213> ORGANISM: Artificial Sequence
<220> FEATURE:
<223> OTHER INFORMATION: Synthetic

<400> SEQUENCE: 72
aagactgctt ga 12

<210> SEQ ID NO 73
<211> LENGTH: 12
<212> TYPE: DNA
<213> ORGANISM: Artificial Sequence
<220> FEATURE:
<223> OTHER INFORMATION: Synthetic

<400> SEQUENCE: 73
gggactgggt ga 12

<210> SEQ ID NO 74
<211> LENGTH: 12
<212> TYPE: DNA
<213> ORGANISM: Artificial Sequence
<220> FEATURE:

<223> OTHER INFORMATION: Synthetic

<400> SEQUENCE: 74
cggactgggt ga 12

<210> SEQ ID NO 75
<211> LENGTH: 12
<212> TYPE: DNA
<213> ORGANISM: Artificial Sequence
<220> FEATURE:
<223> OTHER INFORMATION: Synthetic

<400> SEQUENCE: 75
gagactgggt ga 12

<210> SEQ ID NO 76
<211> LENGTH: 12
<212> TYPE: DNA
<213> ORGANISM: Artificial Sequence
<220> FEATURE:
<223> OTHER INFORMATION: Synthetic

<400> SEQUENCE: 76
gcactgggtg at 12

<210> SEQ ID NO 77
<211> LENGTH: 12
<212> TYPE: DNA
<213> ORGANISM: Artificial Sequence
<220> FEATURE:
<223> OTHER INFORMATION: Synthetic

<400> SEQUENCE: 77
ggactgggtg at 12

<210> SEQ ID NO 78
<211> LENGTH: 12
<212> TYPE: DNA
<213> ORGANISM: Artificial Sequence
<220> FEATURE:
<223> OTHER INFORMATION: Synthetic

<400> SEQUENCE: 78
gcgactgggt ga 12

<210> SEQ ID NO 79
<211> LENGTH: 12
<212> TYPE: DNA
<213> ORGANISM: Artificial Sequence
<220> FEATURE:
<223> OTHER INFORMATION: Synthetic

<400> SEQUENCE: 79
ggcactgggt ga 12

<210> SEQ ID NO 80
<211> LENGTH: 12
<212> TYPE: DNA
<213> ORGANISM: Artificial Sequence
<220> FEATURE:
<223> OTHER INFORMATION: Synthetic

<400> SEQUENCE: 80
cactcggtga tg 12

-continued

<210> SEQ ID NO 81
<211> LENGTH: 12
<212> TYPE: DNA
<213> ORGANISM: Artificial Sequence
<220> FEATURE:
<223> OTHER INFORMATION: Synthetic

<400> SEQUENCE: 81
gactgggtga tg 12

<210> SEQ ID NO 82
<211> LENGTH: 12
<212> TYPE: DNA
<213> ORGANISM: Artificial Sequence
<220> FEATURE:
<223> OTHER INFORMATION: Synthetic

<400> SEQUENCE: 82
gggactgagt ga 12

<210> SEQ ID NO 83
<211> LENGTH: 12
<212> TYPE: DNA
<213> ORGANISM: Artificial Sequence
<220> FEATURE:
<223> OTHER INFORMATION: Synthetic

<400> SEQUENCE: 83
ccgactgggt ga 12

<210> SEQ ID NO 84
<211> LENGTH: 12
<212> TYPE: DNA
<213> ORGANISM: Artificial Sequence
<220> FEATURE:
<223> OTHER INFORMATION: Synthetic

<400> SEQUENCE: 84
cggactcggt ga 12

<210> SEQ ID NO 85
<211> LENGTH: 12
<212> TYPE: DNA
<213> ORGANISM: Artificial Sequence
<220> FEATURE:
<223> OTHER INFORMATION: Synthetic

<400> SEQUENCE: 85
gggactcggt ga 12

<210> SEQ ID NO 86
<211> LENGTH: 12
<212> TYPE: DNA
<213> ORGANISM: Artificial Sequence
<220> FEATURE:
<223> OTHER INFORMATION: Synthetic

<400> SEQUENCE: 86
gggactggct ga 12

<210> SEQ ID NO 87
<211> LENGTH: 12
<212> TYPE: DNA
<213> ORGANISM: Artificial Sequence
<220> FEATURE:
<223> OTHER INFORMATION: Synthetic

<400> SEQUENCE: 87
gtgactgggt ga 12

<210> SEQ ID NO 88
<211> LENGTH: 12
<212> TYPE: DNA
<213> ORGANISM: Artificial Sequence
<220> FEATURE:
<223> OTHER INFORMATION: Synthetic

<400> SEQUENCE: 88
cgtactggct ga 12

<210> SEQ ID NO 89
<211> LENGTH: 12
<212> TYPE: DNA
<213> ORGANISM: Artificial Sequence
<220> FEATURE:
<223> OTHER INFORMATION: Synthetic

<400> SEQUENCE: 89
gctactgggt ga 12

<210> SEQ ID NO 90
<211> LENGTH: 12
<212> TYPE: DNA
<213> ORGANISM: Artificial Sequence
<220> FEATURE:
<223> OTHER INFORMATION: Synthetic

<400> SEQUENCE: 90
ggtactcggt ga 12

<210> SEQ ID NO 91
<211> LENGTH: 12
<212> TYPE: DNA
<213> ORGANISM: Artificial Sequence
<220> FEATURE:
<223> OTHER INFORMATION: Synthetic

<400> SEQUENCE: 91
agcacttgtt ga 12

<210> SEQ ID NO 92
<211> LENGTH: 12
<212> TYPE: DNA
<213> ORGANISM: Artificial Sequence
<220> FEATURE:
<223> OTHER INFORMATION: Synthetic

<400> SEQUENCE: 92
aggactggtt ga 12

<210> SEQ ID NO 93
<211> LENGTH: 12
<212> TYPE: DNA
<213> ORGANISM: Artificial Sequence
<220> FEATURE:
<223> OTHER INFORMATION: Synthetic

<400> SEQUENCE: 93
agtactgatt ga 12

<210> SEQ ID NO 94
<211> LENGTH: 12

<212> TYPE: DNA
<213> ORGANISM: Artificial Sequence
<220> FEATURE:
<223> OTHER INFORMATION: Synthetic

<400> SEQUENCE: 94
ccgactcggt ga 12

<210> SEQ ID NO 95
<211> LENGTH: 12
<212> TYPE: DNA
<213> ORGANISM: Artificial Sequence
<220> FEATURE:
<223> OTHER INFORMATION: Synthetic

<400> SEQUENCE: 95
cctactgtct ga 12

<210> SEQ ID NO 96
<211> LENGTH: 12
<212> TYPE: DNA
<213> ORGANISM: Artificial Sequence
<220> FEATURE:
<223> OTHER INFORMATION: Synthetic

<400> SEQUENCE: 96
cggactggtt ga 12

<210> SEQ ID NO 97
<211> LENGTH: 12
<212> TYPE: DNA
<213> ORGANISM: Artificial Sequence
<220> FEATURE:
<223> OTHER INFORMATION: Synthetic

<400> SEQUENCE: 97
cttactgttt ga 12

<210> SEQ ID NO 98
<211> LENGTH: 12
<212> TYPE: DNA
<213> ORGANISM: Artificial Sequence
<220> FEATURE:
<223> OTHER INFORMATION: Synthetic

<400> SEQUENCE: 98
gacactactt ga 12

<210> SEQ ID NO 99
<211> LENGTH: 12
<212> TYPE: DNA
<213> ORGANISM: Artificial Sequence
<220> FEATURE:
<223> OTHER INFORMATION: Synthetic

<400> SEQUENCE: 99
gcgactggct ga 12

<210> SEQ ID NO 100
<211> LENGTH: 12
<212> TYPE: DNA
<213> ORGANISM: Artificial Sequence
<220> FEATURE:
<223> OTHER INFORMATION: Synthetic

<400> SEQUENCE: 100
gctactcggt ga 12

<210> SEQ ID NO 101
<211> LENGTH: 12
<212> TYPE: DNA
<213> ORGANISM: Artificial Sequence
<220> FEATURE:
<223> OTHER INFORMATION: Synthetic

<400> SEQUENCE: 101
ggaactgggt ga 12

<210> SEQ ID NO 102
<211> LENGTH: 12
<212> TYPE: DNA
<213> ORGANISM: Artificial Sequence
<220> FEATURE:
<223> OTHER INFORMATION: Synthetic

<400> SEQUENCE: 102
gggactatgt ga 12

<210> SEQ ID NO 103
<211> LENGTH: 12
<212> TYPE: DNA
<213> ORGANISM: Artificial Sequence
<220> FEATURE:
<223> OTHER INFORMATION: Synthetic

<400> SEQUENCE: 103
gggactccgt ga 12

<210> SEQ ID NO 104
<211> LENGTH: 12
<212> TYPE: DNA
<213> ORGANISM: Artificial Sequence
<220> FEATURE:
<223> OTHER INFORMATION: Synthetic

<400> SEQUENCE: 104
gggactcgtt ga 12

<210> SEQ ID NO 105
<211> LENGTH: 12
<212> TYPE: DNA
<213> ORGANISM: Artificial Sequence
<220> FEATURE:
<223> OTHER INFORMATION: Synthetic

<400> SEQUENCE: 105
gggactgcgt ga 12

<210> SEQ ID NO 106
<211> LENGTH: 12
<212> TYPE: DNA
<213> ORGANISM: Artificial Sequence
<220> FEATURE:
<223> OTHER INFORMATION: Synthetic

<400> SEQUENCE: 106
gggactggtt ga 12

<210> SEQ ID NO 107
<211> LENGTH: 12
<212> TYPE: DNA
<213> ORGANISM: Artificial Sequence
<220> FEATURE:
<223> OTHER INFORMATION: Synthetic

<400> SEQUENCE: 107
gggactgtgt ga 12

<210> SEQ ID NO 108
<211> LENGTH: 12
<212> TYPE: DNA
<213> ORGANISM: Artificial Sequence
<220> FEATURE:
<223> OTHER INFORMATION: Synthetic

<400> SEQUENCE: 108
gggacttggt ga 12

<210> SEQ ID NO 109
<211> LENGTH: 12
<212> TYPE: DNA
<213> ORGANISM: Artificial Sequence
<220> FEATURE:
<223> OTHER INFORMATION: Synthetic

<400> SEQUENCE: 109
ggggactggg gt 12

<210> SEQ ID NO 110
<211> LENGTH: 12
<212> TYPE: DNA
<213> ORGANISM: Artificial Sequence
<220> FEATURE:
<223> OTHER INFORMATION: Synthetic

<400> SEQUENCE: 110
ggtactgaat ga 12

<210> SEQ ID NO 111
<211> LENGTH: 12
<212> TYPE: DNA
<213> ORGANISM: Artificial Sequence
<220> FEATURE:
<223> OTHER INFORMATION: Synthetic

<400> SEQUENCE: 111
ggtactgttt ga 12

<210> SEQ ID NO 112
<211> LENGTH: 12
<212> TYPE: DNA
<213> ORGANISM: Artificial Sequence
<220> FEATURE:
<223> OTHER INFORMATION: Synthetic

<400> SEQUENCE: 112
taaactggtt ga 12

<210> SEQ ID NO 113
<211> LENGTH: 12
<212> TYPE: DNA
<213> ORGANISM: Artificial Sequence
<220> FEATURE:
<223> OTHER INFORMATION: Synthetic

<400> SEQUENCE: 113
gggactgggt ga 12

<210> SEQ ID NO 114
<211> LENGTH: 12
<212> TYPE: DNA
<213> ORGANISM: Artificial Sequence
<220> FEATURE:
<223> OTHER INFORMATION: Synthetic

<400> SEQUENCE: 114
cggactgggt ga 12

<210> SEQ ID NO 115
<211> LENGTH: 12
<212> TYPE: DNA
<213> ORGANISM: Artificial Sequence
<220> FEATURE:
<223> OTHER INFORMATION: Synthetic

<400> SEQUENCE: 115
gactgggtga tg 12

<210> SEQ ID NO 116
<211> LENGTH: 12
<212> TYPE: DNA
<213> ORGANISM: Artificial Sequence
<220> FEATURE:
<223> OTHER INFORMATION: Synthetic

<400> SEQUENCE: 116
gggactgcgt ga 12

<210> SEQ ID NO 117
<211> LENGTH: 12
<212> TYPE: DNA
<213> ORGANISM: Artificial Sequence
<220> FEATURE:
<223> OTHER INFORMATION: Synthetic

<400> SEQUENCE: 117
gggactcggt ga 12

<210> SEQ ID NO 118
<211> LENGTH: 12
<212> TYPE: DNA
<213> ORGANISM: Artificial Sequence
<220> FEATURE:
<223> OTHER INFORMATION: Synthetic

<400> SEQUENCE: 118
ggtactgggt ga 12

<210> SEQ ID NO 119
<211> LENGTH: 12
<212> TYPE: DNA
<213> ORGANISM: Artificial Sequence
<220> FEATURE:
<223> OTHER INFORMATION: Synthetic

<400> SEQUENCE: 119
agaacttggt ga 12

<210> SEQ ID NO 120
<211> LENGTH: 12
<212> TYPE: DNA
<213> ORGANISM: Artificial Sequence
<220> FEATURE:
<223> OTHER INFORMATION: Synthetic

<400> SEQUENCE: 120
cctactgtct ga 12

<210> SEQ ID NO 121
<211> LENGTH: 12
<212> TYPE: DNA
<213> ORGANISM: Artificial Sequence
<220> FEATURE:
<223> OTHER INFORMATION: Synthetic

<400> SEQUENCE: 121
cgcactgggt ga 12

<210> SEQ ID NO 122
<211> LENGTH: 12
<212> TYPE: DNA
<213> ORGANISM: Artificial Sequence
<220> FEATURE:
<223> OTHER INFORMATION: Synthetic

<400> SEQUENCE: 122
gcgactgggt ga 12

<210> SEQ ID NO 123
<211> LENGTH: 12
<212> TYPE: DNA
<213> ORGANISM: Artificial Sequence
<220> FEATURE:
<223> OTHER INFORMATION: Synthetic

<400> SEQUENCE: 123
ggactgggtg at 12

<210> SEQ ID NO 124
<211> LENGTH: 12
<212> TYPE: DNA
<213> ORGANISM: Artificial Sequence
<220> FEATURE:
<223> OTHER INFORMATION: Synthetic

<400> SEQUENCE: 124
ggcactgcgt ga 12

<210> SEQ ID NO 125
<211> LENGTH: 12
<212> TYPE: DNA
<213> ORGANISM: Artificial Sequence
<220> FEATURE:
<223> OTHER INFORMATION: Synthetic

<400> SEQUENCE: 125
ggcactgggt ga 12

<210> SEQ ID NO 126
<211> LENGTH: 12
<212> TYPE: DNA
<213> ORGANISM: Artificial Sequence
<220> FEATURE:
<223> OTHER INFORMATION: Synthetic

<400> SEQUENCE: 126
gtgactgggt ga 12

<210> SEQ ID NO 127

<211> LENGTH: 12
<212> TYPE: DNA
<213> ORGANISM: Artificial Sequence
<220> FEATURE:
<223> OTHER INFORMATION: Synthetic

<400> SEQUENCE: 127
aggactgagt ga 12

<210> SEQ ID NO 128
<211> LENGTH: 12
<212> TYPE: DNA
<213> ORGANISM: Artificial Sequence
<220> FEATURE:
<223> OTHER INFORMATION: Synthetic

<400> SEQUENCE: 128
aggactgggt ga 12

<210> SEQ ID NO 129
<211> LENGTH: 12
<212> TYPE: DNA
<213> ORGANISM: Artificial Sequence
<220> FEATURE:
<223> OTHER INFORMATION: Synthetic

<400> SEQUENCE: 129
agtactaagt ga 12

<210> SEQ ID NO 130
<211> LENGTH: 12
<212> TYPE: DNA
<213> ORGANISM: Artificial Sequence
<220> FEATURE:
<223> OTHER INFORMATION: Synthetic

<400> SEQUENCE: 130
agtacttgct ga 12

<210> SEQ ID NO 131
<211> LENGTH: 12
<212> TYPE: DNA
<213> ORGANISM: Artificial Sequence
<220> FEATURE:
<223> OTHER INFORMATION: Synthetic

<400> SEQUENCE: 131
cagactgggt ga 12

<210> SEQ ID NO 132
<211> LENGTH: 12
<212> TYPE: DNA
<213> ORGANISM: Artificial Sequence
<220> FEATURE:
<223> OTHER INFORMATION: Synthetic

<400> SEQUENCE: 132
ccgactggct ga 12

<210> SEQ ID NO 133
<211> LENGTH: 12
<212> TYPE: DNA
<213> ORGANISM: Artificial Sequence
<220> FEATURE:
<223> OTHER INFORMATION: Synthetic

<400> SEQUENCE: 133
cggactcggt ga 12

<210> SEQ ID NO 134
<211> LENGTH: 12
<212> TYPE: DNA
<213> ORGANISM: Artificial Sequence
<220> FEATURE:
<223> OTHER INFORMATION: Synthetic

<400> SEQUENCE: 134
gagactgggt ga 12

<210> SEQ ID NO 135
<211> LENGTH: 12
<212> TYPE: DNA
<213> ORGANISM: Artificial Sequence
<220> FEATURE:
<223> OTHER INFORMATION: Synthetic

<400> SEQUENCE: 135
gcgactgtgt ga 12

<210> SEQ ID NO 136
<211> LENGTH: 12
<212> TYPE: DNA
<213> ORGANISM: Artificial Sequence
<220> FEATURE:
<223> OTHER INFORMATION: Synthetic

<400> SEQUENCE: 136
gggactcgtt ga 12

<210> SEQ ID NO 137
<211> LENGTH: 12
<212> TYPE: DNA
<213> ORGANISM: Artificial Sequence
<220> FEATURE:
<223> OTHER INFORMATION: Synthetic

<400> SEQUENCE: 137
gggactgagt ga 12

<210> SEQ ID NO 138
<211> LENGTH: 12
<212> TYPE: DNA
<213> ORGANISM: Artificial Sequence
<220> FEATURE:
<223> OTHER INFORMATION: Synthetic

<400> SEQUENCE: 138
gggactgtgt ga 12

<210> SEQ ID NO 139
<211> LENGTH: 12
<212> TYPE: DNA
<213> ORGANISM: Artificial Sequence
<220> FEATURE:
<223> OTHER INFORMATION: Synthetic

<400> SEQUENCE: 139
ggtactcggt ga 12

<210> SEQ ID NO 140
<211> LENGTH: 12
<212> TYPE: DNA

<213> ORGANISM: Artificial Sequence
<220> FEATURE:
<223> OTHER INFORMATION: Synthetic

<400> SEQUENCE: 140
ggtactggtt ga 12

<210> SEQ ID NO 141
<211> LENGTH: 12
<212> TYPE: DNA
<213> ORGANISM: Artificial Sequence
<220> FEATURE:
<223> OTHER INFORMATION: Synthetic

<400> SEQUENCE: 141
ggtactgtgt ga 12

<210> SEQ ID NO 142
<211> LENGTH: 12
<212> TYPE: DNA
<213> ORGANISM: Artificial Sequence
<220> FEATURE:
<223> OTHER INFORMATION: Synthetic

<400> SEQUENCE: 142
gtgactgcgt ga 12

<210> SEQ ID NO 143
<211> LENGTH: 12
<212> TYPE: DNA
<213> ORGANISM: Artificial Sequence
<220> FEATURE:
<223> OTHER INFORMATION: Synthetic

<400> SEQUENCE: 143
tgtactgcat ga 12

<210> SEQ ID NO 144
<211> LENGTH: 12
<212> TYPE: DNA
<213> ORGANISM: Artificial Sequence
<220> FEATURE:
<223> OTHER INFORMATION: Synthetic

<400> SEQUENCE: 144
aagacttcgt ga 12

<210> SEQ ID NO 145
<211> LENGTH: 12
<212> TYPE: DNA
<213> ORGANISM: Artificial Sequence
<220> FEATURE:
<223> OTHER INFORMATION: Synthetic

<400> SEQUENCE: 145
acactcggtg at 12

<210> SEQ ID NO 146
<211> LENGTH: 12
<212> TYPE: DNA
<213> ORGANISM: Artificial Sequence
<220> FEATURE:
<223> OTHER INFORMATION: Synthetic

<400> SEQUENCE: 146
acccactggg tg 12

<210> SEQ ID NO 147
<211> LENGTH: 12
<212> TYPE: DNA
<213> ORGANISM: Artificial Sequence
<220> FEATURE:
<223> OTHER INFORMATION: Synthetic

<400> SEQUENCE: 147
acgactgcat ga 12

<210> SEQ ID NO 148
<211> LENGTH: 12
<212> TYPE: DNA
<213> ORGANISM: Artificial Sequence
<220> FEATURE:
<223> OTHER INFORMATION: Synthetic

<400> SEQUENCE: 148
acgactgggt ga 12

<210> SEQ ID NO 149
<211> LENGTH: 12
<212> TYPE: DNA
<213> ORGANISM: Artificial Sequence
<220> FEATURE:
<223> OTHER INFORMATION: Synthetic

<400> SEQUENCE: 149
aggactgcgt ga 12

<210> SEQ ID NO 150
<211> LENGTH: 12
<212> TYPE: DNA
<213> ORGANISM: Artificial Sequence
<220> FEATURE:
<223> OTHER INFORMATION: Synthetic

<400> SEQUENCE: 150
aggactgtgt ga 12

<210> SEQ ID NO 151
<211> LENGTH: 12
<212> TYPE: DNA
<213> ORGANISM: Artificial Sequence
<220> FEATURE:
<223> OTHER INFORMATION: Synthetic

<400> SEQUENCE: 151
agtactcagt ga 12

<210> SEQ ID NO 152
<211> LENGTH: 12
<212> TYPE: DNA
<213> ORGANISM: Artificial Sequence
<220> FEATURE:
<223> OTHER INFORMATION: Synthetic

<400> SEQUENCE: 152
agtactgatt ga 12

<210> SEQ ID NO 153
<211> LENGTH: 59
<212> TYPE: DNA
<213> ORGANISM: Artificial Sequence
<220> FEATURE:

<223> OTHER INFORMATION: Synthetic

<400> SEQUENCE: 153
acctgttacc ataaaatcat atgctccact aacaaccctc ctgccatcat attgaacac 59

<210> SEQ ID NO 154
<211> LENGTH: 58
<212> TYPE: DNA
<213> ORGANISM: Artificial Sequence
<220> FEATURE:
<223> OTHER INFORMATION: Synthetic

<400> SEQUENCE: 154
acctgtacgg tcaaggcgta aactccacta acaaccctcc tgccctcata ttgaacac 58

<210> SEQ ID NO 155
<211> LENGTH: 58
<212> TYPE: DNA
<213> ORGANISM: Artificial Sequence
<220> FEATURE:
<223> OTHER INFORMATION: Synthetic

<400> SEQUENCE: 155
acctgtacgg tgacagcgga ttgtgcacta acaaccctcc tgccctcata ttgaacac 58

<210> SEQ ID NO 156
<211> LENGTH: 58
<212> TYPE: DNA
<213> ORGANISM: Artificial Sequence
<220> FEATURE:
<223> OTHER INFORMATION: Synthetic

<400> SEQUENCE: 156
acctgtacgg tgagactact ggatgcacta acaaccctcc tgccctcata ttgaacac 58

<210> SEQ ID NO 157
<211> LENGTH: 58
<212> TYPE: DNA
<213> ORGANISM: Artificial Sequence
<220> FEATURE:
<223> OTHER INFORMATION: Synthetic

<400> SEQUENCE: 157
acctgtacgg tgacataact gagtgcacta acaaccctcc tgccctcata ttgaacac 58

<210> SEQ ID NO 158
<211> LENGTH: 57
<212> TYPE: DNA
<213> ORGANISM: Artificial Sequence
<220> FEATURE:
<223> OTHER INFORMATION: Synthetic

<400> SEQUENCE: 158
acctgtacgg tgacaggact ggatgcacta acaacccct gccctcatat tgaacac 57

<210> SEQ ID NO 159
<211> LENGTH: 58
<212> TYPE: DNA
<213> ORGANISM: Artificial Sequence
<220> FEATURE:
<223> OTHER INFORMATION: Synthetic

<400> SEQUENCE: 159
acctgtacgg tcaaggcgtc tactgcacta acaaccctcc tgccctcata ttgaacac 58

```
<210> SEQ ID NO 160
<211> LENGTH: 58
<212> TYPE: DNA
<213> ORGANISM: Artificial Sequence
<220> FEATURE:
<223> OTHER INFORMATION: Synthetic

<400> SEQUENCE: 160

acctgtacgg tacaaggcga tgctgcacta acaaccctcc tgccctcata ttgaacac        58

<210> SEQ ID NO 161
<211> LENGTH: 58
<212> TYPE: DNA
<213> ORGANISM: Artificial Sequence
<220> FEATURE:
<223> OTHER INFORMATION: Synthetic

<400> SEQUENCE: 161

acctgtacgg tgacagggac tgctgcacta acaaccctcc tgccctcata ttgaacac        58

<210> SEQ ID NO 162
<211> LENGTH: 57
<212> TYPE: DNA
<213> ORGANISM: Artificial Sequence
<220> FEATURE:
<223> OTHER INFORMATION: Synthetic

<400> SEQUENCE: 162

acctgtacgg tgacaggact ggatgcacta acaaccccct gccctcatat tgaacac         57

<210> SEQ ID NO 163
<211> LENGTH: 57
<212> TYPE: DNA
<213> ORGANISM: Artificial Sequence
<220> FEATURE:
<223> OTHER INFORMATION: Synthetic

<400> SEQUENCE: 163

acctgtacgg tgacaggact ggatgcacta acaaccccct gccctcatat tgaacac         57

<210> SEQ ID NO 164
<211> LENGTH: 58
<212> TYPE: DNA
<213> ORGANISM: Artificial Sequence
<220> FEATURE:
<223> OTHER INFORMATION: Synthetic

<400> SEQUENCE: 164

acggtgacca aggcggcgac tggtgcacta acaaccctcc tgccctcata ttgaacac        58

<210> SEQ ID NO 165
<211> LENGTH: 58
<212> TYPE: DNA
<213> ORGANISM: Artificial Sequence
<220> FEATURE:
<223> OTHER INFORMATION: Synthetic

<400> SEQUENCE: 165

acctgtacgg tgacaggact tgatgcacta acaaccctcc tgccctcata ttgaacac        58

<210> SEQ ID NO 166
<211> LENGTH: 58
<212> TYPE: DNA
<213> ORGANISM: Artificial Sequence
<220> FEATURE:
<223> OTHER INFORMATION: Synthetic
```

<400> SEQUENCE: 166
accttgacaa ggcgaccact ggttgcacta acaaccctcc tgccctcata ttgaacac 58

<210> SEQ ID NO 167
<211> LENGTH: 58
<212> TYPE: DNA
<213> ORGANISM: Artificial Sequence
<220> FEATURE:
<223> OTHER INFORMATION: Synthetic

<400> SEQUENCE: 167
acctgtacgg tacaaggcga tgggtgccta acaaccctcc tgccctcata ttgaacac 58

<210> SEQ ID NO 168
<211> LENGTH: 58
<212> TYPE: DNA
<213> ORGANISM: Artificial Sequence
<220> FEATURE:
<223> OTHER INFORMATION: Synthetic

<400> SEQUENCE: 168
acctgtacgg tgacagcgta cgatgcacta acaaccctcc tgccctcata ttgaacac 58

<210> SEQ ID NO 169
<211> LENGTH: 58
<212> TYPE: DNA
<213> ORGANISM: Artificial Sequence
<220> FEATURE:
<223> OTHER INFORMATION: Synthetic

<400> SEQUENCE: 169
acctgtacgg tgacagctta tgctgcacta acaaccctcc tgccctcata ttgaacac 58

<210> SEQ ID NO 170
<211> LENGTH: 58
<212> TYPE: DNA
<213> ORGANISM: Artificial Sequence
<220> FEATURE:
<223> OTHER INFORMATION: Synthetic

<400> SEQUENCE: 170
acctgtacgg tgacagcgga tgatgcacta acaaccctcc tgccctcata ttgaacac 58

<210> SEQ ID NO 171
<211> LENGTH: 58
<212> TYPE: DNA
<213> ORGANISM: Artificial Sequence
<220> FEATURE:
<223> OTHER INFORMATION: Synthetic

<400> SEQUENCE: 171
acctgtacgg tgacacgaac tgctgcacta acaaccctcc tgccctcata ttgaacac 58

<210> SEQ ID NO 172
<211> LENGTH: 58
<212> TYPE: DNA
<213> ORGANISM: Artificial Sequence
<220> FEATURE:
<223> OTHER INFORMATION: Synthetic

<400> SEQUENCE: 172
acctgtacgg tgacagctta tgctgcacta acaaccctcc tgccctcata ttgaacac 58

<210> SEQ ID NO 173
<211> LENGTH: 58

<212> TYPE: DNA
<213> ORGANISM: Artificial Sequence
<220> FEATURE:
<223> OTHER INFORMATION: Synthetic

<400> SEQUENCE: 173
acctgtacgg tcaaggcgta gactccacta acaaccctcc tgccctcata ttgaacac 58

<210> SEQ ID NO 174
<211> LENGTH: 57
<212> TYPE: DNA
<213> ORGANISM: Artificial Sequence
<220> FEATURE:
<223> OTHER INFORMATION: Synthetic

<400> SEQUENCE: 174
acctgtacgg tgacaaacta tgtgcactaa caaccctcct gccctcatat tgaacac 57

<210> SEQ ID NO 175
<211> LENGTH: 58
<212> TYPE: DNA
<213> ORGANISM: Artificial Sequence
<220> FEATURE:
<223> OTHER INFORMATION: Synthetic

<400> SEQUENCE: 175
acctgtacgg tgacagcgga tactgcacta acaaccctcc tgccctcata ttgaacac 58

<210> SEQ ID NO 176
<211> LENGTH: 58
<212> TYPE: DNA
<213> ORGANISM: Artificial Sequence
<220> FEATURE:
<223> OTHER INFORMATION: Synthetic

<400> SEQUENCE: 176
acctgtacgg tgacagcatc tggtgcacta acaaccctcc tgccctcata ttgaacac 58

<210> SEQ ID NO 177
<211> LENGTH: 57
<212> TYPE: DNA
<213> ORGANISM: Artificial Sequence
<220> FEATURE:
<223> OTHER INFORMATION: Synthetic

<400> SEQUENCE: 177
acctgtacgg tgacatcatg tgtgaactaa caaccctcct gccctcatat tgaacac 57

<210> SEQ ID NO 178
<211> LENGTH: 58
<212> TYPE: DNA
<213> ORGANISM: Artificial Sequence
<220> FEATURE:
<223> OTHER INFORMATION: Synthetic

<400> SEQUENCE: 178
acctgtacgg tgacatgact ggctgcacta acaaccctcc tgccctcata ttgaacac 58

<210> SEQ ID NO 179
<211> LENGTH: 44
<212> TYPE: DNA
<213> ORGANISM: Artificial Sequence
<220> FEATURE:
<223> OTHER INFORMATION: Synthetic

<400> SEQUENCE: 179
ctcgtaggct gcactaacaa ccctcctgcc ctcatattga acac 44

<210> SEQ ID NO 180
<211> LENGTH: 55
<212> TYPE: DNA
<213> ORGANISM: Artificial Sequence
<220> FEATURE:
<223> OTHER INFORMATION: Synthetic

<400> SEQUENCE: 180
acctgtacgg tgacaacgtg agtgacacta acaccctcct cctcatattg aacac 55

<210> SEQ ID NO 181
<211> LENGTH: 58
<212> TYPE: DNA
<213> ORGANISM: Artificial Sequence
<220> FEATURE:
<223> OTHER INFORMATION: Synthetic

<400> SEQUENCE: 181
acctgtacgg tgaaacccac tgctgcacta acacccctcc tgccctcata ttgaacac 58

<210> SEQ ID NO 182
<211> LENGTH: 58
<212> TYPE: DNA
<213> ORGANISM: Artificial Sequence
<220> FEATURE:
<223> OTHER INFORMATION: Synthetic

<400> SEQUENCE: 182
acctgtacgg tgacatgact ggatgcacta acaaccctcc tgccctcata ttgaacac 58

<210> SEQ ID NO 183
<211> LENGTH: 55
<212> TYPE: DNA
<213> ORGANISM: Artificial Sequence
<220> FEATURE:
<223> OTHER INFORMATION: Synthetic

<400> SEQUENCE: 183
cttcgtagaa catggcgtgc tgcactaaca accctcctgc cctcatattg aacac 55

<210> SEQ ID NO 184
<211> LENGTH: 54
<212> TYPE: DNA
<213> ORGANISM: Artificial Sequence
<220> FEATURE:
<223> OTHER INFORMATION: Synthetic

<400> SEQUENCE: 184
acctgtacgg tgacagcata agtgcactaa caactctgca ctcatattga acac 54

<210> SEQ ID NO 185
<211> LENGTH: 56
<212> TYPE: DNA
<213> ORGANISM: Artificial Sequence
<220> FEATURE:
<223> OTHER INFORMATION: Synthetic

<400> SEQUENCE: 185
acctgtacgg tgacagcaga aggtgcacta acacctcctg cactcatatt gaacac 56

<210> SEQ ID NO 186
<211> LENGTH: 55
<212> TYPE: DNA
<213> ORGANISM: Artificial Sequence -continued
<220> FEATURE:
<223> OTHER INFORMATION: Synthetic

<400> SEQUENCE: 186
acctgtacgg tgacaggaac tcgtgcacta cacctcacgc actcatattg aacac 55

<210> SEQ ID NO 187
<211> LENGTH: 58
<212> TYPE: DNA
<213> ORGANISM: Artificial Sequence
<220> FEATURE:
<223> OTHER INFORMATION: Synthetic

<400> SEQUENCE: 187
acctgtacgg tgagagaact agctgcacta acaaccctcc tgcactcata ttgaacac 58

<210> SEQ ID NO 188
<211> LENGTH: 57
<212> TYPE: DNA
<213> ORGANISM: Artificial Sequence
<220> FEATURE:
<223> OTHER INFORMATION: Synthetic

<400> SEQUENCE: 188
acctgtacgg tgagaagact gggtgcacta acaacctcct gcactcatat tgaacac 57

<210> SEQ ID NO 189
<211> LENGTH: 56
<212> TYPE: DNA
<213> ORGANISM: Artificial Sequence
<220> FEATURE:
<223> OTHER INFORMATION: Synthetic

<400> SEQUENCE: 189
acctgtacgg tgacagcata gggtgcacta acacctcctg cgctcatatt gaacac 56

<210> SEQ ID NO 190
<211> LENGTH: 55
<212> TYPE: DNA
<213> ORGANISM: Artificial Sequence
<220> FEATURE:
<223> OTHER INFORMATION: Synthetic

<400> SEQUENCE: 190
acctgtacgg tgacagcact gctgcactaa cacctcctgc gctcatattg aacac 55

<210> SEQ ID NO 191
<211> LENGTH: 20
<212> TYPE: PRT
<213> ORGANISM: Artificial Sequence
<220> FEATURE:
<223> OTHER INFORMATION: Synthetic

<400> SEQUENCE: 191

Val Lys Val Met Phe Asp Tyr Ala Gly Ser Val Val Arg Arg Gly Asp
1 5 10 15

Tyr Gln Val Cys
20